(12) United States Patent
Kelly et al.

(10) Patent No.: US 8,703,815 B2
(45) Date of Patent: Apr. 22, 2014

(54) SMALL MOLECULES THAT COVALENTLY MODIFY TRANSTHYRETIN

(75) Inventors: Jeffery W. Kelly, LaJolla, CA (US); Sungwook Choi, Daejeon (KR)

(73) Assignee: The Scripps Research Institute, LaJolla, CA (US)

( * ) Notice: Subject to any disclaimer, the term of this patent is extended or adjusted under 35 U.S.C. 154(b) by 0 days.

(21) Appl. No.: 13/516,963

(22) PCT Filed: Oct. 14, 2010

(86) PCT No.: PCT/US2010/052672
§ 371 (c)(1), (2), (4) Date: Jun. 18, 2012

(87) PCT Pub. No.: WO2011/075210
PCT Pub. Date: Jun. 23, 2011

(65) Prior Publication Data
US 2012/0270938 A1    Oct. 25, 2012

Related U.S. Application Data

(60) Provisional application No. 61/288,128, filed on Dec. 18, 2009.

(51) Int. Cl.
*A61K 31/21*    (2006.01)
*A61K 31/235*   (2006.01)
*A61K 31/19*    (2006.01)
*A61K 31/05*    (2006.01)

(52) U.S. Cl.
USPC ............ 514/513; 514/544; 514/568; 514/733

(58) Field of Classification Search
None
See application file for complete search history.

(56) References Cited

FOREIGN PATENT DOCUMENTS

JP    61-000057 A    1/1986
WO    WO 03-009807    2/2003

OTHER PUBLICATIONS

Johnson et al (J Med Chem 51:6348-6358, 2008).*
Tinnemans et al., J Chem Soc, Perkin II 1976(10):1104-1111.
Hunter et al., Chem Comm 2004(1):108-109.
Dogan et al., J Am Chem Soc 2004 126(15):4762-4763.
Nishioka et al., Chem Comm 2007 (42):4354-4356.
Choi et al., J Am Chem Soc 2010 134(4)1359-1370 (Web pub Dec. 31, 2009).

* cited by examiner

*Primary Examiner* — Craig Ricci
(74) *Attorney, Agent, or Firm* — Husch Blackwell, LLP

(57) ABSTRACT

A family of covalent kinetic stabilizer compounds that selectively and covalently react with the prominent plasma protein transthyretin in preference to more than 4000 other human plasma proteins is disclosed. A contemplated compound corresponds in structure to Formula I, below, where the various substituents are defined within, and

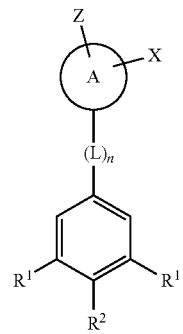

reacts chemoselectively with one or two of four Lys-15 ε-amino groups within the transthyretin tetramer. The crystal structure confirms the binding orientation of the compound substructure and the conjugating amide bond. A covalent transthyretin kinetic stabilizer exhibits superior amyloid inhibition potency, compared to a non-covalent counterpart, and inhibits cytotoxicity associated with amyloidogenesis.

7 Claims, 13 Drawing Sheets

SMALL MOLECULES THAT COVALENTLY MODIFY TRANSTHYRETIN

CROSS-REFERENCE TO RELATED APPLICATION

This application claims priority of provisional application Ser. No. 61/288,128, filed on Dec. 18, 2009, whose disclosures are incorporated by reference.

GOVERNMENTAL SUPPORT

The present invention was made with governmental support under Contract No. DK046335 awarded by the National Institutes of Health. The government has certain rights in this invention.

BACKGROUND ART

Small molecules that react chemoselectively with a unique non-enzyme protein in a complex biological environment are rare. Such molecules are envisioned to have imaging, pharmacology and protein engineering applications. Pharmacologic examples include Plavix® (clopidogrel) and related thienopyridines, which are oxidized in the liver yielding a thiol that forms a disulfide with a Cys residue in the $P2Y_{12}$ receptor, inactivating it. [Savi et al., *Thromb. Haemost.* 84:891-896 (2000)]. There are β-amino ketones identified by high throughput screening that β-eliminate to form α,β-unsaturated ketones and then react with a proximal Cys residue in the thyroid hormone receptor, inhibiting it. [Estebanez-Perpina et al., *Mol. Endocrinol.* 21:2919-2928 (2007)] There are also small molecules that are known to bind to and react with one Lys ε-amino group within a purified antibody in buffer. [Guo et al., *Proc. Natl. Acad. Sci. U.S.A.* 103:11009-11014 (2006)] These conjugates, after purification, are envisioned to become injectable drugs (see, covx.com). However, compounds that react with a specific Lys ε-amino group in a non-enzyme protein in the context of a complex biological sample have not been reported.

For pharmacologic applications, it would be advantageous if an orally bioavailable, appropriately reactive small molecule formed a conjugate with an endogenous non-enzyme protein. This strategy can be used to conjugate potent drug candidate substructures, whose individual pharmacologic properties are undesirable, to an endogenous protein such that the conjugate exhibited activity and a favorable half-life and distribution. Lys ε-amine covalent modifiers can also be used to modulate non-enzyme function. A third application is focused upon in this invention, the creation of Lys ε-amine covalent modifiers that form a conjugate with an endogenous protein inhibiting it from aggregating and leading to a gain-of-toxic-function amyloid disease.

Human amyloid diseases, like the transthyretin (TTR) amyloidoses, are named after the characteristic extracellular cross-β-sheet amyloid fibril deposits that result from the misassembly of a specific protein. [Cohen et al., *Science* 313: 1604-1610 (2006); and Hardy et al., *Science* 297:353-356 (2002)] The amyloidogenesis-associated cytotoxicity that appears to be central to amyloid disease etiology is linked to an aging-associated decline in cellular protein homeostasis, or proteostasis, capacity. [Cohen et al., *Science* 313:1604-1610 (2006); and Balch et al., *Science* 319:916-919 (2008)].

Senile systemic amyloidosis (SSA) affecting >10% of the aged population, results from wild type (WT) TTR amyloidogenesis leading to cardiomyopathy. [Johnson et al., *Acc. Chem. Res.* 38:911-921 (2005); and Westermark et al., *Proc. Natl. Acad. Sci. U.S.A.* 87:2843-2845 (1990)] Deposition of a destabilized TTR mutant causes earlier onset familial amyloid polyneuropathy (FAP) and/or cardiomyopathy (FAC). [Coelho, *Curr. Opin. Neurol.* 9:355-359 (1996); Jacobson et al., *N. Engl. J. Med.* 336:466-473 (1997); and Sekijima et al., *Cell* 121:73-85 (2005)]. No effective treatment is available for SSA or FAC.

The only strategy to ameliorate FAP is gene therapy mediated by liver transplantation, wherein the wild type/mutant TTR (WT-TTR/mutant-TTR) genes in the liver (that synthesize plasma-bound TTR) are replaced by WT-TTR/WT-TTR genes [Holmgren et al., *Lancet* 341:1113-1116 (1993)], resulting in a dramatic reduction in amyloidogenic TTR concentration in the blood. However, continued WT-TTR deposition in the heart post-transplantation results in cardiomyopathy, limiting effectiveness. Thus, general chemotherapeutic approaches for the TTR amyloidoses are sought. [Johnson et al., *Acc. Chem. Res.* 38:911-921 (2005)].

Transthyretin is a 55 kDa homotetrameric protein composed of 127-residue β-sheet-rich subunits. [Klabunde et al., *Nat. Struct. Biol.* 7:312-321 (2000)]. TTR transports thyroxine ($T_4$) and holoretinol binding protein (REP) in the blood and in the cerebrospinal fluid (CSF), using non-overlapping binding sites. [Monaco et al., *Science* 268:1039-1041 (1995); and Wojtczak et al., *J. Biol. Chem.* 267:353-357 (1992)] Transthyretin is also present within neurons. Concentrations of TTR in healthy adults have been reported to be in the range of 0.017-0.025 g/L in the CSF [Davidsson et al., *J. Neural. Transm.* 1997, 104:711-720; Riisoen; *Acta Neurol. Scand.* 1988, 78:455-459; and Ingenbleek et al., *Annu. Rev. Nutr.* 1994, 14:495-533] and 0.20-0.40 g/L in the plasma [Hamilton et al., *Cell Mol Life Sci* 2001, 58:1491-1521].

The more labile dimer-dimer interface of the TTR tetramer creates two funnel-shaped $T_4$ binding sites. Although TTR transports $T_4$ and holoretinol binding protein in the blood and cerebrospinal fluid of mammals, >99% of the $T_4$ sites in human blood are unoccupied because the vast majority of $T_4$ in the blood is carried by thyroid binding globulin and albumin, the latter being most abundant plasma protein. [Klabunde et al., *Nat. Struct. Biol.* 2000, 7:312; Johnson et al., *Acc. Chem. Res.* 2005, 38:911; Monaco et al., *Science* 1995, 268:1039; Wojtczak et al., *J. Biol. Chem.* 1992, 267:353; and Bartalena et al., *Clin. Lab. Med.* 1993, 13: 583]. TTR tetramer dissociation is rate limiting for the generation of partially folded monomers that spontaneously self-assemble into TTR amyloid fibrils. [Johnson et al., *Acc. Chem. Res.* 38:911-921 (2005); Colon et al., *Biochemistry* 31:8654-8660 (1992); Liu et al., *Nat. Struct. Biol.* 7:754-757 (2000); Jiang et al., *Biochemistry* 40:11442-11452 (2001); Hammarstrom et al., *Science* 299:713-716 (2003); Hammarstrom et al., *Science* 293: 2459-2462 (2001); Hurshman et al., *Biochemistry* 43:7365-7381 (2004); and Babbes et al., *Biochemistry* 47:6969-6984 (2008)]. Small molecules that bind to tetrameric TTR and stabilize the ground state more than the dissociative transition state inhibit amyloidogenesis by making the tetramer dissociation barrier insurmountable. [Klabunde et al., *Nat. Struct. Biol.* 2000, 7:312; Petrassi et al., *J. Am. Chem. Soc.* 2000, 122:2178; Razavi et al., *Angew. Chem. Int. Ed. Engl.* 2003, 42:2758; Purkey et al., *Chem. Biol.* 2004, 11:1719; Johnson et al., *Acc. Chem. Res.* 2005, 38:911; Johnson et al., *J. Med. Chem.* 2008, 51:260; Johnson et al., *J. Med. Chem.* 2008, 51:6348; Adamski-Werner et al., *J. Med. Chem.* 2004, 47:355; Oza et al., *J. Med. Chem.* 2002, 45:321; Baures et al., *Bioorg. Med. Chem.* 1999, 7:1339; Green et al., *J. Am. Chem. Soc.* 2003, 125:13404; and Hammarstrom et al., *Science* 2003, 299:713]. These so-called TTR kinetic stabilizers have recently been demonstrated to be efficacious in a phase II/III placebo-controlled clinical trial for familial amyloid polyneuropathy, one of the transthyretin amyloid diseases (See, foldrx.com).

Reversible occupancy of one of the two $T_4$ binding sites by a high affinity small molecule is known to be sufficient to kinetically stabilize the entire TTR tetramer through differential stabilization of the ground state over the dissociative transition state, thus inhibiting amyloidogenesis. [Johnson et al., *Acc. Chem. Res.* 38:911-921 (2005); Hammarstrom et al., *Science* 299:713-716 (2003); Hammarstrom et al., *Science* 293:2459-2462 (2001); Adamski-Werner et al., *J. Med. Chem.* 47:355-374 (2004); Johnson et al., *J. Med. Chem.* 51:6348-6358 (2008); Johnson et al., *J. Med. Chem.* 48:1576-1587 (2005); Miroy et al., *Proc. Natl. Acad. Sci. U.S.A.* 93:15051-15056 (1996); Oza et al., *J. Med. Chem.* 45, 321-332 (2002); Razavi et al., *Angew. Chem. Int. Ed. Engl.* 42, 2758-2761 (2003); Wiseman et al., *J. Am. Chem. Soc.* 127: 5540-5551 (2005); Foss et al., *J. Mol. Biol.* 347, 841-854 (2005); and Foss et al., *Biochemistry* 44:15525-15533 (2005)].

The development of fluorescent biosensors to image processes within living cells with high spatial and temporal resolution has transformed what can be accomplished in biological research. [Tsien, *Angew. Chem., Int. Ed.* 2009, 48:5612]. A commonly used molecule within sensors is the green fluorescent protein (GFP), which must first fold and then undergo an autocatalytic intramolecular chemical reaction to form its chromophore. [Shimomura et al., *J. Cell Comp. Physiol.* 1962, 59:223; Prasher et al., *Gene* 1992, 111:229; Chalfie et al., *Science* 1994, 263:802; Tsien, *Annu Rev Biochem* 1998, 67:509; Morise et al., *Biochemistry* 1974, 13:2656; Heim et al., *Proc. Natl. Acad. Sci. U.S.A.* 1994, 91:12501; and Heim et al., *Nature* 1995, 373:663]. Although mutants of GFP exhibit emission at a variety of wavelengths [Shaner et al., *Nature Biotechnology* 2004, 22:1567], there are limits to what can accomplished using mutagenesis to alter their photophysical properties. [Tsien, *Angew. Chem., Int. Ed.* 2009, 48:5612].

A family of designed compounds are disclosed hereinafter, exemplified by stilbenes that very selectively bind to TTR in human plasma and, when bound, chemoselectively react with the ε-amino group of Lys-15 of TTR, affording an amide bond. These covalent TTR kinetic stabilizers inhibit 10-20 percent more TTR amyloid fibril formation than their non-covalent counterparts, which are exceptional TTR kinetic stabilizers in their own right. The cytotoxicity linked to TTR amyloidogenesis is also inhibited by these covalent TTR kinetic stabilizers.

In addition, certain members of this family of covalent TTR kinetic stabilizers that are themselves non-fluorescent, metal-free compounds bind to and react with TTR creating a fluorophore as a consequence of amide bond conjugation. Owing to the structural plasticity exhibited by the TTR binding site for a wide variety of stilbenes and related molecules, the work underlying the invention disclosed hereinafter indicates that a covalent TTR kinetic stabilizer compound can be extensively modified chemically and the protein modified by mutagenesis to manipulate the excitation and emission wavelengths, the fluorescence lifetime and other photophysical properties of the TTR-conjugate. [Klabunde et al., *Nat. Struct. Biol.* 2000, 7:312; Petrassi et al., *J. Am. Chem. Soc.* 2000, 122:2178; Razavi et al., *Angew. Chem. Int. Ed. Engl.* 2003, 42:2758; Purkey et al., *Chem. Biol.* 2004, 11:1719; Petrassi et al., *J. Am. Chem. Soc.* 2005, 127:6662; Johnson et al., *Acc. Chem. Res.* 2005, 38:911; Johnson et al., *J. Med. Chem.* 2008, 51:260; Johnson et al., *J. Med. Chem.* 2008, 51:6348; and Johnson et al., *J. Med. Chem.* 2009, 52:1115].

BRIEF SUMMARY OF THE INVENTION

The present invention contemplates a covalent TTR kinetic stabilizer compound, a composition for using that compound and several methods for using the compound. Thus, in one aspect, a compound that corresponds in structure to Formula I is contemplated.

I

In a compound of Formula I, $R^1$ is halo, preferably chloro or bromo, a methyl, monofluoro-, difluoro- or trifluoromethyl group; $R^2$ is H, OH or $NH_2$; n is zero or one; L is a linker that is Q=Q or $CH_2$—$CH_2$ when n is one and is absent when n is zero, so that the two depicted cyclic structures are bonded directly to each other, where Q=Q is N=N or HC=CH, with HC=CH being preferred. The circle A is an aromatic or heteroaromatic ring structure containing one 5- or 6-membered ring, which is preferred, or a fused ring system containing one 5- and one 6-membered ring or two 6-membered rings. X is a reactive substituent that reacts with an amine in an aqueous environment to bond the amine to the depicted compound such as carboxylic ester or thioester, an azetidin-2-one, a Michael acceptor, an α-haloacetyl group or an epoxide, an aziridine or an episulfide group. Z is H, which is preferred in some embodiments, or a second linker, $L_2$, such as X that can be the same or different from the previously noted X, or a $NR^3R^4$ group, where $R^3$ and $R^4$ are the same or different and are H, methyl or ethyl, a 1,3-diketo group or a metal ion chelating group.

A particularly preferred compound of Formula I is a compound of Formula Iva 1 shown below, where X is as before defined, and preferably is a carboxylic ester or thioester.

IVa 1

Of the above compounds of Formula IVa 1, two are of particular interest herein and are shown in the Table below along with the name used to refer to the compound of Formula IVa1 that contains the depicted X substituent.

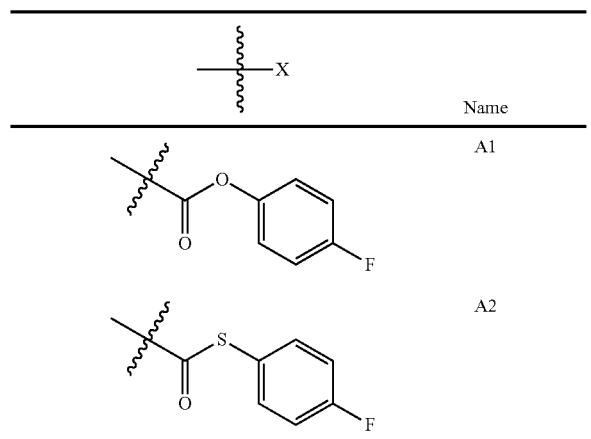

A pharmaceutical composition that comprises a transthyretin (TTR) fibril formation-inhibiting amount of a compound of Formula I dissolved or dispersed in a pharmaceutically acceptable diluent is also contemplated. A pharmaceutical composition is typically an aqueous composition that contains a compound of Formula I dissolved or dispersed therein along with a diluent. The compound of Formula I is present in an amount sufficient to provide a concentration of about 1 nM to about 100 µM, preferably about 1 nM to about 10 µM, when admixed with TTR. Thus, the amount of a compound of Formula I present can be about 1 nM to the limit of solubility of the compound, or about 10 µM. A pharmaceutical composition that contains a TTR fibril formation-inhibiting amount of a compound of Formula I dissolved or dispersed in a physiologically or pharmaceutically acceptable diluent is also contemplated.

A compound of Formula I is useful is several methods. A method of inhibiting TTR fibril formation is contemplated that comprises the steps of contacting an aqueous composition containing TTR with a stabilizing amount of a compound of Formula I and maintaining that contact for a time period sufficient for the compound to bind to, react with and thereby kinetically stabilize TTR.

A method of treating transthyretin (TTR) amyloidosis in a subject in need is contemplated that comprises administering to that subject a contemplated pharmaceutical composition discussed above. That composition can be administered a plurality of times in one week.

A method for identifying a non-covalent TTR kinetic stabilizer compound is also contemplated. This method that comprises the steps of admixing a binding-sufficient amount of a candidate non-covalent TTR kinetic stabilizer compound with an aqueous composition that contains a predetermined amount of TTR to form a first binding admixture. That first binding admixture is maintained for a time period sufficient for the candidate compound to bind to TTR. A binding/reaction sufficient amount of a compound of Formula I in which Q=Q is HC=CH is admixed with the first binding admixture to form a binding/reaction admixture, and that binding/reaction admixture is maintained for a time period sufficient for the compound of step of Formula I to bind to and react with TTR. Whether the reaction of the compound of Formula I with TTR has been inhibited is determined and when inhibition is found, that inhibition identifies the candidate compound as a non-covalent TTR kinetic stabilizer compound.

One method is for assaying for the presence of transthyretin (TTR) in a sample to be assayed. That method comprises the steps of admixing a compound of Formula I with a sample to be assayed such as blood plasma or serum, cells or tissues. The admixture so formed is maintained for a time period sufficient for the compound to bind to TTR present in the sample, react with it and form a conjugate (reacted compound). The presence of conjugate is then determined, as by LC-MS, fluorescence spectroscopy or the like.

BRIEF DESCRIPTION OF THE DRAWINGS

In the drawings forming a part of this disclosure,

FIG. 1 illustrates a reverse phase (RP)-HPLC analysis of the chemoselectivity of Compounds 1-4 in recombinant WT-TTR vs K15A-TTR (wild type TTR vs. a TTR mutant having an alanine at position 15 in place of a lysine residue) homotetramer solutions and human plasma.

FIG. 2 shows a comparison of the potency of covalent kinetic stabilizers and their non-covalent counterparts as TTR amyloid inhibitors and an assessment of WT-TTR tetramer dissociation kinetics in the presence of a covalent kinetic stabilizer.

FIG. 8 contains two graphs that show the linear correlation between assays for a TTR-reacted inhibitor compound conjugate carried out by RP-HPLC and fluorescence measurements. FIG. 8A illustrates the data for the reacted Compound 4-TTR conjugate fluorescence intensity change (X axis) and RP-HPLC intensity of for the same conjugate (Y axis), whereas

Figure 1A:
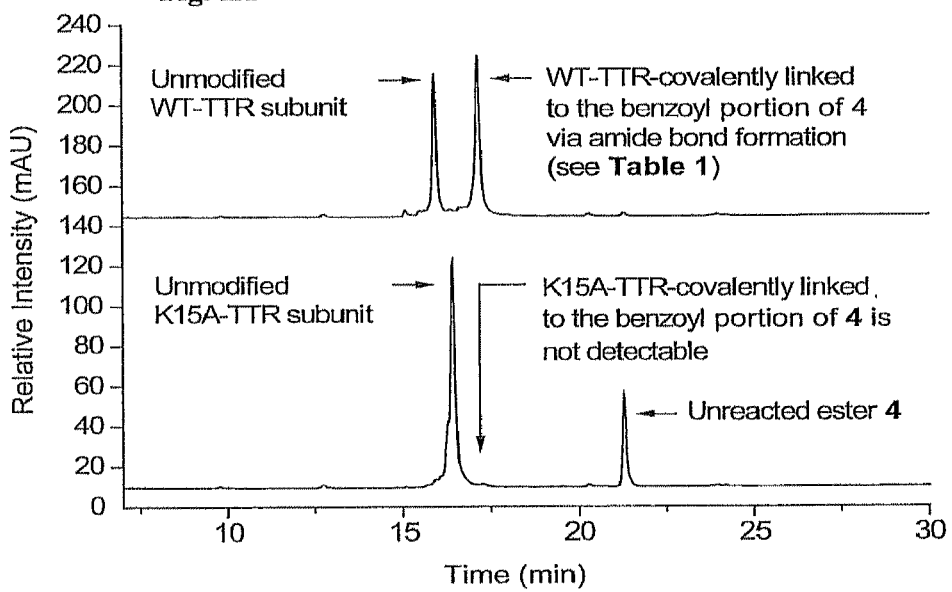
FIG. 1A shows a $C_{18}$-RP-HPLC analysis of WT-TTR (top) or K15A-TTR (bottom) pre-incubated (18 hours) with candidate covalent kinetic stabilizer Compound 4 (analogous data for Compounds 1-3 were also obtained).

The present invention has several benefits and advantages.

One benefit is the provision of a reactive, covalent TTR stabilizer compound that functions like a suicide inhibitor in its irreversible reaction with TTR to stabilize the TTR tetramer and inhibit fibril formation.

An advantage of the invention is that certain of the contemplated compounds only fluoresce when they have reacted with TTR so that the presence of inhibited TTR molecules can be detected readily.

Another benefit of the invention is that a contemplated can select TTR out of the approximately 4000 proteins present in blood plasma or serum as the only protein with which to react.

A further advantage of the invention is that a contemplated compound is relatively easily prepared.

Yet another benefit of the invention is that compound A2 is non-fluorescent as depicted and bound in the TTR tetramer, but upon reaction with the ε-amino group of lysine-15 of TTR, fluoresces at a wavelength of 430 nm when irradiated at a wavelength of 328 nm.

Yet another advantage of the invention is that Compound A2-derived conjugate fluorescence can be used to measure the stoichiometry of kinetic stabilizers bound to TTR in patient plasma using an A2-kinetic stabilizer competition assay.

Still further benefits and advantages will be apparent to the worker of ordinary skill from the disclosure that follows.

DETAILED DESCRIPTION OF THE INVENTION

One aspect of the invention contemplates a covalent TTR kinetic stabilizer compound. A composition for using that compound and several methods for using the compound are also contemplated. Thus, in one aspect, a compound that corresponds in structure to Formula I is contemplated.

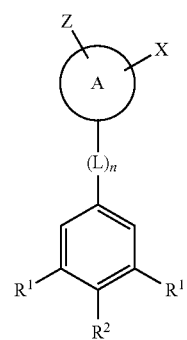

I

In a compound of Formula I, $R^1$ is a halo group, preferably chloro or bromo, a methyl, monofluoro-, difluoro- or trifluoromethyl group; $R^2$ is H, OH or $NH_2$, preferably OH; n is zero or one; L is a linker that is Q=Q or $CH_2$—$CH_2$ when n is one and is absent when n is zero so that the two depicted cyclic structures are bonded directly to each other, where Q=Q is N=N or HC=CH, with HC=CH being preferred. Circle A is an aromatic or heteroaromatic ring structure containing one 5- or 6-membered ring, which is preferred, or a fused ring system containing one 5- and one 6-membered ring or two 6-membered rings. X is a reactive substituent that reacts with an amine in an aqueous environment to bond the amine to the depicted compound such as carboxylic ester or thioester, an azetidin-2-one, a Michael acceptor, an α-haloacetyl group or an epoxide, an aziridine or an episulfide group. Z is H, which is preferred in some embodiments, or a second linker, $L_2$, such as X that can be the same or different from the previously mentioned X group, $NR^3R^4$, where $R^3$ and $R^4$ are the same or different and are H, methyl or ethyl, a 1,3-diketo group or a metal ion chelating group.

In one preferred embodiment, a compound of Formula I corresponds in structure to Formula Ic, below,

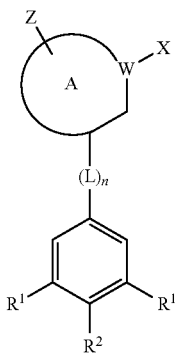

Ic where L, n, X, Z, $R^1$ and $R^2$ are as defined before, W is N or C, preferably C, and the depicted structure A is an aromatic or heteroaromatic ring structure containing one 5- or 6-membered ring, which is preferred. A dashed circle can also be added within the within the ring structure A to further indicate that the depicted ring is aromatic.

In a compound of Formula Ic, the atoms bonded to the linker, L, and the reactive substituent that reacts with an amine in an aqueous environment to bond the amine to the depicted compound, X, are in a 1,3-substitution relationship in the ring to which they are bonded. It is to be understood that this "1,3-substitution" nomenclature does not refer to the formal rules of naming, particularly where heterocyclic compounds are contemplated, but rather to the fact that the bonds to L and to X are separated by three ring atoms. Illustrative Formula Ic compounds are shown in Tables A, B, F, H, J, K, L, M, O, P, Q and R hereinafter.

Another contemplated compound of Formula I (including Formulas Ia, Ib, and Ic) corresponds in structure to Formula II or Formula III, below.

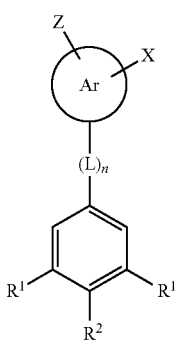

II

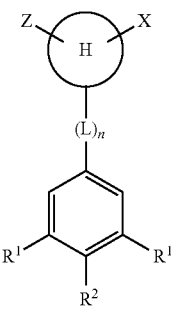

III

In Formulas II and III, L, n, X, Z, $R^1$ and $R^2$ are as defined before, and circle Ar is a hydrocarbyl aromatic ring system, whereas circle H is a heteroaromatic ring system.

Thus, where circle Ar is present, a contemplated compound of Formula II can correspond in structure to one of Formulas IVa, IVb, IVc or IVd that are shown below, where L, n, X, Z, $R^1$ and $R^2$ are as defined before.

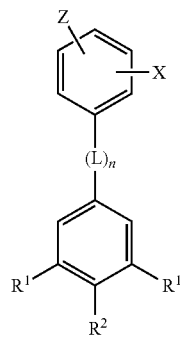

IVa

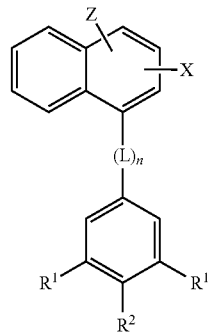

IVb

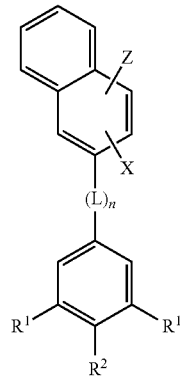

IVc

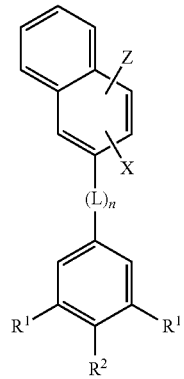

Similarly, where circle H is present, a contemplated compound of Formula III can correspond in structure to one of Formulas Va, Vb, Vc, Vd, Ve, and Vf, that are shown below, and where L, n, X, Z, R¹ and R² are as defined before, and W in Formula Vd is S or O, and M, V, W and Y in Formula Vg are S, N, O or CH, with at least one of M, V, W and Y being other than CH, and the dashed circle within the 5-membered ring indicates that the ring containing M, V, W and Y is a heteroaromatic ring.

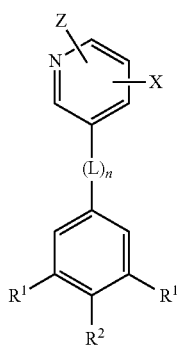

Va

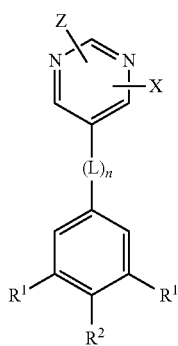

Vb

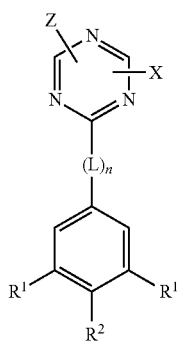

Vc

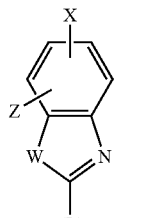

Vd

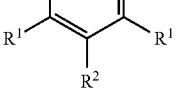

Ve

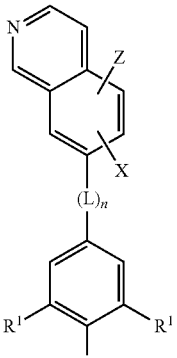

Vf

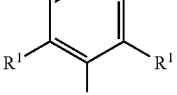

Vg

It is noted that the bonds to L and X are preferably separated by three ring atoms in the above compounds.

A particularly preferred X substituent reactive group is a carboxylic acid ester or thioester prepared using an aromatic or heteroaromatic alcohol or thiol such as a phenol, thiophenol or a pyridinol. It is also preferred that a phenol or thiophenol of such an ester or thioester have a $pK_a$ value that is less than that of phenol itself (about 10.0) down to about 5.0, and preferably about 9.0 to about 6.0. Illustrative p$K_a$ values for suitable esterifiable or thioesterifiable compounds can be found in the *Handbook of Biochemistry*, H. A. Sober Ed., The Chemical Rubber Co., Cleveland, pages J-195, J-215-217 and J-223 (1970), and in Verma et al., *Chem. Res. Toxicol.*, 2003, 16 (3):276-284. Illustrative compounds are shown in the Table below shown as R group portions of compounds of Formula I with p$K_a$ values for the unesterified phenol or thiophenol compound from the above source listed below each structure. The wavy lines indicate the place of bonding between the phenol or thiophenol and the depicted carbonyl group of the circle aromatic or heteroaromatic ring system.

| | |
|---|---|
| 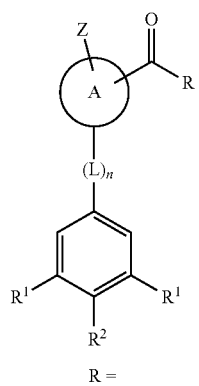 | I |
| R = | |
| 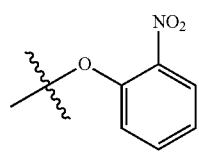 | 7.2 |
| 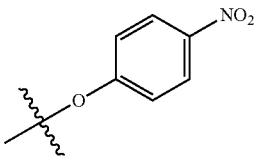 [SMILES: *Oc1ccc([N+](=O)[O-])cc1] | 7.1 |
| 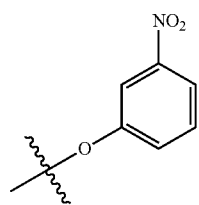 [SMILES: *Oc1cccc([N+](=O)[O-])c1] | 8.4 |
| 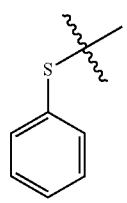 [SMILES: *Sc1ccccc1] | 6.6 |

-continued

| | |
|---|---|
| 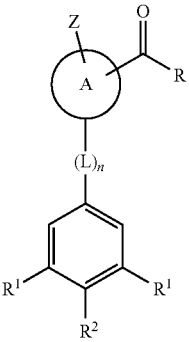 | I |
| R = | |
| 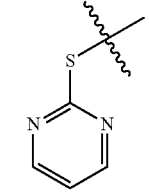 [SMILES: *Sc1ncccn1] | 7.1 |
| 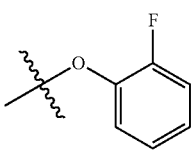 [SMILES: *Oc1ccccc1F] | 8.8 |
| 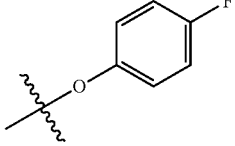 | 9.95 |
| 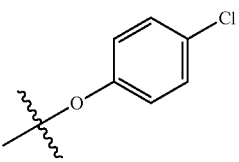 [SMILES: *Oc1ccc(Cl)cc1] | 9.4 |
| 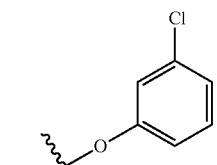 | 9.0 |
| 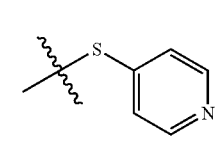 [SMILES: *Sc1ccncc1] | 8.9 |
| 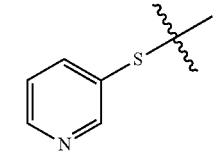 [SMILES: *Sc1cccnc1] | 7.0 |

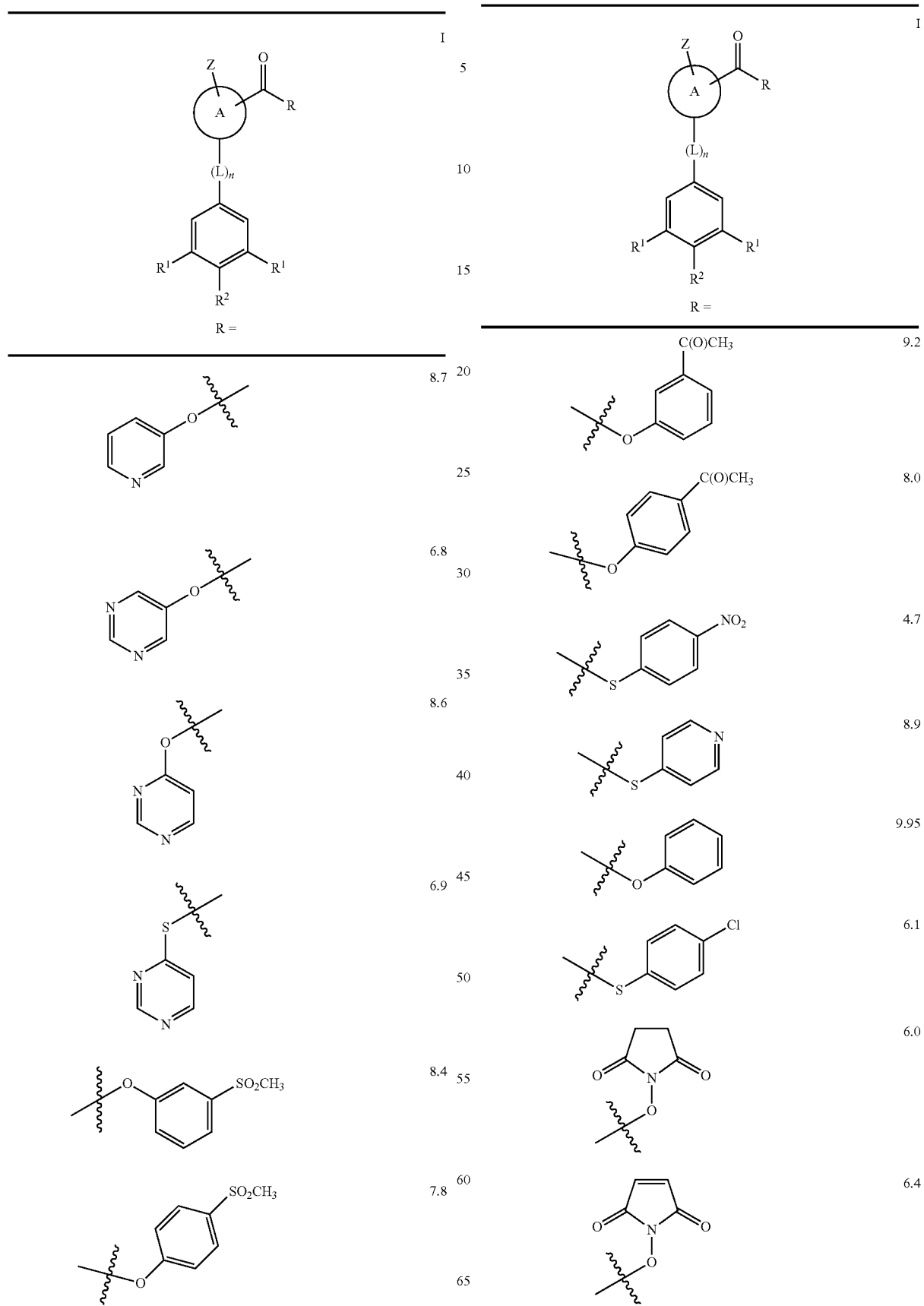

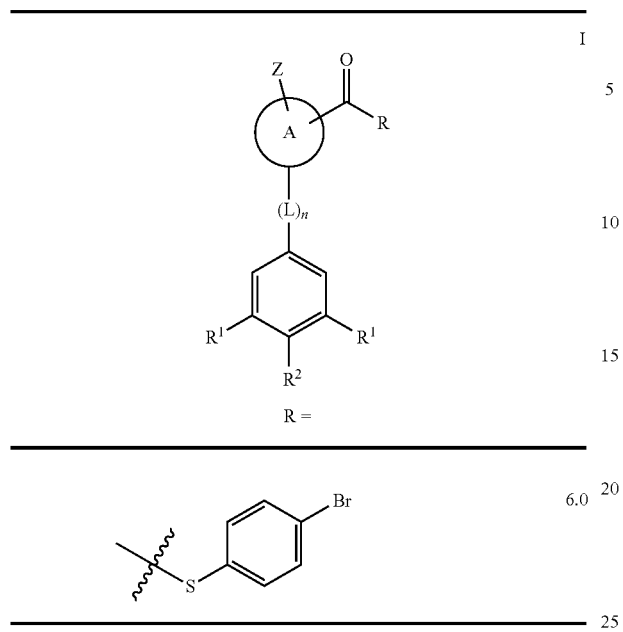

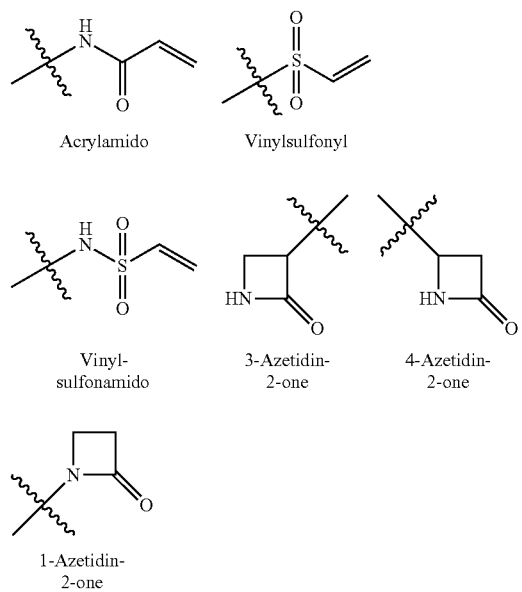

It is to be understood that other leaving groups besides aromatic or heteroaromatic alcohols or thiols are also useful. Additional illustrative leaving groups include the N-hydroxysuccinimido and N-hydroxymaleimido groups shown above. Another useful leaving group is 2-hydroxypropylene (prop-1-en-2-ol).

Another reactive substituent X that reacts with an amine nitrogen in an aqueous medium is a Michael acceptor group; i.e., a substituent that reacts with an amine nitrogen in a Michael addition reaction. Illustrative Michael acceptor groups include a —C(O)CH═CH$_2$ (acryloyl) group, a —S(O)$_2$CH═CH$_2$ (vinylsulfonyl) group, —NHC(O)CH═CH$_2$ (acrylamido) group and —NHS(O)$_2$CH═CH$_2$ (vinylsulfonamido) group.

Still further reactive X substituent groups include a 1-, 3- or 4-azetidine group (collectively, an azetidin-2-one), and an α-halomethylcarbonyl (α-haloacetyl) group, where the halo group is preferably bromo or chloro. An X substituent can also be an epoxide, an aziridine or an episulfide group as are present in a glycidyl, aziridinylmethyl and thiiranylmethyl group (a —CH$_2$CHOCH$_2$, a —CH$_2$CHNHCH$_2$, or a —CH$_2$CHSCH$_2$ group). The structures of these groups and those above are shown below:

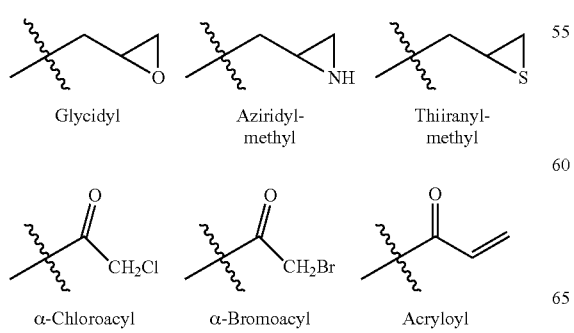

A Z group can be H, which is preferred in some embodiments, and can also be a second linker, L$_2$, such as the same or different X group discussed above, NR$^3$R$^4$, where R$^3$ and R$^4$ are the same or different and are H, methyl or ethyl, a 1,3-diketo group or a metal ion chelating group. Where Z is NR$^3$R$^4$, the linking group function can be via a covalent reaction of the primary or secondary nitrogen atom, or by an ionic bond via a protonated nitrogen atom or a hydrogen bond between the primary, secondary or tertiary nitrogen and a near-by hydroxyl group.

When Z is other than H, a contemplated Z group is linker group L$_2$ of a compound of Formula Ia

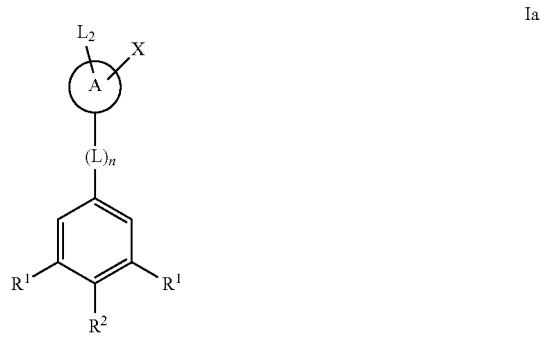

where L, n, X, Z, R$^1$ and R$^2$ are as defined before. That L$_2$ group can conjugate a compound of Formula I to a low molecular weight drug molecule, a peptide containing about 3 to about 35 amino acid residues such as a peptide hormone, and more preferably about 5 to about 25 residues, a peptidomimetic, or to a group for a radionuclide or a contrast agent used in magnetic resonance imaging analyses, as discussed before. Thus, L$_2$ can be an X group that is the same as or different from the previously mentioned X group, a NR$^3$, R$^4$ group where $R^3$ and $R^4$ are the same or different and are H, methyl or ethyl, a 1,3-diketo group or a metal ion chelating group.

A contemplated drug molecule is a low molecular weight compound that typically has a molecular mass of about 1000 Da or less, and preferably a molecular mass of about 700 or less and most preferably about 500 Da or less. Illustrative drug molecules include estrogen and progesterone antagonists, aromatase inhibitors including anastrozole, mycophenolic acid, lisinopril, analapril, captopril, candesartan, eprosartan, ibandronic acid, pamidronic acid, tiludronic acid and the like.

Illustrative peptides and peptide hormones and their analogs include Met- and Leu-enkephalins, dynorphin A, beta-endorphin, ACTH, vasopressin, luteinizing hormone releasing hormone, somatostatin, pancreatic glucagons, parathyroid hormone, amylin, ghrelin, cholecystokinin, erythropioietin, peptide mimetics, tissue factor pathway inhibitor, peptide YY and oxytocin linked to $L_2$ through its carboxyl terminus, an amino acid side chain comprising the peptide hormone or its N-terminal amino group. The tripeptide recognition sequence, ArgGlyAsp (RGD), and a peptide of 5 to about 25 residues containing that sequence is also contemplated.

A contemplated drug, protein, peptide or peptide hormone can be linked to a compound of Formula I using standard conjugation chemistry. For example, each of the above illustrative drug molecules and peptides contains a carboxyl group and that can be conjugated to the amine group via an ester-amide exchange or using carbodiimide chemistry, for example.

The choice of the particular radioisotope (radionuclide) used for labeling can be determined by the size of the of a tumor to be treated or imaged and its localization in the body. Two characteristics are important in the choice of a radioisotope—emission range in the tissue and half-life. Alpha emitters, which have a short emission range in comparison to beta emitters, can be preferable for treatment of small tumors such as melanomas that are disseminated in the body. Examples of alpha emitters include 213-Bismuth (half-life 46 minutes), 223-Radium (half-life 11.3 days), 224-Radium (half-life 3.7 days), 225-Radium (half-life 14.8 days), 225-Actinium (half-life 10 days), 212-Lead (half-life 10.6 hours), 212-Bismuth (half-life 60 minutes), 211-Astatine (half-life 7.2 hours), and 255-Fermium (half-life 20 hours).

In a preferred embodiment, the alpha-emitting radioisotope is 213-Bismuth. $^{213}$Bi emits a high LET α-particle with E=5.9 MeV with a path length in tissue of 50-80 μm. Theoretically a cell can be killed with one or two α-particle hits to the nucleus. $^{213}$Bi is the only α-emitter that is currently available in generator form, which allows transportation of this isotope from the source to clinical centers within the United States and abroad. Another alpha-emitting radioisotope is $^{212}$Bi that emits an α-particle with an energy of about 8 MeV with a path length in tissue of 50-80 μm.

Beta emitters, with their longer emission range, can be preferable for the treatment of large tumors. Examples of beta emitters include 188-Rhenium (half-life 16.7 hours), 90-Yttrium (half-life 2.7 days), 32-Phosphorous (half-life 14.3 days), 47-Scandium (half-life 3.4 days), 67-Copper (half-life 62 hours), 64-Copper (half-life 13 hours), 77-Arsenic (half-life 38.8 hours), 89-Strontium (half-life 51 days), 105-Rhodium (half-life 35 hours), 109-Palladium (half-life 13 hours), 111-Silver (half-life 7.5 days), 131-Iodine (half-life 8 days), 177-Lutetium (half-life 6.7 days), 153-Samarium (half-life 46.7 hours), 159-Gadolinium (half-life 18.6 hours), 186-Rhenium (half-life 3.7 days), 166-Holmium (half-life 26.8 hours), 166-Dysprosium (half-life 81.6 hours), 140-Lantanum (half-life 40.3 hours), 194-Irridium (half-life 19 hours), 198-Gold (half-life 2.7 days), and 199-Gold (half-life 3.1 days).

In one preferred embodiment, the beta-emitting radioisotope is 188-Rhenium. $^{188}$Re is a high-energy β-emitter ($E_{max}$=2.12 MeV) that has recently emerged as an attractive therapeutic radionuclide in diverse therapeutic trials including cancer radioimmunotherapy, palliation of skeletal bone pain, and endovascular brachytherapy to inhibit restenosis after angioplasty. $^{188}$Re has the additional advantage that it emits γ-rays that can be used for imaging studies. For access to sites deep in the body, longer-lived isotopes such as 90-Yttrium (half-life 2.7 days), 177-Lutetium (half-life 6.7 days) or 131-Iodine (half-life 8 days) may also be preferred.

Positron emitters can also be used, such as (half-life in parenthesis): $^{52m}$Mn (21.1 minutes); $^{62}$Cu (9.74 minutes); $^{68}$Ga (68.1 minutes); $^{11}$C (20 minutes); $^{82}$Rb (1.27 minutes); $^{110}$In (1.15 hours); $^{118}$Sb (3.5 minutes); $^{122}$I (3.63 minutes); $^{18}$F (1.83 hours); $^{34m}$Cl (32.2 minutes); $^{36}$K (7.64 minutes); $^{51}$Mn (46.2 minutes); $^{52}$Mn (5.59 days); $^{52}$Fe (8.28 hours); $^{55}$Co (17.5 hours); $^{61}$Cu (3.41 hours); $^{64}$Cu (12.7 hours); $^{72}$As (1.08 days); $^{75}$Br (1.62 hours); $^{76}$Br (16.2 hours); $^{82m}$Rb (6.47 hours); $^{83}$Sr (1.35 days); $^{86}$Y (14.7 hours); $^{89}$Zr (3.27 days); $^{94m}$Tc (52.0 minutes); $^{120}$I (1.35 hours); $^{124}$I (4.18 days). 64-Copper is a mixed positron, electron and Auger electron emitter.

Any of the radioisotopes, except alpha emitters, that are used for radioimmunotherapy can also be used at lower doses for radioimmunoimaging, for example a beta emitter, a positron emitter or an admixture of a beta emitter and a positron emitter. Preferred radioisotopes for use in radioimmunoimaging include 99m-Technetium, 111-Indium, 67-Gallium, 123-Iodine, 124-Iodine, 131-Iodine and 18-Fluorine. For imaging, one can use a dose range of 1-30 mCi for diagnostic isotopes (e.g., 99m-Tc) and 1-10 mCi for therapeutic isotopes to avoid unnecessary dose to a patient.

A radionuclide can be linked to a compound of Formula I using a covalently linked chelating group. For example, $^{212}$Bi or $^{213}$Bi can be linked to a Formula I compound using the isobutylcarboxycarbonic anhydride of diethylenetriaminepentaacetic acid as discussed in Kozak et al., *Proc. Natl. Acad. Sci. USA* 83:474-478 (1986). Similar chelating agents and linkage procedures are well known to skilled workers.

Further useful chelators contain an isothiocyanate group that can react with a primary amine group of a compound of Formula I are illustrated and discussed in Zhu et al., *Bioorg. Med. Chem. Let.* 18:2679-2683 (2008). Those chelators include those known as CHX-A"-DTPA {N—[(R)-2-amino-3-(p-aminophenyl)propyl]-trans-(S,S)-cyclohexane-1,2-diamine-N,N',N",N'''-pentaacetic acid}, 1B4M-DTPA [2-(4-isothiocyanatobenzyl)-6-methyldiethylenetriamine-pentaacetic acid], c-DOTA [2-(p-isothiocyanato-benzyl)-1,4,7,10-tetraazacyclododecane tetraacetic acid] and PA-DOTA [1,4,7,10-Tetraaza-N-(1-carboxy-3-(4-nitrophenyl)propyl)-

N',N'',N'''-tris(acetic acid) cyclododecane] have been found to be excellent at sequestering radionuclides such as $^{86/90}$Y, $^{212/213}$Bi, $^{111}$In and $^{177}$Lu.

Illustrative magnetic resonance contrast agents include both paramagnetic and diamagnetic agents. Gadolinium is paramagnetic and is most widely used. Barium sulfate, which is diamagnetic, has been studied for use in the intestines.

Illustrative chelating agents for gadolinium include CHX-A''-DTPA, 1B4M-DTPA, c-DOTA and PA-DOTA noted above.

An illustrative 1,3-diketone has the structure —C(O)CH$_2$C(O)CH$_3$ or —CH$_2$C(O)CH$_2$C(O)CH$_3$. A 1,3-diketonecan react with two moles of amine to form a diketimine. A 1,3-diketone can also function as a metal ion chelator, but is not used as such herein.

A contemplated Compound of Formula I or Ia can form a conjugate of Formula Ib in which L$_{2'}$ is the reacted L$_2$ group, "E" is a conjugated small molecule drug, a peptide, a peptide hormone or a chelated metal ion that can be a radionuclide or contrast agent as discussed above, and where L, n, X, Z, R$^1$ and R$^2$ are as defined before.

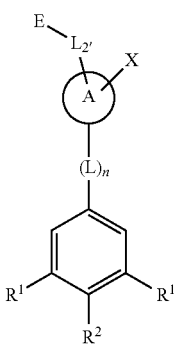

Ib

It is to be understood that as used herein, a chelating group can be covalently linked to a depicted compound of Formula Ia, and once so linked as an E group, is "reacted" as part of a compound of Formula Ib with or without its bound metal ion. Thus, only one of E and L$_{2'}$ is a chelator for a metal ion Tables A-R hereinafter illustrate several contemplated compounds having various linking groups L, circle A aromatic and heteroaromatic ring systems. Except in Tables O and Q, substituent Z on the aromatic or heteroaromatic ring systems is omitted for added clarity with the understanding that such a substituent can be present as discussed previously. Substituents R$^1$ and R$^2$ are held constant as methyl groups also for added clarity, with the understanding that those substituents can be as noted before. Tables J-M illustrate several compounds of structural Formula Vg that are labeled Vg1, Vg2, Vg3 and Vg4 for convenience. Table N illustrates a number of compounds of Formula VA that are referred to there as Formula Va1 in which the X substituent is at the 4-position of a circle A phenyl ring relative to the L group. Tables O and Q illustrate a preferred Z group [—N(CH$_3$)$_2$] and its preferred position in a 6-membered aromatic ring, A. Table R illustrates further compounds of Formula Vg3 (and Ic) in which a nitrogen heteroatom is bonded to X, the reactive substituent that reacts with an amine in an aqueous environment to bond the amine to the depicted compound, in a urethane or thiourethane linkage that forms a urea group after reaction with an amine.

TABLE A

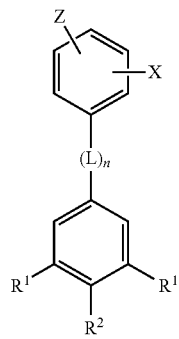

IVa

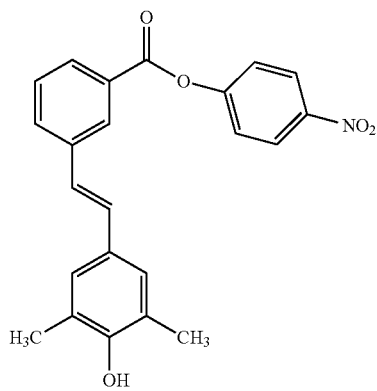 [SMILES: Cc1cc(/C=C/c2cccc(C(=O)Oc3ccc([N+](=O)[O-])cc3)c2)cc(C)c1O]

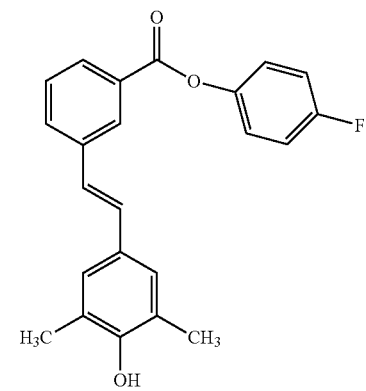 [SMILES: Cc1cc(/C=C/c2cccc(C(=O)Oc3ccc(F)cc3)c2)cc(C)c1O]

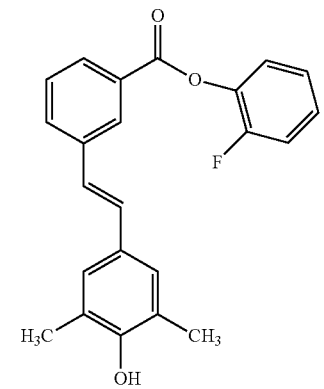 [SMILES: Cc1cc(/C=C/c2cccc(C(=O)Oc3ccccc3F)c2)cc(C)c1O]

TABLE A-continued
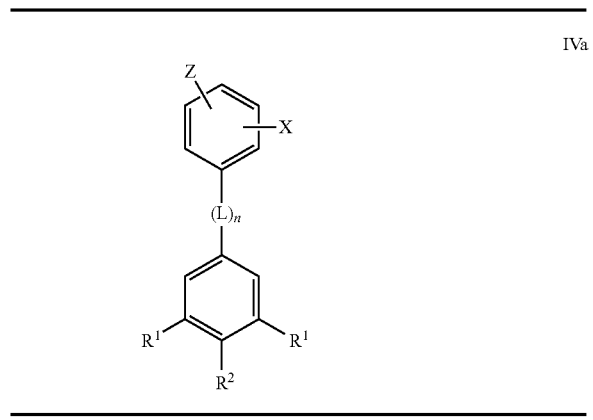
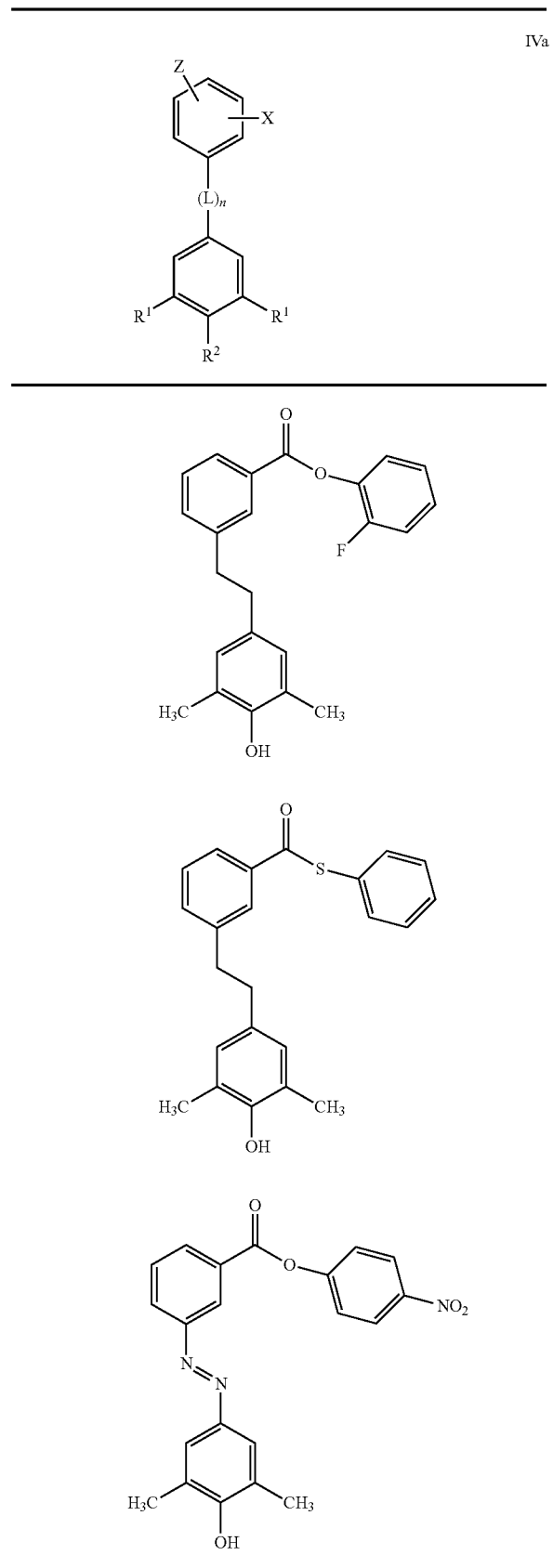

TABLE A-continued
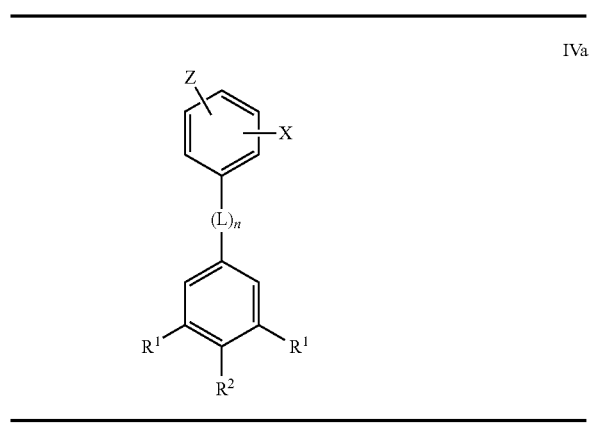
IVa
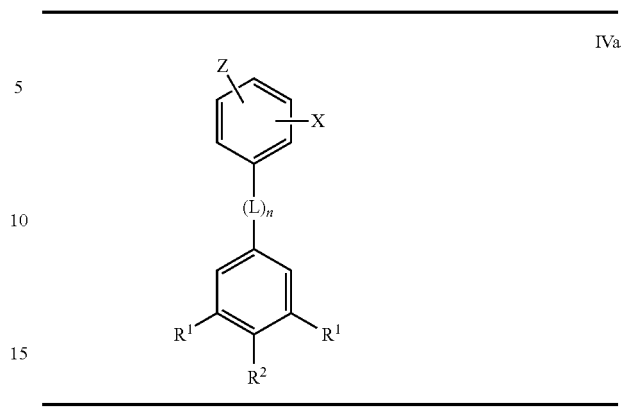
IVa
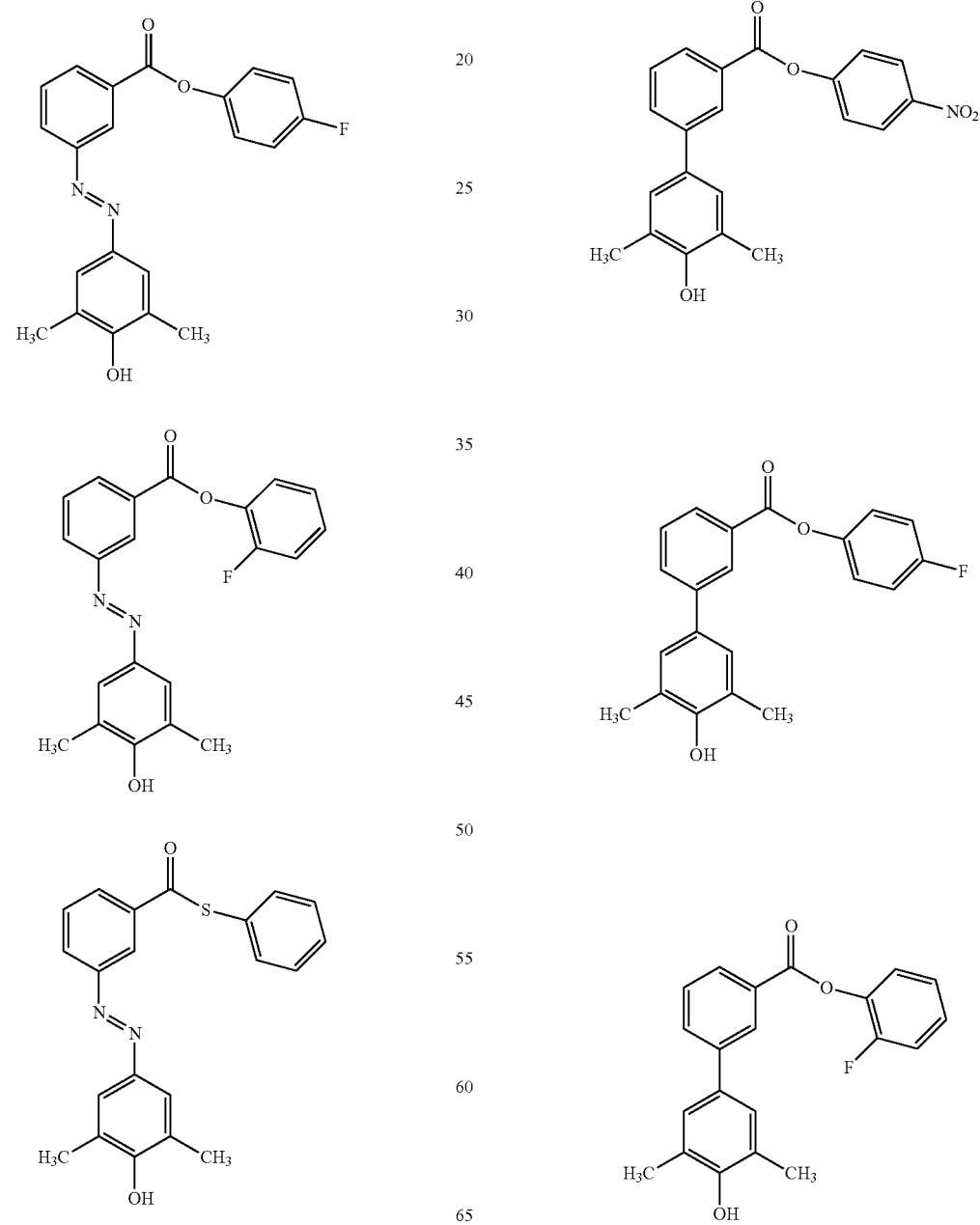

TABLE A-continued
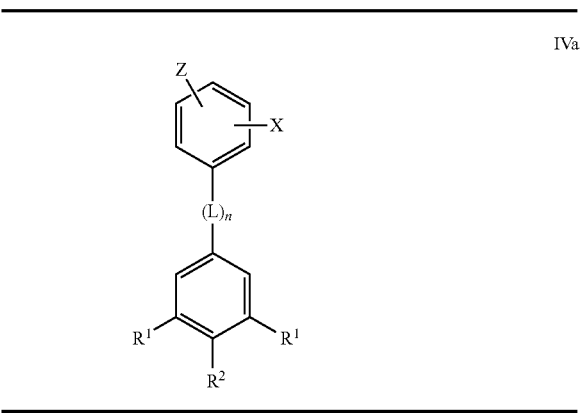
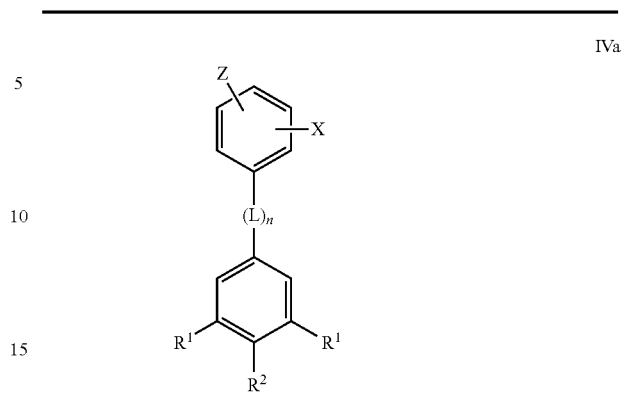
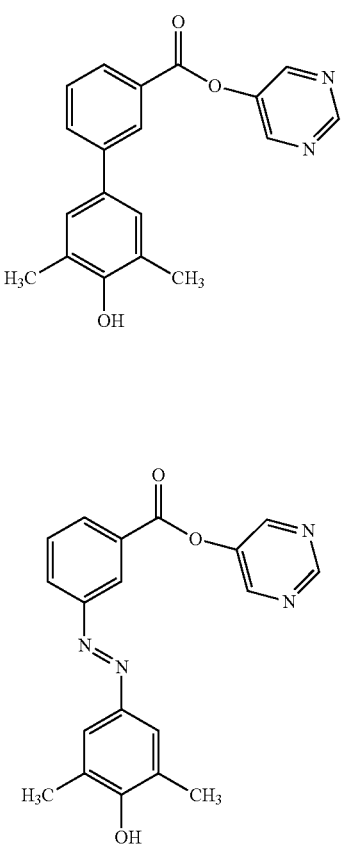
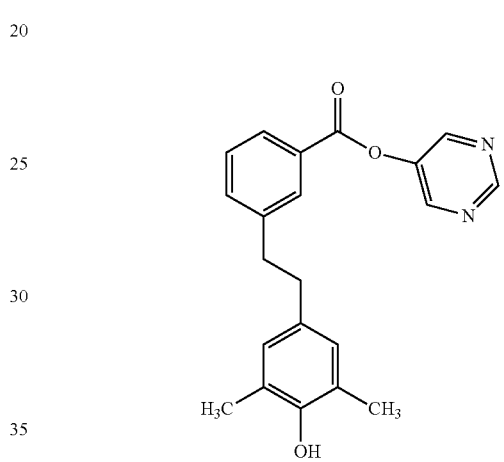
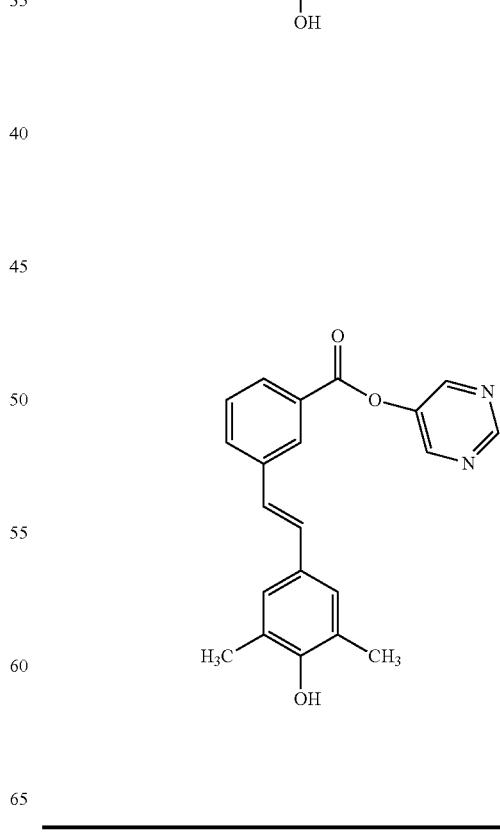

TABLE B
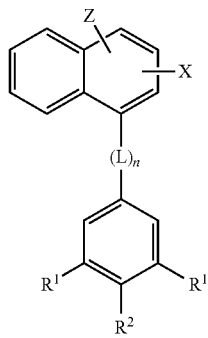
TABLE B-continued
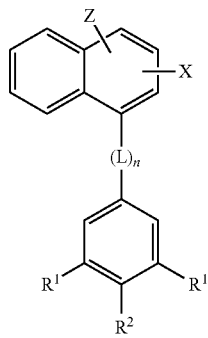
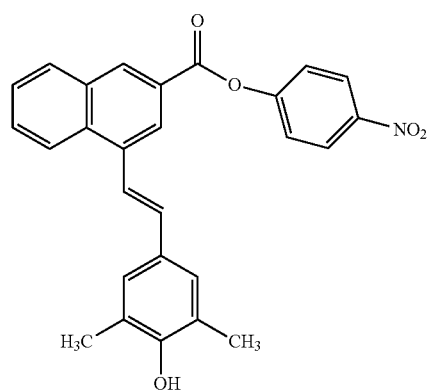 [SMILES: Cc1cc(/C=C/c2cc(C(=O)Oc3ccc([N+](=O)[O-])cc3)cc3ccccc23)cc(C)c1O]
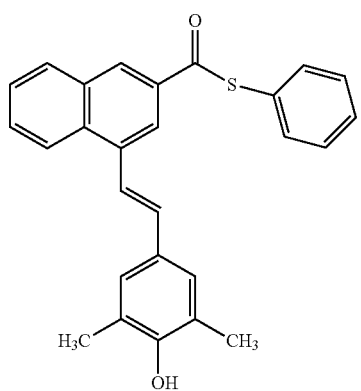
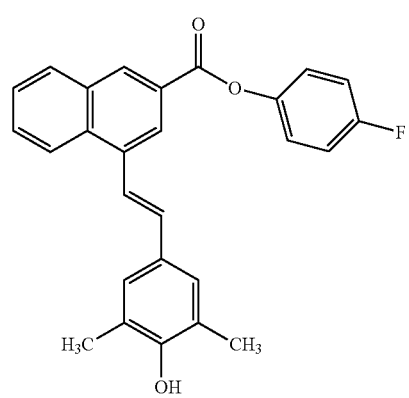 [SMILES: Cc1cc(/C=C/c2cc(C(=O)Oc3ccc(F)cc3)cc3ccccc23)cc(C)c1O]
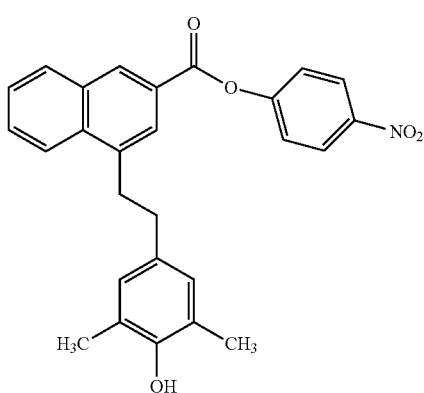
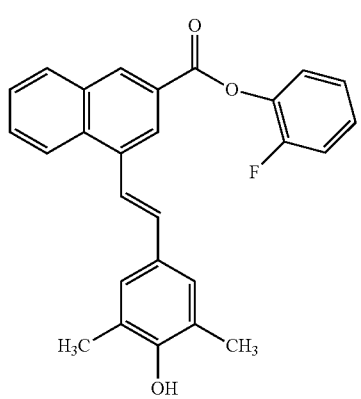 [SMILES: Cc1cc(/C=C/c2cc(C(=O)Oc3ccccc3F)cc3ccccc23)cc(C)c1O]
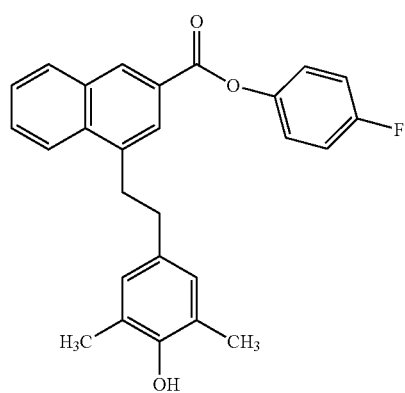 [SMILES: Cc1cc(CCc2cc(C(=O)Oc3ccc(F)cc3)cc3ccccc23)cc(C)c1O]

TABLE B-continued
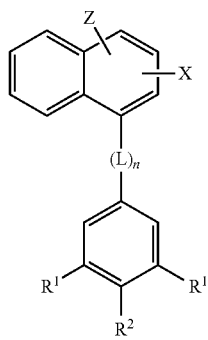
IVb
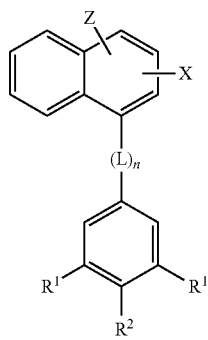
IVb
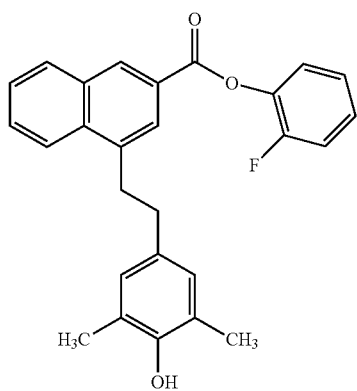 [SMILES: Cc1cc(CCc2cc(C(=O)Oc3ccccc3F)cc3ccccc23)cc(C)c1O]
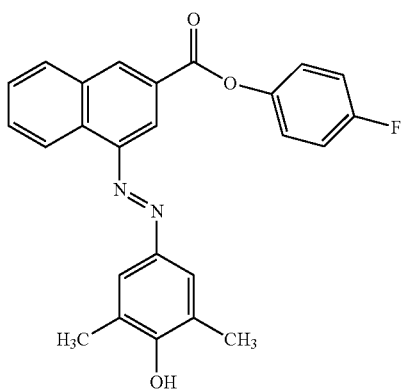
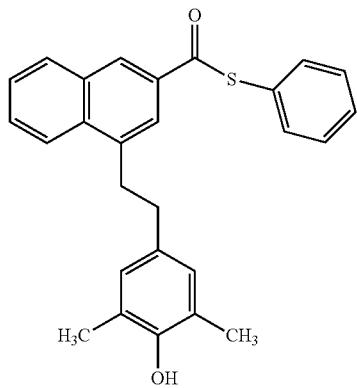 [SMILES: Cc1cc(CCc2cc(C(=O)Sc3ccccc3)cc3ccccc23)cc(C)c1O]
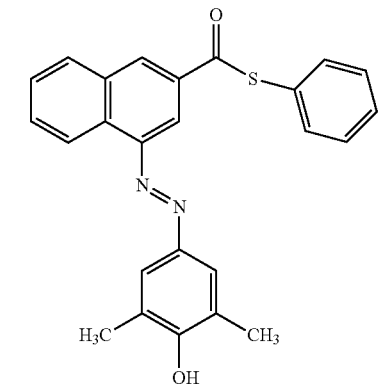 [SMILES: Cc1cc(/N=N/c2cc(C(=O)Sc3ccccc3)cc3ccccc23)cc(C)c1O]
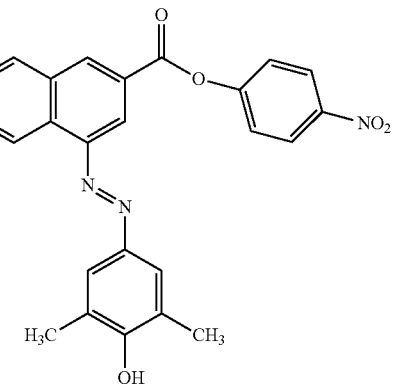
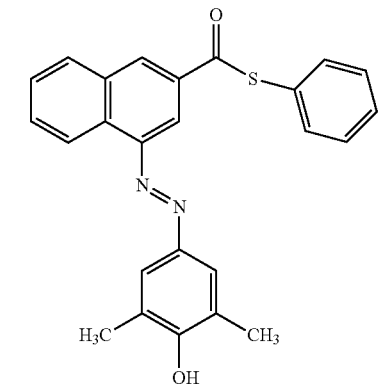 [SMILES: Cc1cc(/N=N/c2cc(C(=O)Sc3ccccc3)cc3ccccc23)cc(C)c1O]

TABLE B-continued
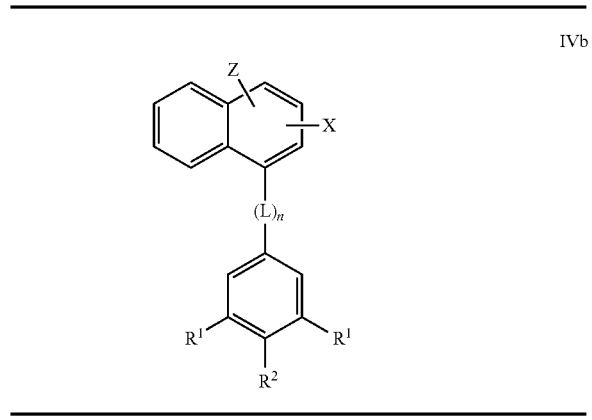
IVb
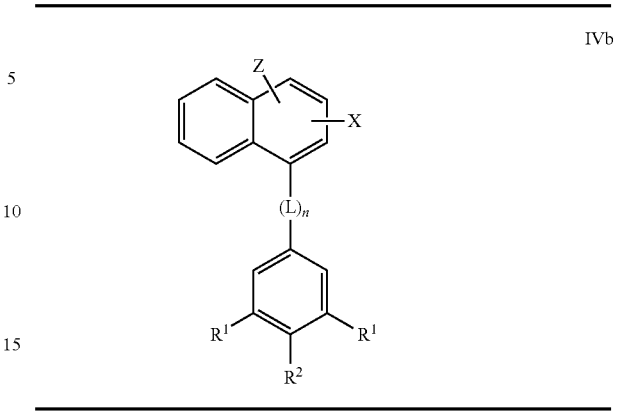
IVb
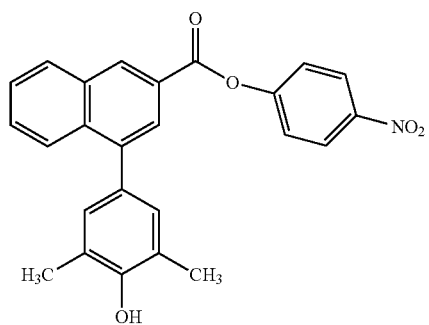 [SMILES: Cc1cc(-c2cc(C(=O)Oc3ccc([N+](=O)[O-])cc3)cc3ccccc23)cc(C)c1O]
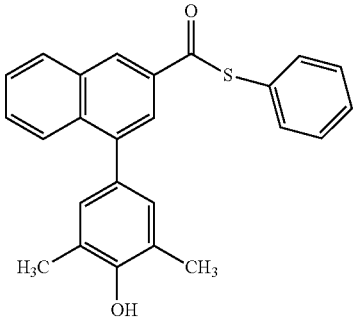
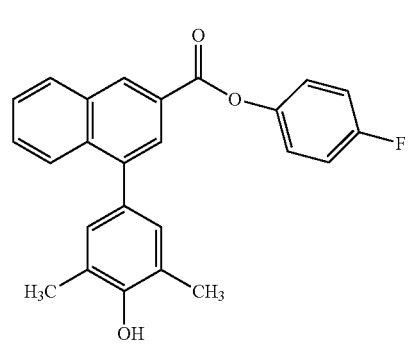 [SMILES: Cc1cc(-c2cc(C(=O)Oc3ccc(F)cc3)cc3ccccc23)cc(C)c1O]
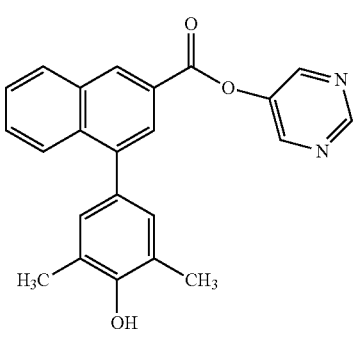
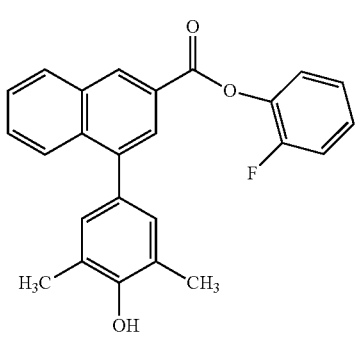 [SMILES: Cc1cc(-c2cc(C(=O)Oc3ccccc3F)cc3ccccc23)cc(C)c1O]
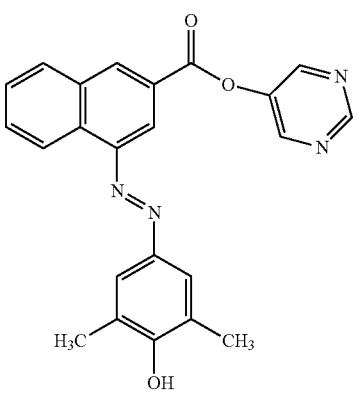 [SMILES: Cc1cc(/N=N/c2cc(C(=O)Oc3cncnc3)cc3ccccc23)cc(C)c1O]

TABLE B-continued
IVb
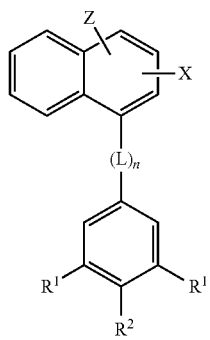
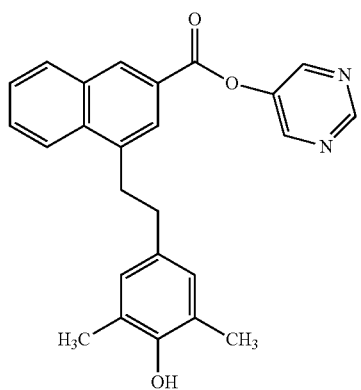 [SMILES: Cc1cc(CCc2cc(C(=O)Oc3cncnc3)cc3ccccc23)cc(C)c1O]
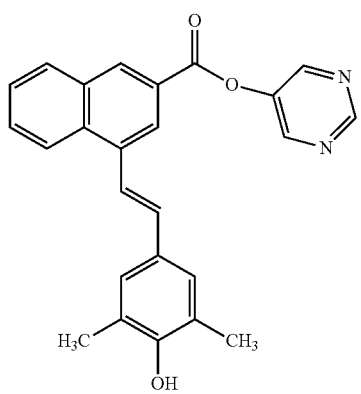 [SMILES: Cc1cc(/C=C/c2cc(C(=O)Oc3cncnc3)cc3ccccc23)cc(C)c1O]
TABLE C
IVc
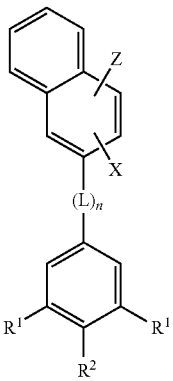
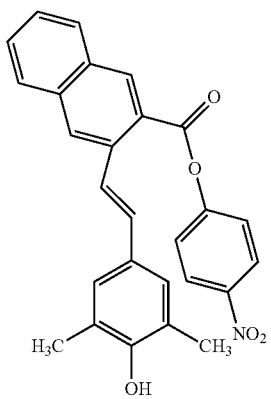 [SMILES: Cc1cc(/C=C/c2cc3ccccc3cc2C(=O)Oc2ccc([N+](=O)[O-])cc2)cc(C)c1O]
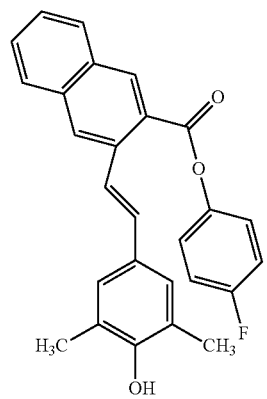 [SMILES: Cc1cc(/C=C/c2cc3ccccc3cc2C(=O)Oc2ccc(F)cc2)cc(C)c1O]
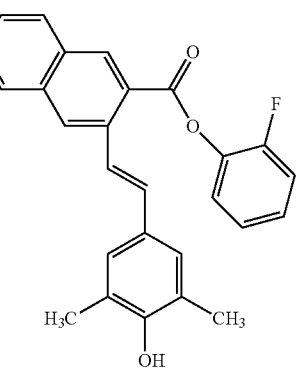

TABLE C-continued
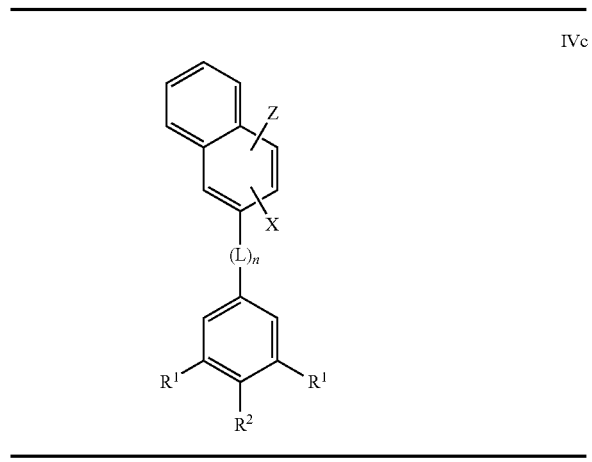
IVc
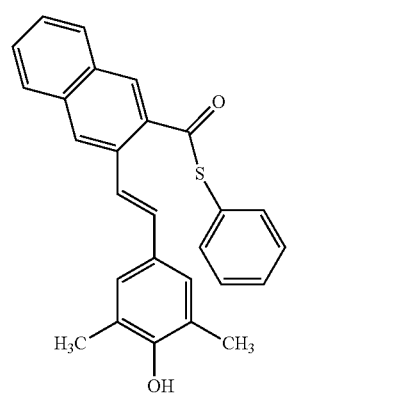 [SMILES: Cc1cc(/C=C/c2cc3ccccc3cc2C(=O)Sc2ccccc2)cc(C)c1O]
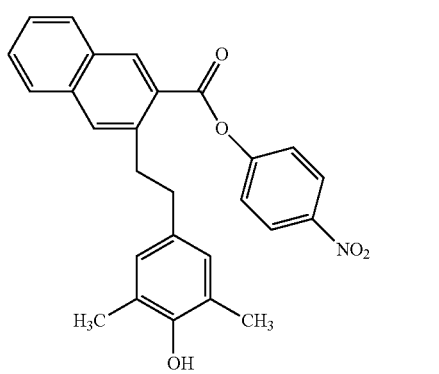 [SMILES: Cc1cc(CCc2cc3ccccc3cc2C(=O)Oc2ccc([N+](=O)[O-])cc2)cc(C)c1O]
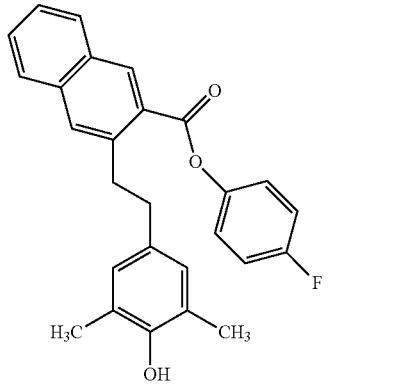 [SMILES: Cc1cc(CCc2cc3ccccc3cc2C(=O)Oc2ccc(F)cc2)cc(C)c1O]
TABLE C-continued
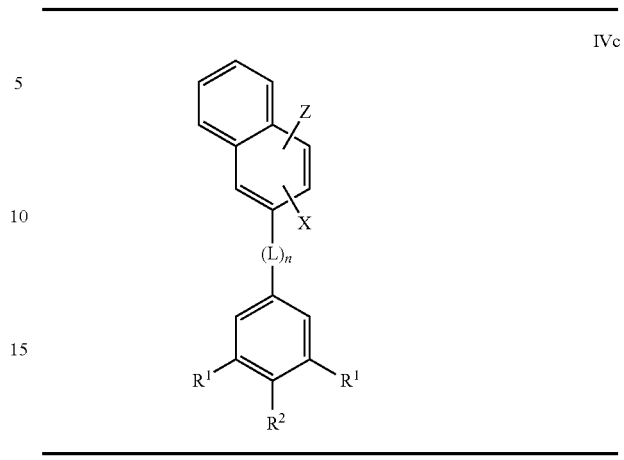
IVc
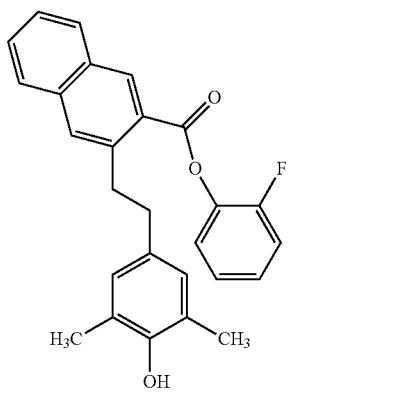 [SMILES: Cc1cc(CCc2cc3ccccc3cc2C(=O)Oc2ccccc2F)cc(C)c1O]
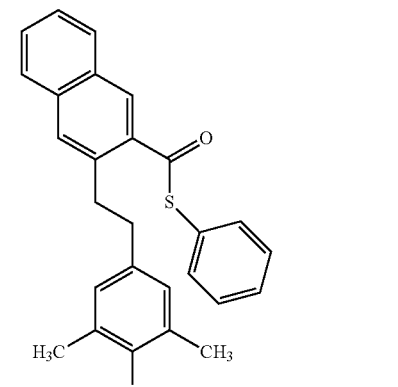
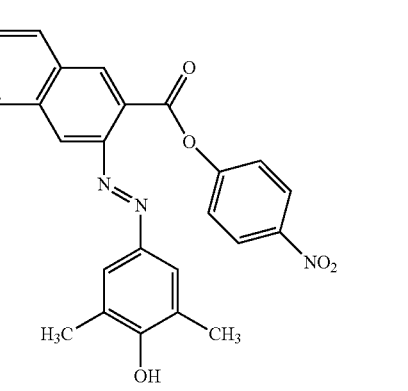

TABLE C-continued
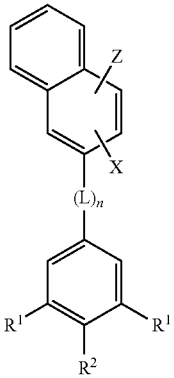
IVc
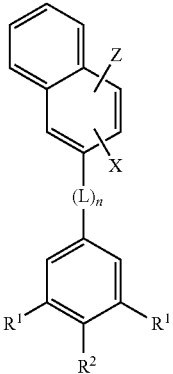
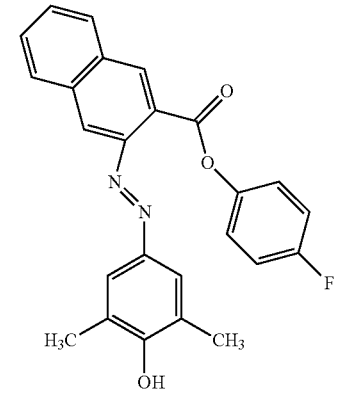 [SMILES: Cc1cc(/N=N/c2cc3ccccc3cc2C(=O)Oc2ccc(F)cc2)cc(C)c1O]
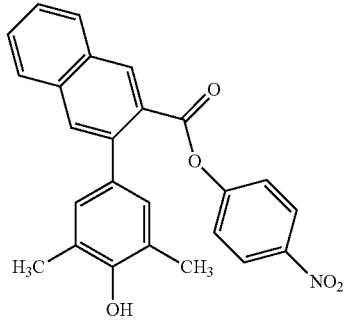
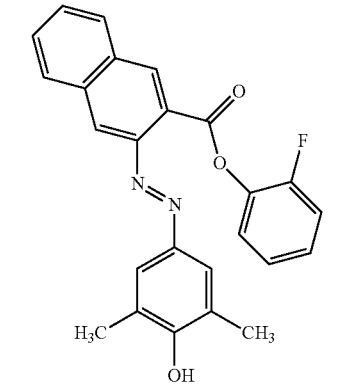 [SMILES: Cc1cc(/N=N/c2cc3ccccc3cc2C(=O)Oc2ccccc2F)cc(C)c1O]
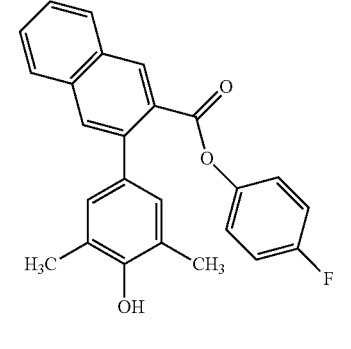
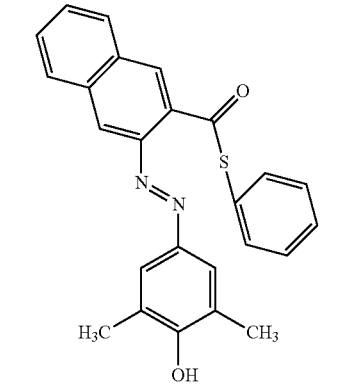 [SMILES: Cc1cc(/N=N/c2cc3ccccc3cc2C(=O)Sc2ccccc2)cc(C)c1O]
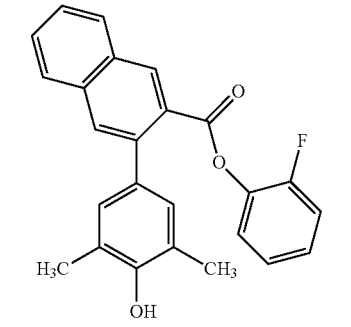 [SMILES: Cc1cc(-c2cc3ccccc3cc2C(=O)Oc2ccccc2F)cc(C)c1O]

TABLE C-continued
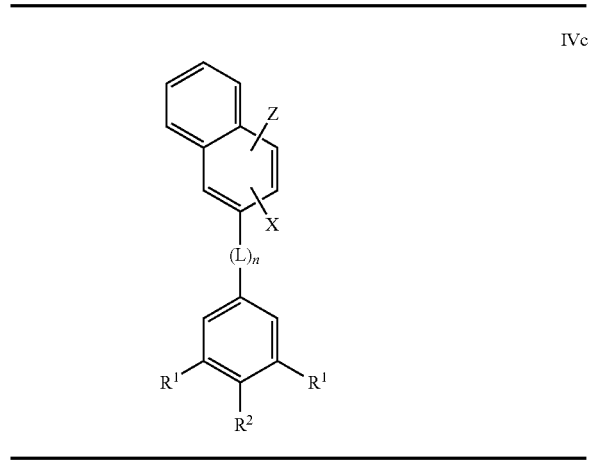
IVc
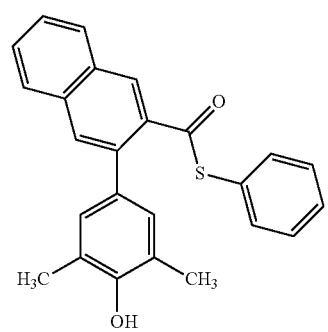 [SMILES: Cc1cc(-c2cc3ccccc3cc2C(=O)Sc2ccccc2)cc(C)c1O]
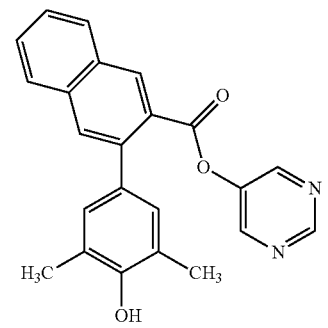 [SMILES: Cc1cc(-c2cc3ccccc3cc2C(=O)Oc2cncnc2)cc(C)c1O]
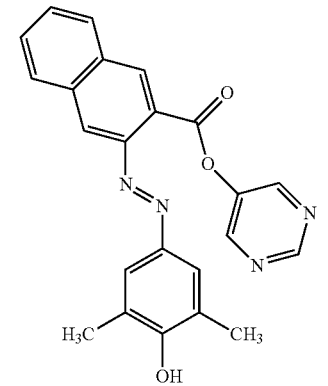 [SMILES: Cc1cc(/N=N/c2cc3ccccc3cc2C(=O)Oc2cncnc2)cc(C)c1O]
TABLE C-continued
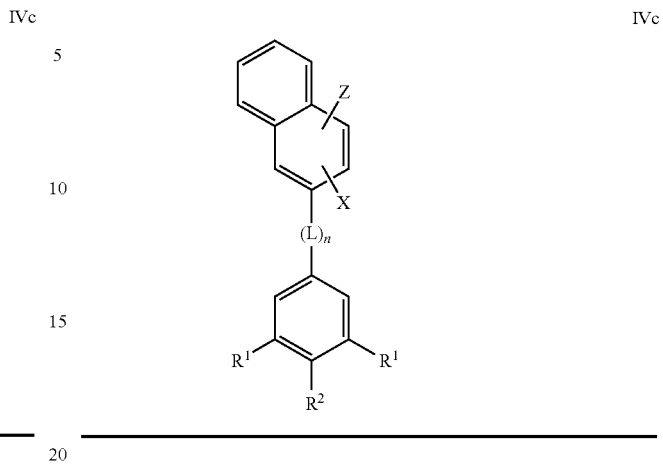
IVc
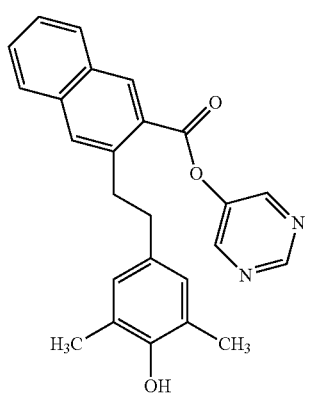 [SMILES: Cc1cc(CCc2cc3ccccc3cc2C(=O)Oc2cncnc2)cc(C)c1O]
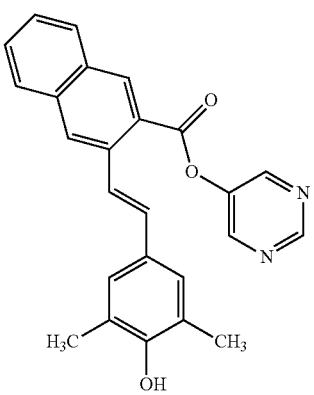 [SMILES: Cc1cc(/C=C/c2cc3ccccc3cc2C(=O)Oc2cncnc2)cc(C)c1O]

TABLE D
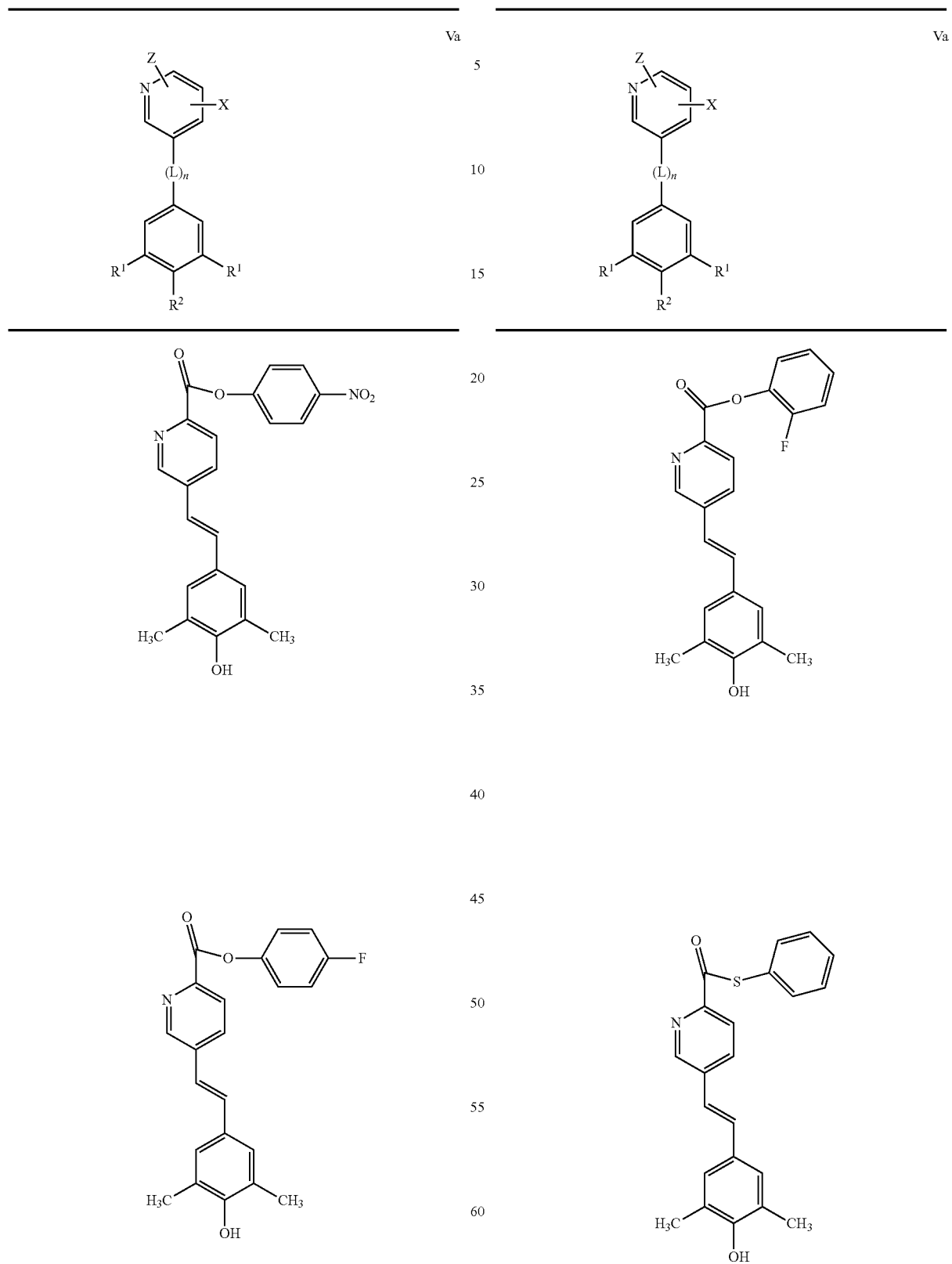

TABLE D-continued
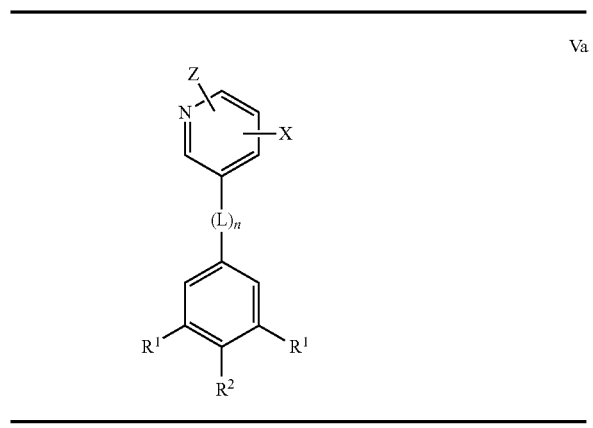
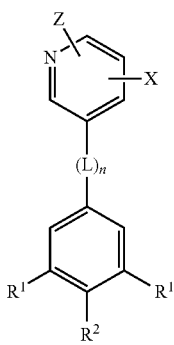
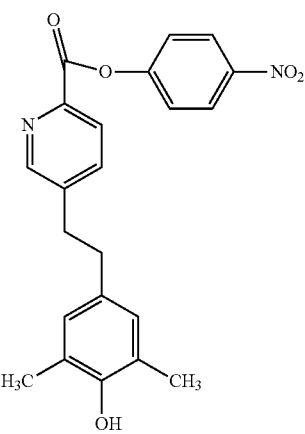
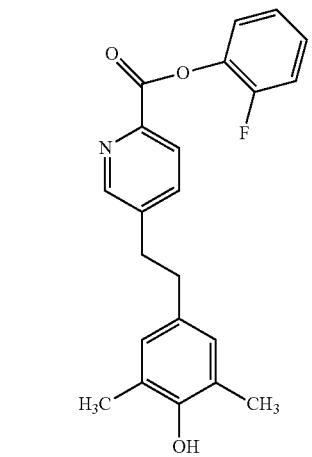
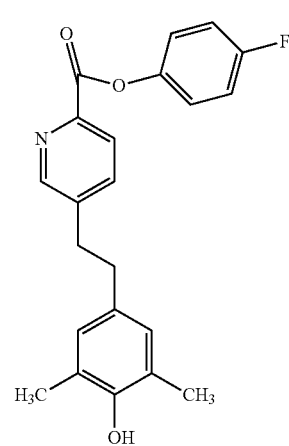 [SMILES: Cc1cc(CCc2ccc(C(=O)Oc3ccc(F)cc3)nc2)cc(C)c1O]
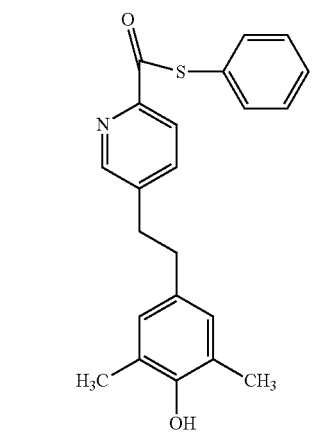 [SMILES: Cc1cc(CCc2ccc(C(=O)Sc3ccccc3)nc2)cc(C)c1O]

TABLE D-continued
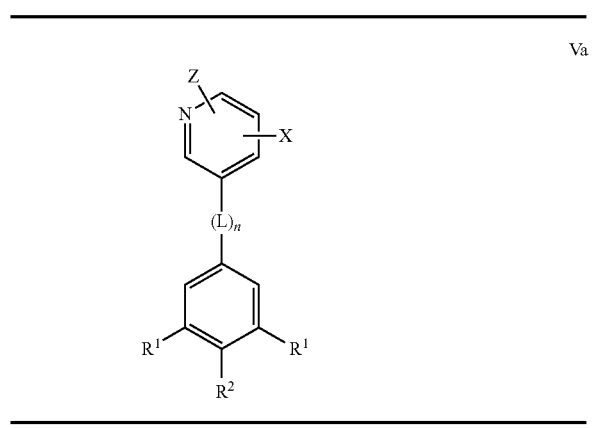
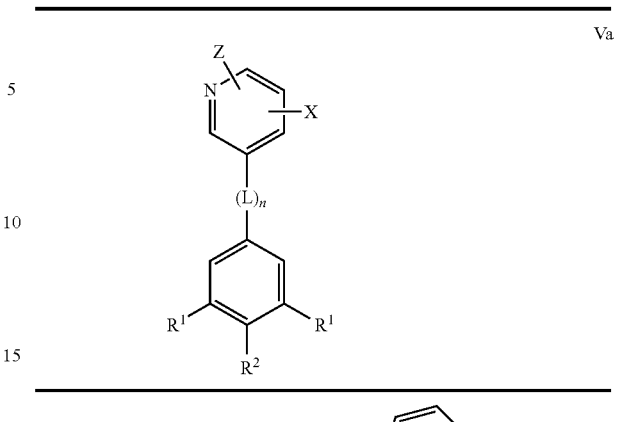
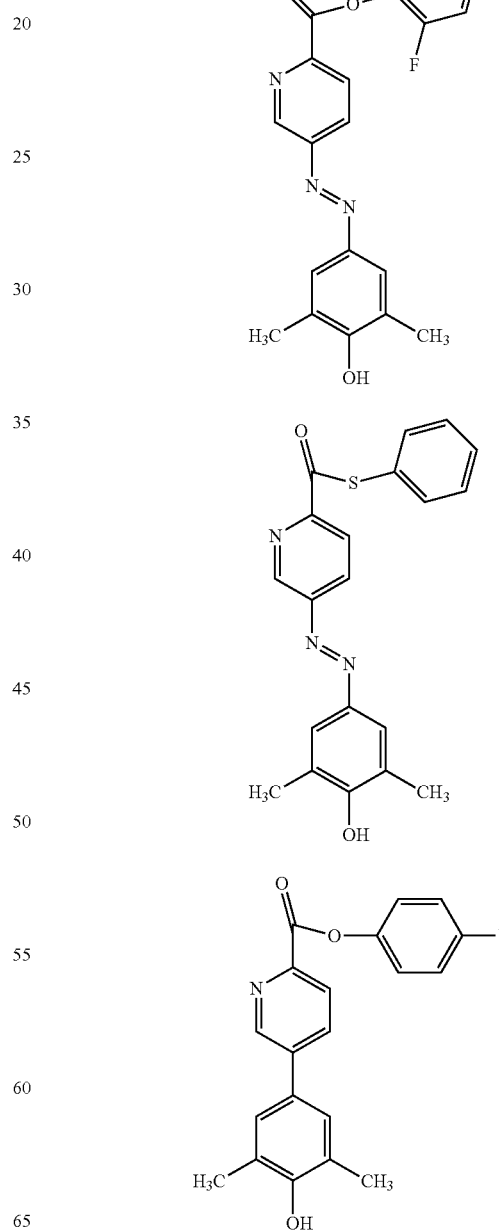

TABLE D-continued
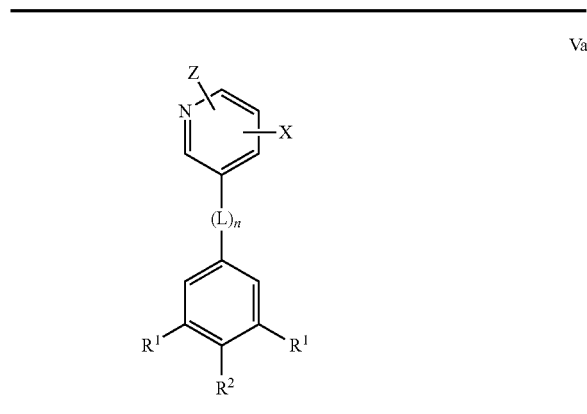
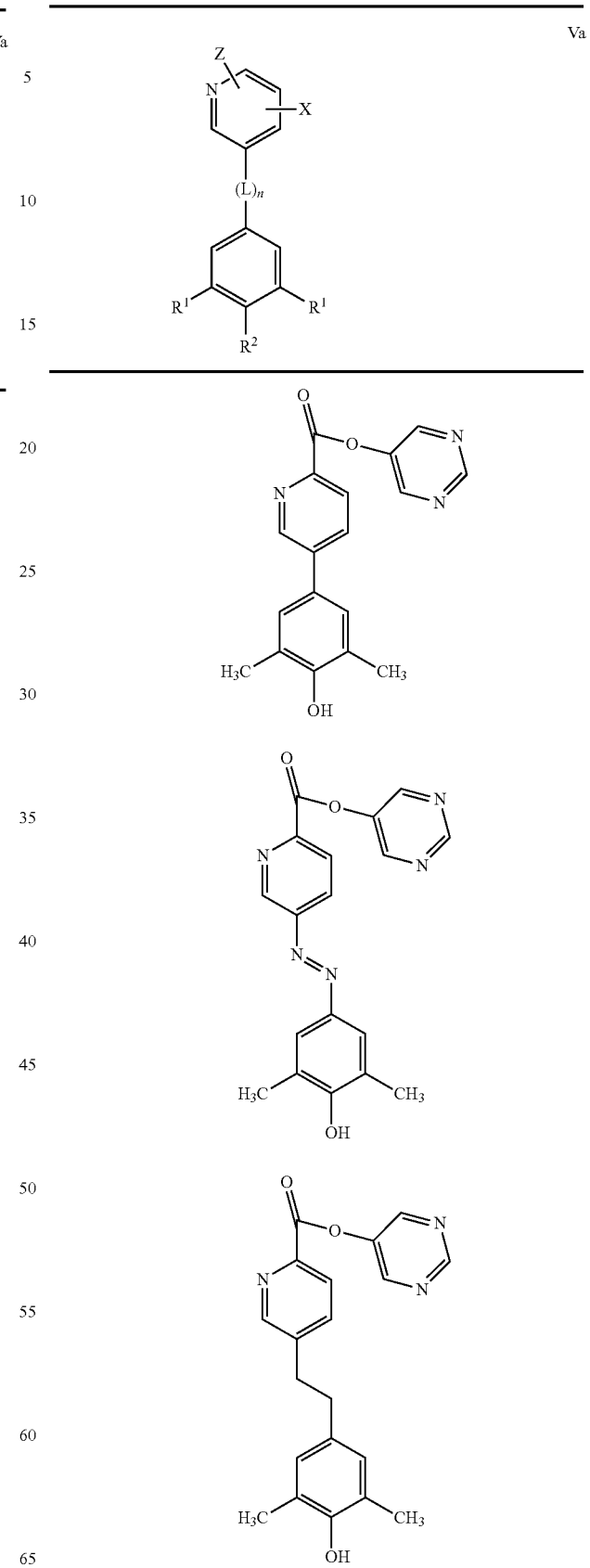

TABLE D-continued
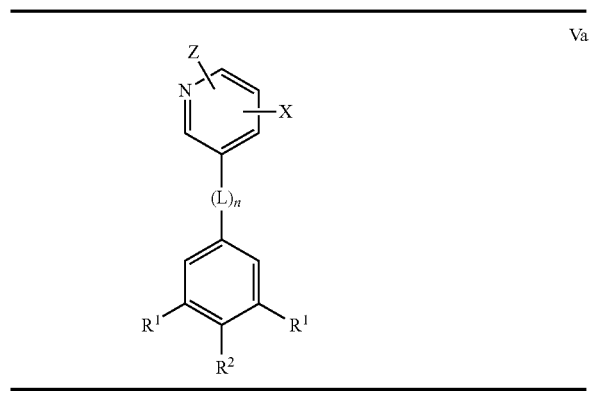
Va
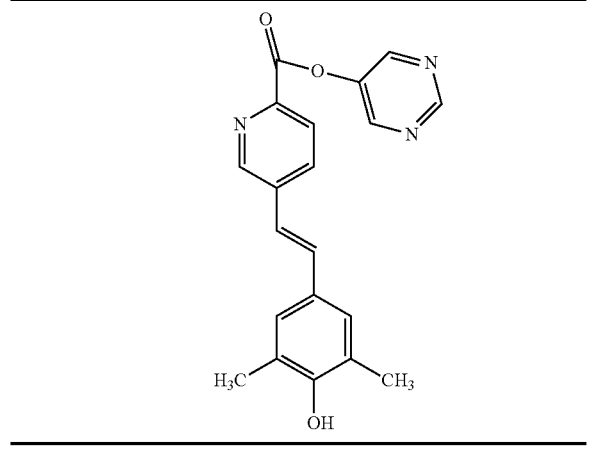
TABLE E
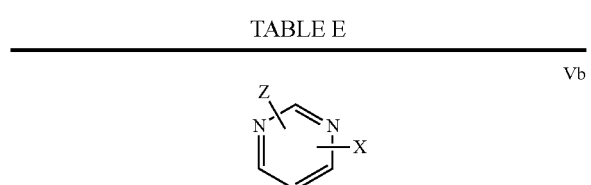
Vb
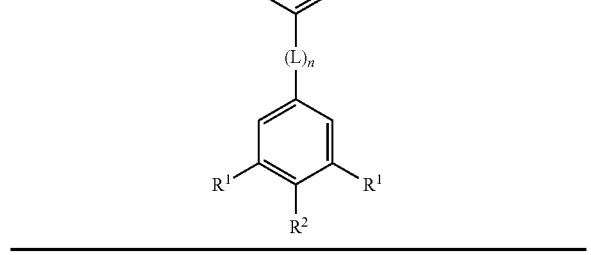
TABLE E-continued
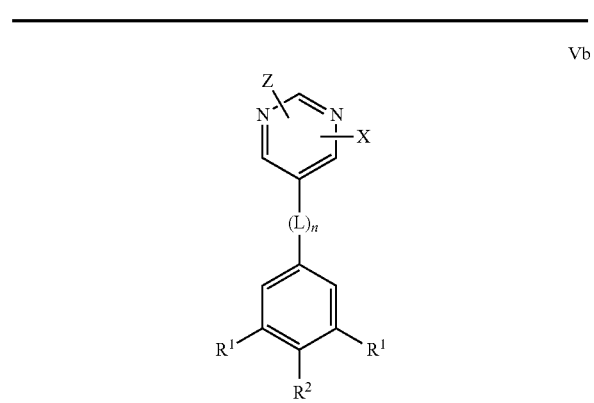
Vb
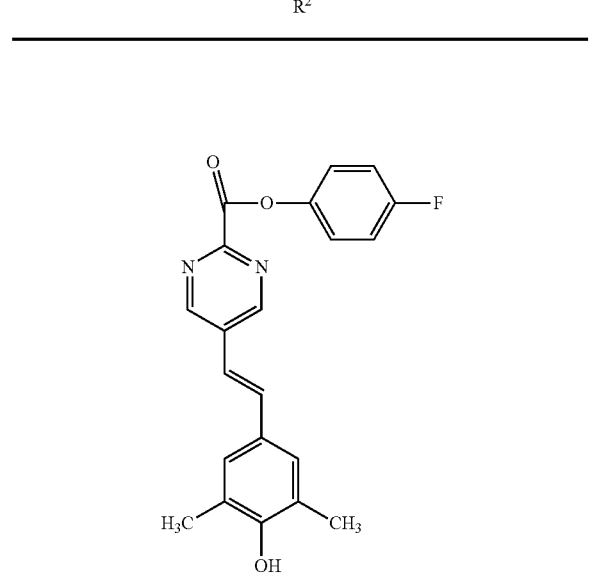
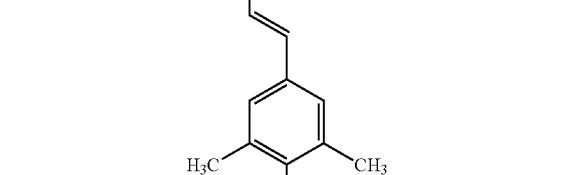

TABLE E-continued
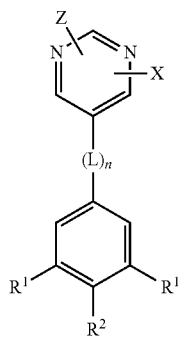
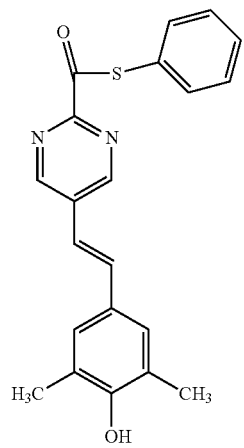 [SMILES: Cc1cc(/C=C/c2cnc(C(=O)Sc3ccccc3)nc2)cc(C)c1O]
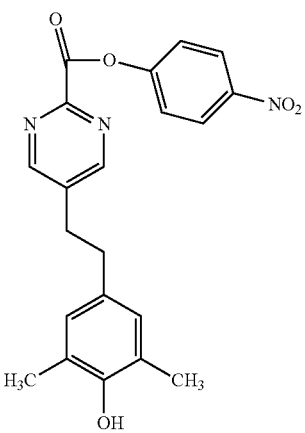 [SMILES: Cc1cc(CCc2cnc(C(=O)Oc3ccc([N+](=O)[O-])cc3)nc2)cc(C)c1O]
TABLE E-continued
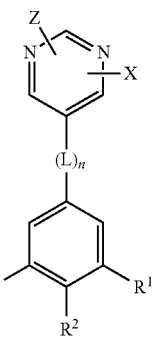
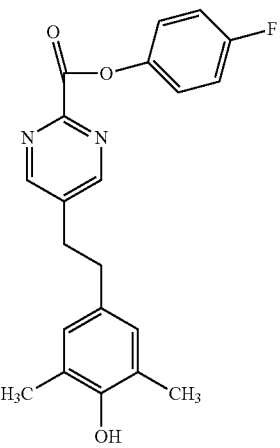 [SMILES: Cc1cc(CCc2cnc(C(=O)Oc3ccc(F)cc3)nc2)cc(C)c1O]
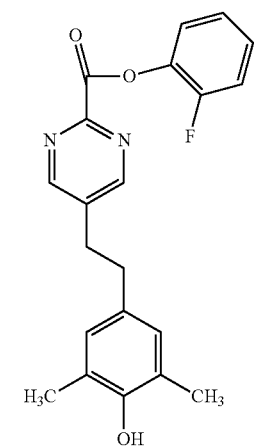 [SMILES: Cc1cc(CCc2cnc(C(=O)Oc3ccccc3F)nc2)cc(C)c1O]

TABLE E-continued
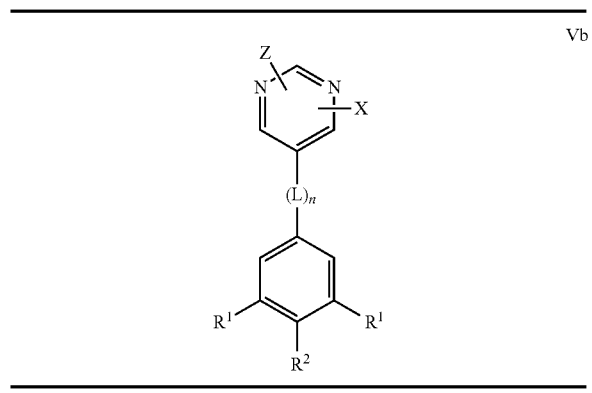
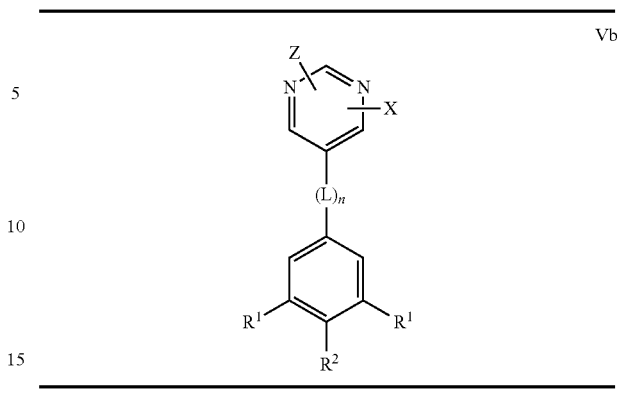
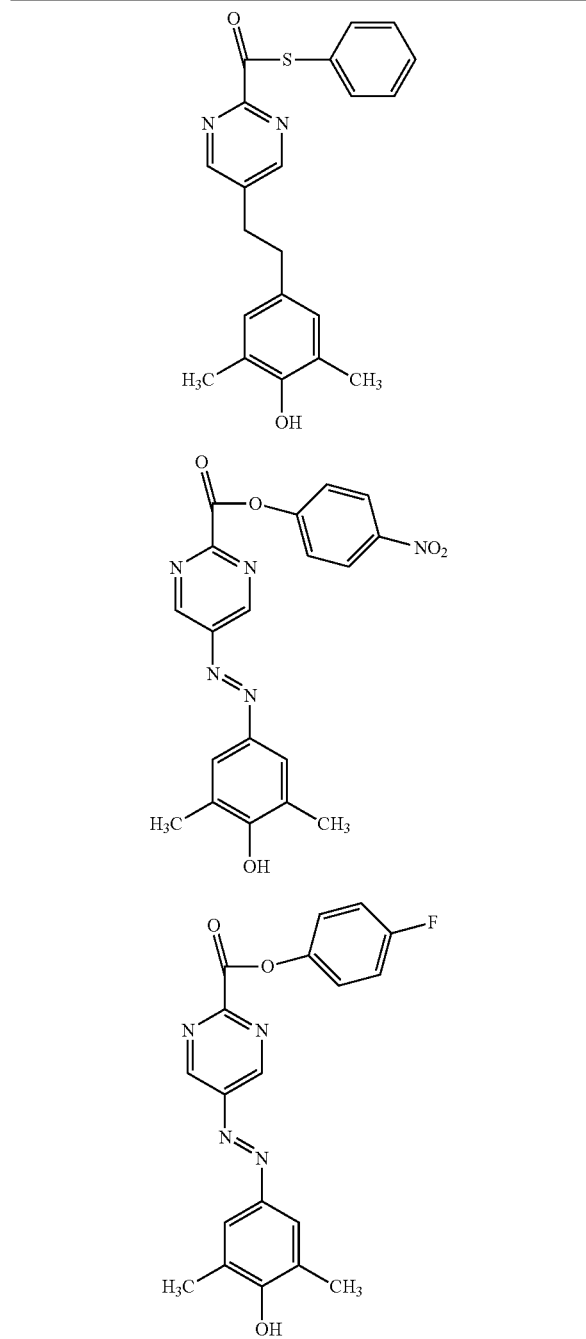
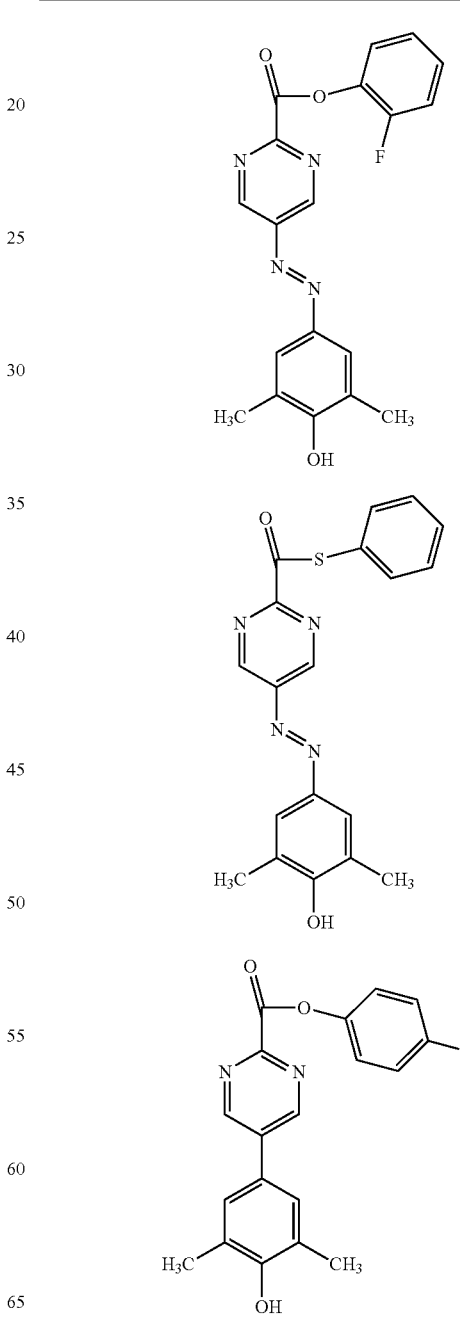

TABLE E-continued
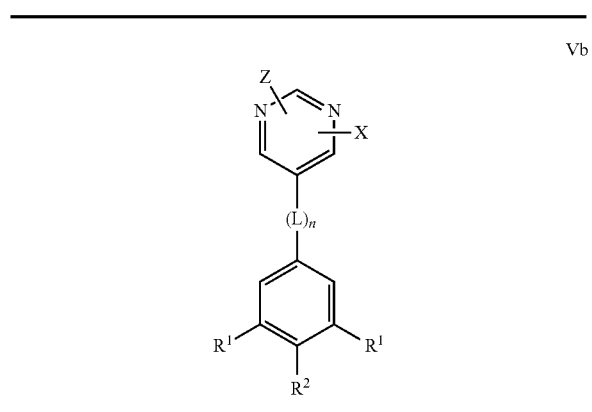
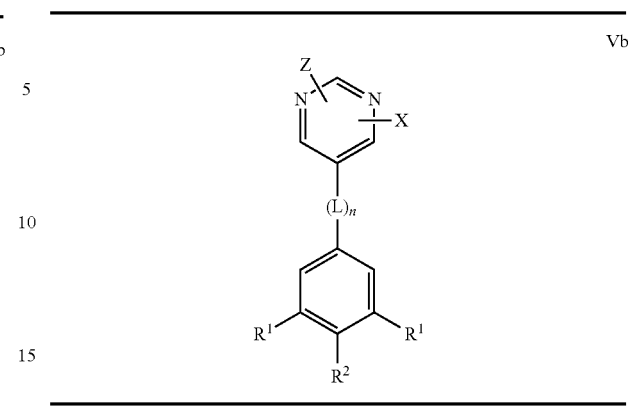
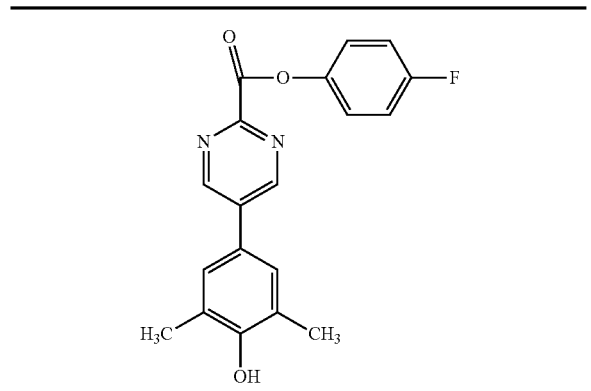
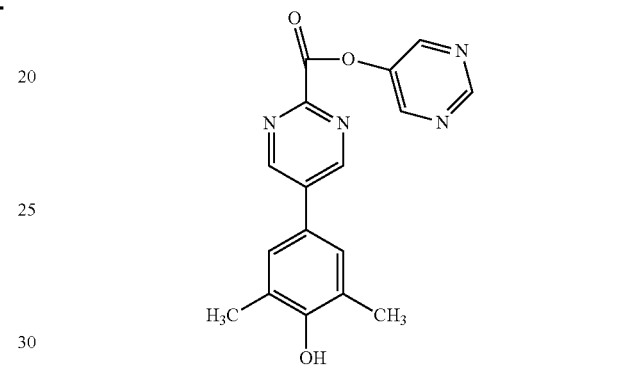
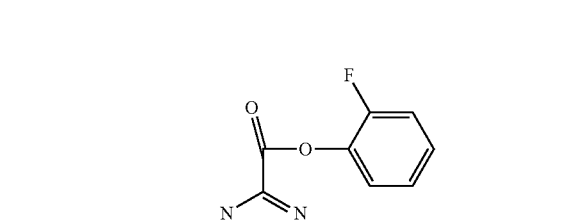
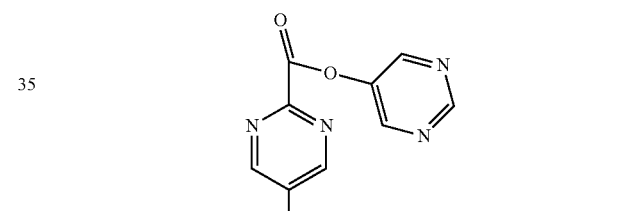
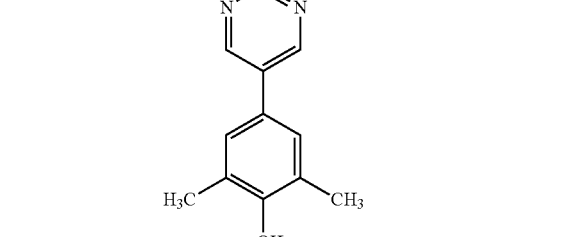
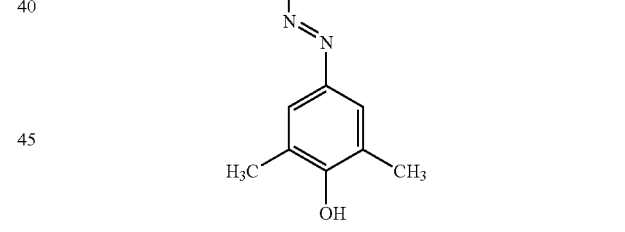
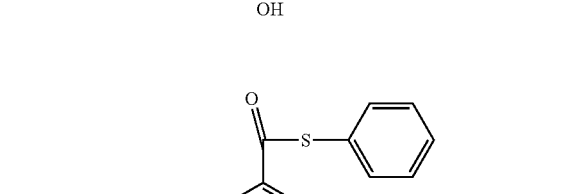
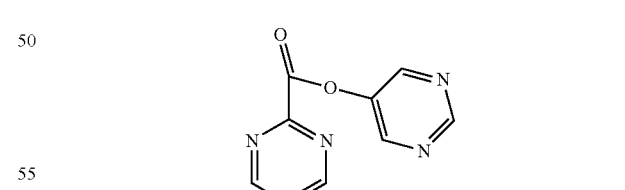
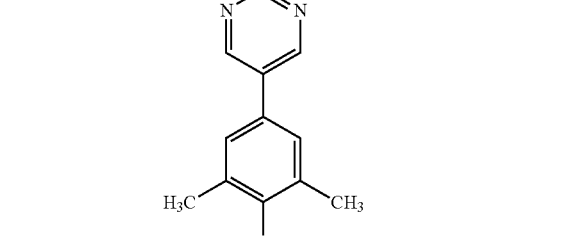
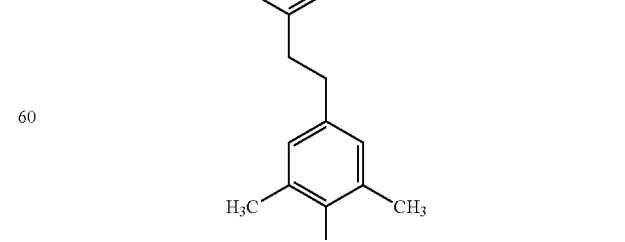

TABLE E-continued
Vb
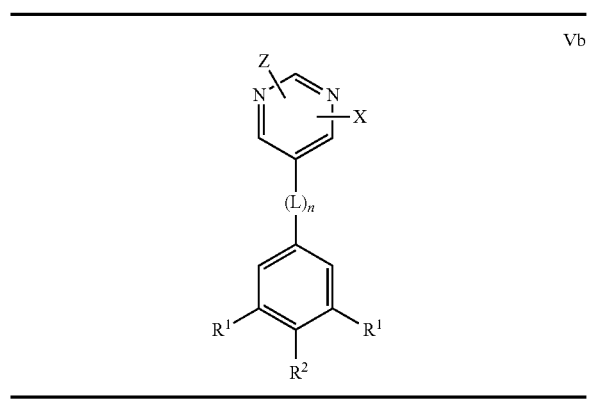
TABLE F
Vc
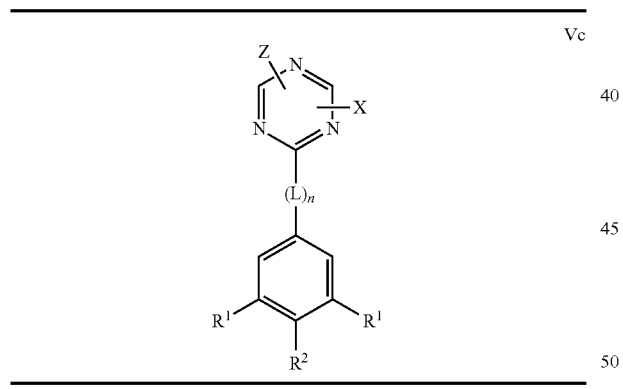
TABLE F-continued
Vc
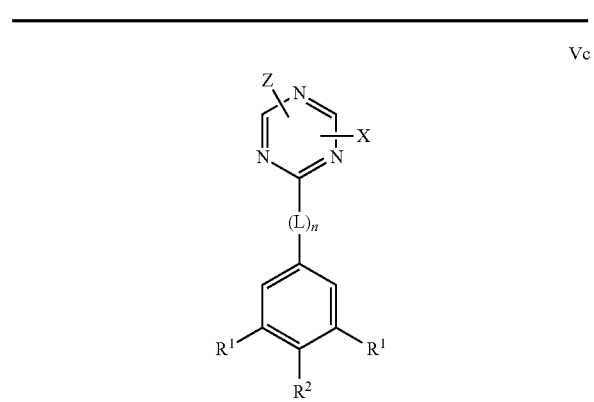
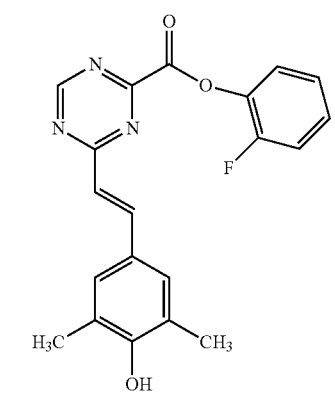

TABLE F-continued
Vc
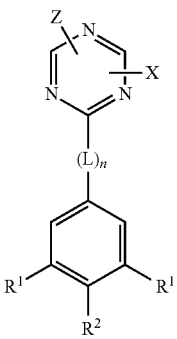
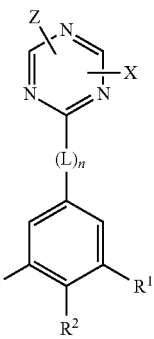
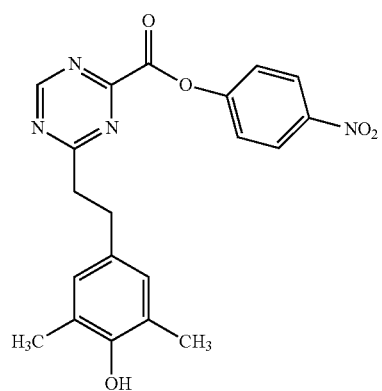 [SMILES: Cc1cc(CCc2ncnc(C(=O)Oc3ccc([N+](=O)[O-])cc3)n2)cc(C)c1O]
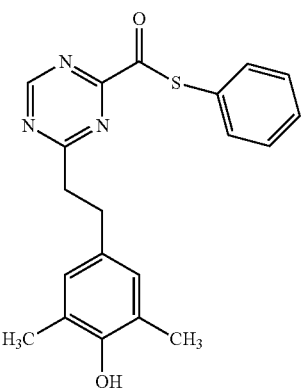
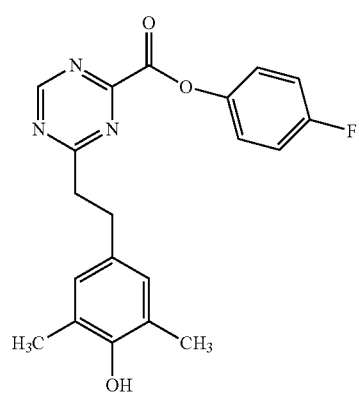 [SMILES: Cc1cc(CCc2ncnc(C(=O)Oc3ccc(F)cc3)n2)cc(C)c1O]
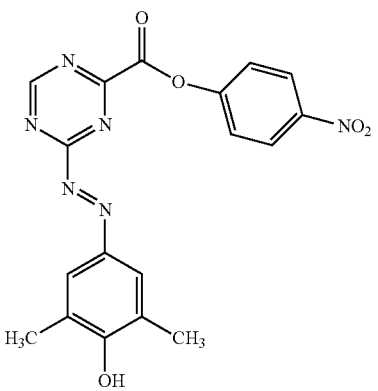
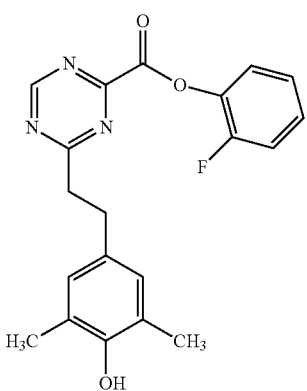 [SMILES: Cc1cc(CCc2ncnc(C(=O)Oc3ccccc3F)n2)cc(C)c1O]
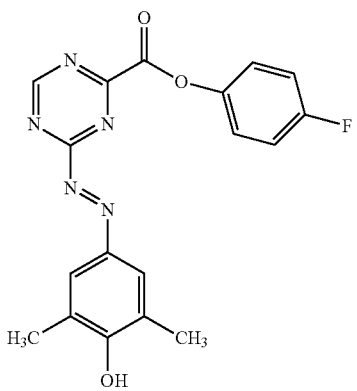 [SMILES: Cc1cc(/N=N/c2ncnc(C(=O)Oc3ccc(F)cc3)n2)cc(C)c1O]

TABLE F-continued
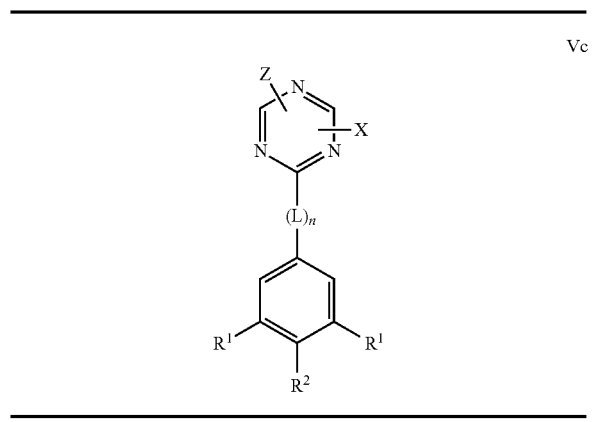
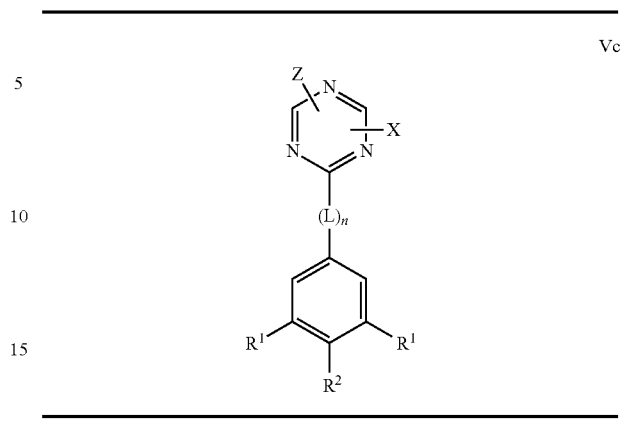
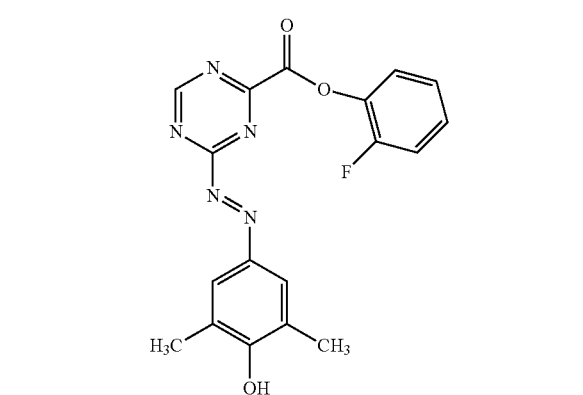 [SMILES: Cc1cc(/N=N/c2ncnc(C(=O)Oc3ccccc3F)n2)cc(C)c1O]
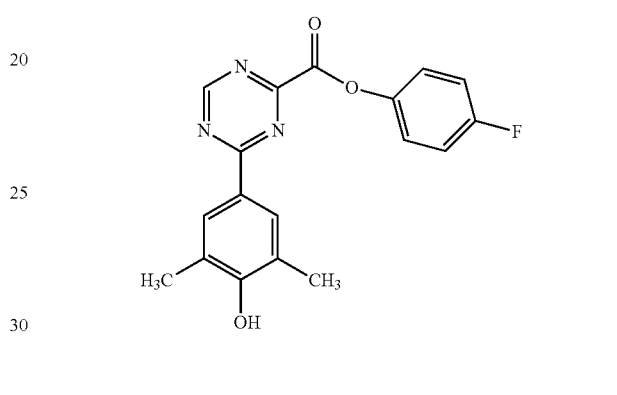
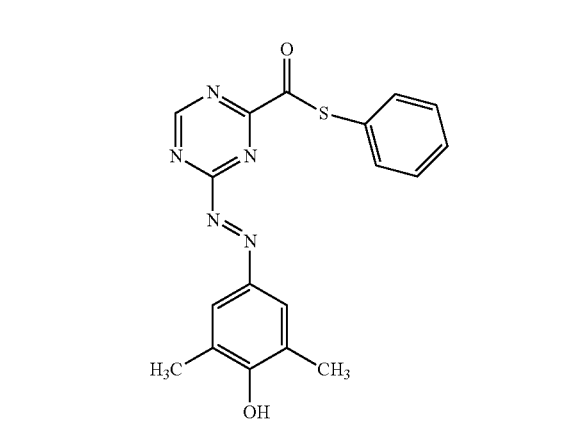 [SMILES: Cc1cc(/N=N/c2ncnc(C(=O)Sc3ccccc3)n2)cc(C)c1O]
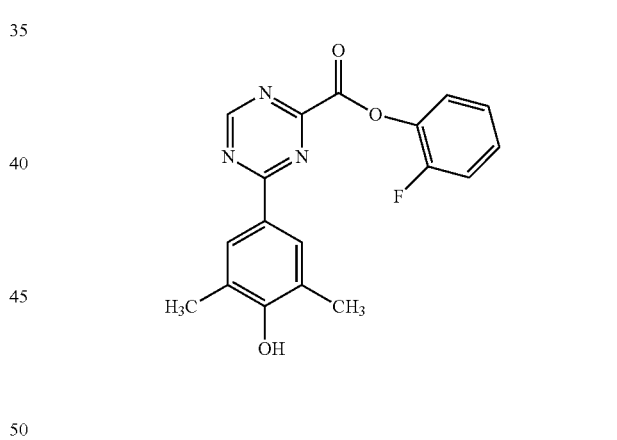
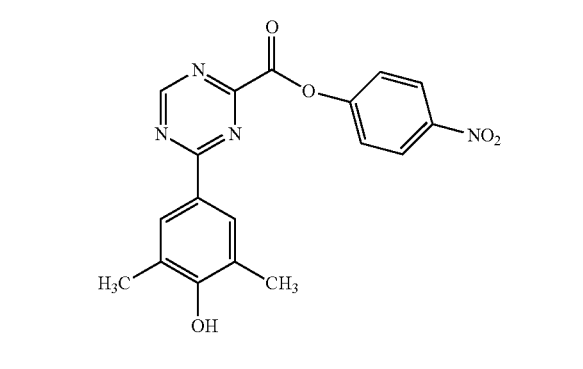 [SMILES: Cc1cc(-c2ncnc(C(=O)Oc3ccc([N+](=O)[O-])cc3)n2)cc(C)c1O]
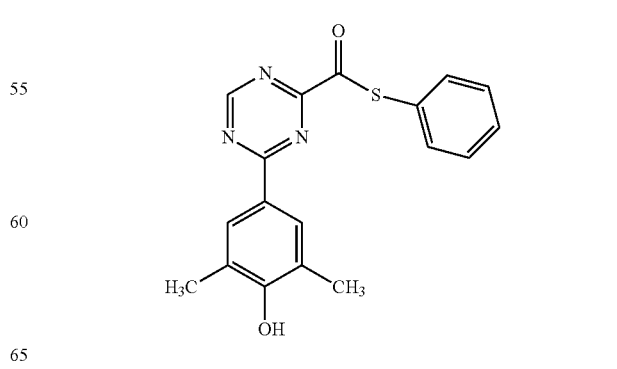

TABLE F-continued
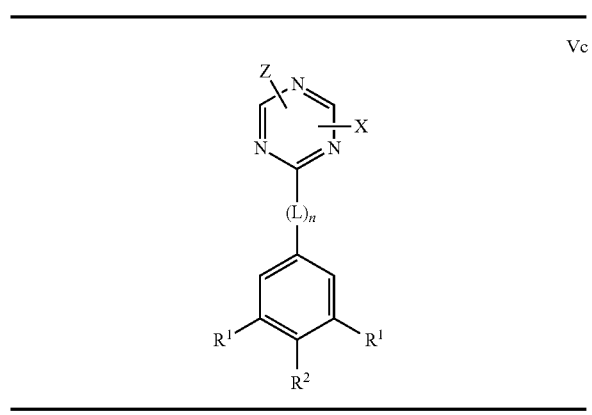
Vc
TABLE F-continued
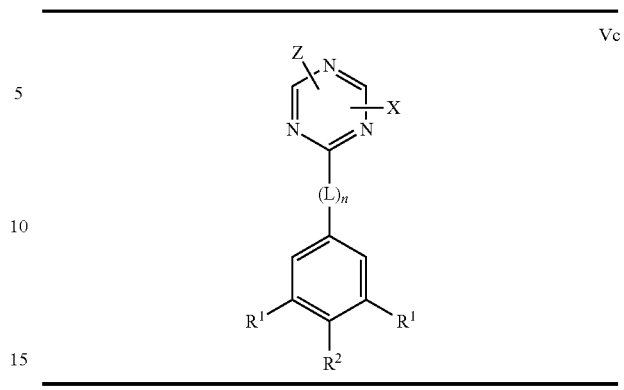
Vc
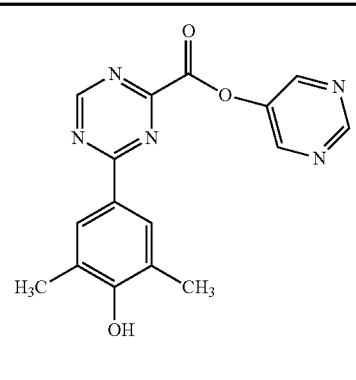
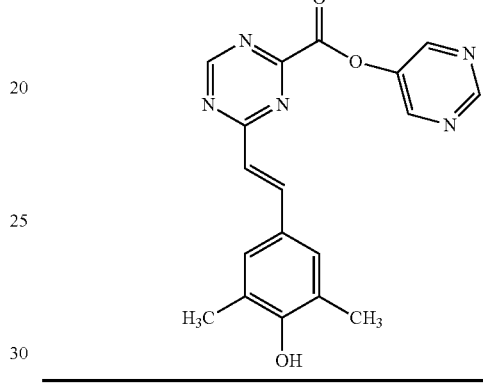
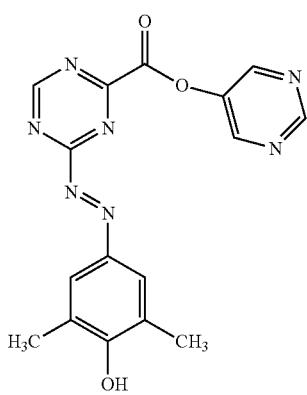 [SMILES: Cc1cc(/N=N/c2ncnc(C(=O)Oc3cncnc3)n2)cc(C)c1O]
TABLE G
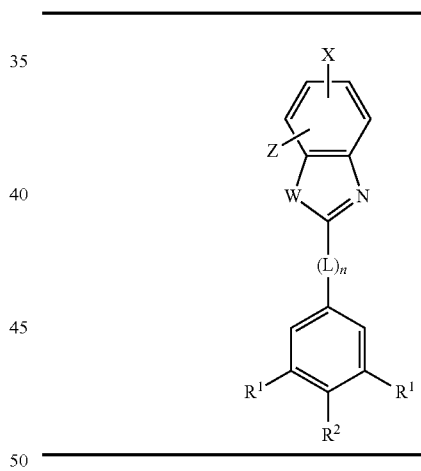
Vd
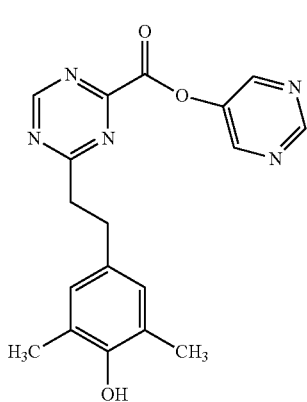 [SMILES: Cc1cc(CCc2ncnc(C(=O)Oc3cncnc3)n2)cc(C)c1O]
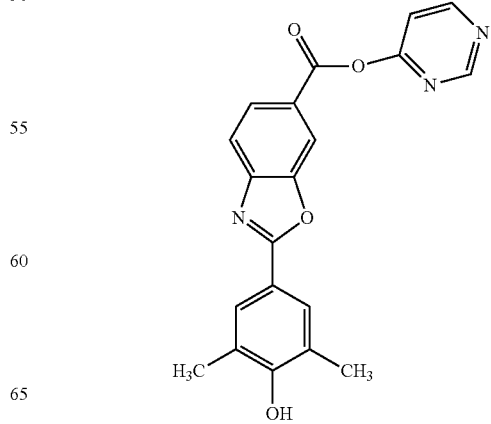

TABLE G-continued
Vd
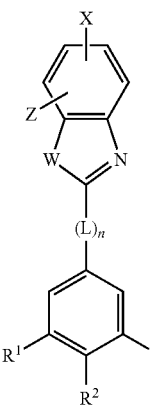
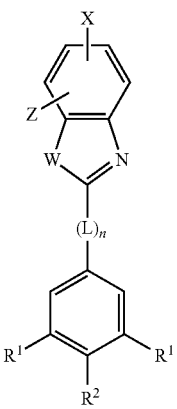
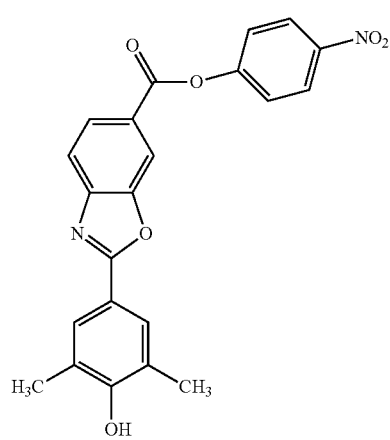 [SMILES: Cc1cc(-c2nc3ccc(C(=O)Oc4ccc([N+](=O)[O-])cc4)cc3o2)cc(C)c1O]
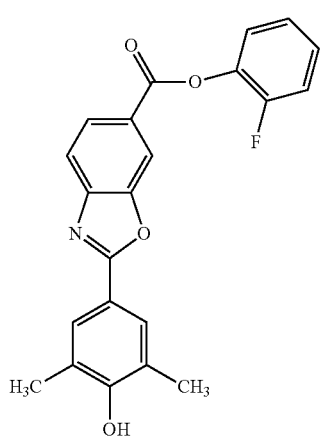
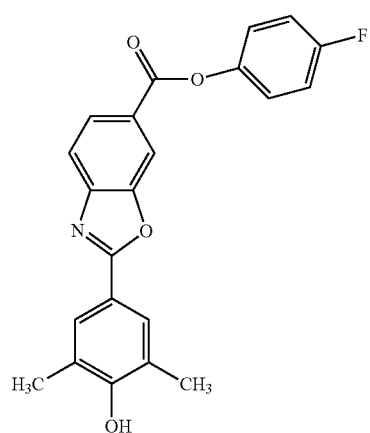 [SMILES: Cc1cc(-c2nc3ccc(C(=O)Oc4ccc(F)cc4)cc3o2)cc(C)c1O]
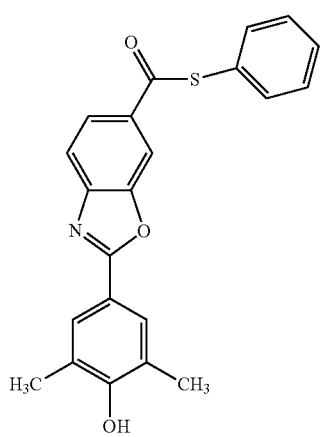 [SMILES: Cc1cc(-c2nc3ccc(C(=O)Sc4ccccc4)cc3o2)cc(C)c1O]

TABLE G-continued
Vd
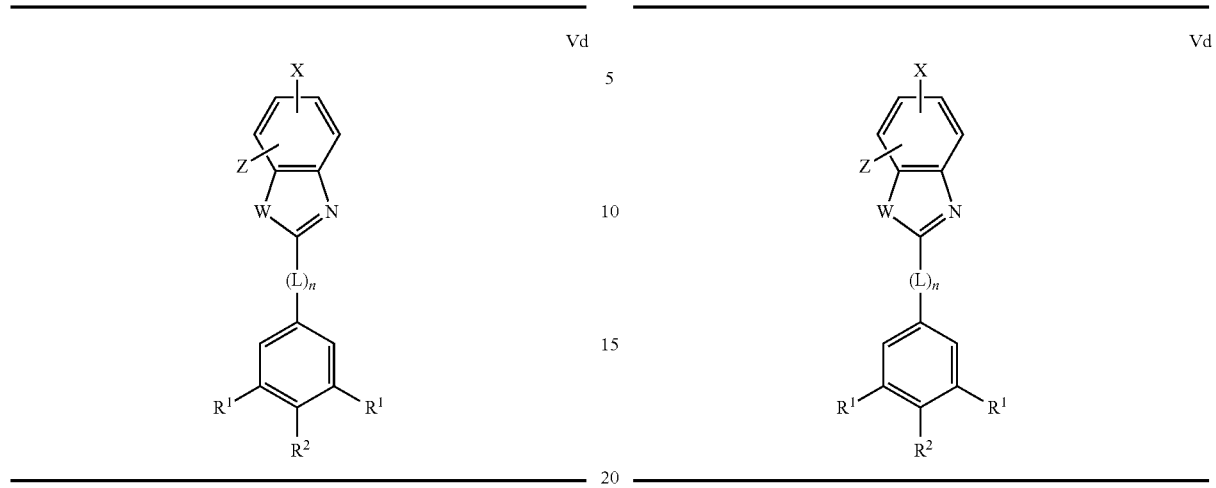
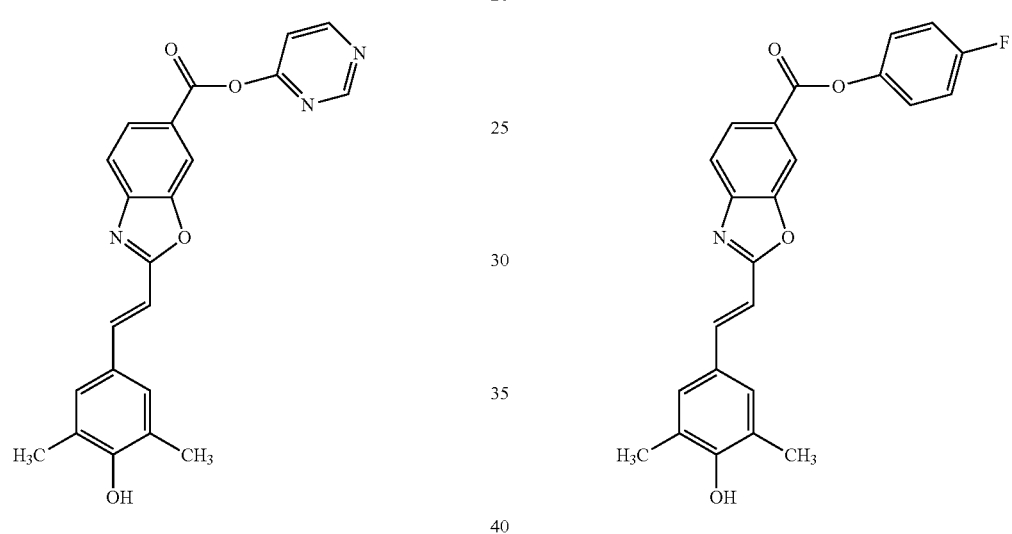
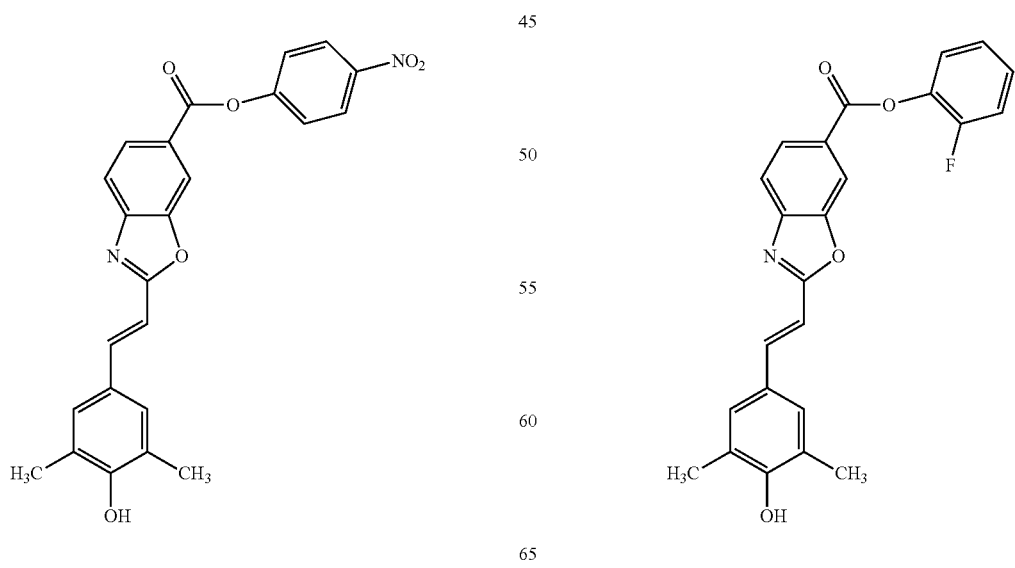

TABLE G-continued
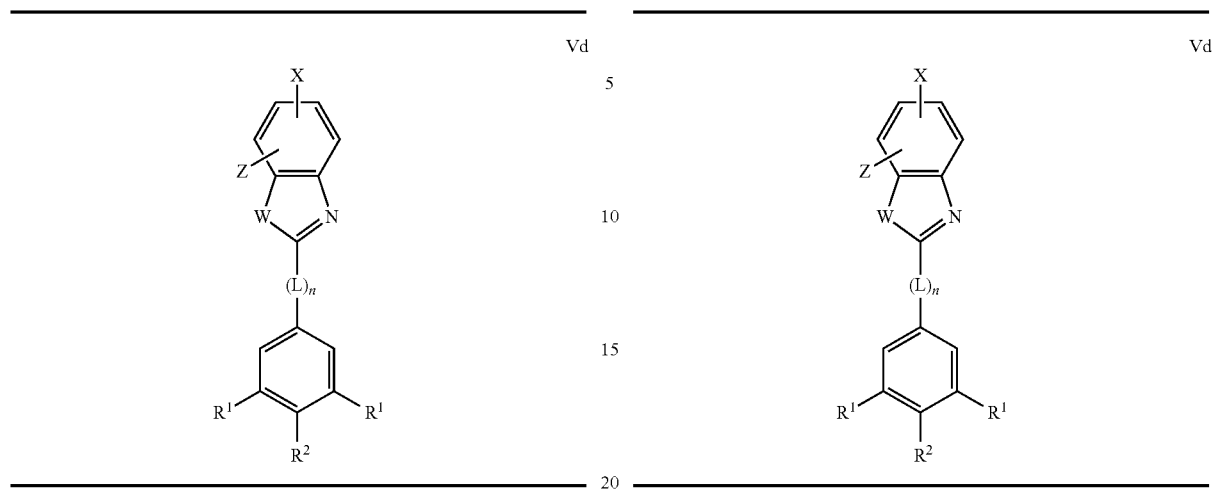
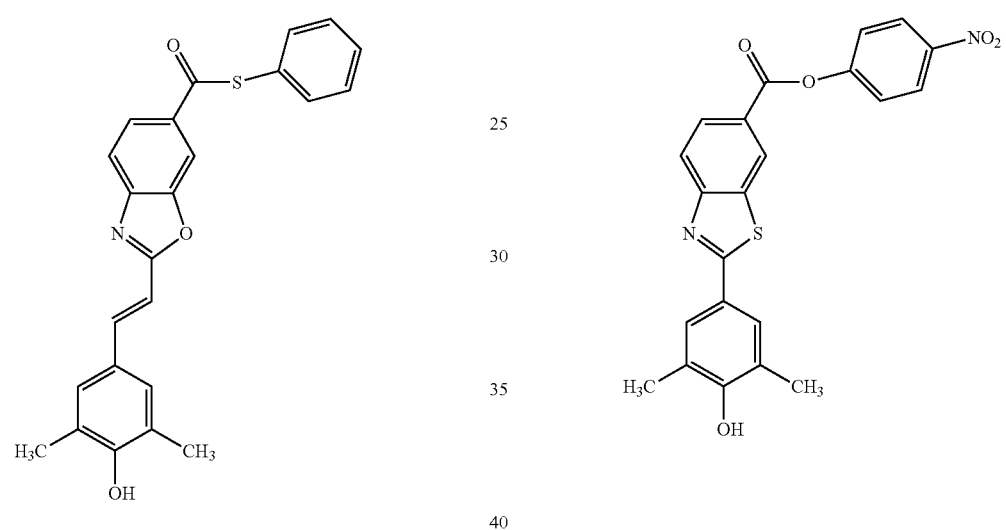
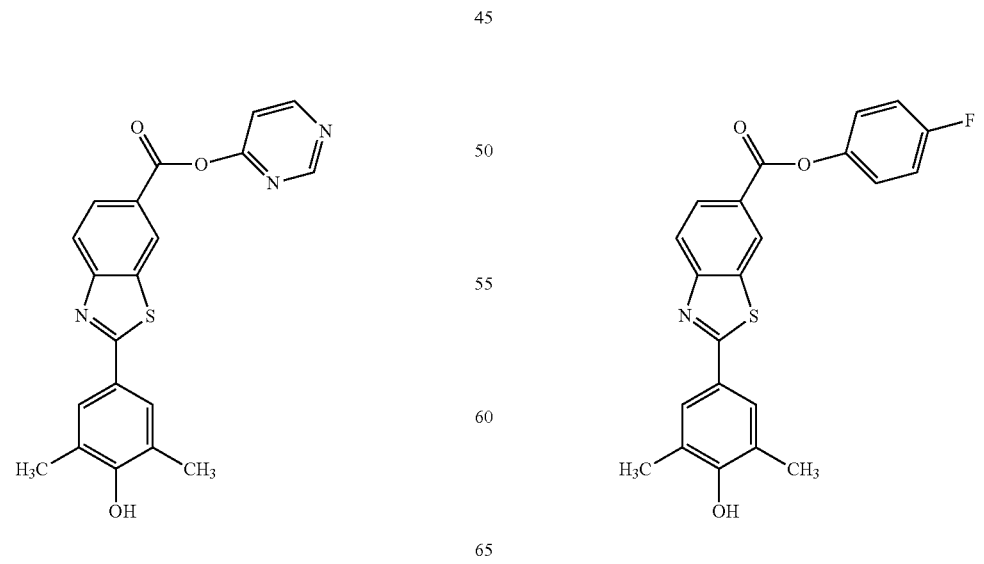

TABLE G-continued
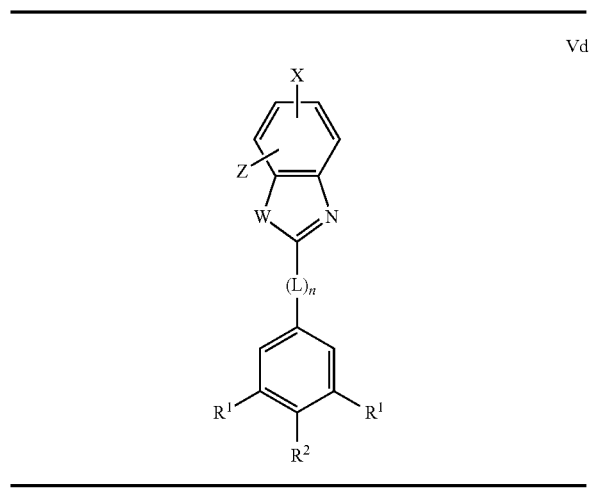
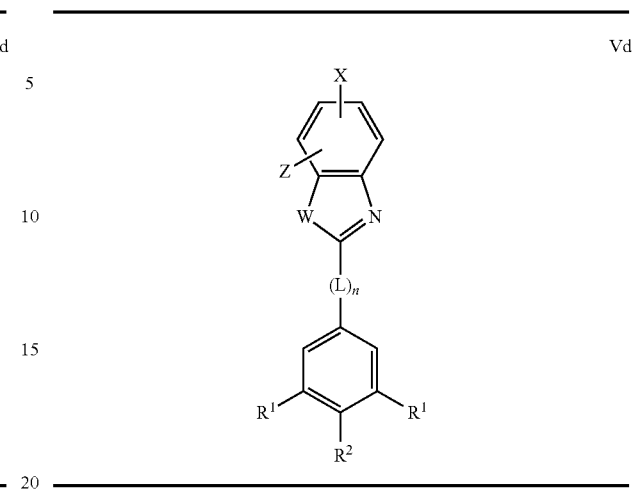
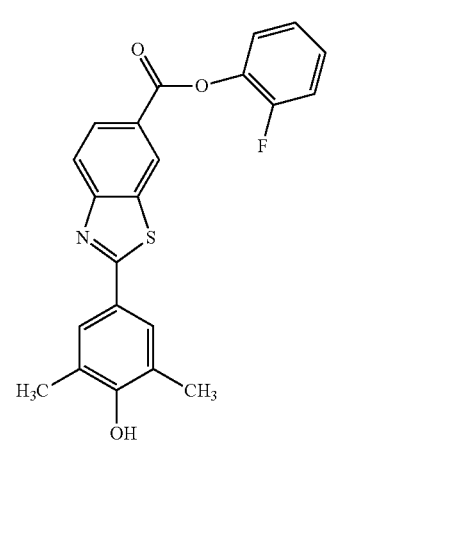
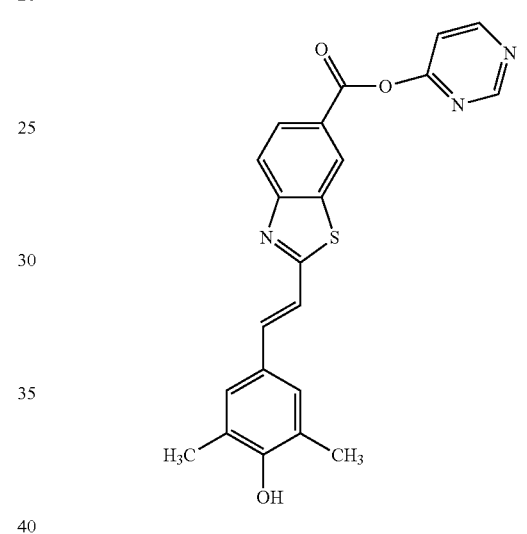
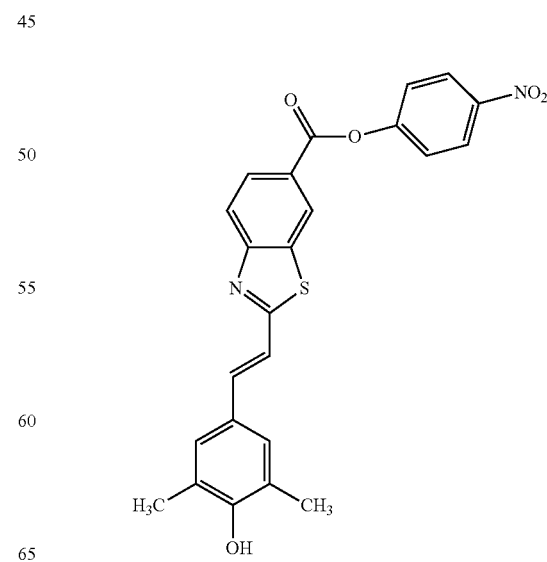

TABLE G-continued
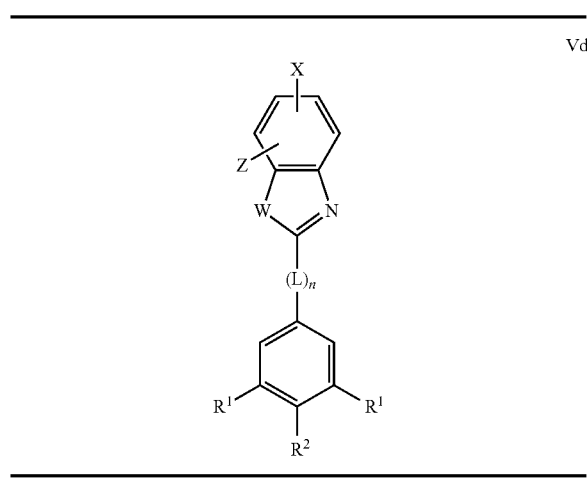
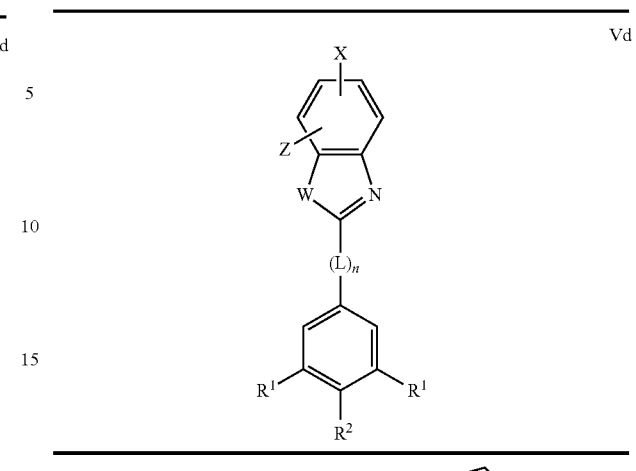
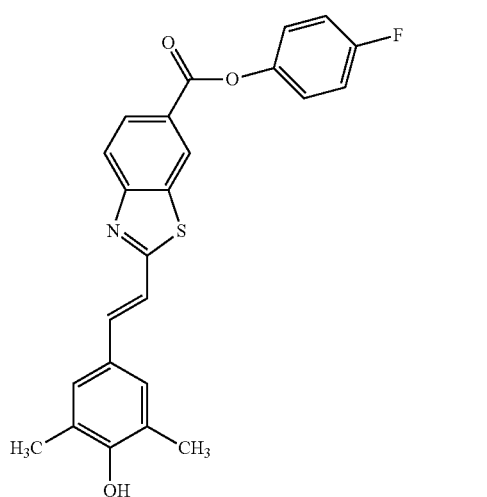 [SMILES: Cc1cc(/C=C/c2nc3ccc(C(=O)Oc4ccc(F)cc4)cc3o2)cc(C)c1O]
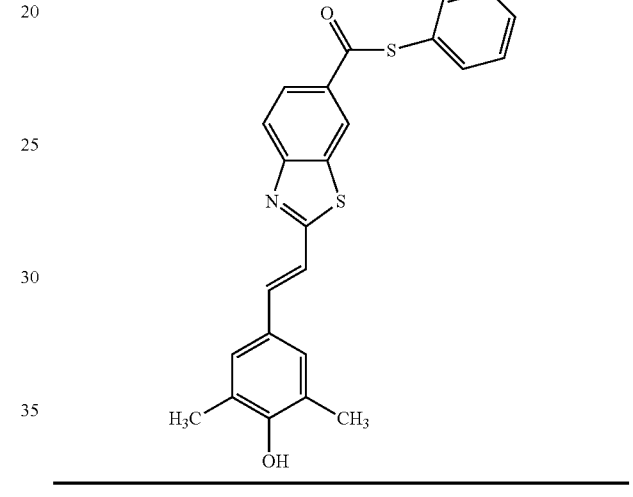
TABLE H
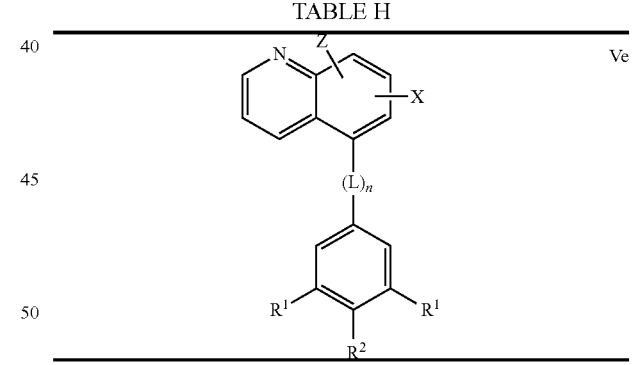
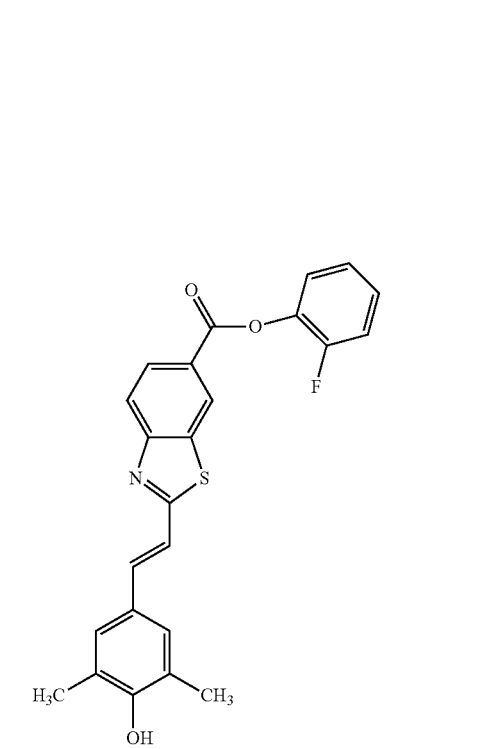 [SMILES: Cc1cc(/C=C/c2nc3ccc(C(=O)Oc4ccccc4F)cc3o2)cc(C)c1O]
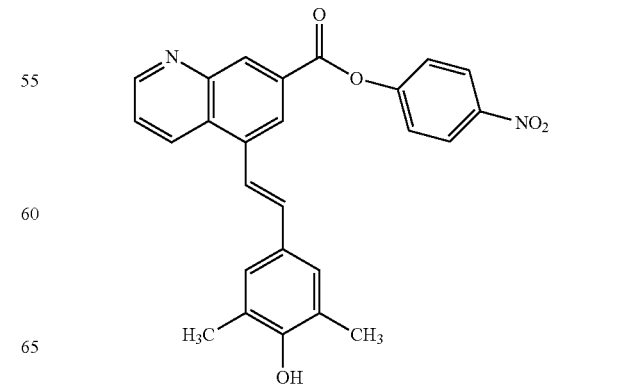

TABLE H-continued
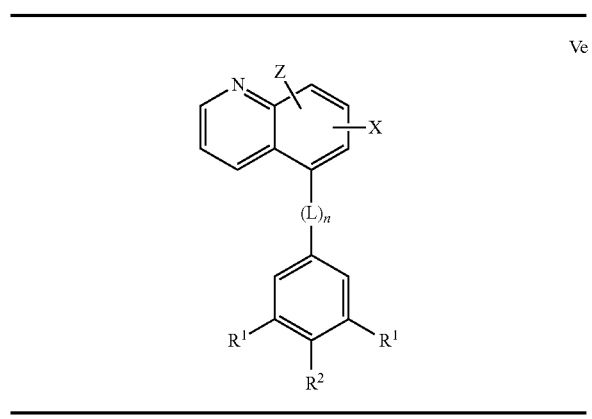
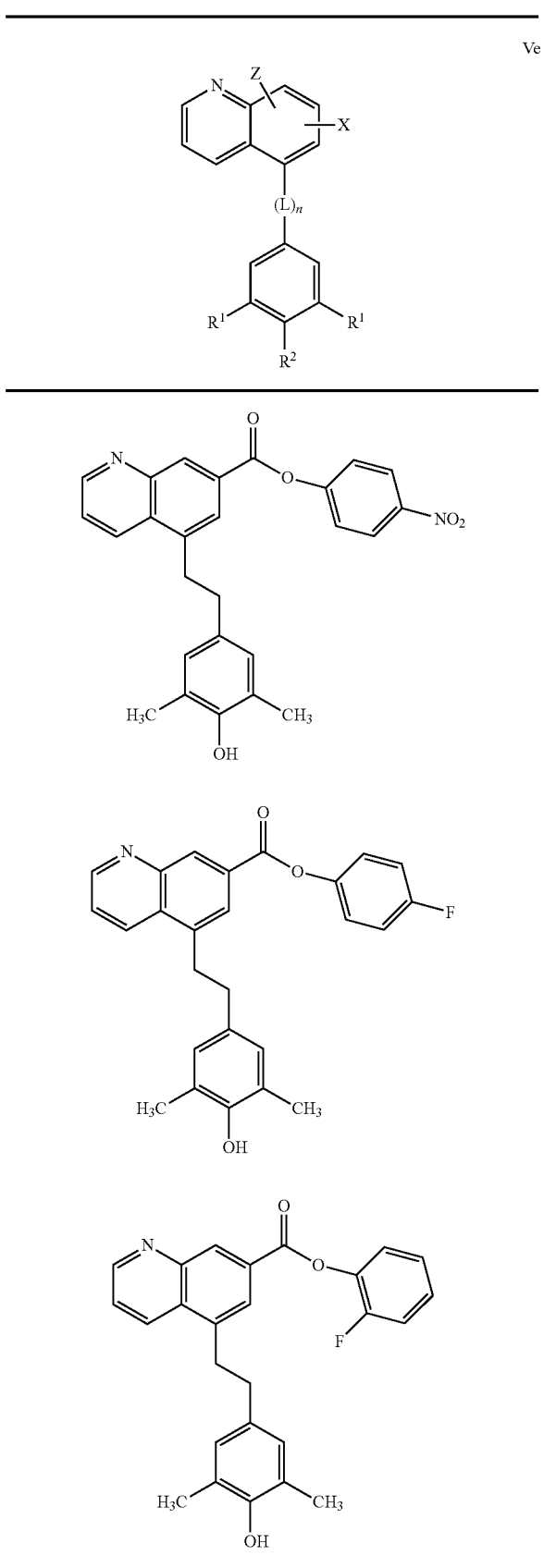

TABLE H-continued
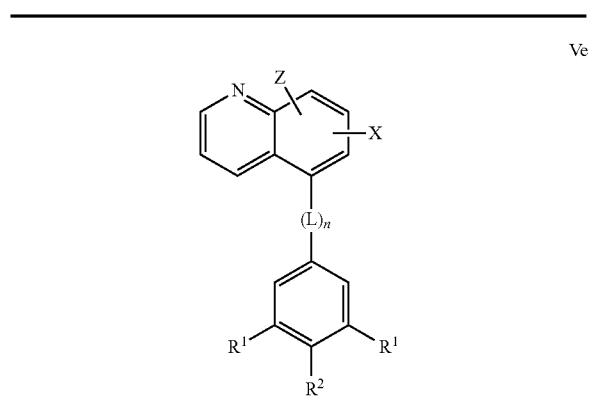
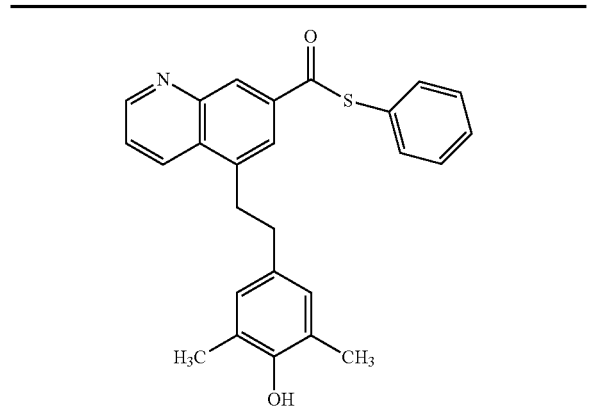
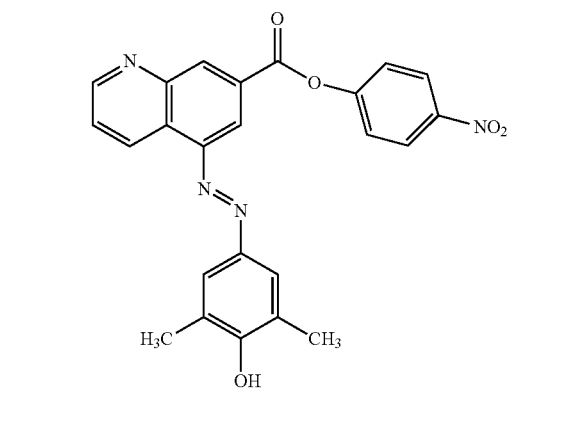 [SMILES: Cc1cc(/N=N/c2cc(C(=O)Oc3ccc([N+](=O)[O-])cc3)cc3ncccc23)cc(C)c1O]
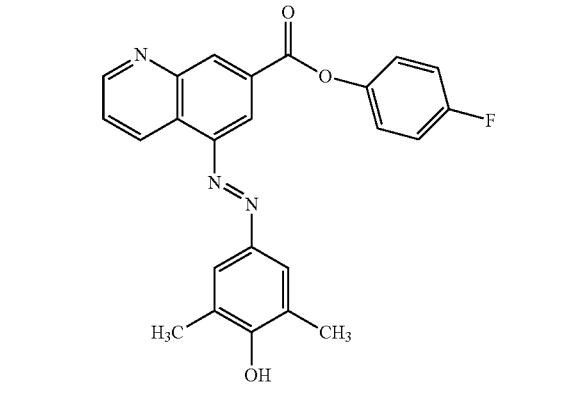 [SMILES: Cc1cc(/N=N/c2cc(C(=O)Oc3ccc(F)cc3)cc3ncccc23)cc(C)c1O]
TABLE H-continued
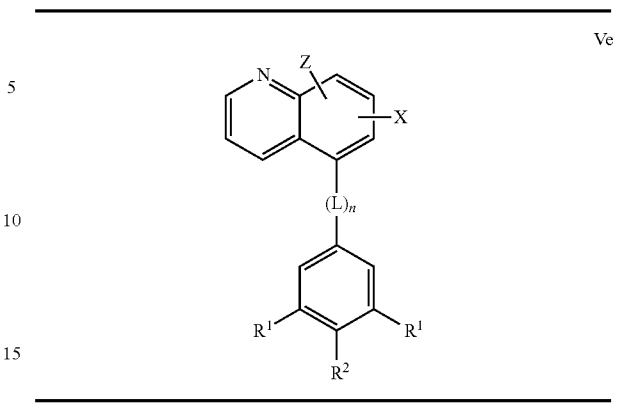
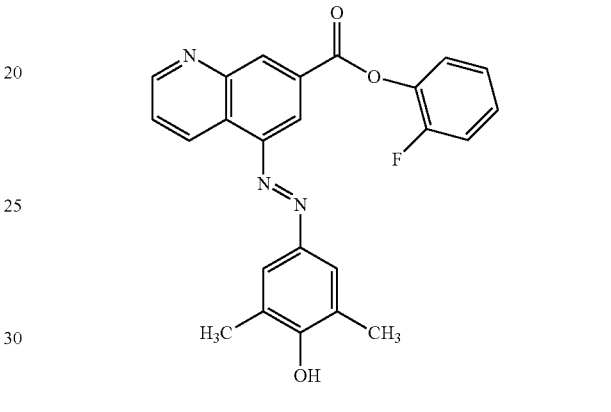
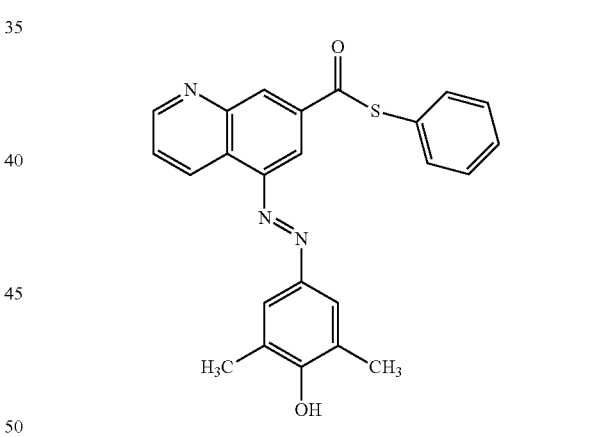
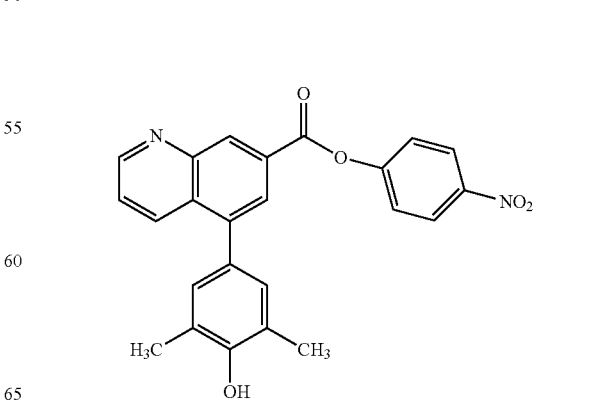

TABLE H-continued
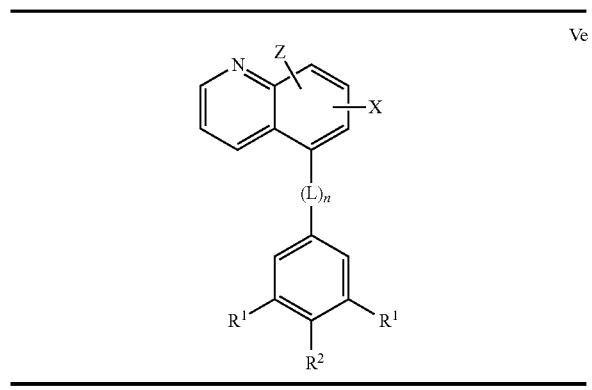
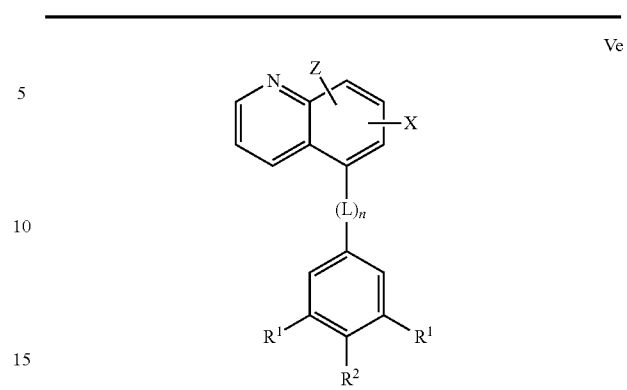
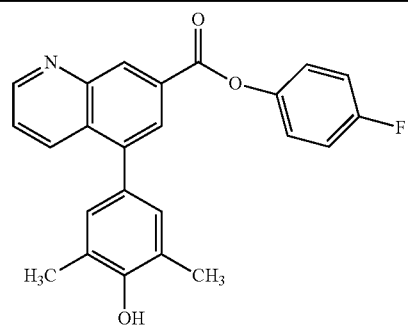
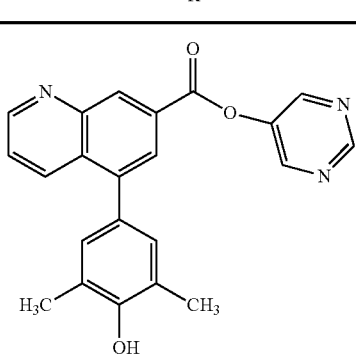
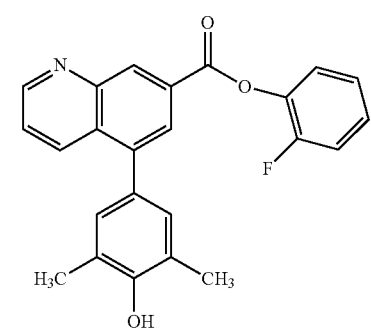 [SMILES: Cc1cc(-c2cc(C(=O)Oc3ccccc3F)cc3ncccc23)cc(C)c1O]
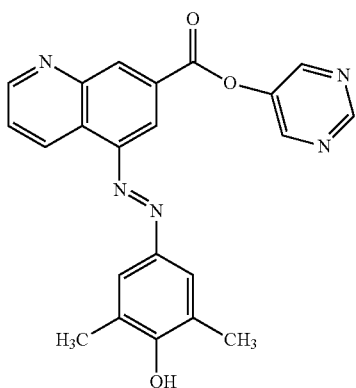
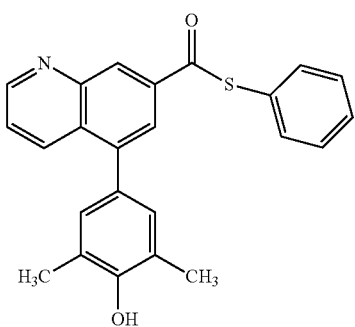 [SMILES: Cc1cc(-c2cc(C(=O)Sc3ccccc3)cc3ncccc23)cc(C)c1O]
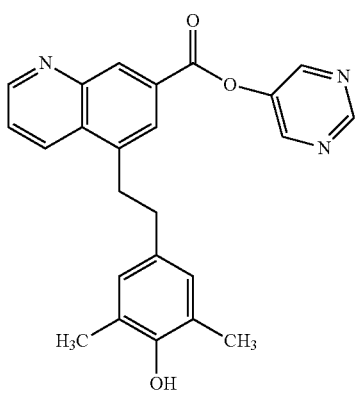 [SMILES: Cc1cc(CCc2cc(C(=O)Oc3cncnc3)cc3ncccc23)cc(C)c1O]

TABLE H-continued
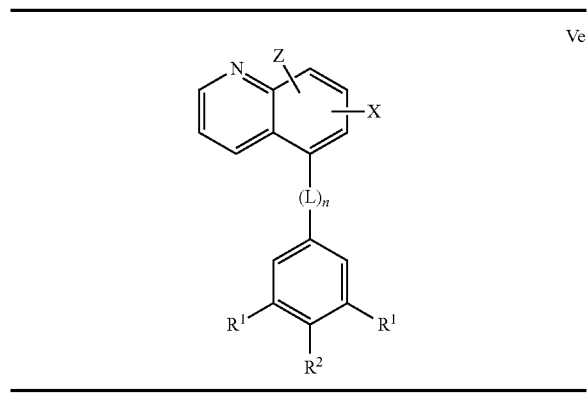
Ve
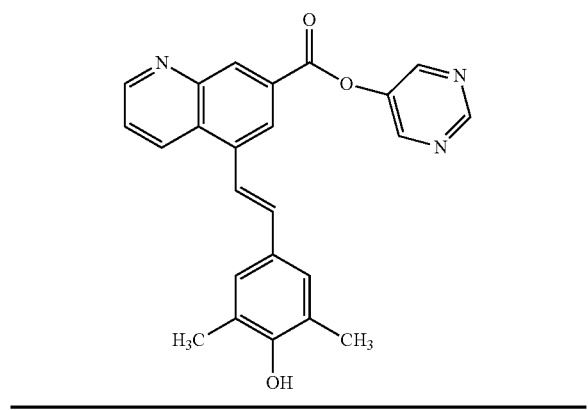
TABLE I
Vf
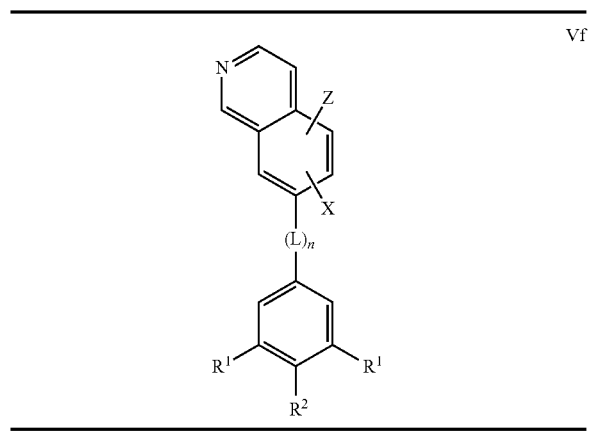
TABLE I-continued
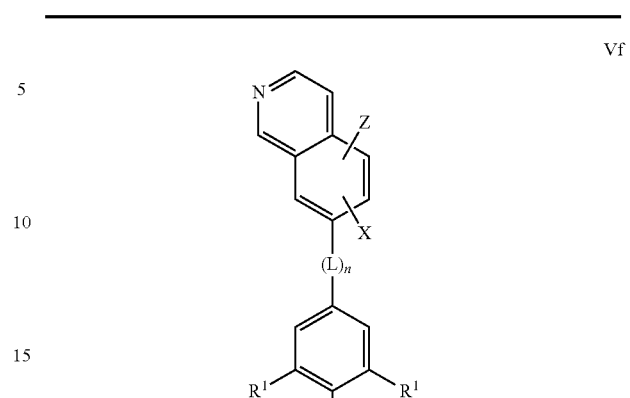
Vf
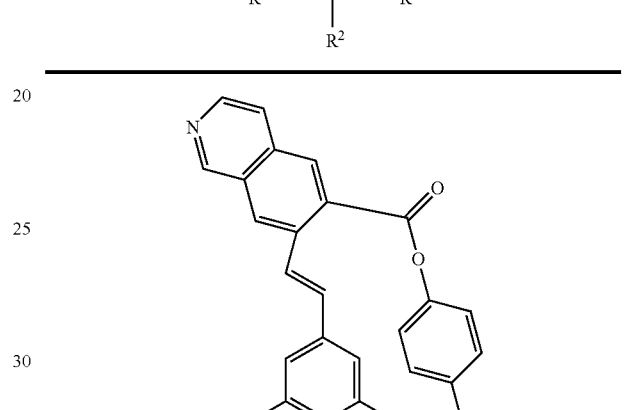
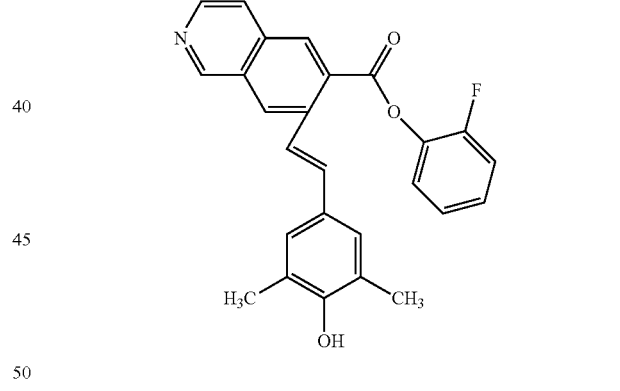
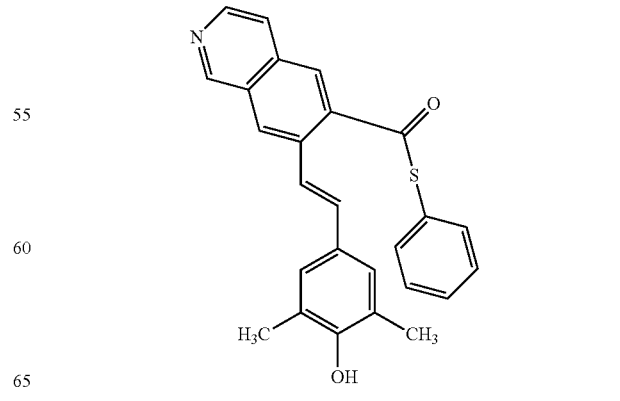

TABLE I-continued
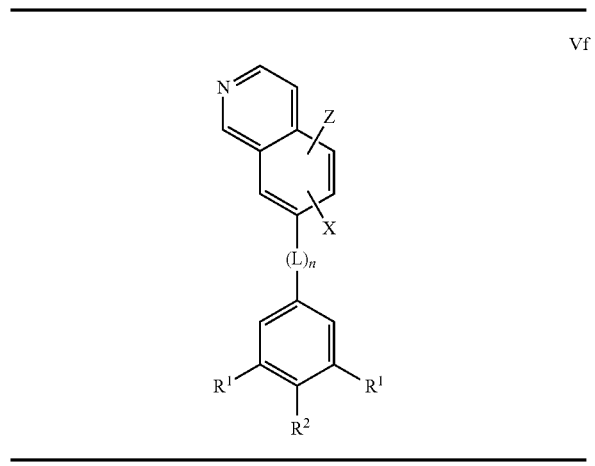
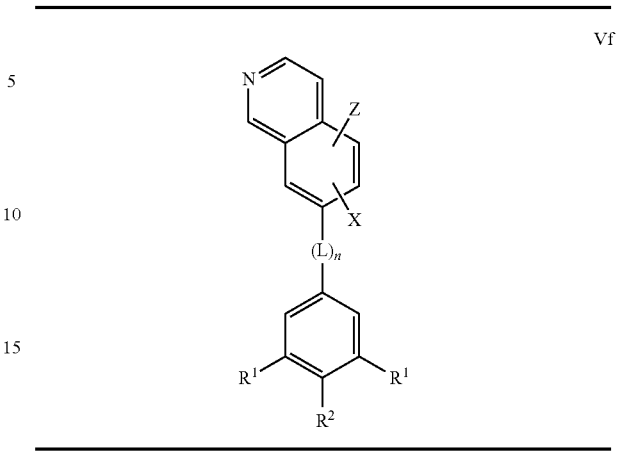
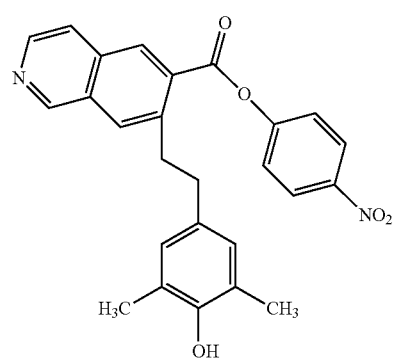 [SMILES: Cc1cc(CCc2cc3cnccc3cc2C(=O)Oc2ccc([N+](=O)[O-])cc2)cc(C)c1O]
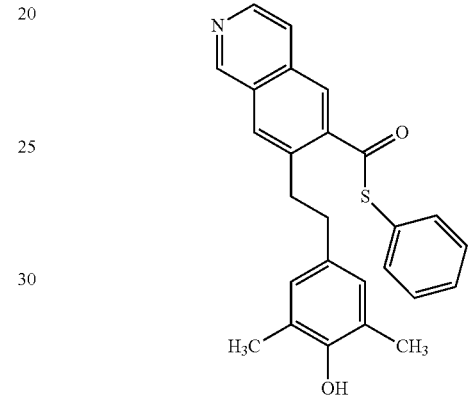
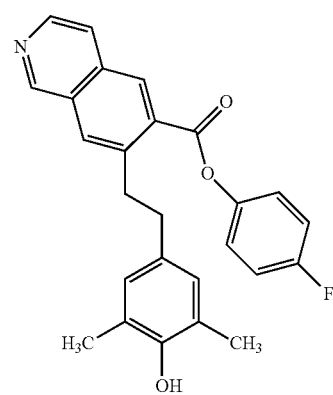 [SMILES: Cc1cc(CCc2cc3cnccc3cc2C(=O)Oc2ccc(F)cc2)cc(C)c1O]
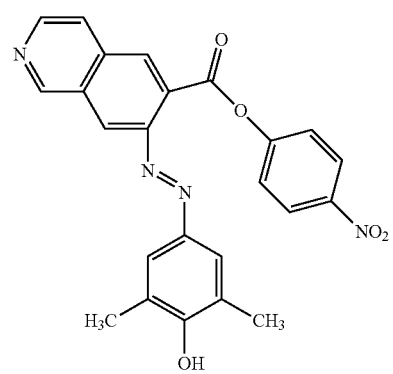
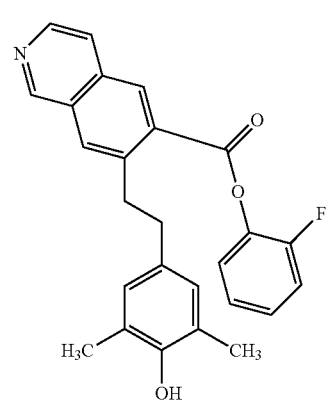 [SMILES: Cc1cc(CCc2cc3cnccc3cc2C(=O)Oc2ccccc2F)cc(C)c1O]
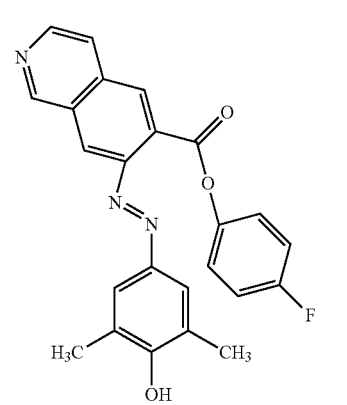 [SMILES: Cc1cc(/N=N/c2cc3cnccc3cc2C(=O)Oc2ccc(F)cc2)cc(C)c1O]

TABLE I-continued
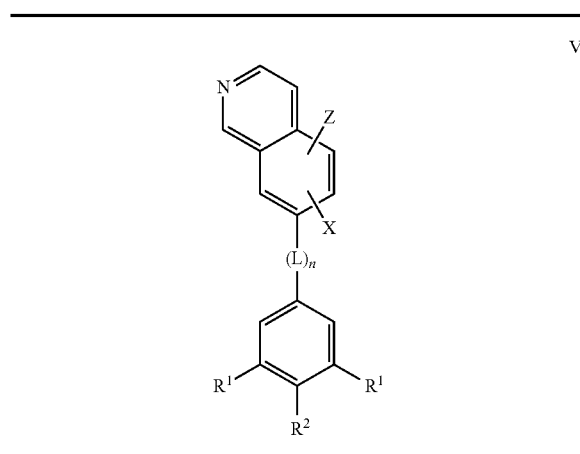
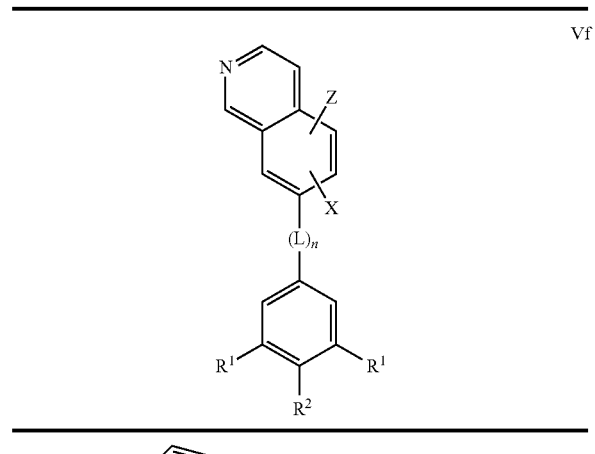
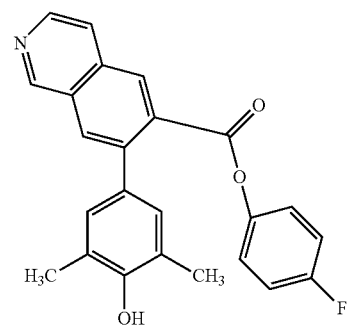 [SMILES: Cc1cc(-c2cc3cnccc3cc2C(=O)Oc2ccc(F)cc2)cc(C)c1O]
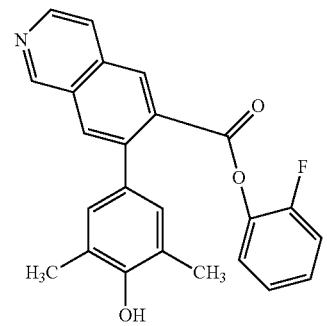 [SMILES: Cc1cc(-c2cc3cnccc3cc2C(=O)Oc2ccccc2F)cc(C)c1O]
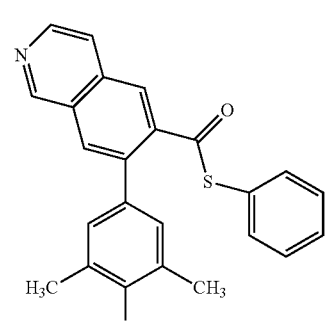

TABLE I-continued
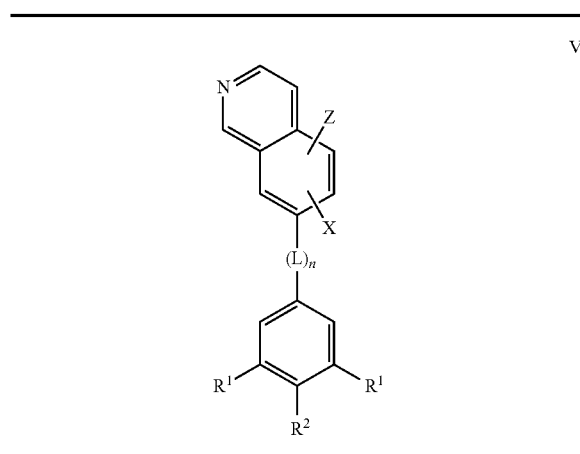
Vf
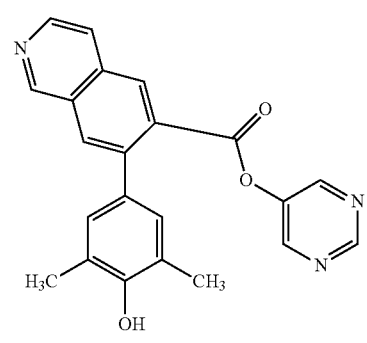 [SMILES: Cc1cc(-c2cc3cnccc3cc2C(=O)Oc2cncnc2)cc(C)c1O]
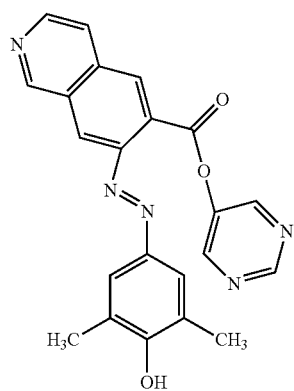 [SMILES: Cc1cc(/N=N/c2cc3cnccc3cc2C(=O)Oc2cncnc2)cc(C)c1O]
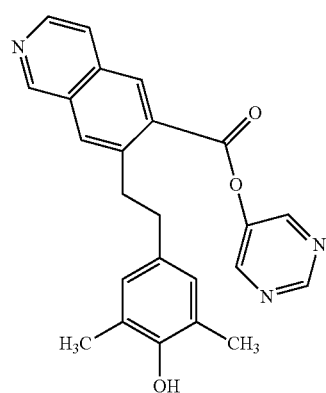 [SMILES: Cc1cc(CCc2cc3cnccc3cc2C(=O)Oc2cncnc2)cc(C)c1O]
TABLE I-continued
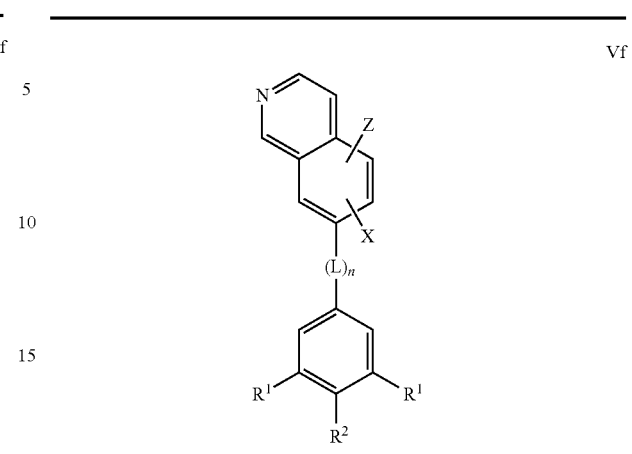
Vf
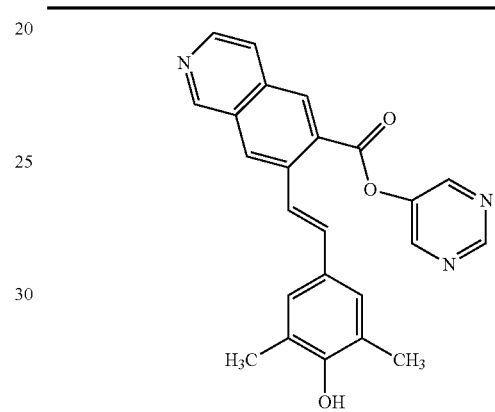
TABLE J
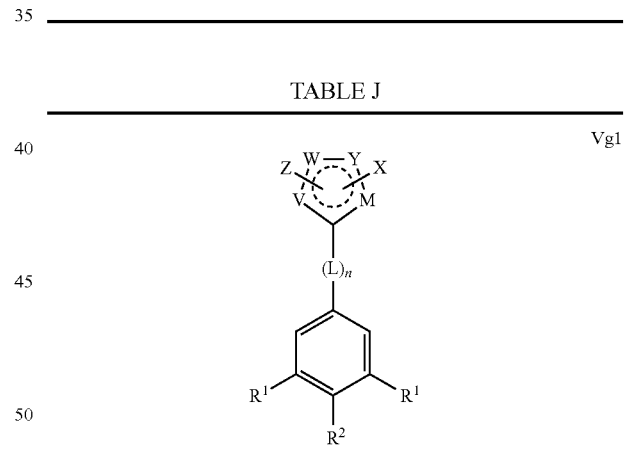
Vg1
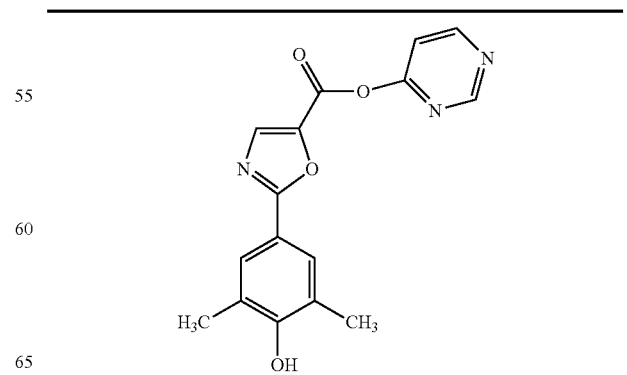

| TABLE J-continued | TABLE J-continued |
|---|---|
| 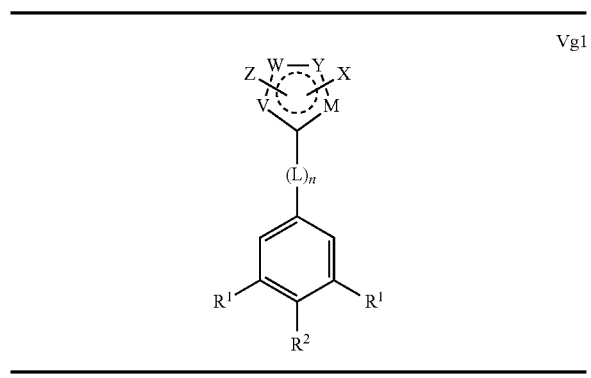 Vg1 | 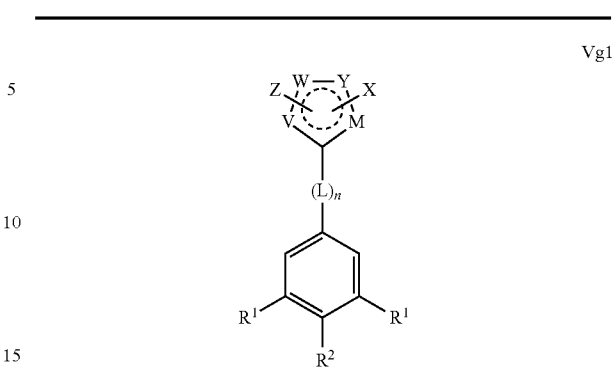 Vg1 |
| 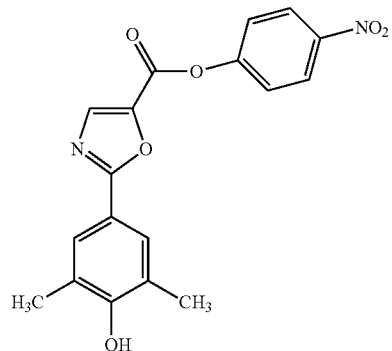 [SMILES: Cc1cc(-c2ncc(C(=O)Oc3ccc([N+](=O)[O-])cc3)o2)cc(C)c1O] | 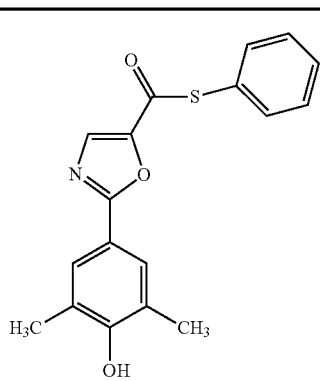 |
| 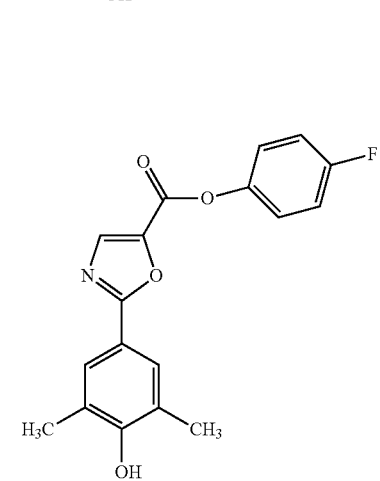 [SMILES: Cc1cc(-c2ncc(C(=O)Oc3ccc(F)cc3)o2)cc(C)c1O] | 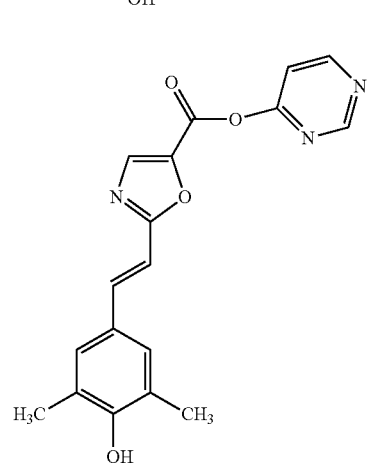 |
| 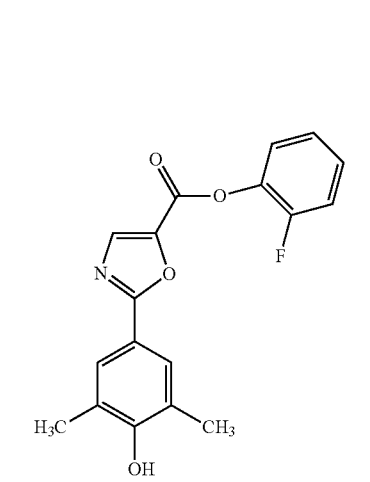 [SMILES: Cc1cc(-c2ccc(C(=O)Oc3ccccc3F)o2)cc(C)c1O] | 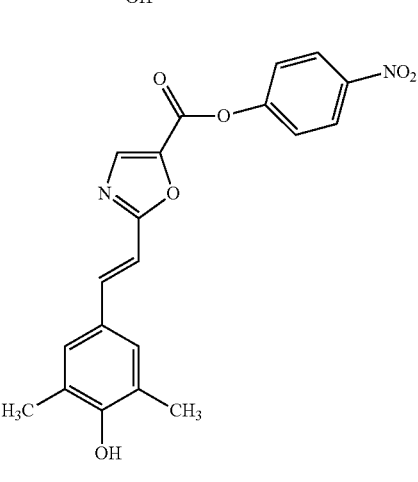 |

TABLE J-continued
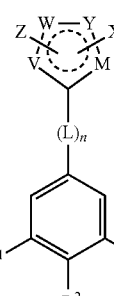
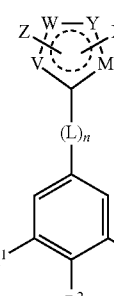
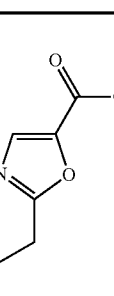
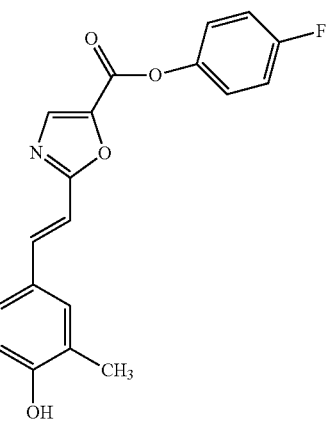
TABLE J-continued
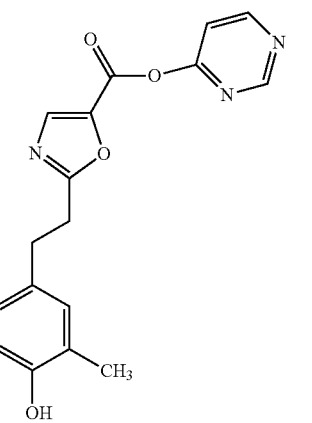
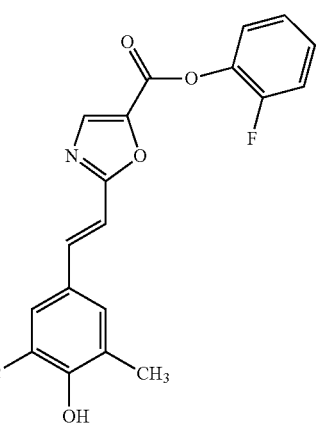
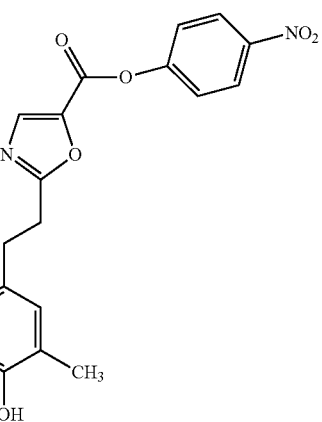
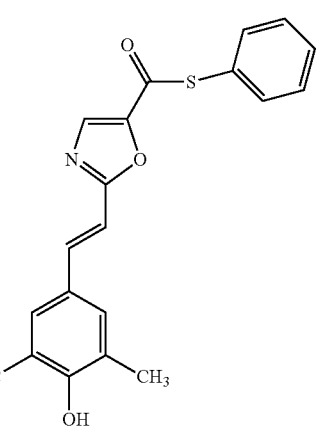

TABLE J-continued
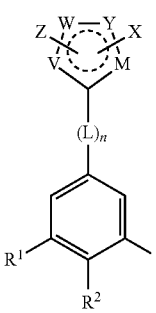
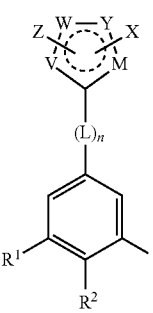
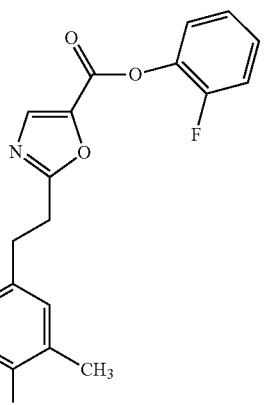
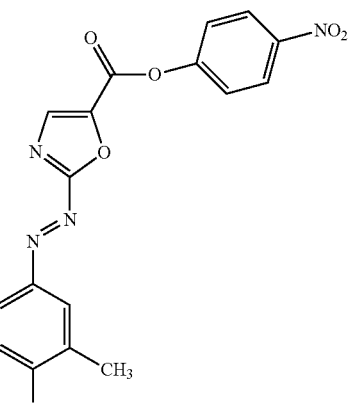
TABLE J-continued
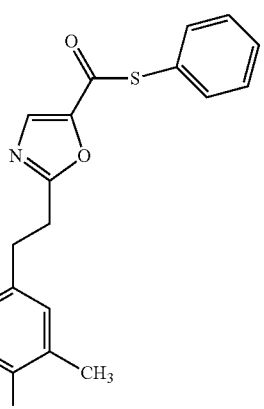
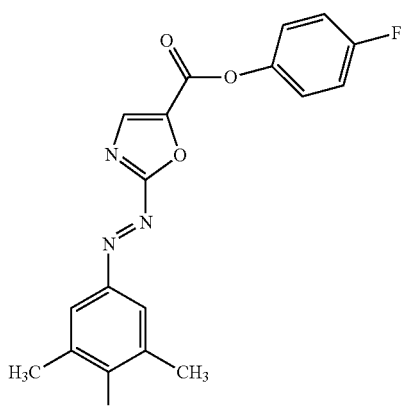
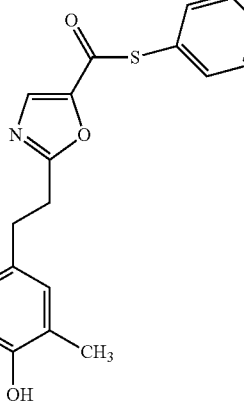
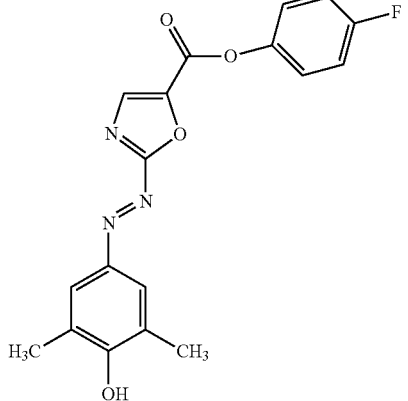

TABLE J-continued
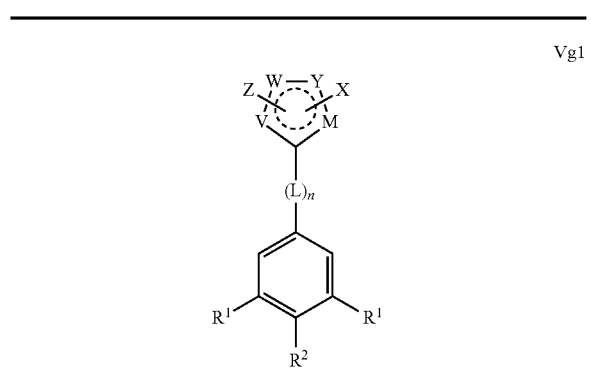
Vg1
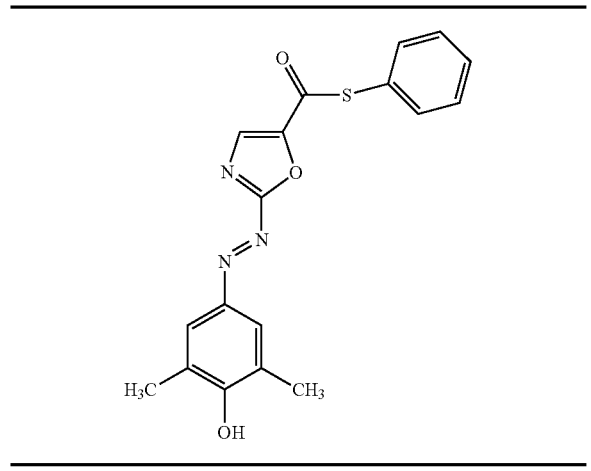
TABLE K
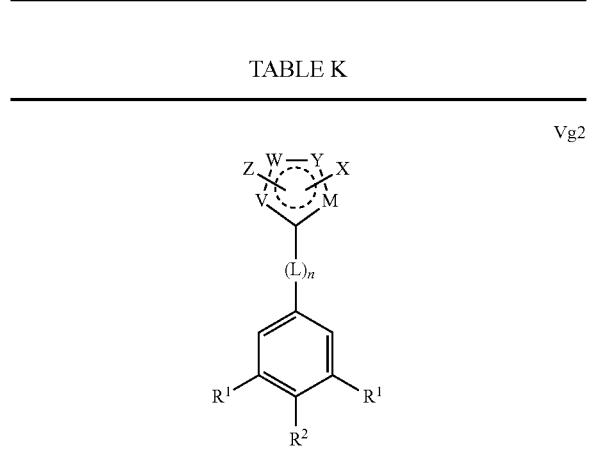
Vg2
TABLE K-continued
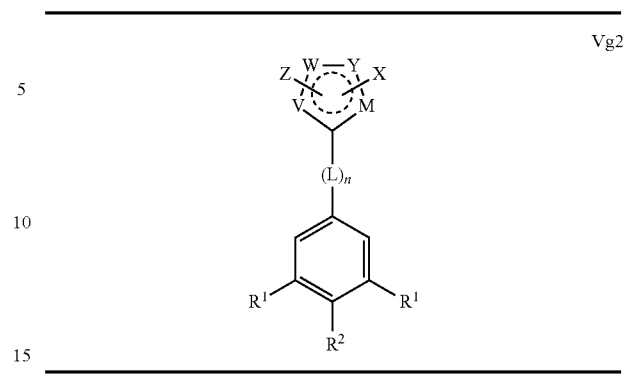
Vg2
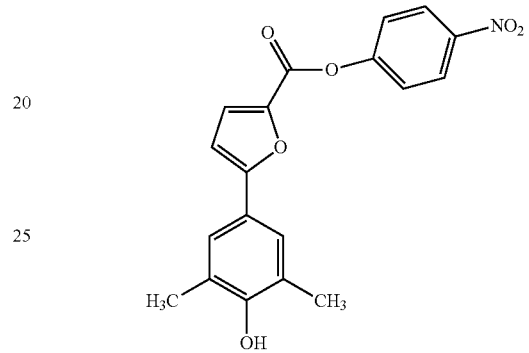
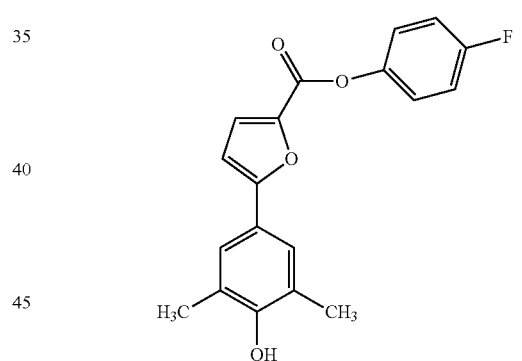
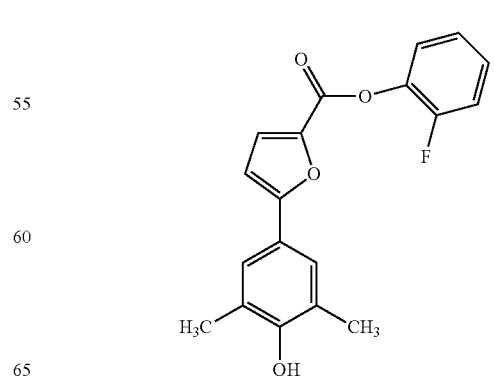

US 8,703,815 B2
| 99 | 100 |
|---|---|
| TABLE K-continued | TABLE K-continued |
| 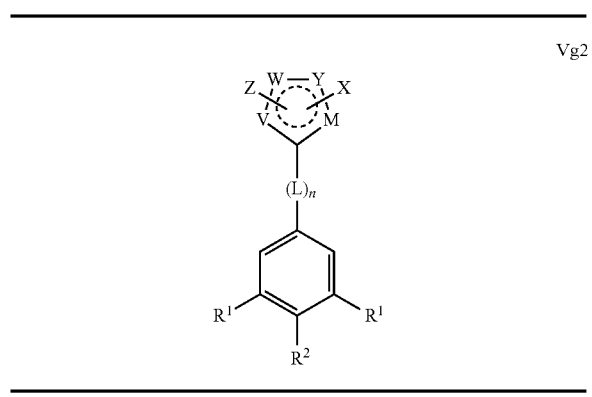 Vg2 | 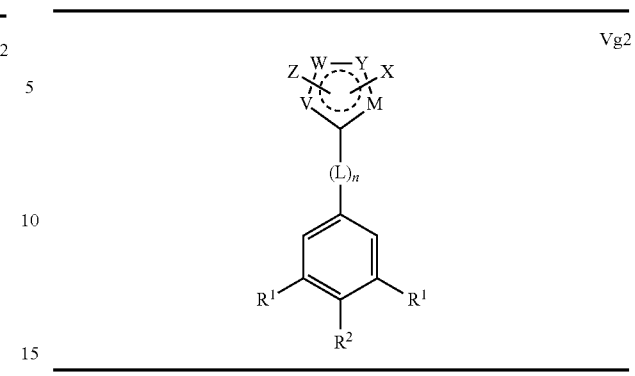 Vg2 |
| 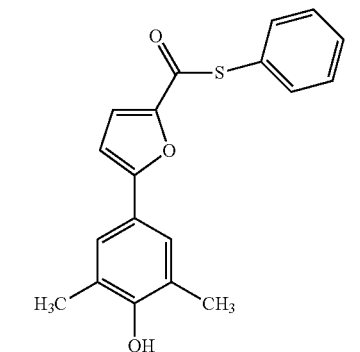 [SMILES: Cc1cc(-c2ccc(C(=O)Sc3ccccc3)o2)cc(C)c1O] | 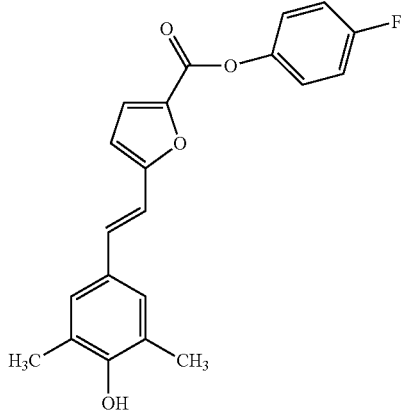 |
| 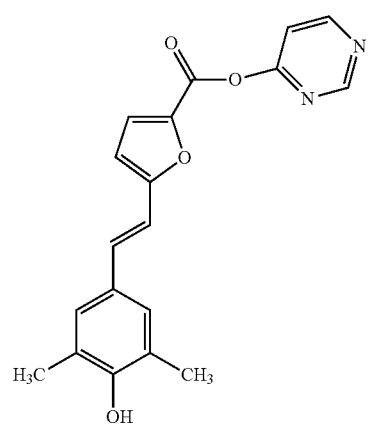 [SMILES: Cc1cc(/C=C/c2ccc(C(=O)Oc3ccncn3)o2)cc(C)c1O] | 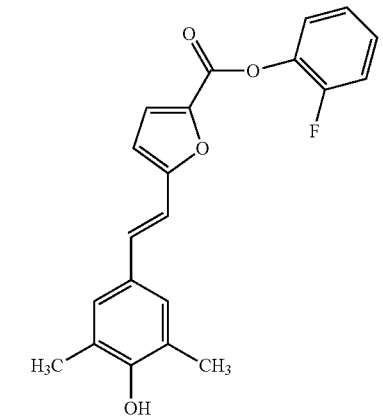 |
| 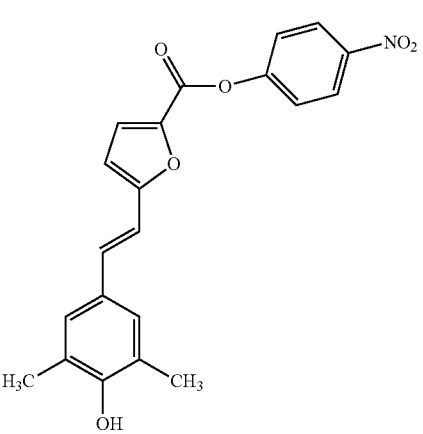 [SMILES: Cc1cc(/C=C/c2ccc(C(=O)Oc3ccc([N+](=O)[O-])cc3)o2)cc(C)c1O] | 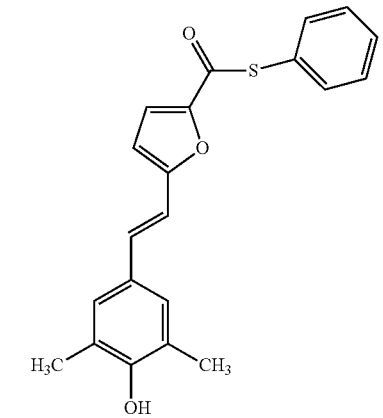 [SMILES: Cc1cc(/C=C/c2ccc(C(=O)Sc3ccccc3)o2)cc(C)c1O] |

TABLE K-continued
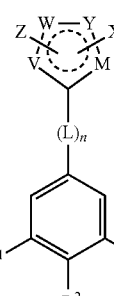

103
TABLE K-continued
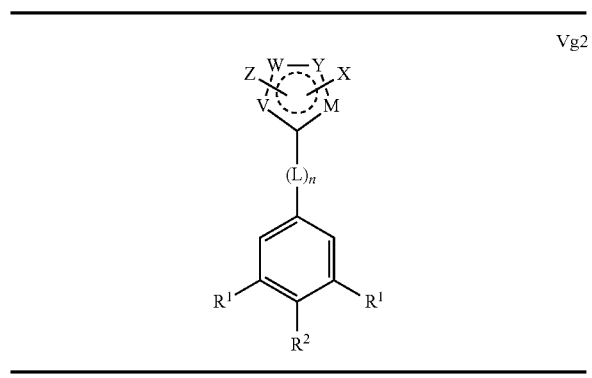
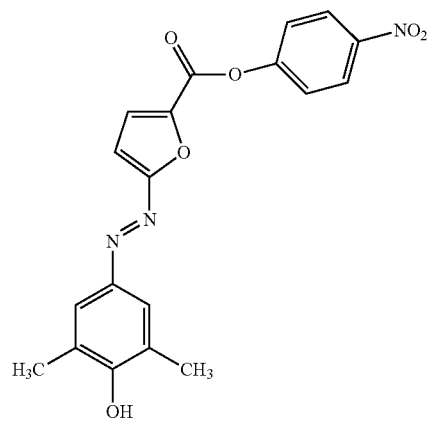 [SMILES: Cc1cc(/N=N/c2ccc(C(=O)Oc3ccc([N+](=O)[O-])cc3)o2)cc(C)c1O]
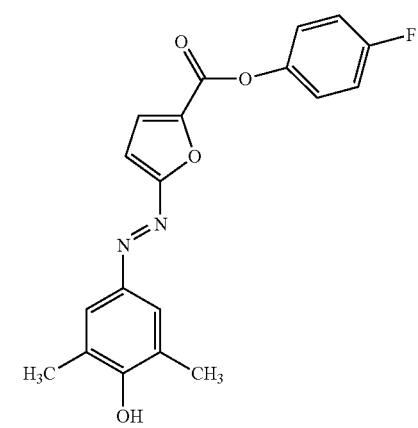
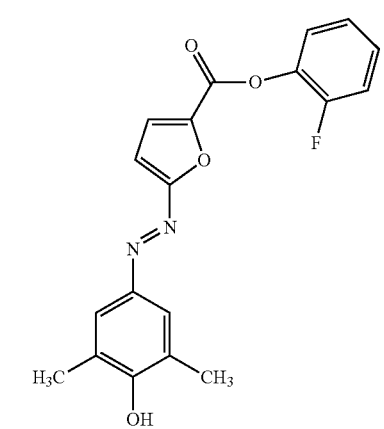 [SMILES: Cc1cc(/N=N/c2ccc(C(=O)Oc3ccccc3F)o2)cc(C)c1O]
104
TABLE K-continued
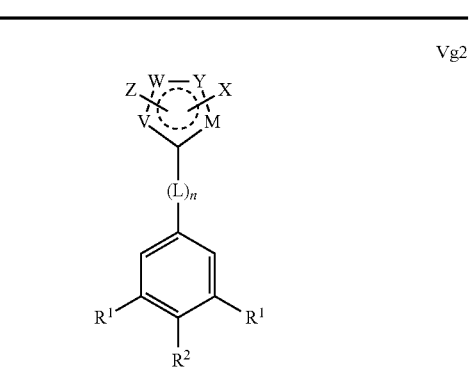
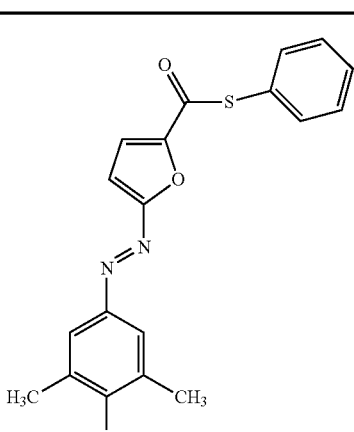
TABLE L
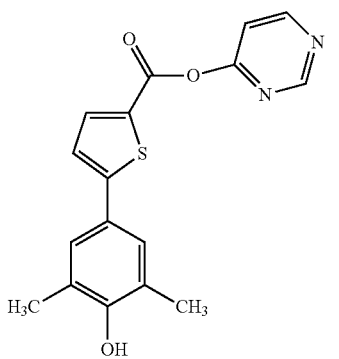 [SMILES: Cc1cc(-c2ccc(C(=O)Oc3ccncn3)s2)cc(C)c1O]

TABLE L-continued
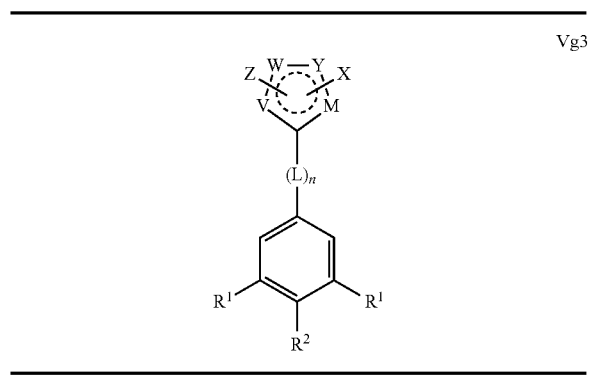
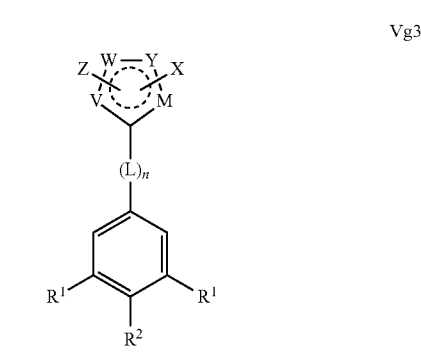
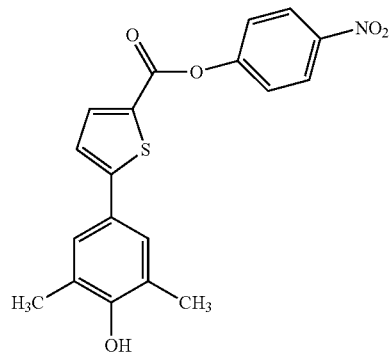
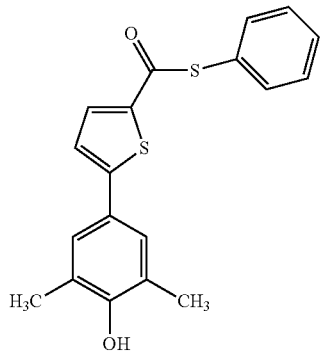
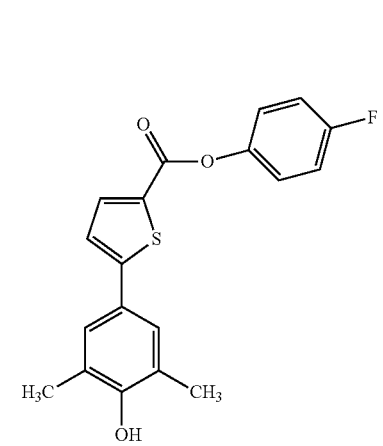 [SMILES: Cc1cc(-c2ccc(C(=O)Oc3ccc(F)cc3)s2)cc(C)c1O]
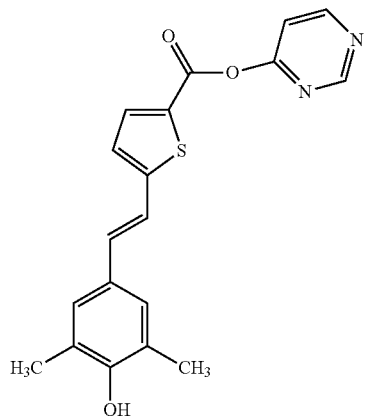
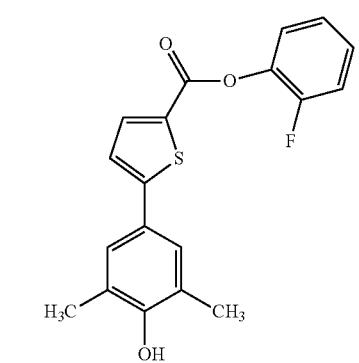
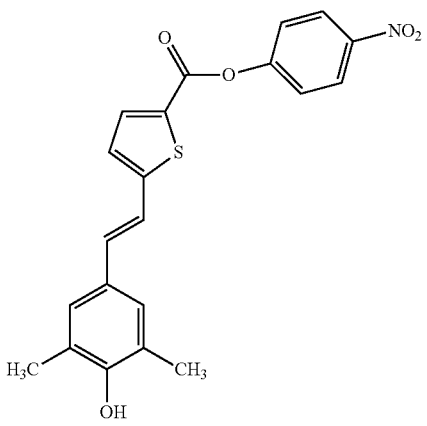 [SMILES: Cc1cc(/C=C/c2ccc(C(=O)Oc3ccc([N+](=O)[O-])cc3)s2)cc(C)c1O]

TABLE L-continued
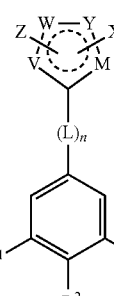
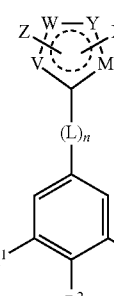
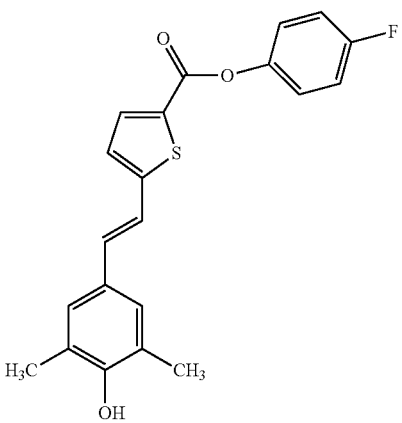 [SMILES: Cc1cc(/C=C/c2ccc(C(=O)Oc3ccc(F)cc3)s2)cc(C)c1O]
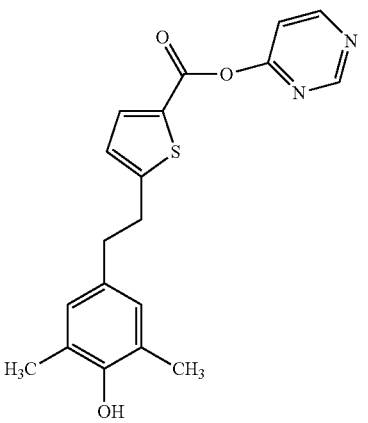
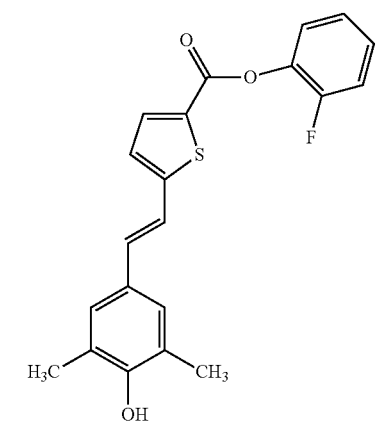
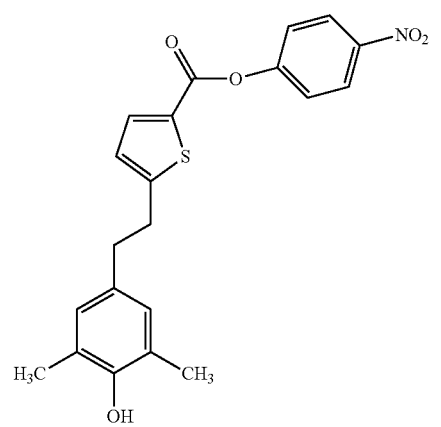
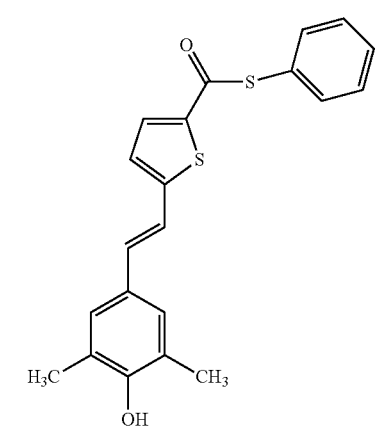
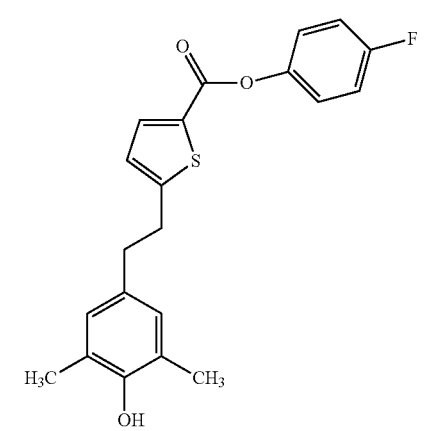

109
TABLE L-continued
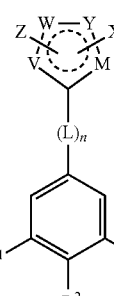
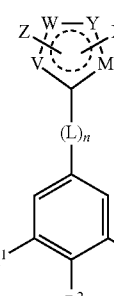
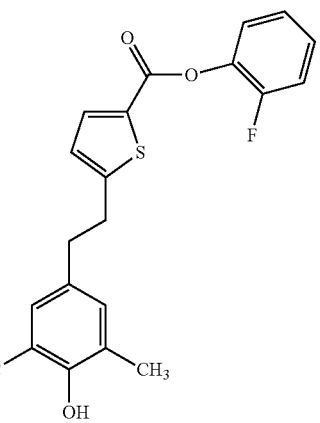
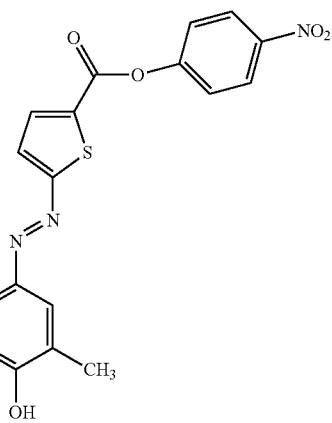
110
TABLE L-continued
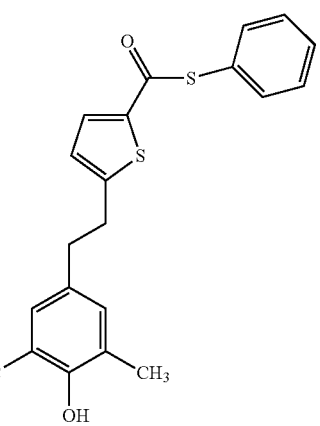
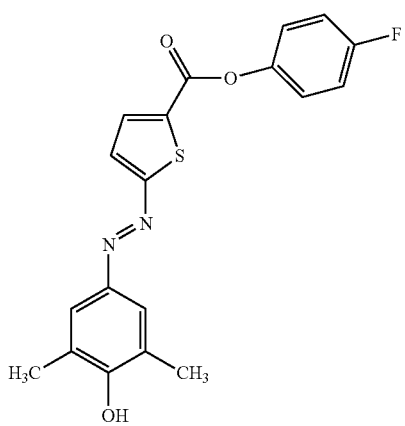
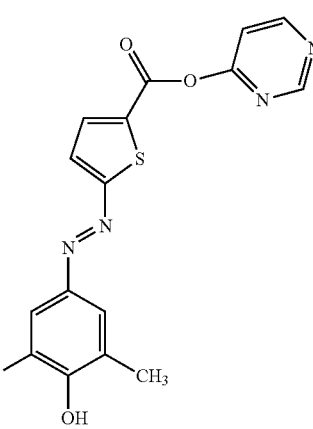
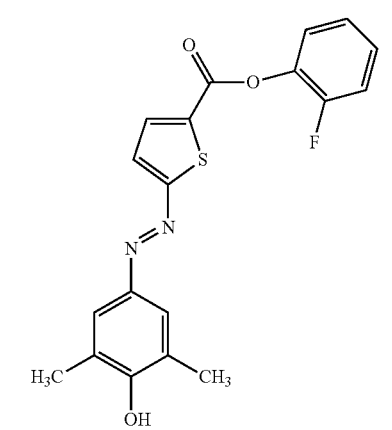 [SMILES: Cc1cc(/N=N/c2ccc(C(=O)Oc3ccccc3F)s2)cc(C)c1O]

TABLE L-continued
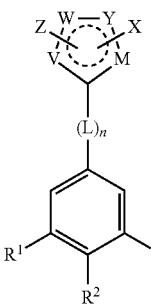
Vg3
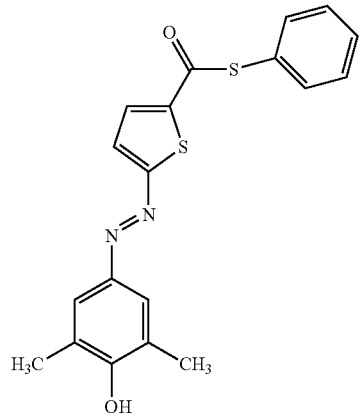
TABLE M
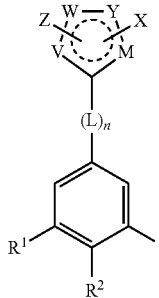
Vg4
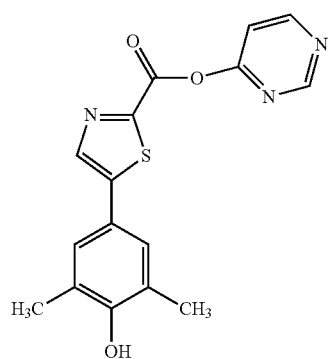 [SMILES: Cc1cc(-c2cnc(C(=O)Oc3ccncn3)s2)cc(C)c1O]
TABLE M-continued
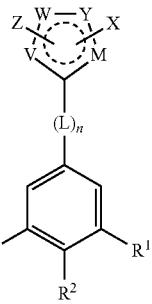
Vg4
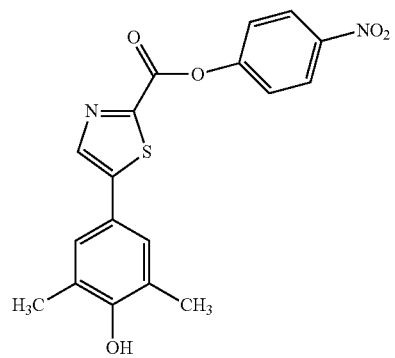 [SMILES: Cc1cc(-c2cnc(C(=O)Oc3ccc([N+](=O)[O-])cc3)s2)cc(C)c1O]
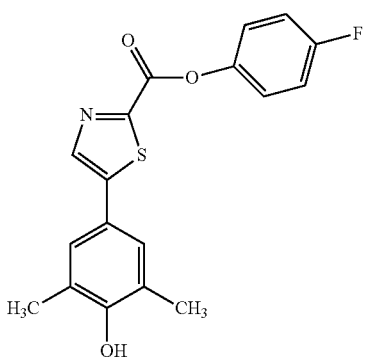 [SMILES: Cc1cc(-c2cnc(C(=O)Oc3ccc(F)cc3)s2)cc(C)c1O]
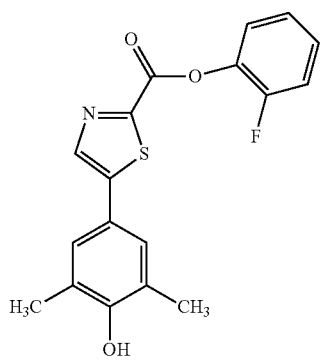 [SMILES: Cc1cc(-c2cnc(C(=O)Oc3ccccc3F)s2)cc(C)c1O]

TABLE M-continued
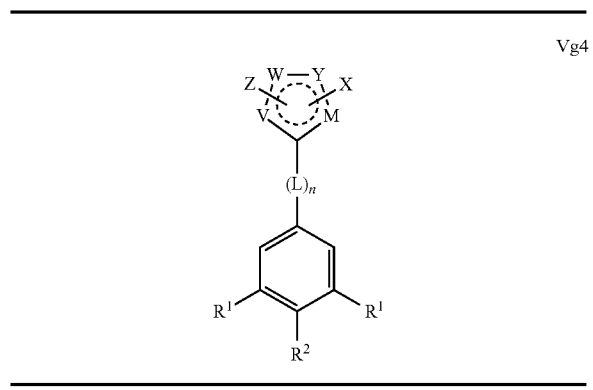
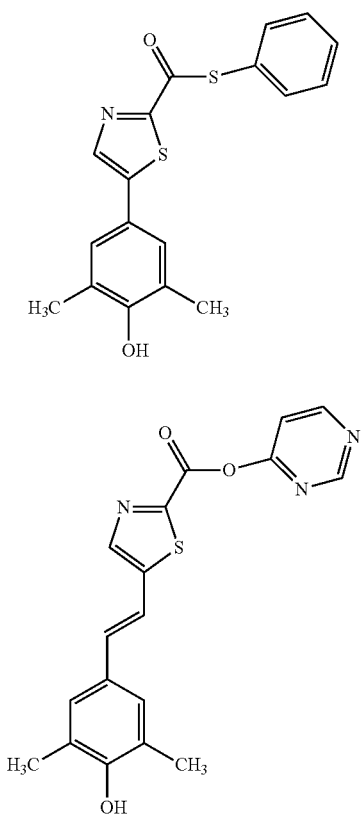
TABLE M-continued
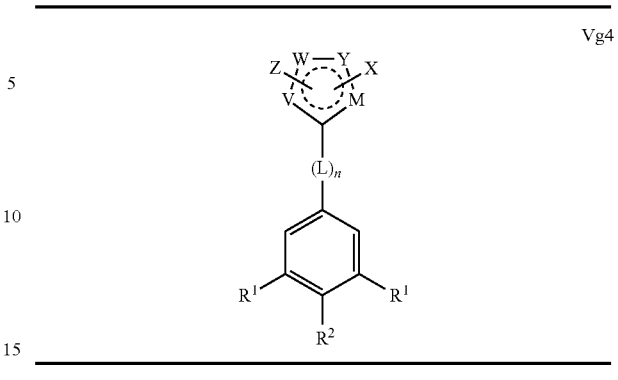
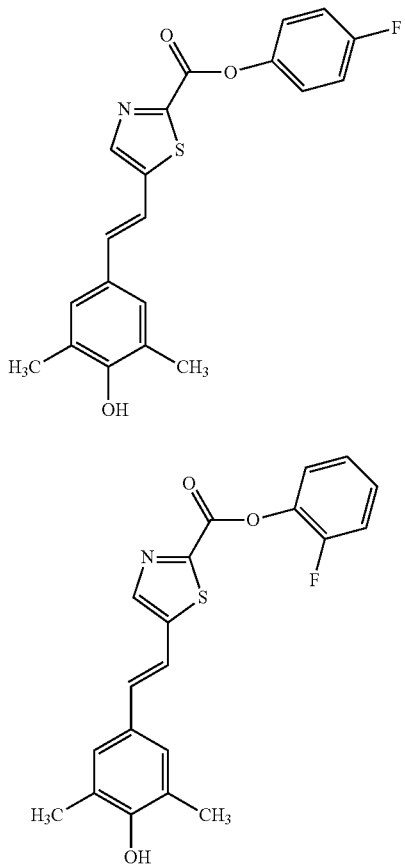

| 115 | 116 |
|---|---|
| TABLE M-continued | TABLE M-continued |
| 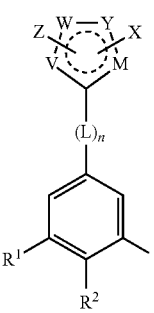 Vg4 | 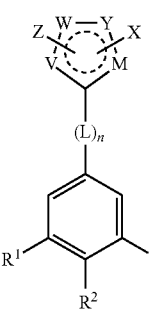 Vg4 |
| 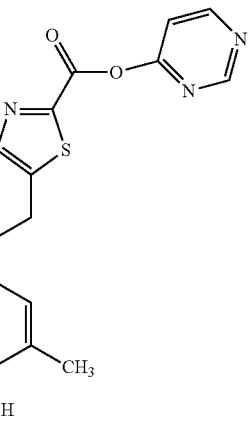 | 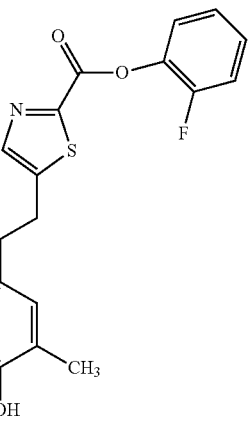 |
| 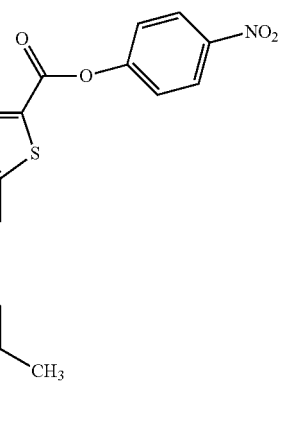 | 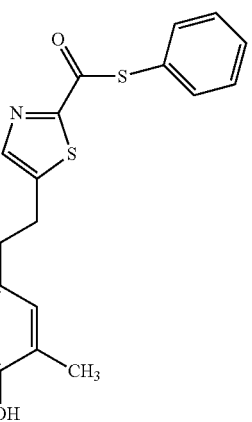 |
| 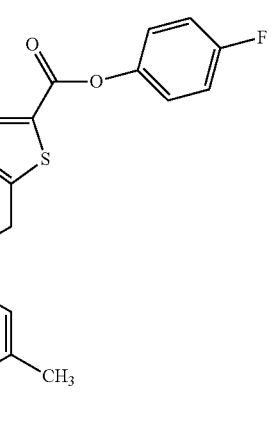 | 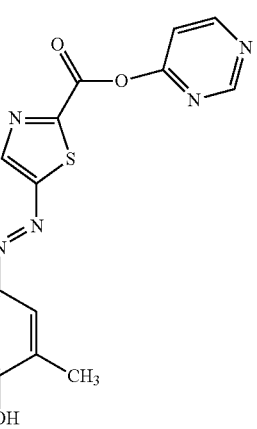 |

TABLE M-continued
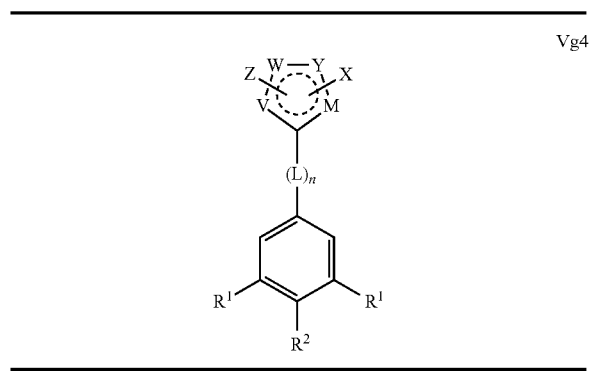
Vg4
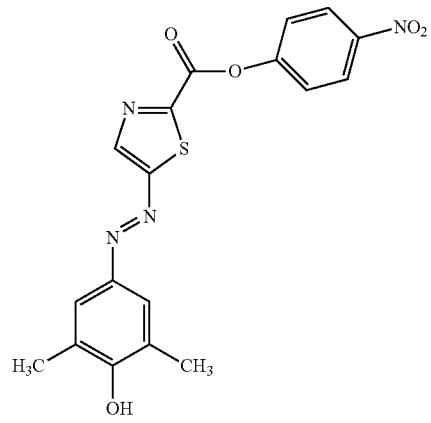
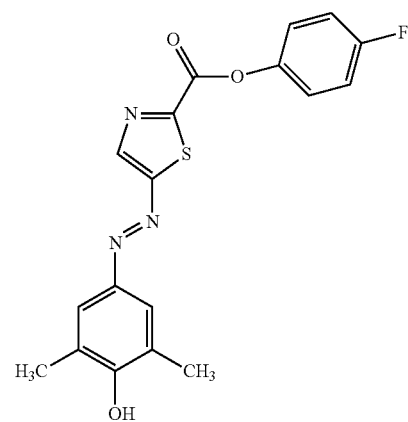
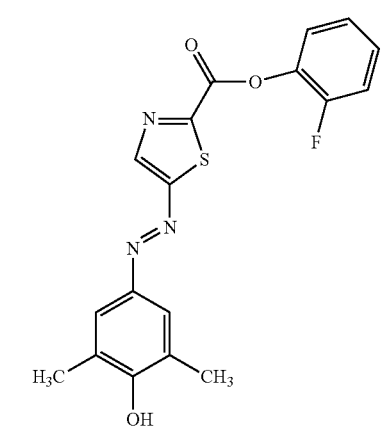 [SMILES: Cc1cc(/N=N/c2cnc(C(=O)Oc3ccccc3F)s2)cc(C)c1O]
TABLE M-continued
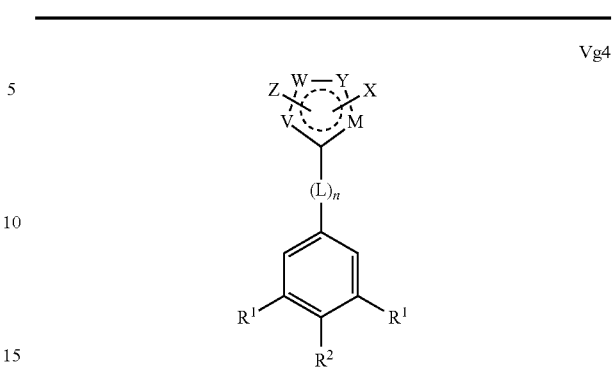
Vg4
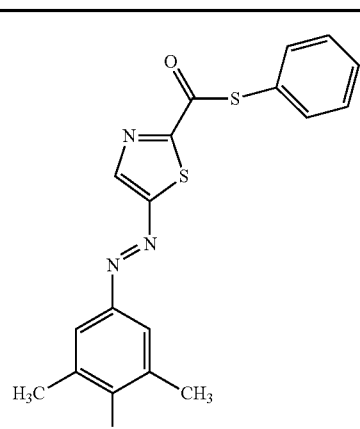
TABLE N
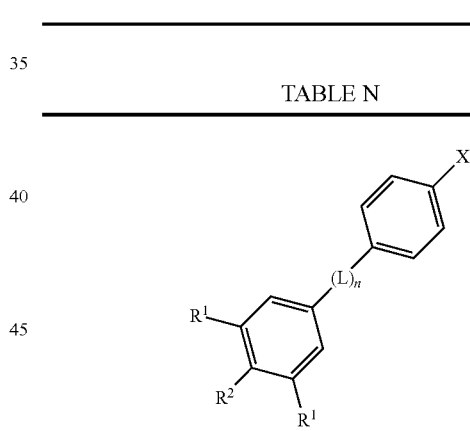
Va1
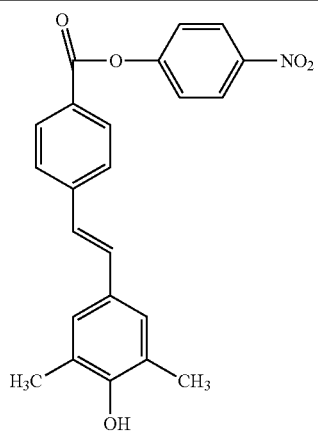

TABLE N-continued
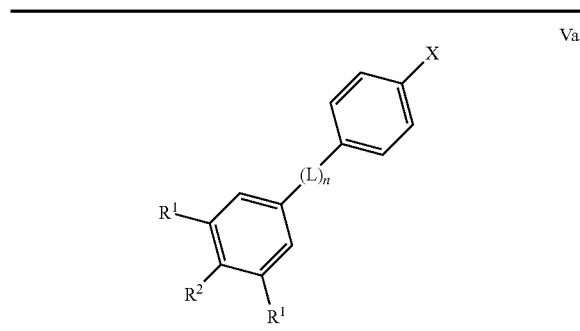
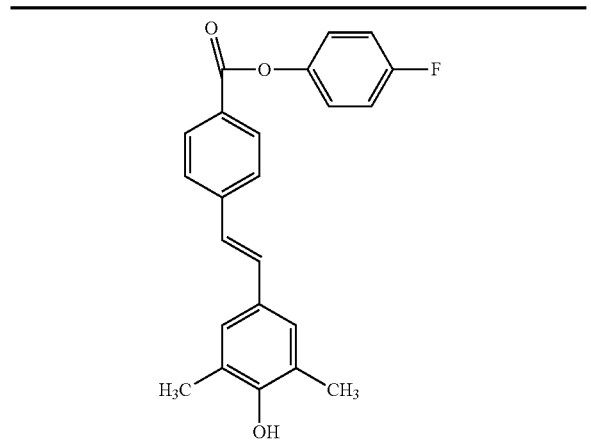
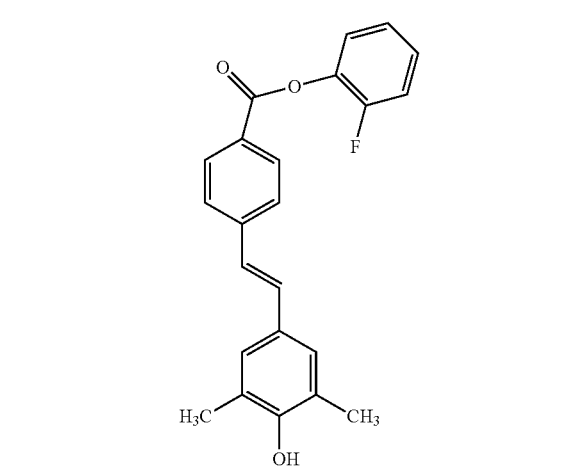
TABLE N-continued
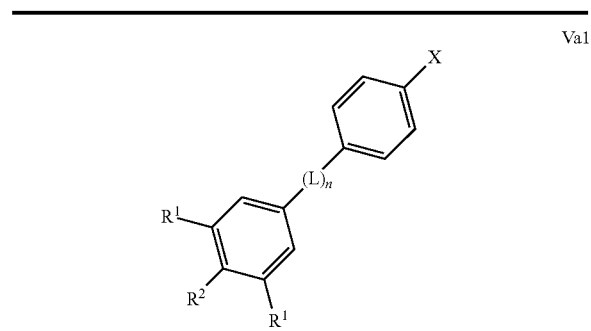
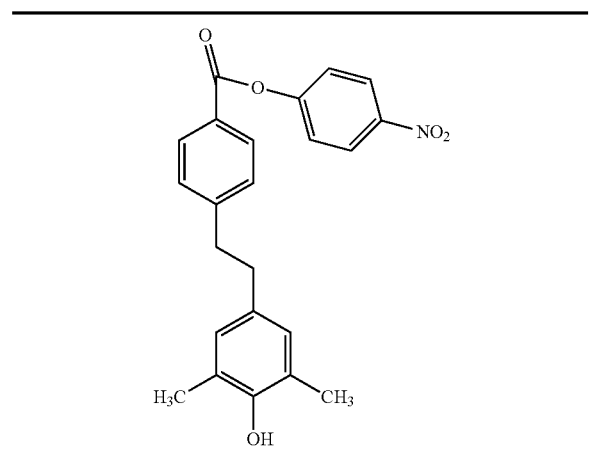
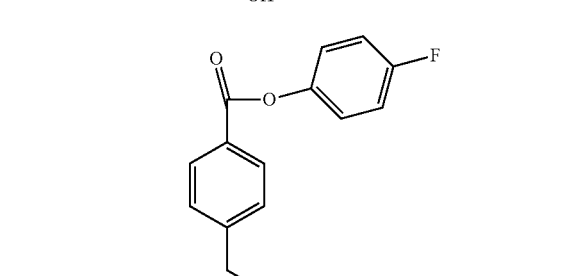
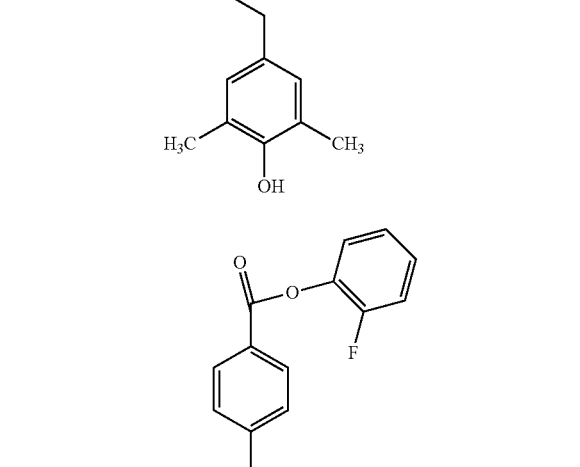

TABLE N-continued
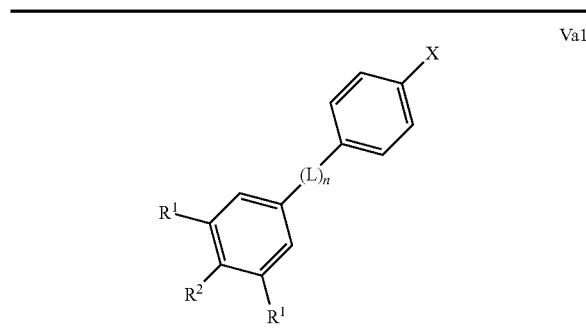
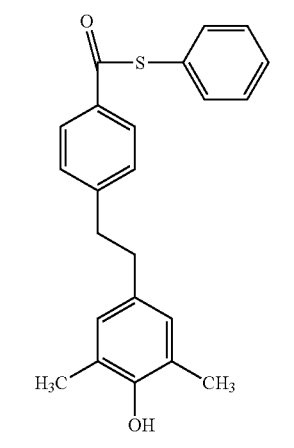 [SMILES: Cc1cc(CCc2ccc(C(=O)Sc3ccccc3)cc2)cc(C)c1O]
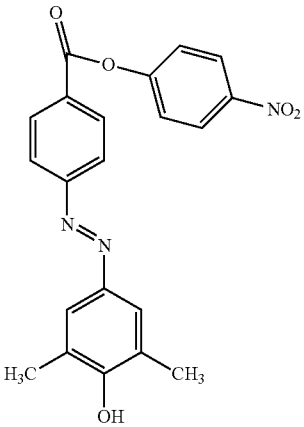 [SMILES: Cc1cc(/N=N/c2ccc(C(=O)Oc3ccc([N+](=O)[O-])cc3)cc2)cc(C)c1O]
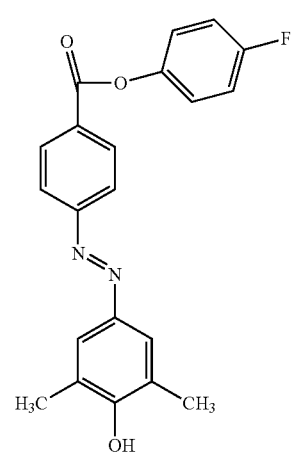 [SMILES: Cc1cc(/N=N/c2ccc(C(=O)Oc3ccc(F)cc3)cc2)cc(C)c1O]
TABLE N-continued
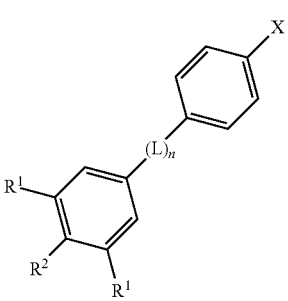
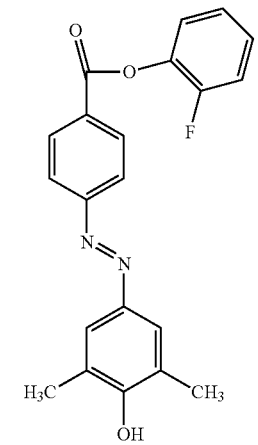 [SMILES: Cc1cc(/N=N/c2ccc(C(=O)Oc3ccccc3F)cc2)cc(C)c1O]
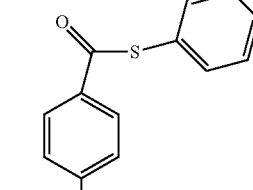
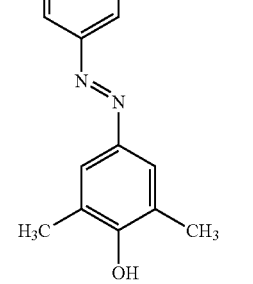
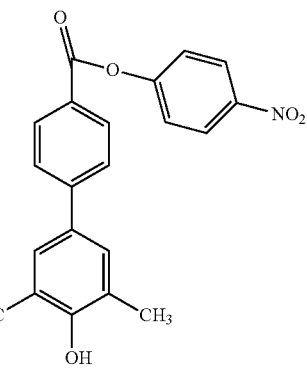

TABLE N-continued
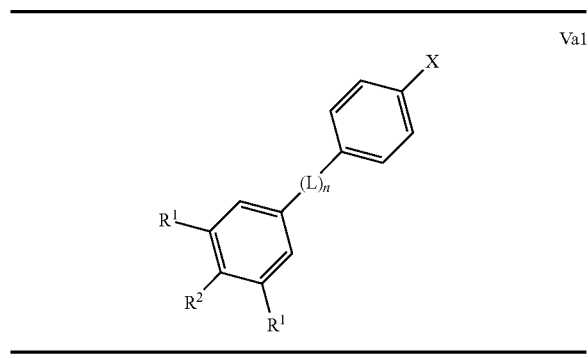
Va1
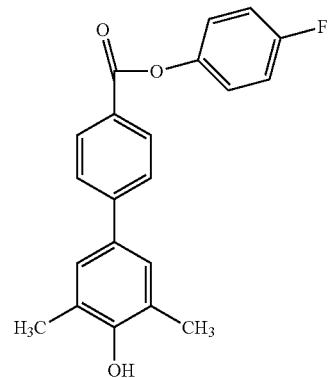 [SMILES: Cc1cc(-c2ccc(C(=O)Oc3ccc(F)cc3)cc2)cc(C)c1O]
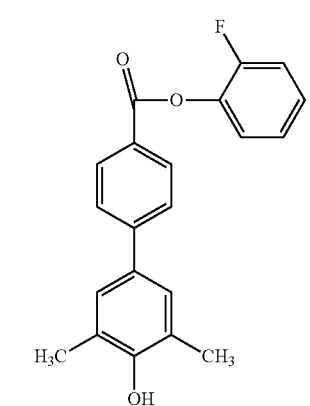 [SMILES: Cc1cc(-c2ccc(C(=O)Oc3ccccc3F)cc2)cc(C)c1O]
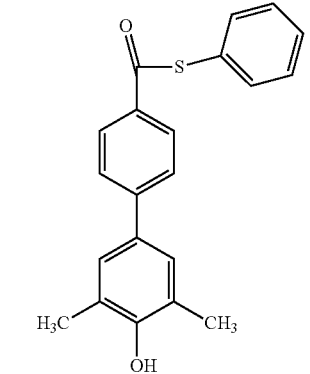 [SMILES: Cc1cc(-c2ccc(C(=O)Sc3ccccc3)cc2)cc(C)c1O]
TABLE N-continued
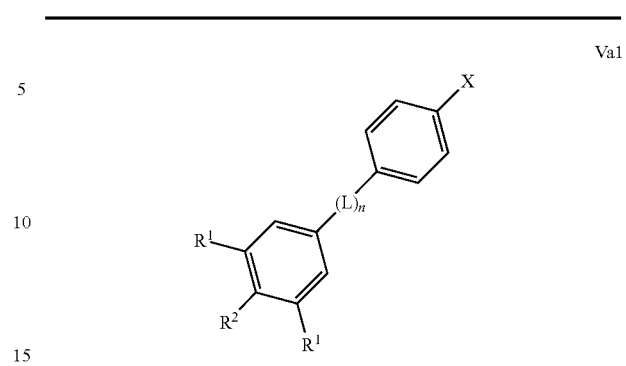
Va1
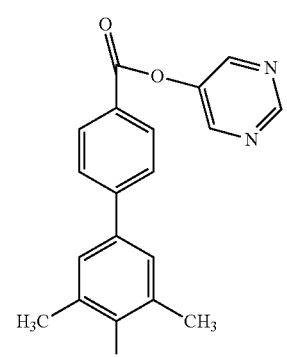
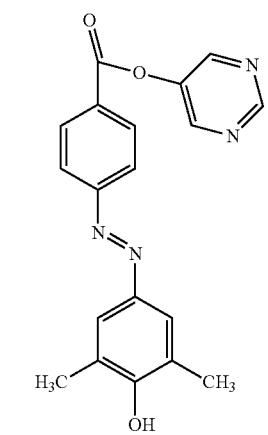 [SMILES: Cc1cc(/N=N/c2ccc(C(=O)Oc3cncnc3)cc2)cc(C)c1O]
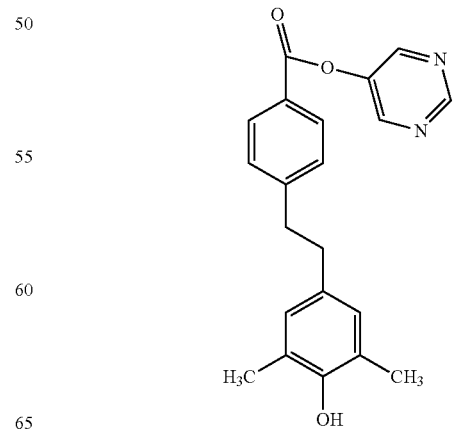

TABLE N-continued
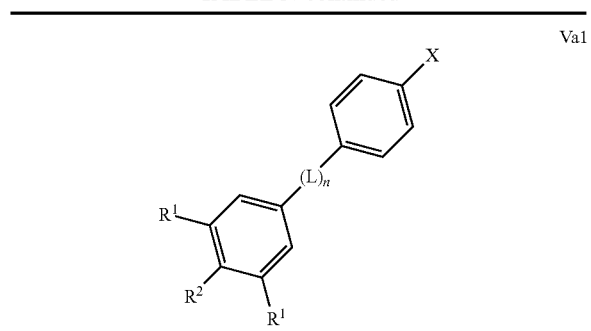
Va1
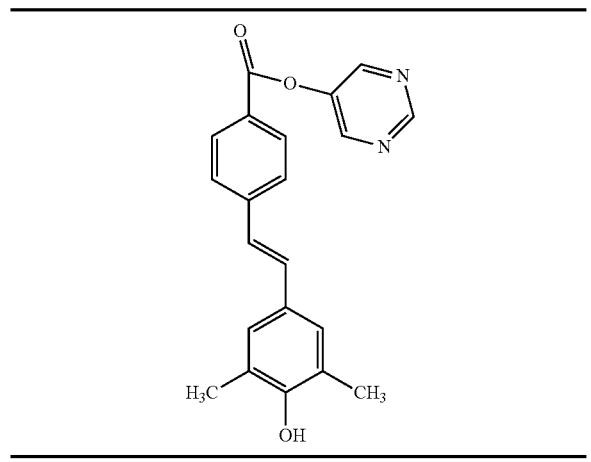
TABLE O
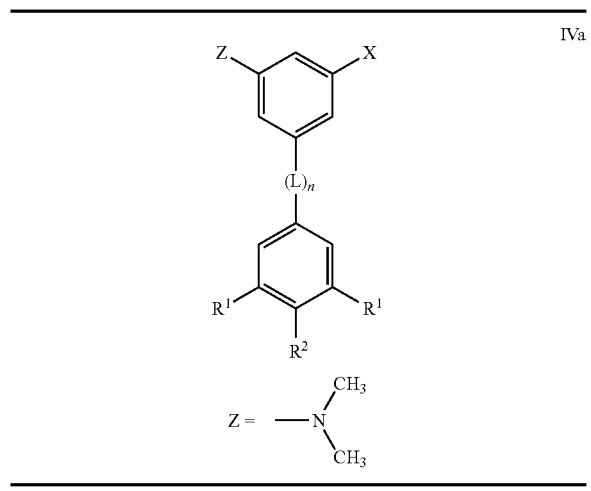
IVa
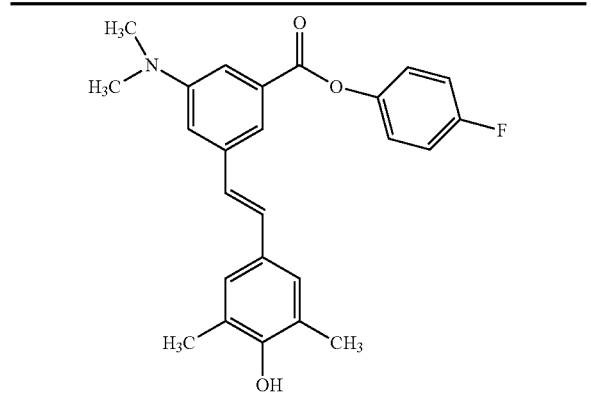
TABLE O-continued
IVa
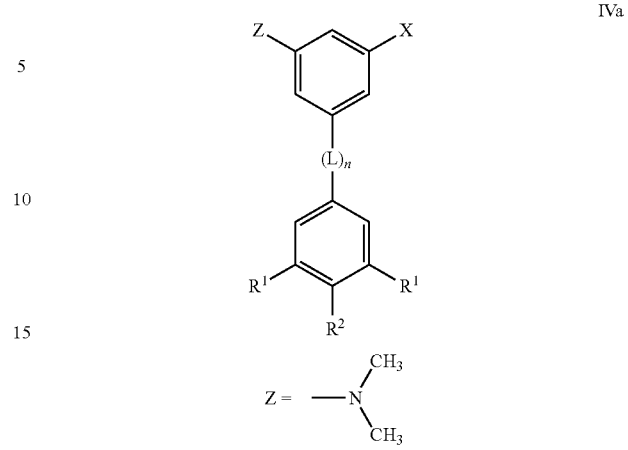
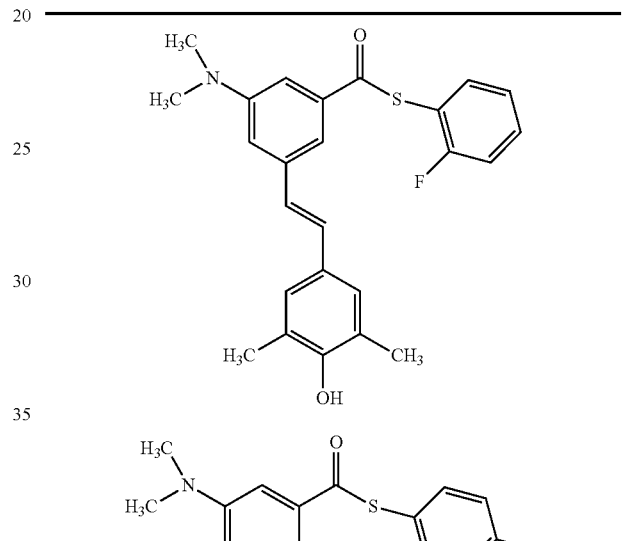
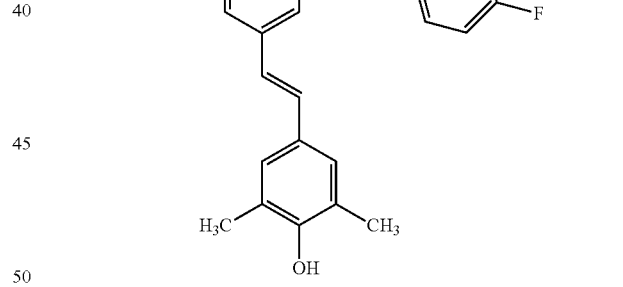
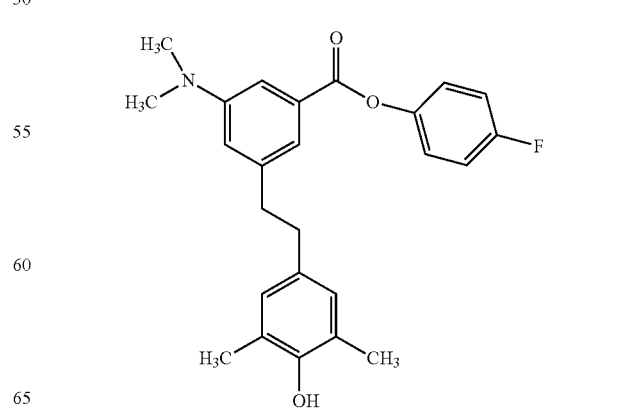

TABLE O-continued
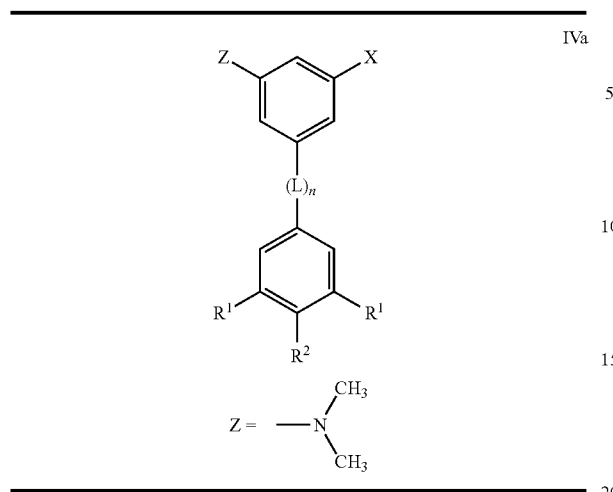
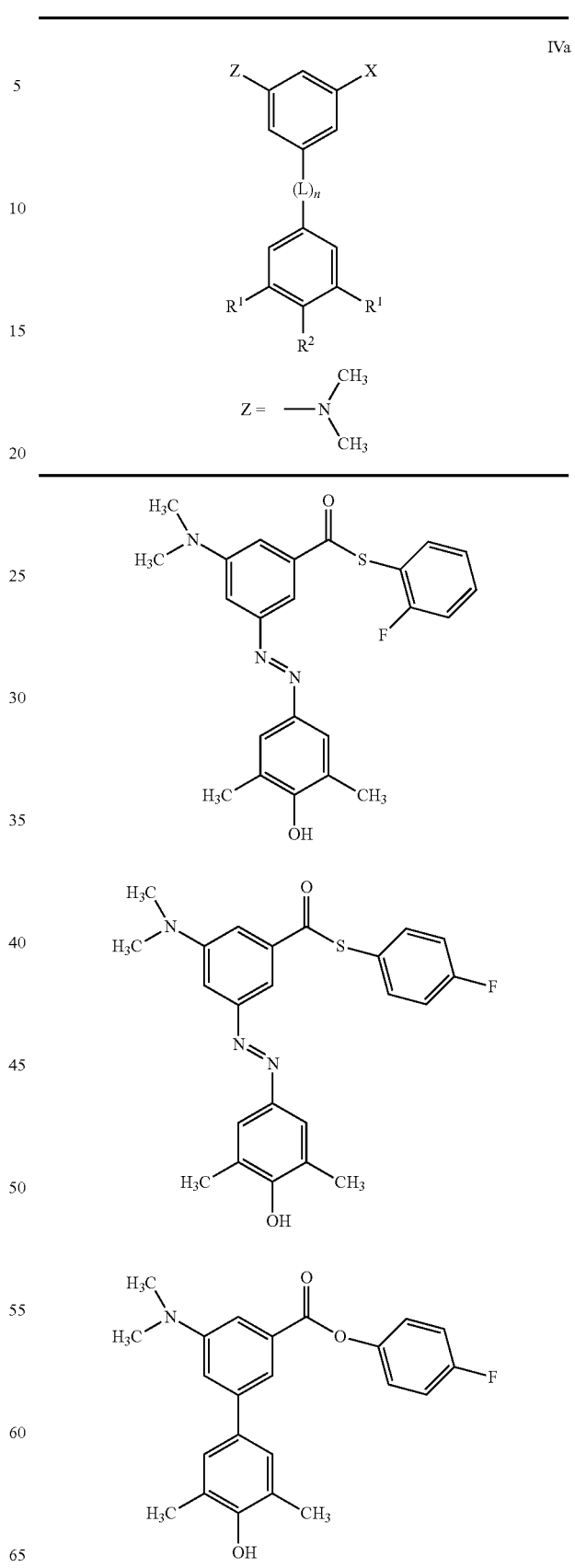

TABLE O-continued
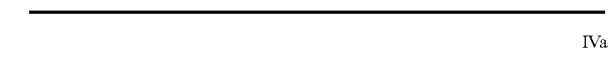
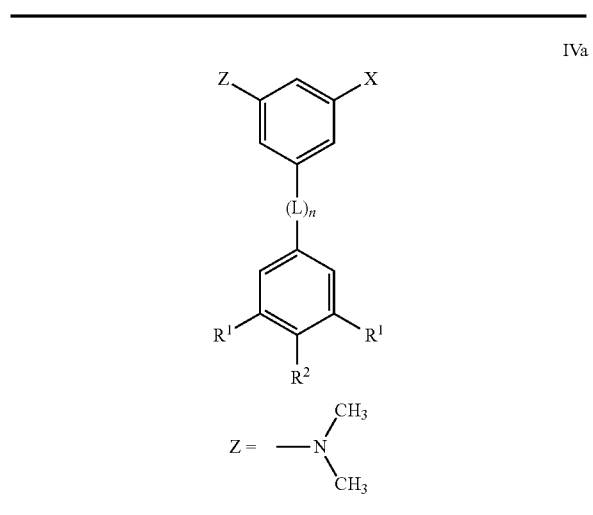
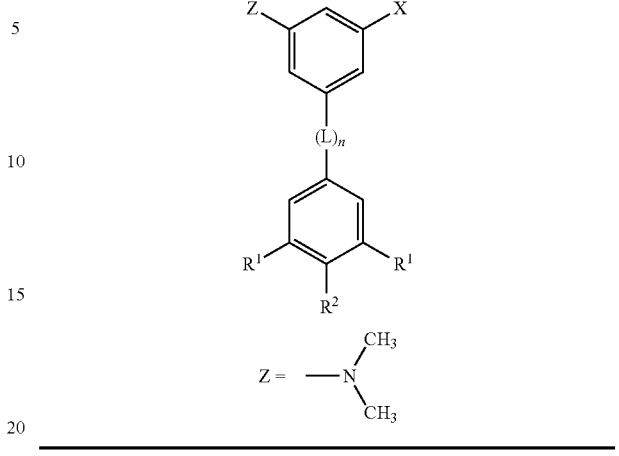
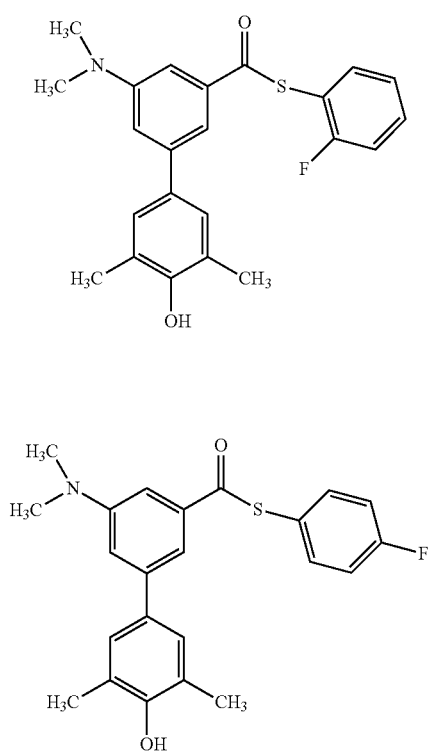
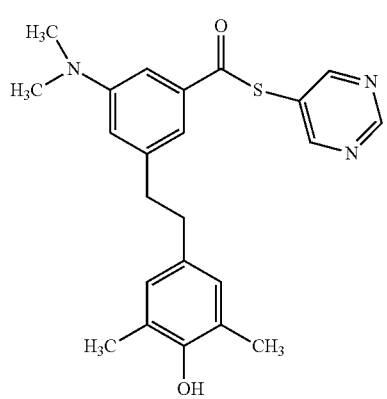
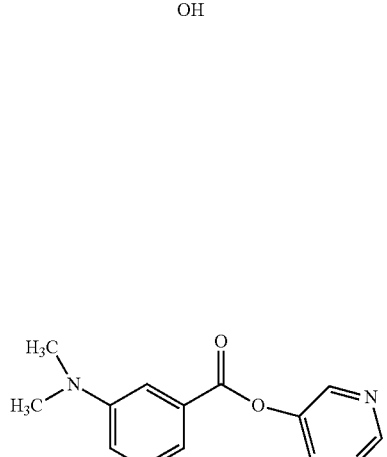
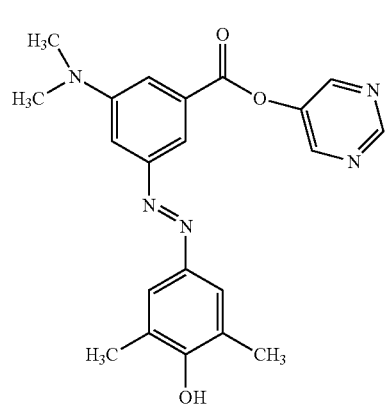 [SMILES: Cc1cc(/N=N/c2cc(C(=O)Oc3cncnc3)cc(N(C)C)c2)cc(C)c1O]
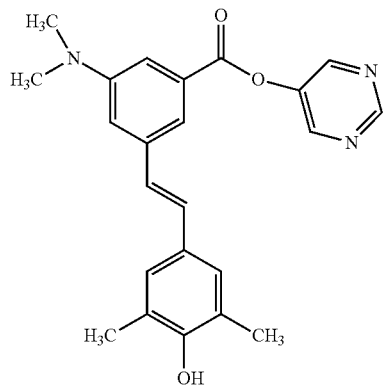 [SMILES: Cc1cc(/C=C/c2cc(C(=O)Oc3cncnc3)cc(N(C)C)c2)cc(C)c1O]

TABLE P
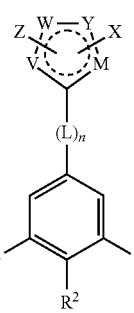
TABLE P-continued
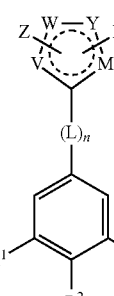

TABLE P-continued
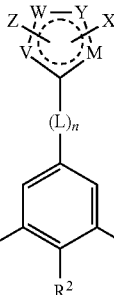
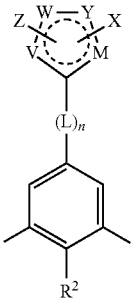
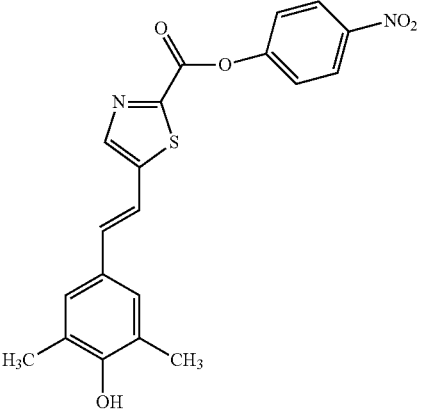
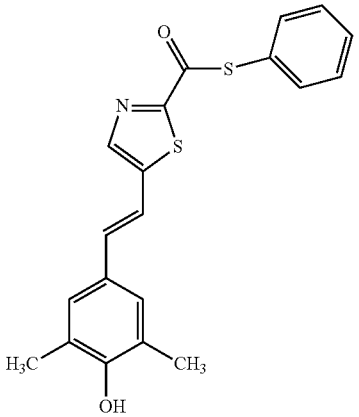 [SMILES: Cc1cc(/C=C/c2cnc(C(=O)Sc3ccccc3)s2)cc(C)c1O]
TABLE P-continued
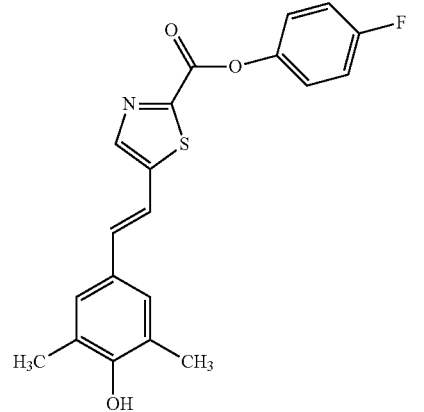
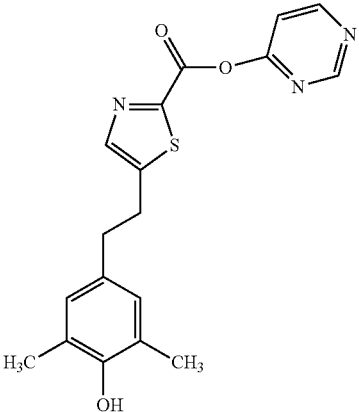 [SMILES: Cc1cc(CCc2cnc(C(=O)Oc3ccncn3)s2)cc(C)c1O]

TABLE P-continued
| | Vg4 |
|---|---|
| 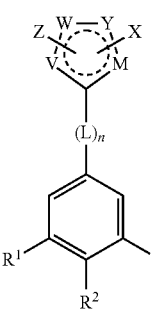 | |
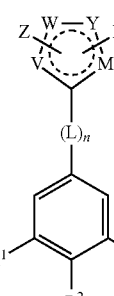
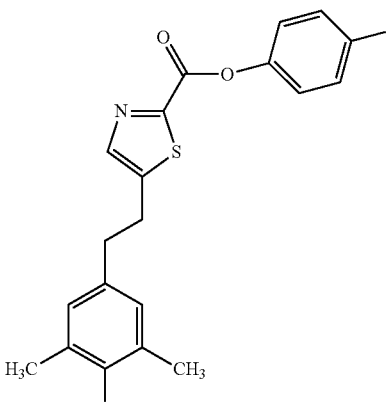
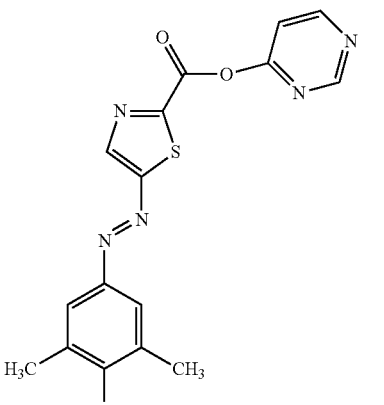
TABLE P-continued
| | Vg4 |
|---|---|
| 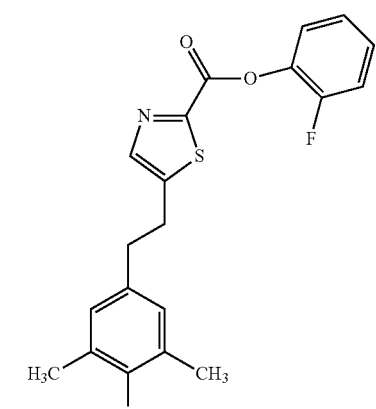 | |
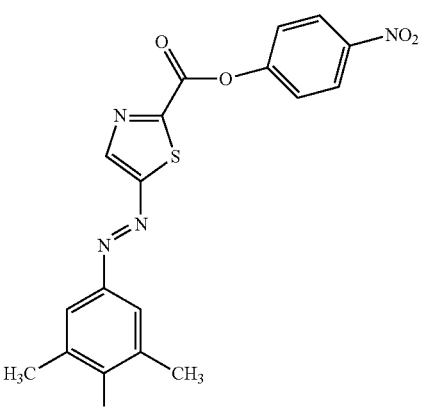
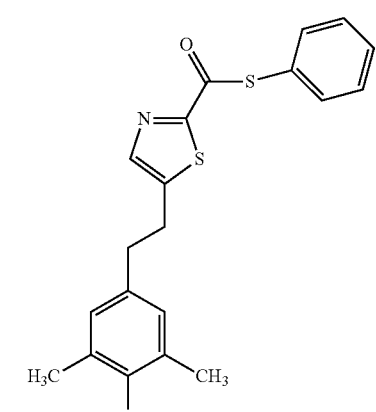
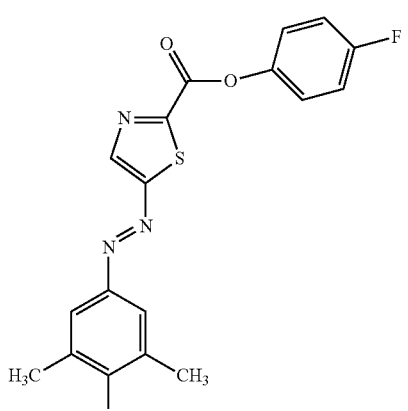

| 137 | 138 |
|---|---|
| TABLE P-continued | TABLE P-continued |
| 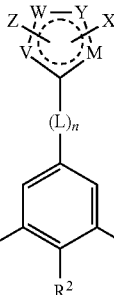 Vg4 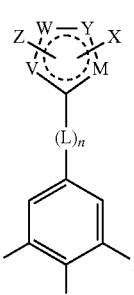 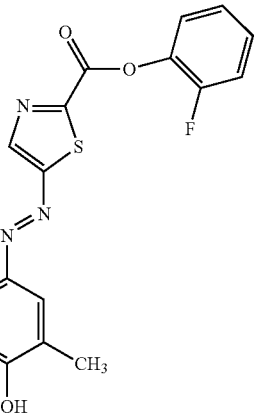 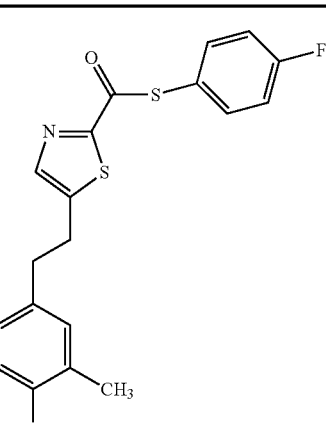 | 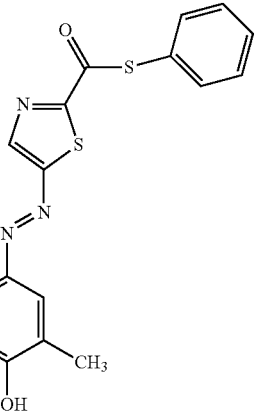 Vg4 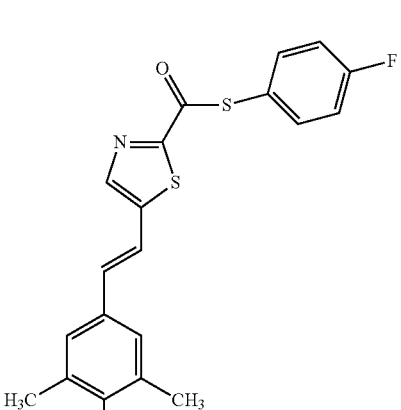 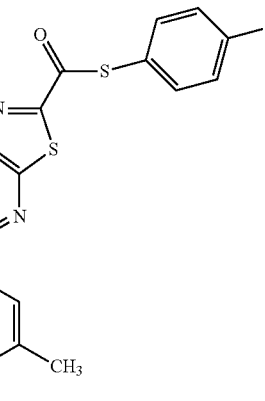 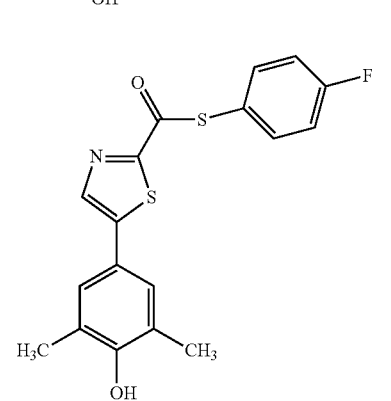 |

TABLE Q
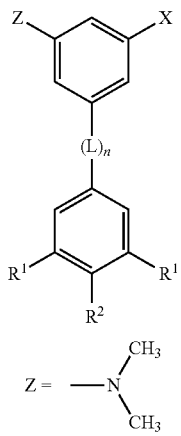
IVa
Z = —N(CH₃)₂
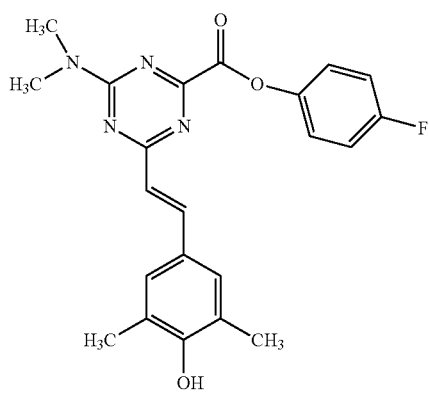 [SMILES: Cc1cc(/C=C/c2nc(C(=O)Oc3ccc(F)cc3)nc(N(C)C)n2)cc(C)c1O]
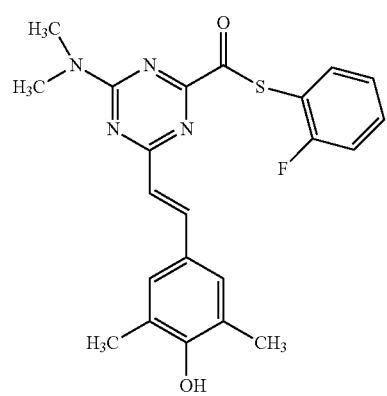 [SMILES: Cc1cc(/C=C/c2nc(C(=O)Sc3ccccc3F)nc(N(C)C)n2)cc(C)c1O]
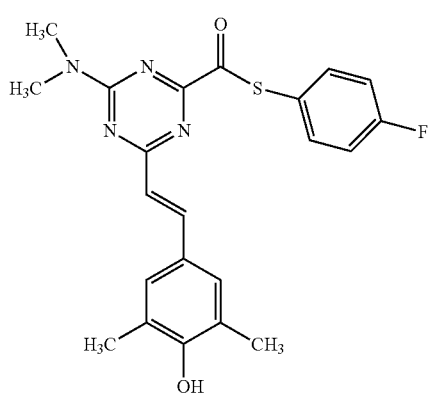
TABLE Q-continued
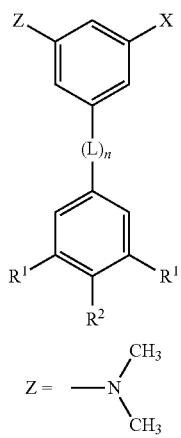
IVa
Z = —N(CH₃)₂
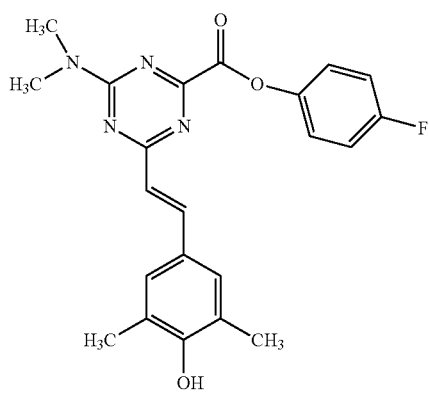 [SMILES: Cc1cc(/C=C/c2nc(C(=O)Oc3ccc(F)cc3)nc(N(C)C)n2)cc(C)c1O]
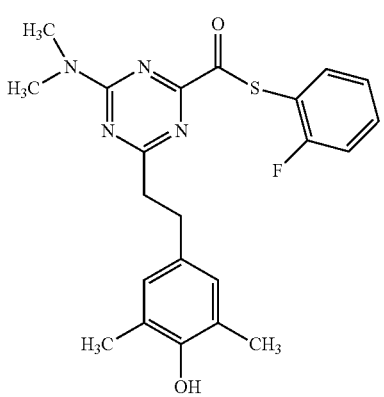 [SMILES: Cc1cc(CCc2nc(C(=O)Sc3ccccc3F)nc(N(C)C)n2)cc(C)c1O]
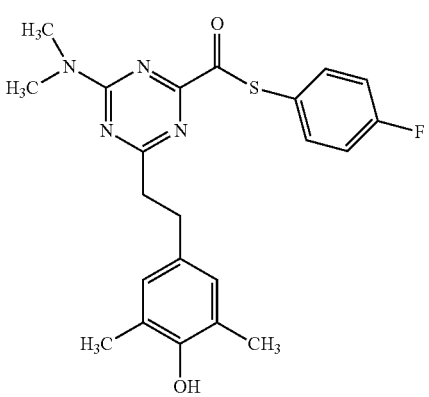 [SMILES: Cc1cc(CCc2nc(C(=O)Sc3ccc(F)cc3)nc(N(C)C)n2)cc(C)c1O]

TABLE Q-continued
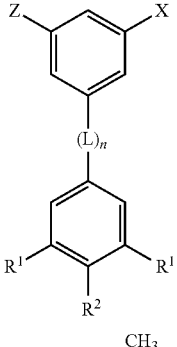
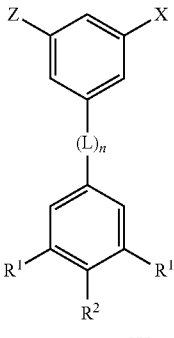
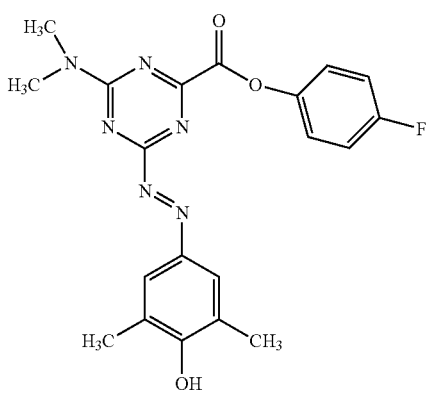 [SMILES: Cc1cc(/N=N/c2nc(C(=O)Oc3ccc(F)cc3)nc(N(C)C)n2)cc(C)c1O]
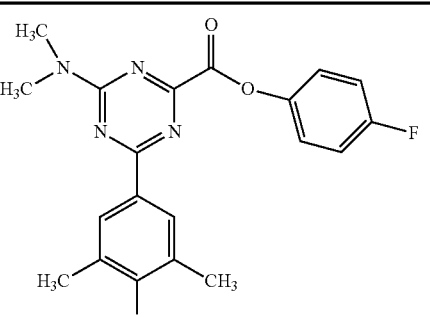
TABLE Q-continued
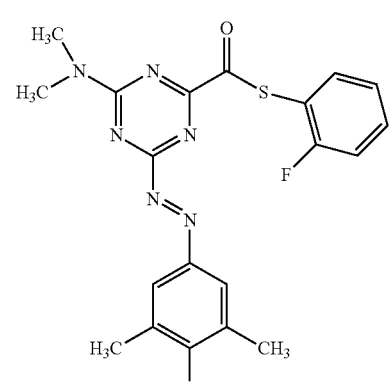
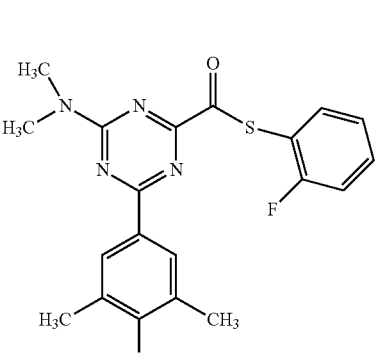
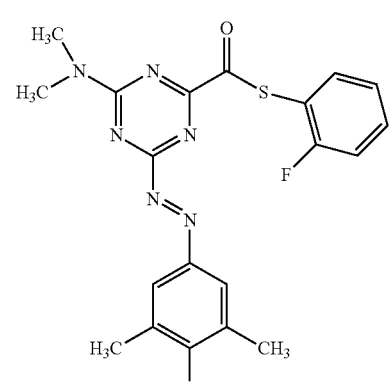
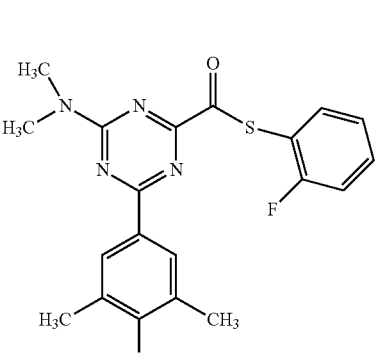

TABLE Q-continued
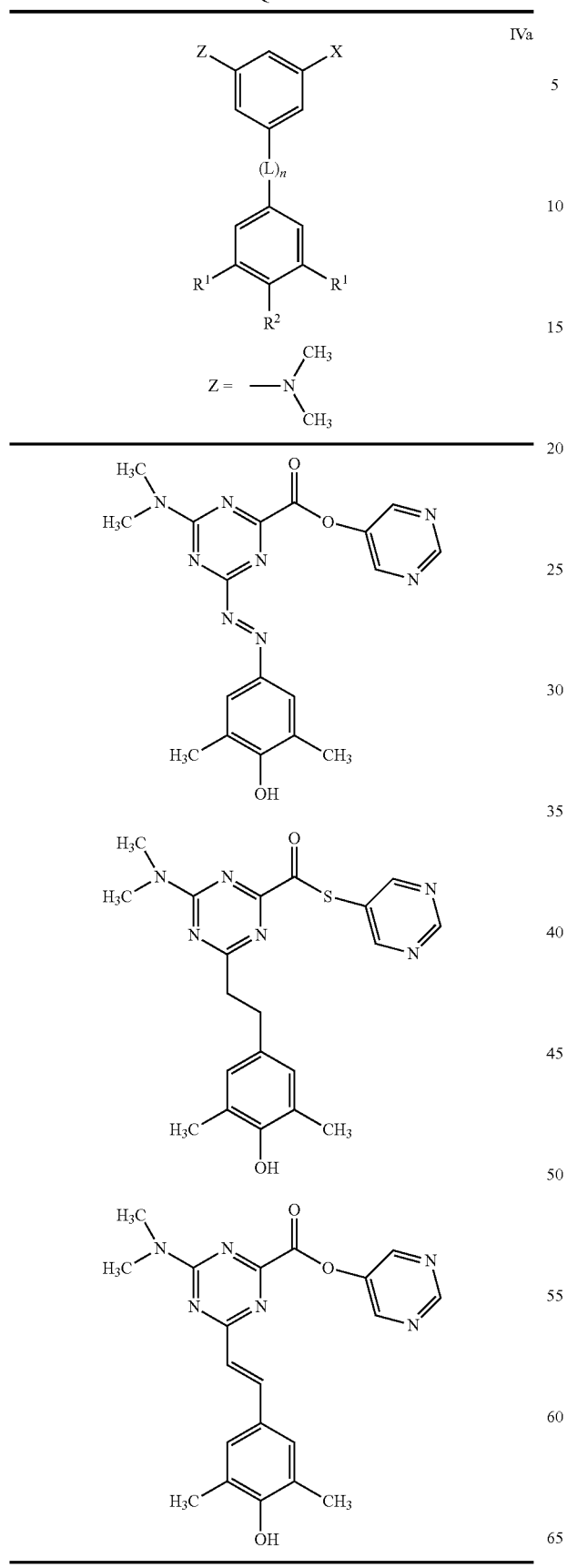
TABLE R
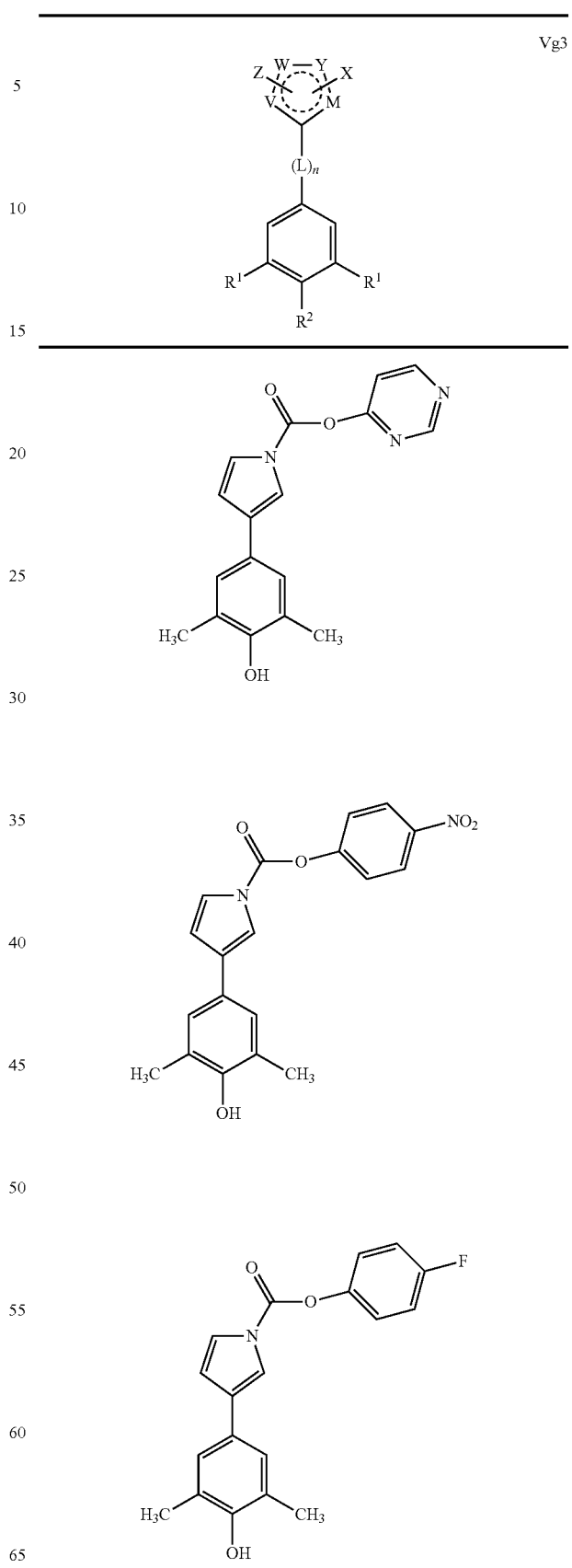

TABLE R-continued
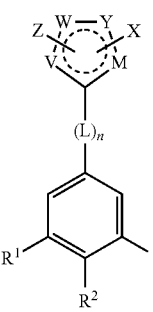
TABLE R-continued
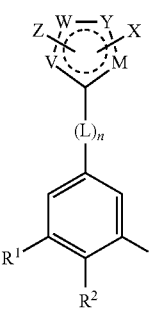

147
TABLE R-continued
148
TABLE R-continued
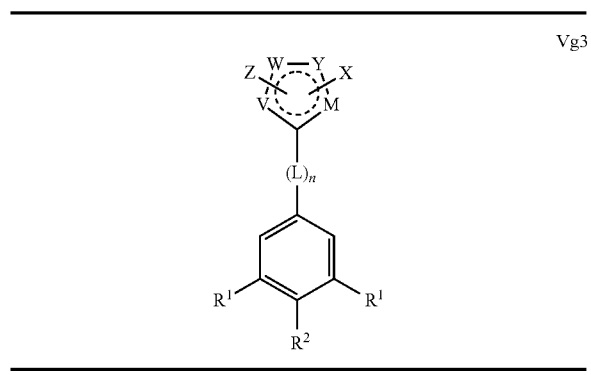
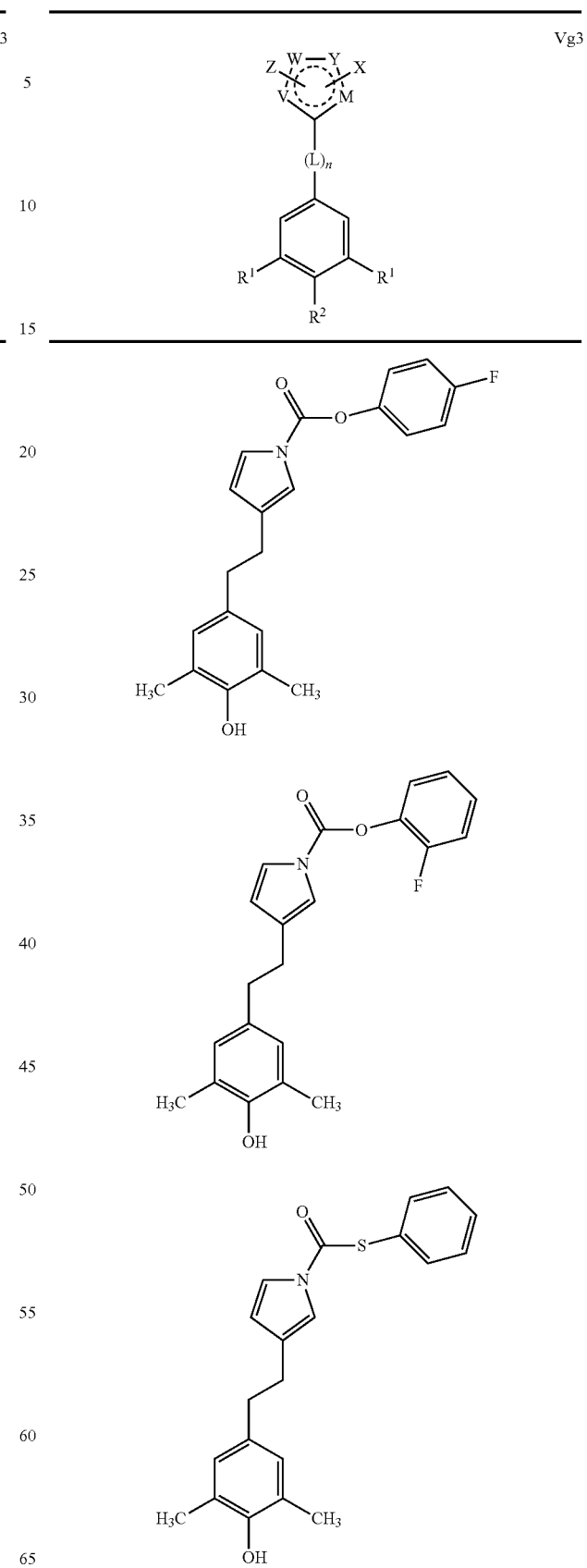

TABLE R-continued

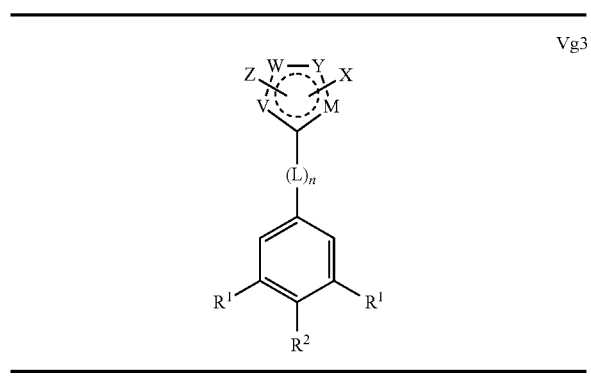

Vg3

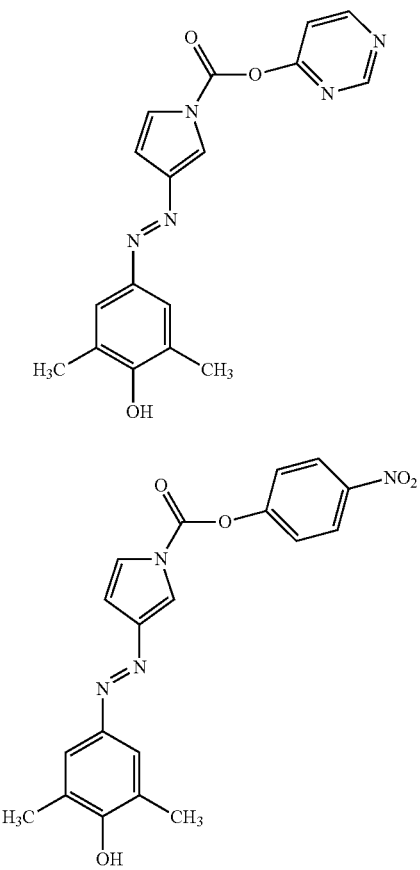

TABLE R-continued

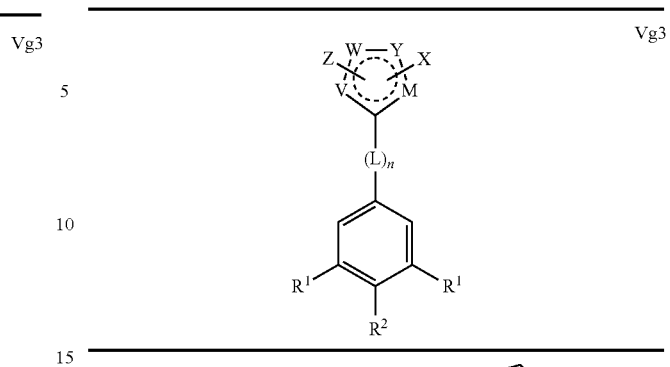

Vg3

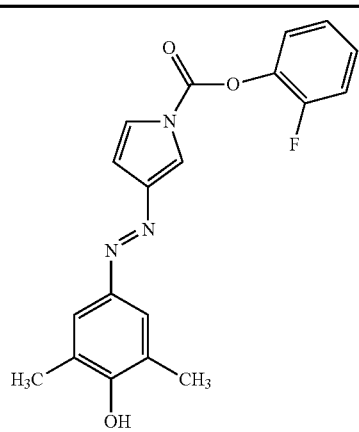

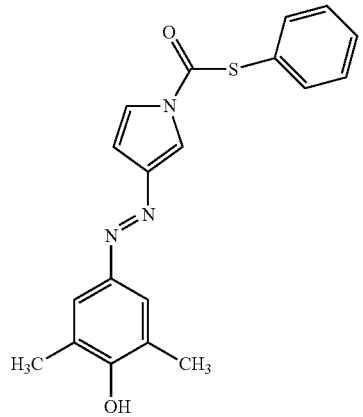 [SMILES: Cc1cc(/N=N/c2ccn(C(=O)Sc3ccccc3)c2)cc(C)c1O]

Compositions

A contemplated compound of Formula I is typically utilized dissolved or dispersed in an aqueous composition that also contains a diluent such as a salt like one or more of $MgCl_2$, $CaCl_2$, NaCl or KCl and/or one or more buffer salts such as sodium or potassium phosphate salts, HEPES [4-(2-hydroxyethyl)-1-piperazine-ethanesulfonic acid], sodium or potassium acetate, Tris or other buffers as are well known in the art, optional other ingredients such as a chelating agent like EDTA can also be present. A contemplated compound is present in an amount that provides about a 1 nM to about a 100 μM concentration when admixed with TTR. The pH value of such a composition is typically about pH 4.0 to about 8.5. The amount of a compound of Formula I present can be about 500 nM to the limit of solubility of the compound or 10 μM. The solubility of a contemplated compound can be enhanced by incorporation of up to about 2 volume percent, and more preferably up to about 1 volume percent, of a water-miscible organic solvent such as methanol, ethanol, DMF, DMSO, acetone, propylene glycol, 1,3-butanediol or acetonitrile.

As is seen from the data herein, a contemplated compound binds well and reacts with TTR when both are present at micromolar concentrations. Inasmuch as the typical healthy adult concentration of TTR in blood plasma is at the micromolar level, an amount of a compound of Formula I present in a contemplated pharmaceutical composition is that which provides about 1 nM to about 100 µM concentration in blood plasma or serum upon administration to bind and react with TTR to inhibit fibril formation. More preferably, that amount is sufficient to provide a concentration of about 1 to about 10 µM. That amount is referred to herein as a stabilizing amount or a fibril formation-inhibiting amount.

A contemplated composition can also be used in the manufacture of a medicament (pharmaceutical composition) that is useful at least for treating transthyretin (TTR) amyloidosis in a subject in need thereof. A contemplated composition can also be used in the manufacture of a medicament that is useful in inhibiting transthyretin fibril formation. When so used, pharmaceutically acceptable salts, buffers and the like are present that collectively are referred to as pharmaceutically acceptable diluents as compared to those that can be present in a composition that is not intended for pharmaceutical use, as in an in vitro assay.

A compound of the invention can be provided for use by itself, or as a pharmaceutically acceptable salt. Most of the contemplated compounds are electronically uncharged at pH 7.2-7.4. Amine-containing substituent groups (Z and $R^2$) can be present and a compound used in the form of an acid addition salt derived from an inorganic or organic acid. Exemplary salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxy-ethanesulfonate, lactate, maleate, methanesulfonate, nicotinate, 2-naphthalenesulfonate, oxalate, palmoate, pectinate, persulfate, 3-phenylpropionate, picrate, pivalate, propionate, succinate, tartrate, thiocyanate, tosylate, mesylate and undecanoate.

The reader is directed to Berge, 1977 *J. Pharm. Sci.* 68(1): 1-19 for lists of commonly used pharmaceutically acceptable acids and bases that form pharmaceutically acceptable salts with pharmaceutical compounds.

In some cases, the salts can also be used as an aid in the isolation, purification or resolution of the compounds of this invention. In such uses, the acid used and the salt prepared need not be pharmaceutically acceptable.

A contemplated composition can also be used in a method for assaying for TTR in a sample to be assayed, as well as in a method of identifying a non-covalent TTR kinetic stabilizer compound. The assay for TTR can be quantitative as well as quantitative and can be carried out in a complex biological sample such as blood plasma or serum as well as in an aqueous sample that is substantially of biological materials other than TTR.

As is seen from the data that follow, a contemplated compound is active in in vitro assay studies at micromolar amounts. When used in an assay for identifying a non-covalent transthyretin kinetic stabilizer compound, such as an in vitro assay, a compound of Formula I is present in the composition in a binding/reaction sufficient amount that is sufficient to provide a concentration of about 1 nM to about 100 µM, preferably about 1 nM to about 10 µM.

A contemplated pharmaceutical composition contains a transthyretin fibril formation-inhibiting amount of a compound of Formula I or a pharmaceutically acceptable salt thereof dissolved or dispersed in a physiologically (pharmaceutically) acceptable carrier. Such a composition can be administered to a sample to be assayed such as blood plasma or serum, to mammalian cells in vitro as in a cell culture, or in vivo as in a living, host mammal in need.

A contemplated composition is typically administered to a subject in need thereof a plurality of times within one week. More usually, a contemplated composition is administered a plurality of times in one day.

A contemplated pharmaceutical composition can be administered orally (perorally), which is preferred, parenterally, by inhalation spray in a formulation containing conventional nontoxic pharmaceutically acceptable carriers, adjuvants, and vehicles as desired. The term parenteral as used herein includes subcutaneous injections, intravenous, intramuscular, intrasternal injection, or infusion techniques. Formulation of drugs is discussed in, for example, Hoover, John E., *Remington's Pharmaceutical Sciences*, Mack Publishing Co., Easton, Pa.; 1975 and Liberman, H. A. and Lachman, L., Eds., *Pharmaceutical Dosage Forms*, Marcel Decker, New York, N.Y., 1980.

Solid dosage forms for oral administration can include capsules, tablets, pills, powders, and granules. The amount of a compound of Formula I in a solid dosage form is as discussed previously, an amount sufficient to provide a concentration of about 1 nM to about 100 µM, preferably about 1 nM to about 10 µM, in the serum or blood plasma. A solid dosage form can also be administered a plurality of times during a one week time period.

In such solid dosage forms, the compounds of this invention are ordinarily combined with one or more adjuvants appropriate to the indicated route of administration. If administered per os, the compounds can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation as can be provided in a dispersion of active compound in hydroxypropylmethyl cellulose. In the case of capsules, tablets, and pills, the dosage forms can also comprise buffering agents such as sodium citrate, magnesium or calcium carbonate or bicarbonate. Tablets and pills can additionally be prepared with enteric coatings.

Injectable preparations, for example, sterile injectable aqueous or oleaginous suspensions can be formulated according to the known art using suitable dispersing or wetting agents and suspending agents. The sterile injectable preparation can also be a sterile injectable solution or suspension in a nontoxic parenterally acceptable diluent or solvent, for example, as a solution in 1,3-butanediol. Among the acceptable vehicles and solvents that can be employed are water, Ringer's solution, and isotonic sodium chloride solution, phosphate-buffered saline. Liquid pharmaceutical compositions include, for example, solutions suitable for parenteral administration. Sterile water solutions of an active component or sterile solution of the active component in solvents comprising water, ethanol, or propylene glycol are examples of liquid compositions suitable for parenteral administration.

In addition, sterile, fixed oils are conventionally employed as a solvent or suspending medium. For this purpose any bland fixed oil can be employed including synthetic mono- or diglycerides. In addition, fatty acids such as oleic acid find use in the preparation of injectables. Dimethyl acetamide, surfactants including ionic and non-ionic detergents, polyethylene glycols can be used. Mixtures of solvents and wetting agents such as those discussed above are also useful.

Sterile solutions can be prepared by dissolving the active component in the desired solvent system, and then passing the resulting solution through a membrane filter to sterilize it or, alternatively, by dissolving the sterile compound in a previously sterilized solvent under sterile conditions.

A mammal in need of treatment (a subject) and to which a pharmaceutical composition containing a contemplated compound is administered can be a primate such as a human, an ape such as a chimpanzee or gorilla, a monkey such as a cynomolgus monkey or a macaque, a laboratory animal such as a rat, mouse or rabbit, a companion animal such as a dog, cat, horse, or a food animal such as a cow or steer, sheep, lamb, pig, goat, llama or the like.

Where an in vitro assay is contemplated, a sample to be assayed such as blood plasma or serum, cells and tissue can be used. The sample can also contain an aqueous composition of recombinant TTR that can be a wild type (WT) or a mutant form in which one or more amino acid residues present in the WT form is replaced by one or more different amino acid residues, as is the case in the V30M-TTR and K15A-TTR mutant TTR molecules, and in the more than about 100 other pathogenic variants. These in vitro compositions typically contain the protein, water, sodium or potassium chloride, and one or more buffer salts such as and acetate and phosphate salts, Hepes or the like, a metal ion chelator such as EDTA that are buffered to a desired pH value such as pH 4.0-8.5, depending on the assay to be performed, as is well known.

Preferably, the pharmaceutical composition is in unit dosage form. In such form, the composition is divided into unit doses containing appropriate quantities of the active urea. The unit dosage form can be a packaged preparation, the package containing discrete quantities of the preparation, for example, in vials or ampules.

Results and Discussion

Small molecules that bind selectively to and then react with a specific Lys ε-amino group composing a specific non-enzyme protein in a complex biological sample are rare. A designed small family of such compounds is disclosed herein that should be useful for a range of applications, beyond the amelioration of TTR amyloidosis. Another application of small molecule TTR conjugating structures includes their covalent attachment to low molecular weight drugs that exhibit unfavorable pharmacokinetic (PK) or pharmacodynamic (PD) properties by themselves [Marinec et al., *Proc Natl Acad Sci USA* 106:1336-1341 (2009)].

Ideally, the small molecule TTR covalent modifier-drug fusion would be orally bioavailable. Upon formation of the TTR-(covalent modifier-drug)$_{n<2}$ conjugate in plasma, the covalently linked drug protrudes from the surface of TTR and takes on the favorable PK and PD properties of TTR (conjugated drug concentration up to 10 μM with a half-life of 24 hours). Such TTR-small molecule covalent modifier substructure-drug conjugates can significantly expand the chemical diversity of pharmacologic agents for the treatment of disease.

Design of Chemoselective Covalent TTR Kinetic Stabilizers

Previous non-covalent TTR kinetic stabilizer structure-based design and/or structure-activity relationship studies demonstrate the efficacy of non-covalent TTR kinetic stabilizers [Klabunde et al., *Nat. Struct. Biol.* 7:312-321 (2000); Adamski-Werner et al., *J. Med. Chem.* 47:355-374 (2004); Johnson et al., *J. Med. Chem.* 51:6348-6358 (2008); Oza et al., *J. Med. Chem.* 45, 321-332 (2002); Razavi et al., *Angew. Chem. Int. Ed. Engl.* 42, 2758-2761 (2003); Johnson et al., *J. Med. Chem.* 51:260-270 (2008); Petrassi et al., *J. Am. Chem. Soc.* 122:2178-2192 (2000); Purkey et al., *Chem. Biol.* 11:1719-1728 (2004); Baures et al., *Bioorg. Med. Chem.* 7:1339-1347 (1999); Green et al., *J. Am. Chem. Soc.* 125: 13404-13414 (2003); and Miller et al., *Lab. Invest.* 84:545-552 (2004)]. Ester and thioester derivatives of previously optimized trans-stilbene-based non-covalent TTR kinetic stabilizers [Johnson et al., *J. Med. Chem.* 51, 6348-6358 (2008)] (Table 1) were prepared utilizing Horner-Wadsworth-Emmons couplings between a benzaldehyde and benzyl halide (see, Scheme 2 hereinafter).

One of the two $T_4$ binding sites comprising two subunits of TTR is shown schematically below containing a bound but unreacted kinetic stabilizer compound and a covalently-bound, reacted, form of the same kinetic stabilizer.

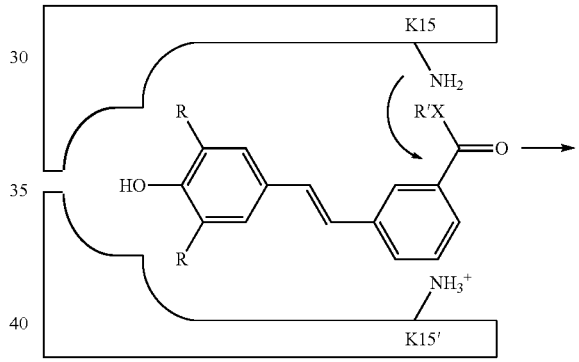

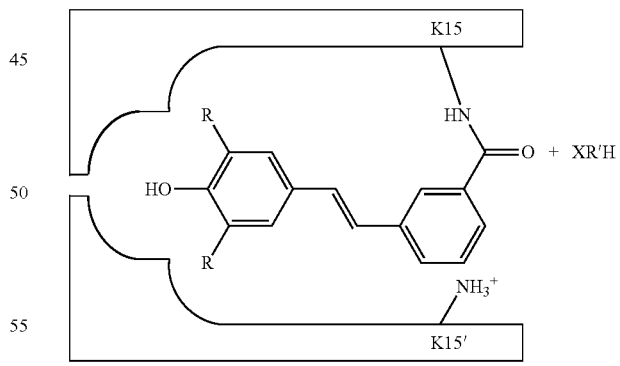

Table 1, below, illustrates in vitro inhibition of purified recombinant WT-TTR and V30M-TTR amyloidogenesis by covalent kinetic stabilizer Compounds 1-4 and quantification of the chemoselective covalent modification of TTR in blood plasma by the candidate covalent kinetic stabilizers 1-4 ex vivo. Data for results with WT-TTR are shown above those for use of the V30M-TTR mutant.

TABLE 1

| Compound | R | XR' | % Fibril Formation[a] 7.2 μM | % Fibril Formation[a] 3.6 μM | IC$_{50}$ (μM)[b] | % Modification of TTR subunits in Human Blood Plasma[c] |
|---|---|---|---|---|---|---|
| 1 | Br | —S-phenyl | 2% (±1%) 3% (±0.3%) | 12% (±1%) 17% (±0.2%) | 2.00 | 36% (±0.4%) |
| 2 | CH$_3$ | —S-phenyl | 2% (±1%) 3% (±0.2%) | 16% (±2%) 34% (±0.5%) | 2.00 | 48% (±1.3%) |
| 3 | CH$_3$ | —O-(2-nitrophenyl) | 4% (±1%) 3% (±0.2%) | 21% (±2%) 33% (±2%) | 2.26 | 49% (±0.7%) |
| 4 | CH$_3$ | —O-(4-fluorophenyl) | 1% (±1%) 7% (±0.2%) | 16% (±1%) 36% (±3%) | 1.96 | 32% (±3.3%) |

[a] Percent fibril formation of WT-TTR (3.6 μM) and V30M-TTR (3.6 μM) in the presence of candidate covalent kinetic stabilizers (7.2 and 3.6 μM) at pH 4.4, 72 hours, 37° C.
[b] IC$_{50}$ reported is apparent, because these compounds bind and then react with WT-TTR.
[c] Maximum modification percent by candidate covalent kinetic stabilizers is 50% because only 2/4 TTR subunits can be modified in each tetramer after incubation (18 hours).

Placement of the ester or thioester group at the 3-position on the aromatic ring expected to occupy the outer T$_4$ binding cavity [Johnson et al., *J. Med. Chem.* 51:6348-6358 (2008)] enables the TTR lysine 15 (K15) ε-amine to approach the carbonyl at the Burgi-Dunitz angle, facilitating amide bond conjugation (Table 1) [Burgi et al., *Tetrahedron* 30:1563-1572 (1974)]. The K15 and K15' side chains are in proximity in each T$_4$ binding site in the tetramer. Thus, putative pK$_a$ perturbation leads to one K15 ε-amine group and one K15' ε-ammonium group at pH 7. [Hammarstrom et al., *Biochemistry* 40:11453-11459 (2001)].

COMPOUNDS

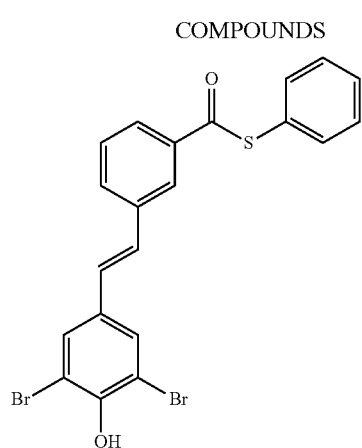

1

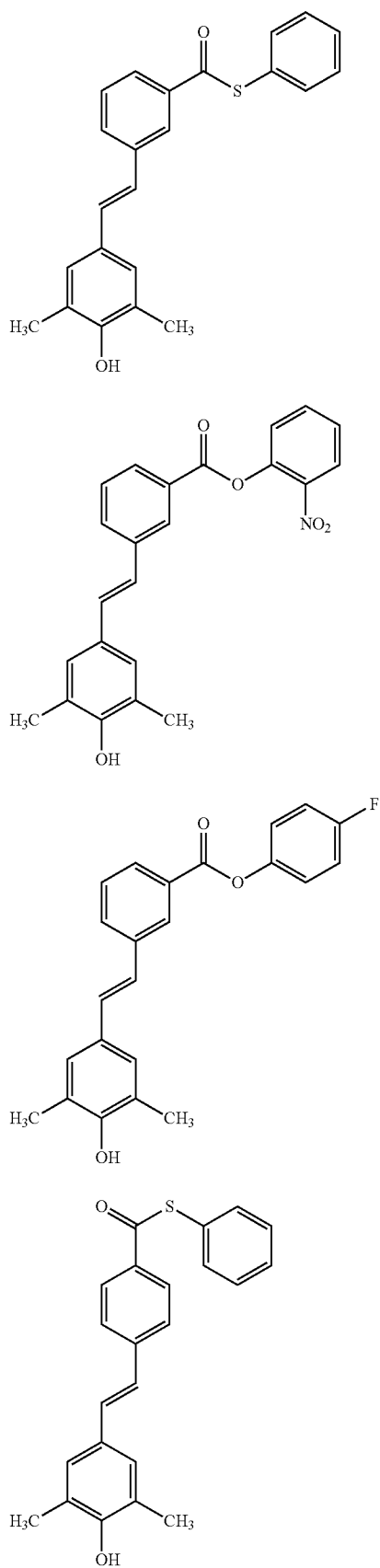
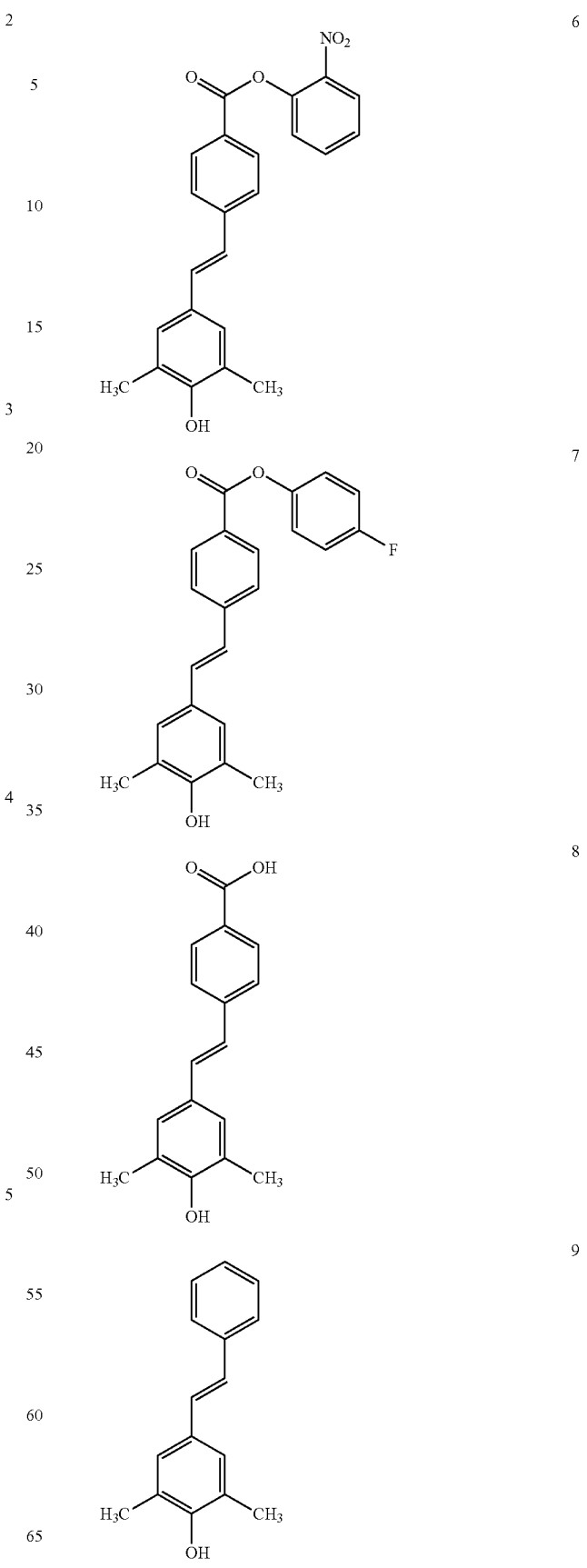

-continued

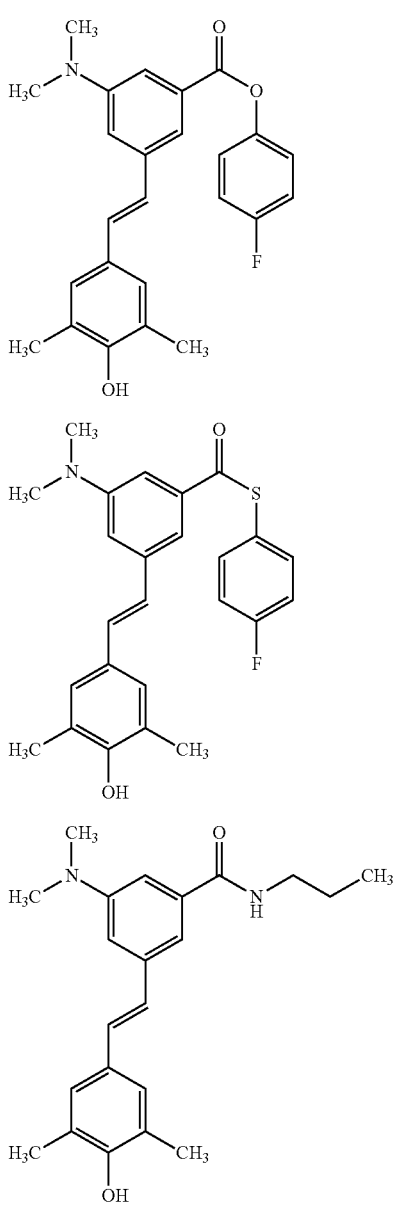

The Chemoselectivity of the Conjugation Reaction of Compounds 1-4

The ability of candidate covalent kinetic stabilizers Compounds 1-4 to form a chemoselective amide bond with the K15 residue of WT-TTR was assessed by incubating the recombinant WT-TTR tetramer (3.6 μM) with Compounds 1-4 (7.2 μM, the minimum concentration required to covalently modify both $T_4$ binding sites) for 18 hours at 25° C. The stilbene-TTR conjugate was quantified by reverse-phase (RP)-HPLC using a denaturing acetonitrile gradient.

The resulting chromatograms exhibit two peaks of nearly equal intensity in the case of highly chemoselective compounds (FIG. 1A, top chromatogram), as it is only possible to benzoylate two of the four subunits at K15 (Table 1), affording conjugation yields of 90-100% (the molar absorptivity changes associated with benzoylation were accounted for). Liquid chromatography-mass spectrometry (LC-MS) analysis confirmed that the first peak is the unmodified WT-TTR subunit (13893 m/z [M+2H]$^+$ calculated, 13893 m/z observed), whereas the second peak is the stilbene-WT-TTR conjugate (14271 m/z M$^+$ for benzoylation by Compound 1 and 14143 m/z [M+2H]$^+$ for benzoylation by Compounds 2-4 (see Table 1, top right)).

Figure 1B:
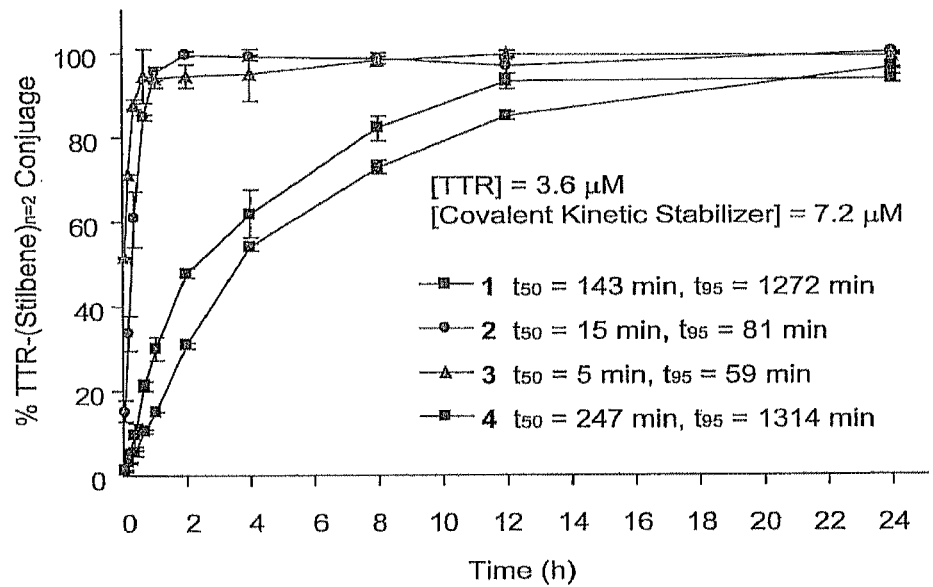
FIG. 1B shows the rate of WT-TTR-(stilbene)$_n$ conjugate formation analyzed by $C_{18}$-RP-HPLC. Samples were analyzed in triplicate and the error bars represent standard deviations.

Analysis of the kinetics of the TTR conjugation reaction demonstrates that the rate of conjugation can vary dramatically, even when the leaving group is identical (FIG. 1B, Compounds 1 and 2). This is not surprising because the reaction rate is dependent on the binding constants, the leaving group potential, and the exact binding geometry; the latter two are envisioned to be the major contributors to the differences in reaction rates observed. Covalent kinetic stabilizers Compounds 2 and 3 exhibit a conjugation half-life ($t_{50s}$) of 5-15 minutes (FIG. 1B), whereas Compounds 1 and 4 exhibit $t_{50}$, of 143 and 247 minutes, respectively. Importantly, all the TTR covalent kinetic stabilizers react completely with TTR within 24 hours, the half-life of TTR in plasma.

A strictly analogous study performed with the K15A homotetrameric TTR mutant confirmed that K15 was essential for the observed chemoselective reaction between TTR and Compounds 1-4 (FIG. 1A, bottom trace). Compound 4 was the most chemoselective covalent kinetic stabilizer identified in vitro, as no reaction could be detected between it and K15A-TTR mutant (FIG. 1A, bottom trace). However, it is important to note that Compounds 1-3 were only slightly less chemoselective (<5% reaction with K15A).

Figure 11:
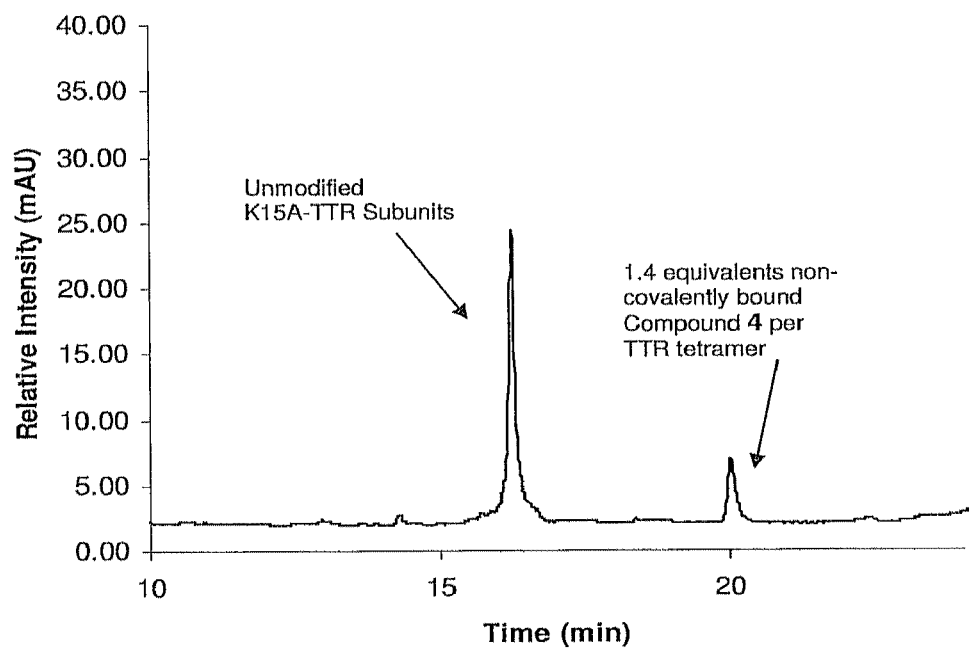
FIG. 11 is a RP-HPLC chromatogram showing the non-covalent binding stoichiometry of Compound 4 to the recombinant K15A-TTR homotetramer after immunocapture utilizing an anti-TTR antibody conjugated to Sepharose® resin, demonstrating that the covalent kinetic stabilizers can bind to K15A TTR but they do not react because lysine-15 is missing.

To demonstrate that the covalent kinetic stabilizers can bind to K15A-TTR like they do to WT-TTR, Compound 4 was pre-incubated with K15A-TTR. K15A-TTR and any compound bound to it was immunocaptured using a Sepharose-resin-conjugated anti-TTR antibody. [Purkey et al., Proc. Natl. Acad. Sci. U.S.A. 98:5566-5571 (2001] After high-pH-mediated dissociation, HPLC analysis showed that 1.4 out of a maximum of 2 equivalents of Compound 4 were non-covalently bound to the K15A-TTR homotetramer (See, FIG. 11), demonstrating that covalent kinetic stabilizer binding to K15A-TTR is not impaired. Therefore, Compounds 1-4 do not react with K15A-TTR simply because the Lys-15 ε-amino group is absent, not because they cannot bind.

Placement of the ester or thioester at the 4-position of the stilbene aryl ring putatively occupying the outer $T_4$ binding pocket (e.g., Compounds 5-7) either resulted in more non-chemoselective conjugation, as exemplified by the reactivity of Compound 6 with the K15A mutant subunits, or lower reactivity, as exemplified by the lower modification yield of the WT-TTR subunits by Compound 7 (data not shown).

However, Compound 5 exhibits promising results, suggesting that it may be possible to place a conjugating functional group at the 4-position in another context. There are numerous examples of transforming non-covalent enzyme inhibitors into covalent inhibitors, and it is likely that additional functional groups at the 3- or 4-position will find utility in covalent kinetic stabilization of TTR.

The Potency of Compounds 1-4 as Amyloid Inhibitors Relative to their Non-Covalent Counterpart Compounds 8 and 9

The utility of the chemoselective covalent kinetic stabilizers Compounds 1-4 to inhibit WT-TTR amyloidogenesis was evaluated next utilizing the previously validated acid-mediated fibril formation assay. [Lashuel et al., Biochemistry 38:13560-13573 (1999)]. Compounds 1-4 (3.6 or 7.2 μM) were pre-incubated with WT-TTR (3.6 μM) for 18 hours (the half-life of TTR in plasma is 24 hours) before initiating TTR amyloidogenesis (pH jump to 4.4). The extent of amyloidogenesis was quantified at a fixed time point (72 hours), as done previously, by measuring sample turbidity (400 nm), shown to be equivalent to thioflavin T monitoring of amyloidogenesis. [Hurshman et al., *Biochemistry* 43:7365-7381 (2004)].

Potent non-covalent kinetic stabilizers, many exhibiting subnanomolar dissociation constants, permit about 10% WT-TTR fibril formation at a concentration of 7.2 µM and about 40% WT-TTR fibril formation at a concentration equal to that of the TTR tetramer (3.6 µM). [Adamski-Werner et al., *J. Med. Chem.* 47:355-374 (2004); Johnson et al., *J. Med. Chem.* 51:6348-6358 (2008); Johnson et al., *J. Med. Chem.* 48:1576-1587 (2005); Miroy et al., *Proc. Natl. Acad. Sci. U.S.A.* 93:15051-15056 (1996); Oza et al., *J. Med. Chem.* 45:321-332 (2002); Razavi et al., *Angew. Chem. Int. Ed. Engl.* 42:2758-2761 (2003); Johnson et al., *J. Med. Chem.* 51:260-270 (2008); Petrassi et al., *J. Am. Chem. Soc.* 122:2178-2192 (2000); Green et al., *J. Am. Chem. Soc.* 125:13404-13414 (2003); and Baures et al., *Med. Chem.* 6:1389-1401 (1998)]. TTR incubated individually with each of Compounds 1-4 exhibits <4% (7.2 µM) and 12-21 percent (3.6 µM) of the fibril formation exhibited by WT-TTR alone after 72 hours (Table 1), less than half of the TTR amyloidogenesis allowed by the best non-covalent kinetic stabilizers after 72 hours [Adamski-Werner et al., *J. Med. Chem.* 47:355-374 (2004); Johnson et al., *J. Med. Chem.* 51:6348-6358 (2008); Johnson et al., *J. Med. Chem.* 48:1576-1587 (2005); Miroy, G. J. et al., *Proc. Natl. Acad. Sci. U.S.A.* 93:15051-15056 (1996); Oza et al., *J. Med. Chem.* 45:321-332 (2002); Razavi et al., *Angew. Chem. Int. Ed. Engl.* 42:2758-2761 (2003); Johnson et al., *J. Med. Chem.* 51:260-270 (2008); Petrassi et al., *J. Am. Chem. Soc.* 122:2178-2192 (2000); Green et al., *J. Am. Chem. Soc.* 125:13404-13414 (2003); and Baures et al., *Bioorg. Med. Chem.* 6:1389-1401 (1998)].

To further scrutinize the potency of covalent kinetic stabilizer Compounds 2 and 4, not against a spectrum of non-covalent kinetic stabilizers as above, but relative to their strictly structurally analogous highly potent and selective non-covalent counterparts Compounds 8 and 9 [Johnson et al., *J. Med. Chem.* 51:6348-6358 (2008)] (FIG. 2B), the extent of inhibition of acid-mediated WT-TTR (3.6 µM) fibril formation by lower concentrations (2.7 µM and 1.8 µM) of the kinetic stabilizers was compared over a 120 hour time course instead of at a fixed time (72 hours).

Figure 2A:
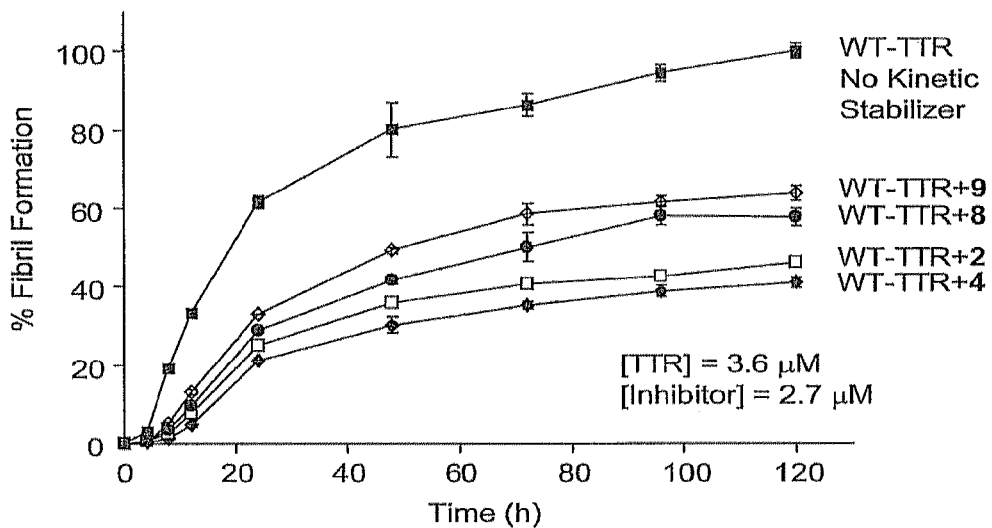
FIG. 2A shows a comparison of the potency of structurally similar non-covalent kinetic stabilizer Compounds 8 and 9 (2.7 µM) with that of covalent kinetic stabilizer Compounds 2 and 4 (2.7 µM) assessed by their capacity to inhibit recombinant WT-TTR (3.6 µM) amyloidogenesis over a 120 hour time course.
Figure 7:
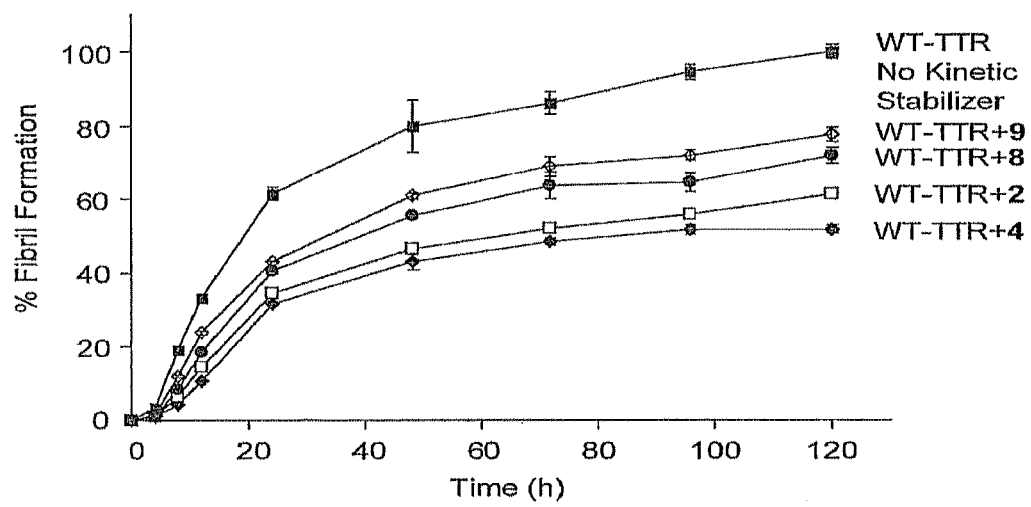
FIG. 7 is a graph showing inhibition of recombinant WT-TTR (3.6 µM) amyloidogenesis by covalent kinetic stabilizers Compounds 2 and 4 and non-covalent kinetic stabilizers Compounds 8 and 9 at a concentration of 1.8 µM, strictly analogous to FIG. 2A but at a different concentration.

The covalent kinetic stabilizers inhibited 10-20 percent more fibril formation than their non-covalent counterparts when applied at 2.7 µM (FIG. 2A) or 1.8 µM (FIG. 7). This result is highly significant, given that the non-covalent inhibitors have been previously optimized for potency and selectivity [Johnson et al., *J. Med. Chem.* 51:6348-6358 (2008)].

Figure 2B:
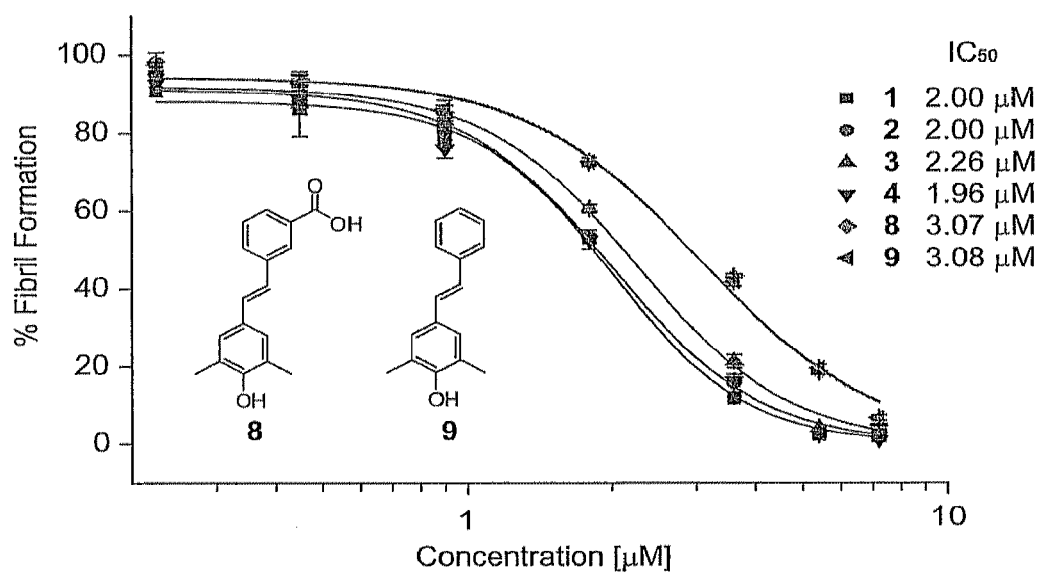
FIG. 2B shows the concentration-dependent kinetic stabilization of recombinant WT-TTR by Compounds 1-4 and their non-covalent counterparts Compounds 8 and 9 assessed by % fibril formation after 72 hours.

The inhibition of WT-TTR (3.6 µM) amyloidogenesis by Compounds 1-4 is dose dependent, with apparent $IC_{50}$ values in the range of 1.96-2.26 µM, whereas the previously optimized [Johnson et al., *J. Med. Chem.* 51:6348-6358 (2008)] non-covalent kinetic stabilizer Compounds 8 and 9 exhibited higher $IC_{50}$ values around 3 µM (FIG. 2B). The exquisitely high binding affinity of Compounds 8 and 9 to TTR necessarily renders the apparent $IC_{50}$ of Compounds 8 and 9 similar to that of stabilizer Compounds 1-4 in vitro.

In order for the incorporation of covalency into the TTR kinetic stabilization mechanism to translate into potency in vivo, the compound must bind with very high selectivity to TTR in plasma (demonstrated below), react with TTR rapidly relative to its 24 hour half-life (demonstrated in vitro), and exhibit a plasma distribution, concentration and half-life facilitating a near quantitative conjugation yield.

Compounds 1-4 Inhibit V30M-TTR Amyloidogenesis

Covalent kinetic stabilizer Compounds 1-4 (3.6 and 7.2 µM) also efficiently inhibit V30M-TTR (3.6 µM) amyloidogenesis associated with FAP (Table 1, lower values). As expected, Compounds 1-4 exhibited decreased potency relative to WT-TTR amyloidogenesis, owing to the decreased thermodynamic stability of the V30M-TTR tetramer.

Benzoylation of K15 and Occupancy of the $T_4$ Site Together Contribute to the Superiority of the Covalent Kinetic Stabilizers Previous studies demonstrated that electrostatic repulsions between the proximal pairs of K15 and K15' residues destabilize the TTR tetramer structure [Hammarstrom et al., *Biochemistry* 40:11453-11459 (2001)]. In an attempt to understand whether the kinetic stabilization of TTR by conjugation to one of Compounds 1-4 results solely from benzoylation-induced reduction of the K15-mediated electrostatic repulsions or whether bridging hydrophobic interactions between proximal TTR subunits mediated by the stilbene component of the kinetic stabilizers also contribute, WT-TTR or K15A-TTR (3.6 µM) was incubated with the non-covalent kinetic stabilizers Compounds 8 or 9 (7.2 µM) for 72 hours at pH 4.4.

Although K15A-TTR is much less amyloidogenic than WT-TTR (demonstrating that reduction of the charge-charge repulsions by benzoylation is likely stabilizing), additional stabilization of K15A-TTR was observed in the absence of benzoylation (Compounds 8 and 9 cannot covalently modify TTR; Example FIG. 6). This study demonstrates that both diminishing the K15-K15' electrostatic repulsions through benzoylation and subunit bridging through non-covalent hydrophobic interactions with neighboring subunits comprising the weaker dimer interface of TTR together contribute to the kinetic stabilization of TTR.

Assessing the Selectivity of 1-4 for Binding to TTR Over Other Plasma Proteins

Figure 1C:
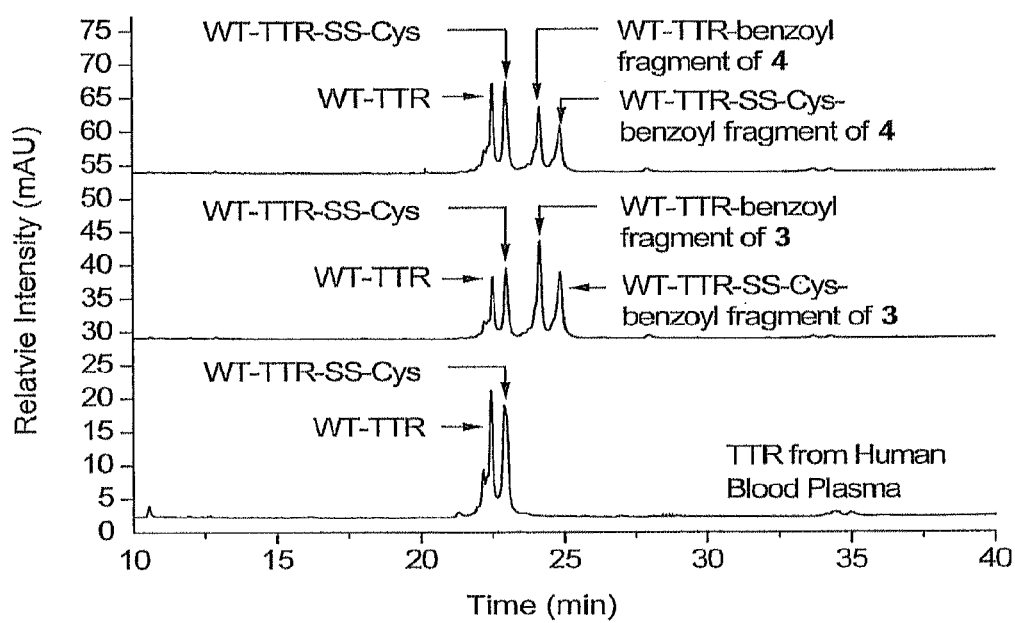
FIG. 1C shows a $C_{18}$-RP-HPLC assessment of the modification of TTR in human blood plasma by Compounds 3 and 4.
Figure 9:
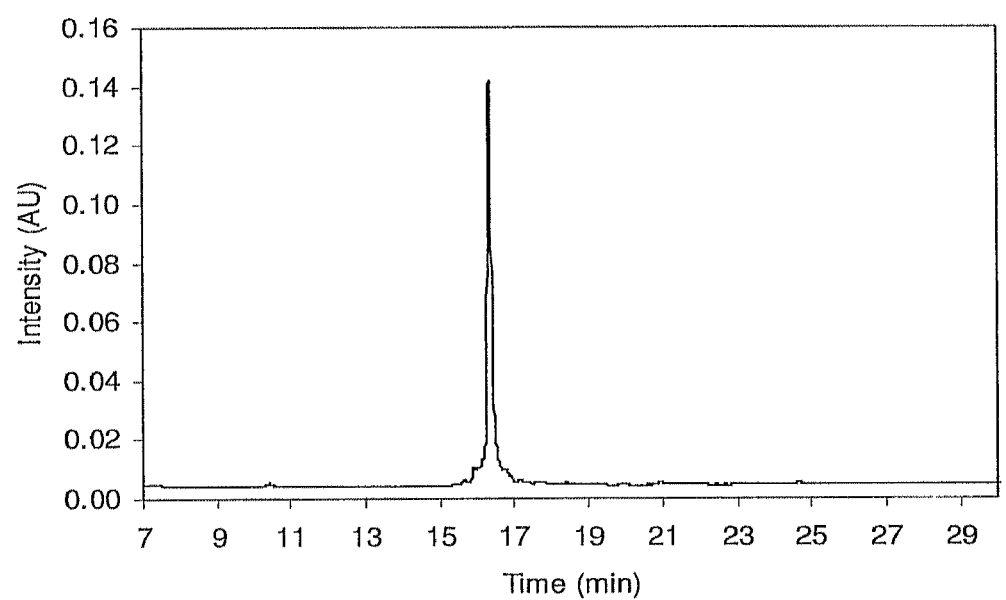
FIG. 9 shows a RP-HPLC trace of recombinant WT-TTR, demonstrating that it is homogeneous, unlike TTR isolated from human plasma that exhibits two peaks because half is disulfide bonded to Cys, and to a lesser extent, other SH-containing small molecules.

The ability of each of Compounds 1-4 to bind to and then react with TTR over the >4000 other human proteins in blood plasma was assessed next. Untreated recombinant TTR in buffer is homogeneous and, thus, its subunits exhibit a single RP-HPLC peak under denaturing conditions (FIG. 9). RP-HPLC analysis of TTR captured from human plasma, using a Sepharose®-resin-conjugated anti-TTR antibody [Purkey et al., *Proc. Natl. Acad. Sci. U.S.A.* 98:5566-5571 (2001)], and dissociated with a high pH treatment revealed two RP-HPLC peaks of nearly equal intensity (FIG. 1C, bottom chromatogram), because about one-half of the TTR subunits form a disulfide bond with the amino acid Cys, and a very small amount of the Cys in TTR gets S-sulfonated, —$C_\alpha H$—$C_\beta H_2$—S—$SO_3(H)$ [Zhang et al., *Biochemistry* 42:8756-8761 (2003)].

Compounds 1-4 (10.8 µM) were incubated for 24 hours at 37° C. with human plasma, wherein the TTR concentration is 3.6-5.4 µM. Immunocapture/HPLC analysis of TTR [Purkey et al., *Proc. Natl. Acad. Sci. U.S.A.* 98:5566-5571 (2001)] revealed the ratio of the TTR monomer to the TTR-stilbene-conjugate (FIG. 1C and Table 1, rightmost column), demonstrating selective binding to and reaction with plasma TTR. Covalent kinetic stabilizer Compounds 2 (Table 1) and 3 (Table 1 and FIG. 1C, middle chromatogram) exhibited the highest modification yield in plasma, very close to the maximum of 50 percent (the molar absorptivity changes associated with benzoylation were accounted for). It is not surprising that the two TTR kinetic stabilizers exhibiting rapid (FIG. 1B) and selective (FIG. 1C) TTR conjugation reactions perform best in human plasma.

Figure 10:
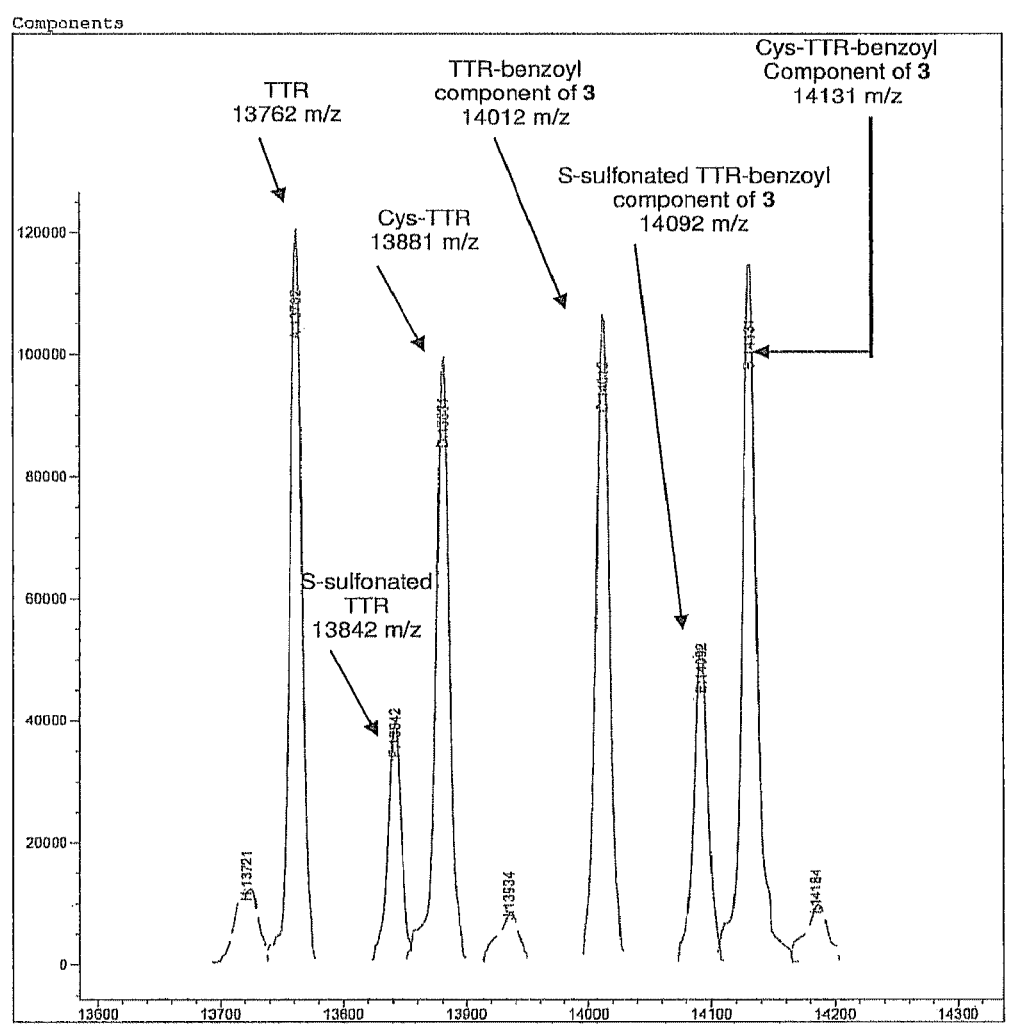
FIG. 10 is a mass spectrum of human plasma TTR and the thiol-modified forms of TTR found in human plasma, as well as the TTR-(benzoyl substructure of Compound 3) and its corresponding TTR modifications in human plasma.

Mass spectrometry is an especially gratifying method for the assessment of covalent kinetic stabilizer modification of TTR. LC-MS analysis (FIG. 10) following treatment by Compound 3 reveals peaks at 13762 m/z for TTR, 13842 m/z for S-sulfonated TTR, and 13881 m/z for Cys-TTR. That spectrum also shows the additional peaks in the chromatogram (FIG. 1C; middle chromatogram) correspond to the TTR-benzoyl component of Compound 3=14012 m/z, and under the rightmost broad peak is the Cys-SS-TTR-benzoyl component of Compound 3=14131 m/z and the S-sulfonated-TTR-benzoyl component of 3=14092 m/z.

Similar LC-MS analysis of the benzoylation of TTR by Compound 1 (not shown) reveals strictly analogous species with peaks at 13762 m/z for TTR, 13842 m/z for S-sulfonated TTR, and 13881 m/z for Cys-TTR. Here, the TTR-benzoyl component of Compound 1=14142 m/z, and under the rightmost broad peak is the Cys-SS-TTR-benzoyl component of Compound 1=14261 m/z and the S-sulfonated-TTR-benzoyl component of 3=14222 m/z.

Dose-Dependent Kinetic Stabilization of the TTR Tetramer by Compound 4

Because TTR tetramer dissociation is rate limiting for amyloidogenesis [Hammarstrom et al., *Science* 299:713-716 (2003)], the extent of TTR kinetic stabilization is revealed by measuring tetramer dissociation rates and the degree of dissociation as a function of the concentration of Compound 4. Tetramer dissociation kinetics are measured by linking the slow dissociation step to the rapid monomer unfolding step-assessed by far-UV circular dichroism (CD) spectroscopy. [Johnson et al., *Acc. Chem. Res.* 38, 911-921 (2005); Hammarstrom et al., *Science* 299:713-716 (2003); and Foss et al., *J. Mol. Biol.* 347:841-854 (2005)].

Figure 2C:
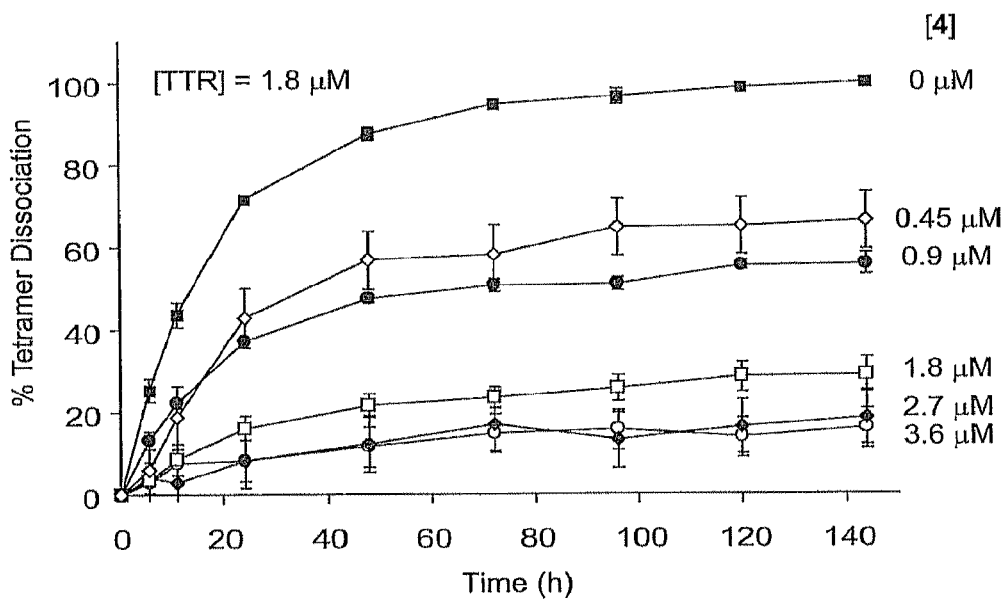
FIG. 2C illustrates that covalent kinetic stabilizer Compound 4 inhibits WT-TTR dissociation in a concentration-dependent manner. Urea-mediated WT-TTR (1.8 µM) dissociation time course in the absence and presence of Compound 4 as a function of the indicated concentrations, was evaluated by linking slow tetramer dissociation to rapid and irreversible monomer denaturation in 6 M urea measured by far-UV circular dichroism at 215-218 nm. [Hammarstrom et al., Science 299:713-716 (2003)]. Samples were analyzed in triplicate and the error bars represent standard deviations.

Recombinant TTR (1.8 µM) was pre-incubated for 18 hours as a function of the concentration of Compound 4 (0.45-3.6 µM). Dissociation (accelerated by the addition of 6 M urea) and denaturation of TTR, monitored over 144 hours by far-UV CD, was diminished proportionally to the concentration of Compound 4 added (FIG. 2C). Only slightly less TTR kinetic stabilization was observed at 1.8 vs 3.6 µM, indicating that covalent attachment of Compound 4 to one $T_4$ site in the TTR tetramer is sufficient to impose kinetic stability on the entire tetramer, as demonstrated previously. [Wiseman et al., *J. Am. Chem. Soc.* 127:5540-5551 (2005)].

Covalent kinetic stabilizers inhibit TTR-amyloidogenesis-associated cytotoxicity WT-TTR purified at 4° C. is cytotoxic to IMR-32 human neuroblastoma cells, possibly because of an altered tetramer structure that facilitates amyloidogenesis. [Reixach et al., *Proc. Natl. Acad. Sci. U.S.A.* 101:2817-2822 (2004); and Reixach et al., *Biochem. Biophys. Res. Commun.* 348:889-897 (2006)]. Non-covalent TTR kinetic stabilizers (e.g., resveratrol) are known to inhibit amyloid-formation-associated cytotoxicity, whereas structurally related compounds with poor TTR binding capacity do not inhibit cytotoxicity. [Reixach et al., *Proc. Natl. Acad. Sci. U.S.A.* 101:2817-2822 (2004); and Reixach et al., *Biochem. Biophys. Res. Commun.* 348:889-897 (2006)].

Compounds 2 and 4 or the corresponding non-covalent kinetic stabilizers Compounds 8 and 9 (2, 4, 6 and 8 µM) were pre-incubated with WT-TTR (8 µM) for 18 hours at 37° C. and added to IMR-32 cells. Cell viability was measured after 24 hours by a resazurin reduction assay.

Figure 3:
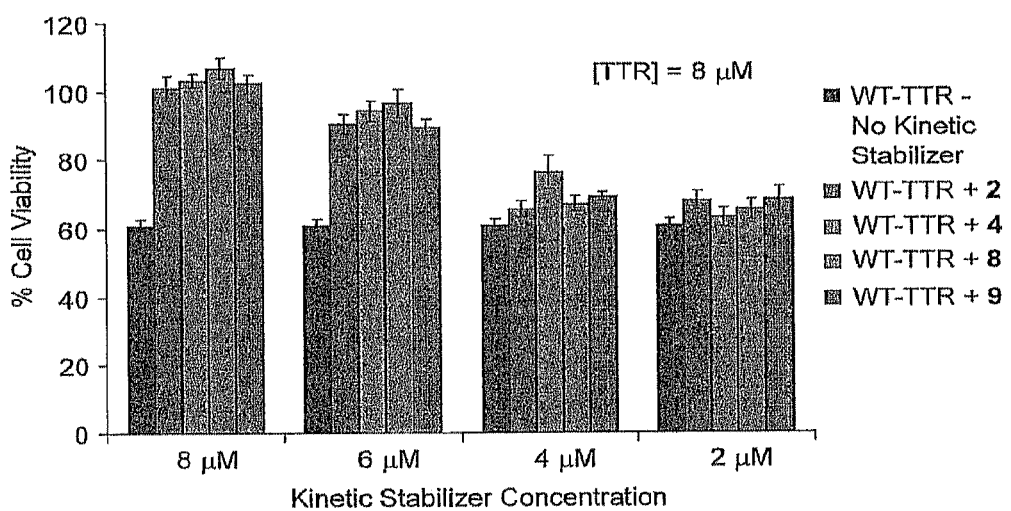
FIG. 3 contains sets of bar graphs that illustrate inhibition of WT-TTR cytotoxicity in human IMR-32 neuroblastoma cells as a function of the dose of covalent and non-covalent TTR kinetic stabilizers. WT-TTR was pre-incubated at 37° C. in the absence (black bars, left-most of each set of bars) or presence of Compounds 2, 4, 8 and 9 (left to right bars in each set) for 18 hours and then added to the cell culture media. The final concentration of WT-TTR was 8 µM and the final concentrations of compounds were 8, 6, 4 and 2 µM, as indicated. Cell viability was assessed using the resazurin reduction assay after 24 hours. Cell viability results are reported relative to cells treated with vehicle only (100% cell viability). [Reixach et al., Proc. Natl. Acad. Sci. U.S.A. 101:2817-2822 (2004)]. Columns represent the means of 2 independently performed experiments (n=6) and the error bars represent standard errors.

Metabolically active cells reduce the resazurin redox dye to resorufin, a soluble fluorescent compound. [O'Brien et al., *Eur. J. Biochem.* 267:5421-5426 (2002)] The percentage of viable cells was calculated relative to cells treated with vehicle only (cell culture media and DMSO=100% viable). Pre-incubation of WT-TTR with Compounds 2, 4, 8, or 9 clearly and dose-dependently inhibits IMR-32 cytotoxicity (FIG. 3). However, this assay is not capable of uncovering the differences between the covalent (Compounds 2 and 4) and the non-covalent (Compounds 8 and 9) kinetic stabilizers, which is not surprising given the high selectivity and the potency of the non-covalent kinetic stabilizer Compounds 8 and 9. None of these compounds were cytotoxic to IMR-32 cells in the absence of WT-TTR.

Crystal Structure of the WT-TTR-(Benzoyl Substructure of Compound 4)$_2$ Complex The crystal structure of the WT-TTR-(benzoyl substructure of Compound 4)$_2$ covalent conjugate was determined to 1.35 Å resolution (Table 2). Because the conjugated ligand resides on the crystallographic 2-fold axis, the observed electron density represents an average of the two possible symmetry-related conformations. [Wojtczak et al., *Acta Crystallogr. D Biol. Crystallogr.* 57:1061-1070 (2001)].

Electron density for the benzoyl substructure of Compound 4 and the K15 (K15') side chain up to the δ methylene are clear and unambiguous. Although the electron density for the amide bond is clearly visible, symmetry averaging makes it difficult to be absolutely certain whether the amide bond is in a cis or trans conformation. Modeling with a trans amide bond did not agree as well as modeling the amide in a cis conformation. Moreover, the trans bond angles and lengths were atypical and the crystallographic R-values were higher, suggesting that the cis amide affords a lower overall energy structure in the crystal given the constraints on the orientation of the bound stilbene and the K15 (K15') side chain. Future NMR studies are warranted to explore this subject in more detail.

The 3,5-dimethyl-4-hydroxyphenyl substructure of the TTR conjugate occupies the inner thyroxine binding cavity, consistent with the preferred binding orientation of non-covalent stilbene-based high $pK_a$ phenols. [Johnson et al., *J. Med. Chem.* 51:6348-6358 (2008); and Johnson et al., *J. Med. Chem.* 48, 1576-1587 (2005)]. The methyl substituents extend into the two symmetry-related halogen binding pockets 3 and 3'. The 4-OH substituent on the aryl makes bridging hydrogen bonds with the Ser-117 and -117' side chains of adjacent TTR subunits.

The conjugating amide bond orders the ordinarily flexible K15 side chain and the substructure of Compound 4 such that their B-values (18.4 Å$^2$) approach those of the protein (13 Å$^2$), suggesting that the stilbene substructure is rigidly held in the pocket. As the p-fluorophenol leaving group of Compound 4 is not observed in the density, all bound Compound 4 must have reacted covalently with the lysine ε-NH$_2$ nucleophile. Even though a 5-fold excess of Compound 4 was used in formation of the TTR•4 conjugate crystals, the electron density indicated that the other 7 lysines, and all other residues, were unmodified, consistent with the high chemoselectivity of Compound 4, as demonstrated above.

A structurally homologous, non-covalent TTR kinetic stabilizer recently completed a successful phase II/III placebo-controlled clinical trial for the amelioration of FAP, demonstrating that it is unlikely that $T_4$ or holoretinol binding protein or retinol homeostasis will be perturbed in any significant fashion upon TTR conjugate formation with Compounds 1-4 (foldrx.com). Comparisons of the structures of WT-TTR-(benzoyl substructure of Compound 4)$_2$ (PDB accession code 3HJ0) and WT-TTR with two non-covalently bound resveratrol molecules (Compound 10; PDB accession code 1DVS) (0.389A RMSD) and WT-TTR in complex with RBP (PDB accession code 1QAB) further support this hypothesis.

Fluorescence Studies with Compounds 2 and 4

Figure 4A:
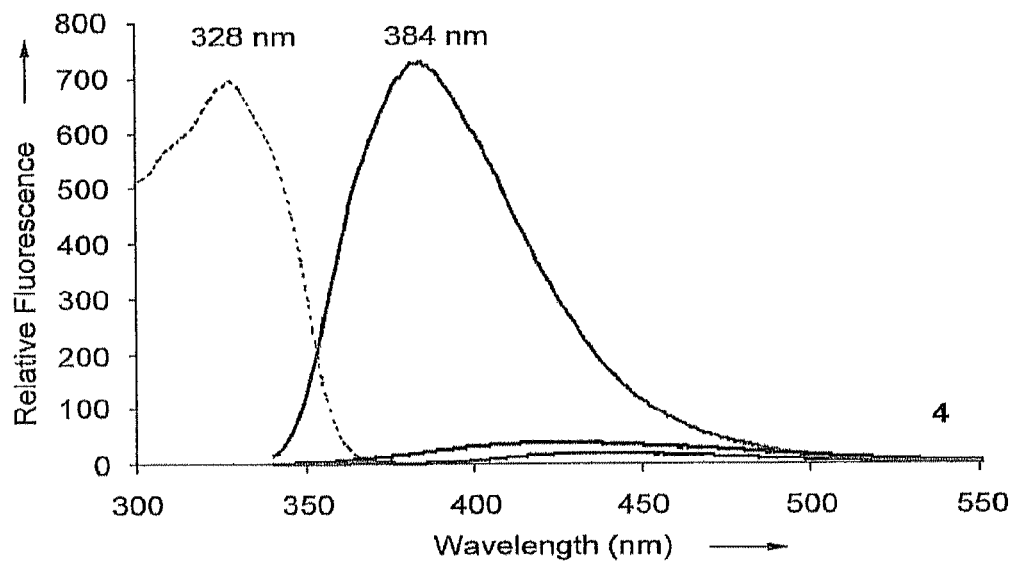
FIG. 4 in three panels shows fluorescence observed ($\lambda_{max}$ at 384 nm) after a 24 hour incubation of the reactive stilbene-based TTR modifiers FIG. 4A (Compound 4) and FIG. 4B (Compound 2) with WT-TTR.
FIG. 4C shows a similar fluorescence spectrum of the non-reactive stilbene-amide Compound B1 is also shown upon incubation with WT-TTR (plot with $\lambda_{max}$ at 384 nm and maximal emission at about 600 units). Each stilbene (7.2 µM) was also incubated with recombinant K15A-TTR (3.6 µM) for 24 hours [plots in FIG. 4A and FIG. 4B barely above the X-axis], and that in FIG. 4C with maximal emission at about 300 units, respectively. The fluorescence spectra of the stilbenes (7.2 µM) alone in aqueous buffer are also shown, but all plots are substantially on the X-axis, whereas the excitation spectra ($\lambda_{max}$ at 328 nm) are presented as dotted traces.
Figure 4B:
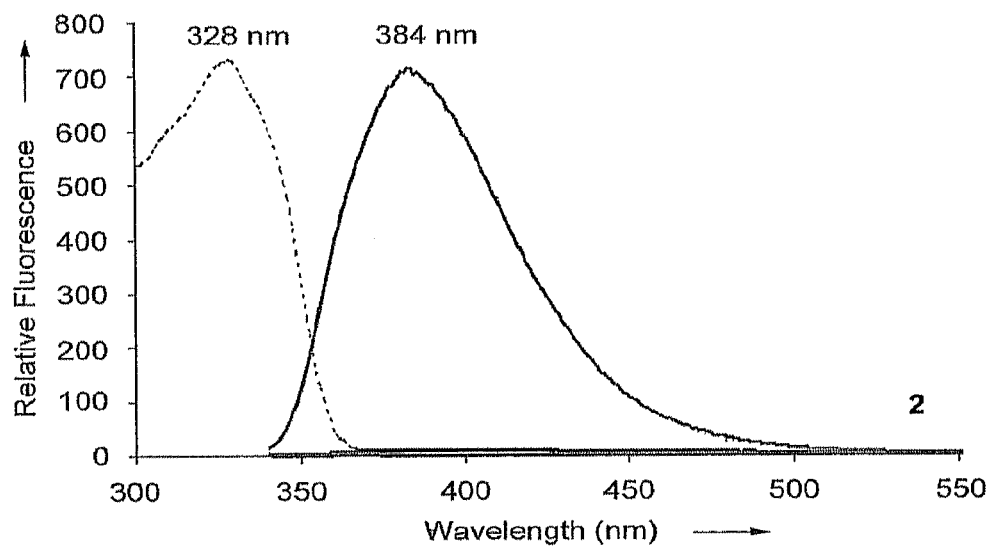

The ester substructure of Compound 4 and, particularly, the thioester substructure of Compound 2 quench the fluorescence of these small molecules when bound to the thyroxine binding site of TTR. Incubation of recombinant wild type (WT)-TTR or the amyloid disease-associated mutant V30M-TTR with Compound 4 or Compound 2 for 24 hours produced fluorescence resulting from amide bond conjugation. The fluorescence spectra are shown in FIGS. 4A and 4B for Compounds 4 and 2, respectively, when WT-TTR was used, and the spectra were substantially the same when V30M-TTR was used.

The excitation spectra are shown with dotted traces ($\lambda_{max}$=328 nm), and emission spectra are adjacently ($\lambda_{max}$=384 nm). Very low fluorescence resulted from 328 nm excitation of stilbene Compounds 4 or 2 alone in buffer (FIGS. 4A and 4B; traces substantially on the X-axis). No significant increase in the fluorescence intensity was observed when Compound 4 or Compound 2 was incubated with the recombinant Lys15Ala-TTR homotetramer that enables binding of Compound 4 or Compound 2, but not amide bond conjugation (FIGS. 4A and 4B, traces slightly above the X-axis).

A blue shift in the very weak fluorescence of Compound 4 was observed with K15A-TTR, providing evidence that it is binding to the $T_4$ binding sites within TTR (additional evidence is provided below). Binding of Compound 4 to the K15A-TTR homotetramer demonstrates that the intense 384 nm fluorescence from the stilbene-WT-TTR conjugate does not simply result from placement of the stilbene in the unique environment of the $T_4$ binding site.

Figure 5A:
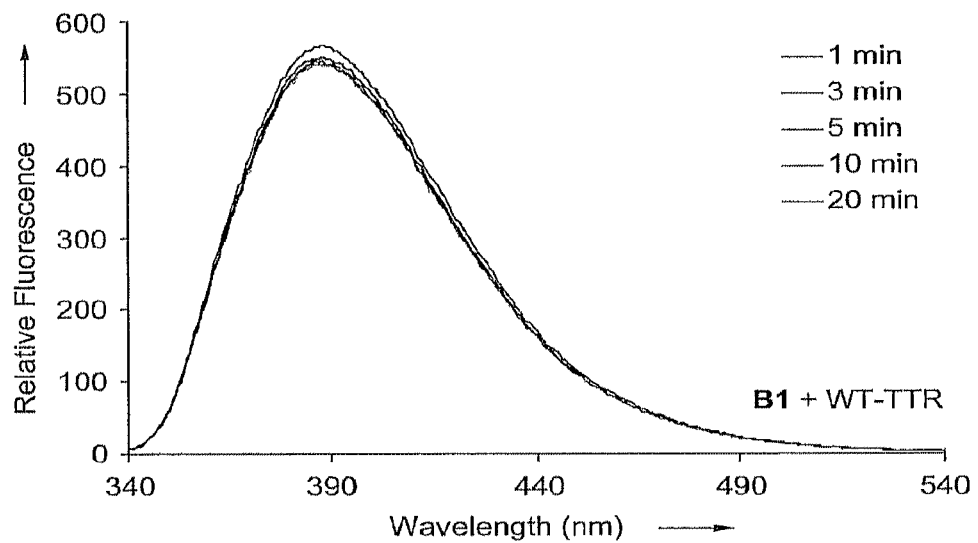
FIG. 5 in three panels shows time-dependent TTR-bound stilbene compound fluorescence spectra from recombinant WT-TTR (3.6 µM) treated with Compound B1 at 7.2 µM in FIG. 5A, with plots at 1, 3, 5, 10, and 20 minutes (min) in the direction from top to bottom; Compound 4 at 7.2 µM in FIG. 5B, with plots at 3, 10, 20, 40 minutes (min) and 1, 2, 4, 8, 12, and 24 hours (H) in the direction from bottom to top; and Compound 2 at 7.2 µM in FIG. 5C, with plots at 1, 3, 5, 10, 20, 40 minutes (min) and 1, 2, and 4 hours (H) also in the direction from bottom to top.
Figure 5B:
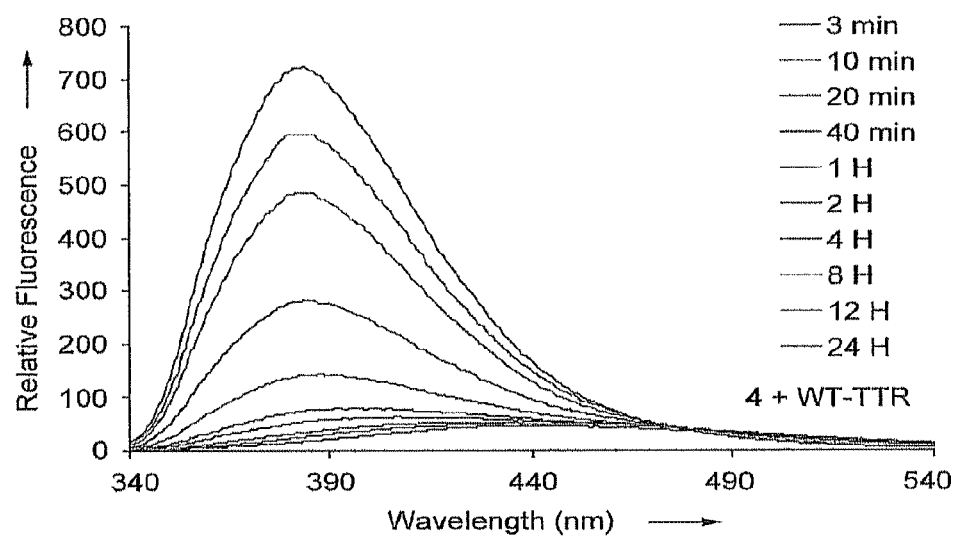
Figure 5C:
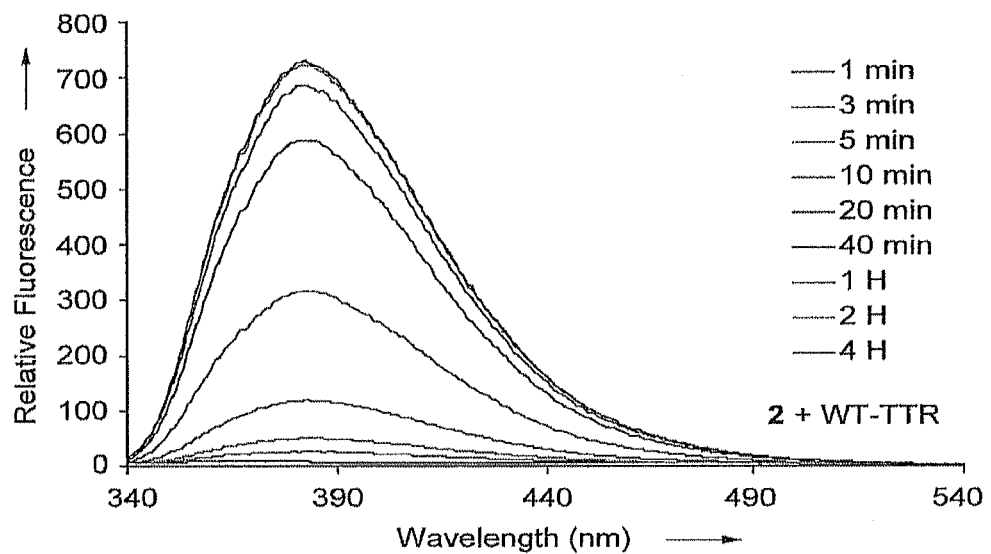

To confirm that chemoselective Lys-15 amide bond conjugation creates the blue-shifted, about 560-fold (Compound 4) and about 1100-fold (Compound 2) increase in fluorescence intensity displayed in FIGS. 5B and 5C (compared to Compounds 4 and 2 alone in buffer), recombinant WT-TTR and K15A-TTR homotetramers were incubated with a stilbene analog already possessing an amide bond (propylamide Compound B1, below) that turns on the fluorescence of this chromophore. Addition of unreactive Compound B1 to recombinant WT-TTR for 24 hours reveals an about 400-fold increase in fluorescence intensity (compared to Compound B1 alone in buffer, FIG. 5A), supporting the hypothesis that amide bond linkage of Compounds 4 or 2 to TTR turns on the TTR-(stilbene)$_2$ conjugate fluorescence.

In stark contrast to Compounds 4 and 2 that remain non-fluorescent upon binding to K15A-TTR, Compound B1 (below) exhibited an about 190-fold

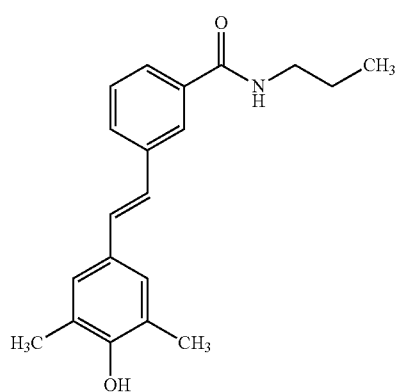

B1 increase in fluorescence intensity upon binding to K15A-TTR (24 hour incubation). The fluorescence intensity was slightly diminished relative to WT-TTR binding, presumably due to changes in the $T_4$ binding site environment of mutant K15A-TTR. It is notable the Compound B1 fluorescence in buffer is undetectable (not shown), strongly suggesting that binding to and amide bond conjugation to TTR are both required to observe maximal conjugate fluorescence from Compounds 4 and 2. Apparently, the ester substructure of Compound 4 and particularly the thioester substructure of Compound 2 quench the fluorescence of the stilbene.

Time-Dependent Fluorescence Studies

The requirements for stilbene-TTR conjugate fluorescence were further probed by adding Compounds 4, 2, or B1 to recombinant WT-TTR and recording time-dependent emission spectra. Addition of Compound B1 to WT-TTR confirmed that stilbenes bind rapidly to TTR (within 1 minute), resulting in an about 360-fold increase in fluorescence intensity (FIG. 5A) relative to Compound B1 alone in buffer. The slight time-dependent decrease in intensity is likely due to photobleaching.

Addition of Compound 4 to WT-TTR reveals that binding was not sufficient to afford fluorescence within 3 minutes. Instead, amide-bond-mediated conjugate formation is required, which proceeded with a 24 hour time-course (FIG. 5A), as discerned by the progressive increase in TTR-(stilbene)$_2$ conjugate fluorescence. The addition of Compound 2 to WT-TTR further demonstrated that binding alone (within 1 minute) was insufficient for the acquisition of fluorescence. Instead conjugation was required, which occurred over a much faster time course ($t_{50}$=22 minutes) owing to the more reactive thioester in Compound 2 relative to the ester in Compound 4 (FIG. 5C).

Figure 8A:
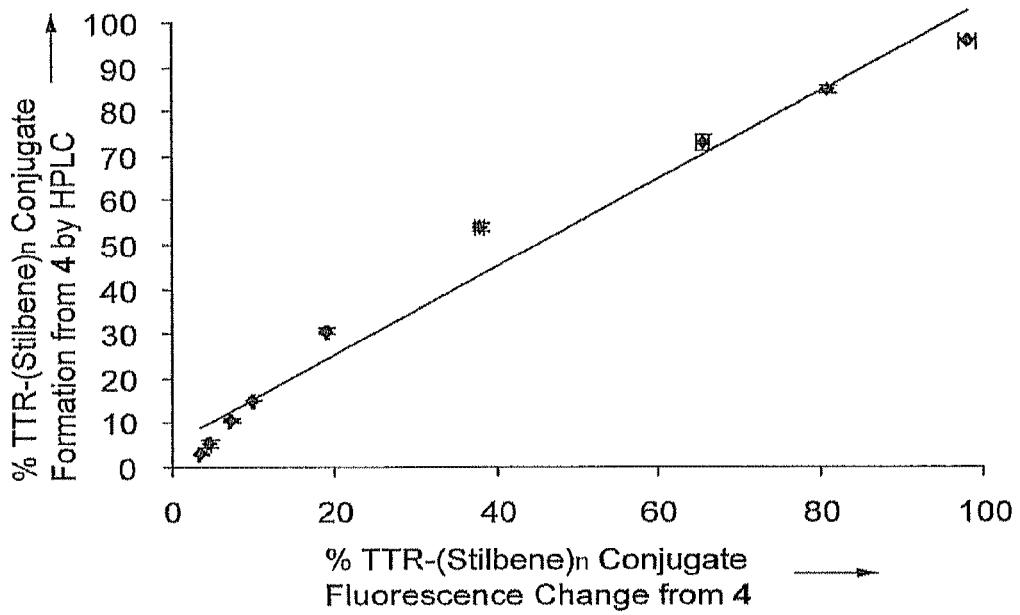
Figure 8B:
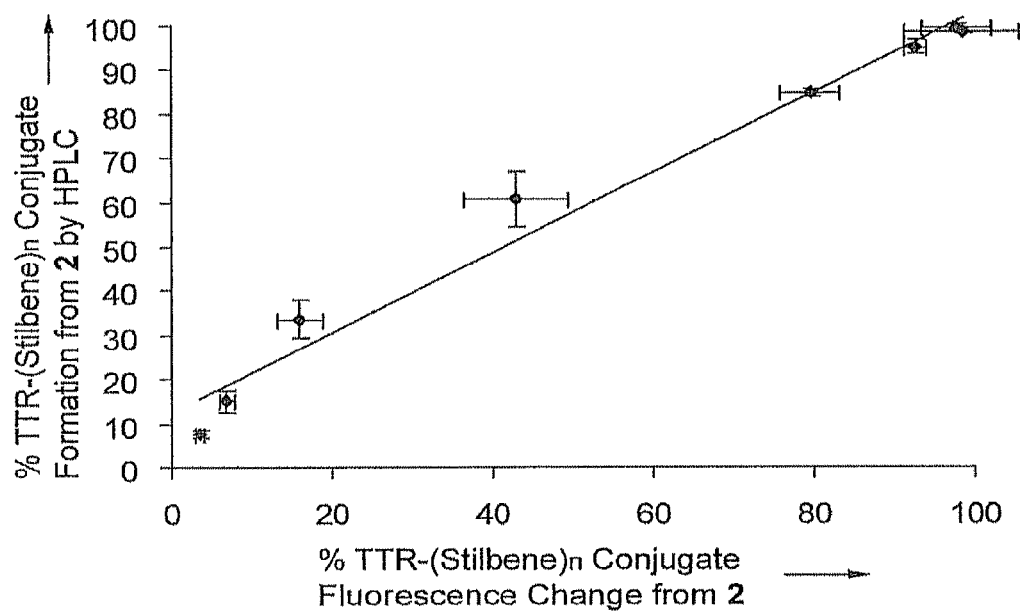
FIG. 8B shows the similar relationship for the reacted Compound 2-TTR conjugate.

The data of FIG. 8 show that the rate of Compound 4 or Compound 2 amide bond conjugation to recombinant WT-TTR, monitored by RP-HPLC, correlates precisely with the time-dependent increase in TTR-(stilbene)$_2$ conjugate fluorescence. These data provide further evidence that both binding and amide-bond-mediated TTR conjugation are required to observe fluorescence.

Fluorescence-Based Assay of for Binding Non-Fluorescent, Non-Covalent TTR Kinetic Stabilizers One application of these non-fluorescent stilbenes that bind to and modify TTR to create a fluorescent stilbene-TTR conjugate is demonstrated by development of an assay for the discovery of non-covalent TTR kinetic stabilizers. The process of TTR tetramer dissociation, monomer mis-folding and aggregation into cross-β-sheet amyloid fibrils is thought to cause the transthyretin amyloid diseases. [Johnson et al., *Acc. Chem. Res.* 2005, 38:911; Sekijima et al., *Cell* 2005, 121:73; and Reixach et al., *Proc. Natl. Acad. Sci. U.S.A.* 2004, 101: 2817].

Previously, the identification of promising kinetic TTR stabilizers required two separate assays: the acid-mediated TTR fibril formation assay [Lashuel et al., *Biochemistry* 1999, 38:13560] and the plasma TTR binding selectivity assay. [Purkey et al., *Proc. Natl. Acad. Sci. U.S.A.* 2001, 98:5566]. Data from these 2 assays were integrated to create an individual efficacy score, (Equation 1, below) that reliably ranks potent and selective TTR kinetic stabilizers. [Johnson et al., *J. Med. Chem.* 2008, 51:6348; and Johnson et al., *J. Med. Chem.* 2009, 52:1115].

$$\text{Individual Efficacy Score} = (100\% - \% \text{ FF}) \times (1 + \text{PS})/300\% \quad \text{(Equation 1)}$$

where FF=Fibril Formation, and
PS=Plasma TTR Binding Stoichiometry.

The efficacy score exhibits a maximum of 1 for the most potent and selective TTR kinetic stabilizers and a minimum of 0 for a poor compound.

Figure 6A:
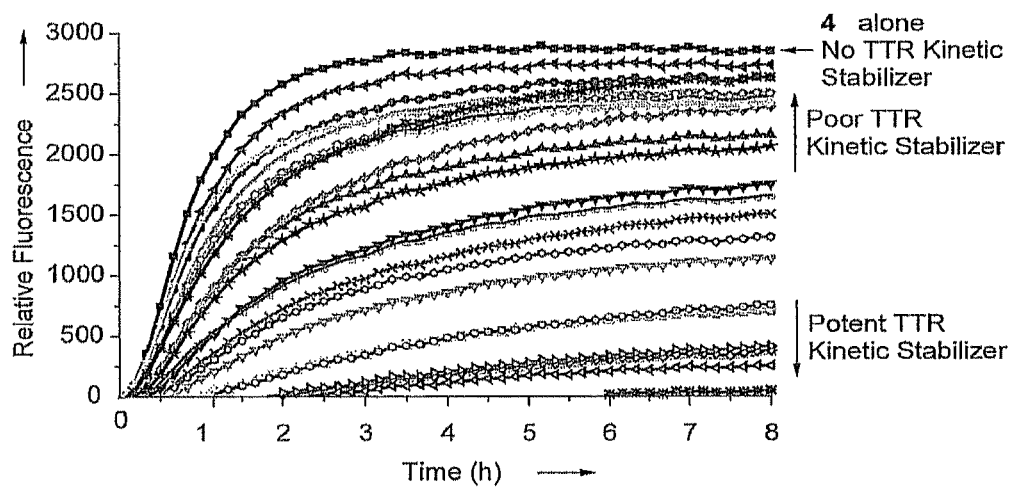
FIG. 6A shows results from a series of TTR fluorescence conjugation competition assays useful for discovering non-covalent TTR kinetic stabilizers using a competition between covalent TTR modifier Compound 4 and established non-covalent TTR kinetic stabilizers with known amyloid inhibition potencies and plasma binding stoichiometries in which the TTR-(stilbene)$_{\leq 2}$ conjugate fluorescence over an 8 hour time course from Compound 4 alone is shown in the uppermost line, whereas fluorescence over the same time course resulting from competition of Compound 4 with noncovalent TTR kinetic stabilizers with known individual efficacy scores comprising amyloid inhibition potency and plasma binding stoichiometry is shown in the remaining traces.
Figure 6B:
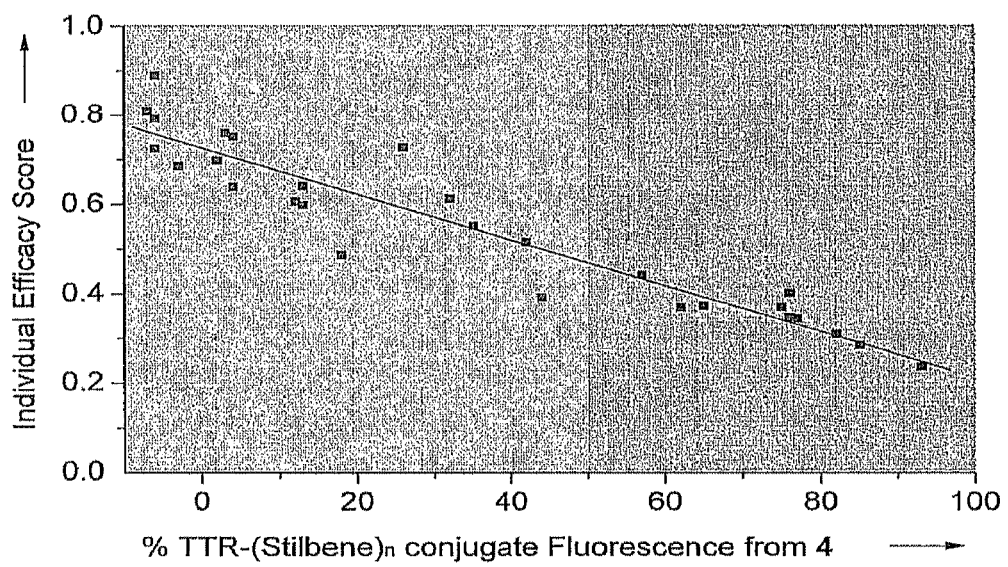
FIG. 6B illustrates the correlation between the extent of TTR conjugate fluorescence from reacted Compound 4 and the kinetic stabilizer efficacy scores after 3 hours of competition.

The suitability of the "TTR fluorescence conjugation competition assay", revealed here, to discover potent and selective non-covalent TTR kinetic stabilizers was probed in FIG. 6A. This assay is centered around a competition between Compound 4 (7.2 μM) binding to and reacting with recombinant WT-TTR (3.6 μM) to create a fluorescent conjugate versus the binding of unreactive kinetic stabilizers (7.2 μM) in buffer to inhibit binding and conjugation by Compound 4.

This assay was validated by use of twenty-eight unreactive kinetic stabilizers that exhibit a wide range of previously determined efficacy scores (structures and scores are shown below). The linear correlation between the decrease in TTR-(stilbene)$_2$ conjugate fluorescence (measured after a 3 hours of competition) and the increase in the efficacy score of the kinetic stabilizers [Johnson et al., J. Med. Chem. 2008, 51:6348; and Johnson et al., J. Med. Chem. 2009, 52:1115] was striking (FIG. 6B), demonstrating that the lower the stilbene-TTR conjugate fluorescence, the greater the binding affinity and selectivity the non-covalent TTR kinetic stabilizer. Similar findings were made using human plasma as the TTR source and the same group of unreactive kinetic stabilizers and covalent kinetic stabilizers.

Chemical structures of the previously characterized TTR kinetic stabilizer Compounds S1-S28 and their individual efficacy scores, shown as a decimal fraction, are shown below.

S1
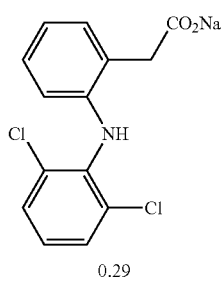
0.29

S2
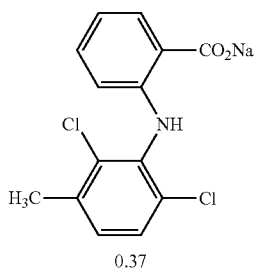
0.37

S3
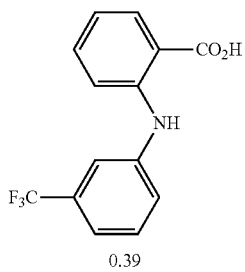
0.39

-continued

S4
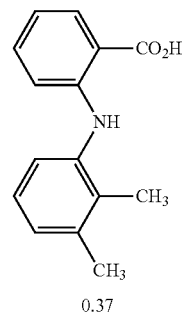
0.37

S5
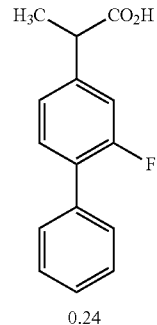
0.24

S6
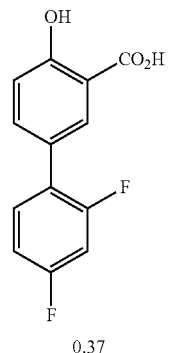
0.37

S7
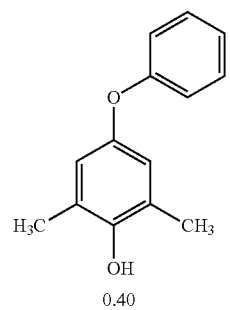
0.40

-continued
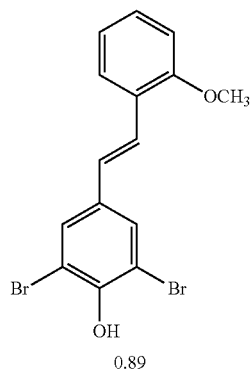
0.89
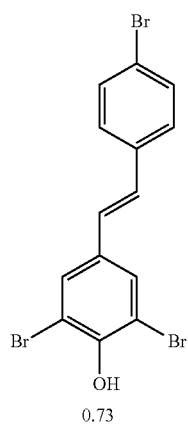
0.73
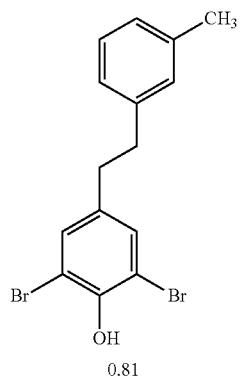
0.81
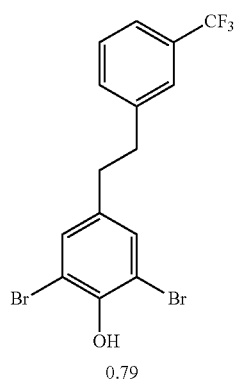
0.79
-continued
S8
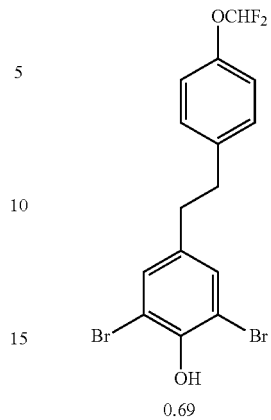
0.69
S9
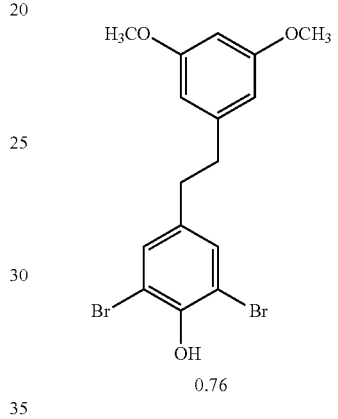
0.76
S10
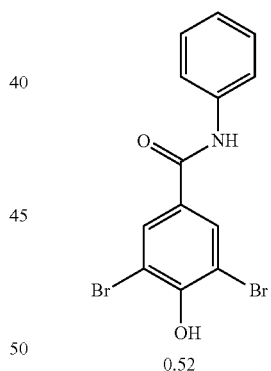
0.52
S11
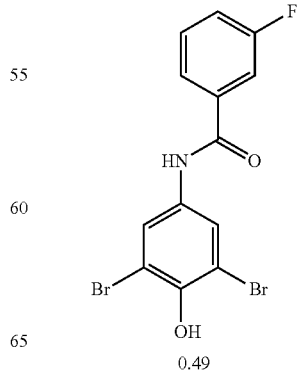
0.49
S12
S13
S14
S15

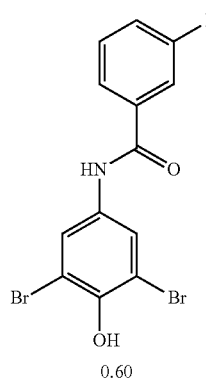
0.60
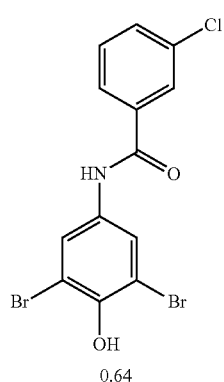
0.64
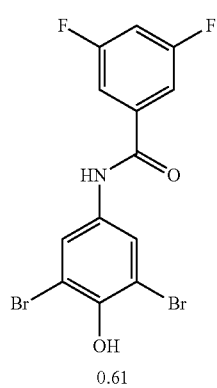
0.61
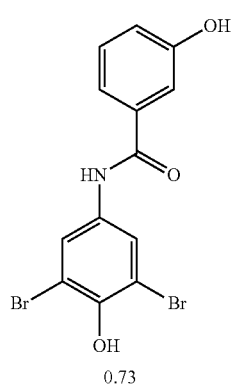
0.73
S16
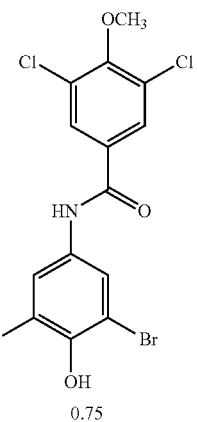
0.75
S17
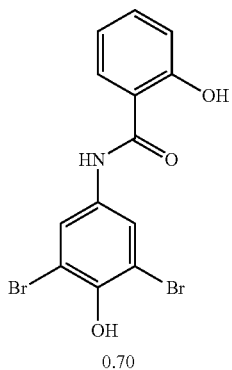
0.70
S18
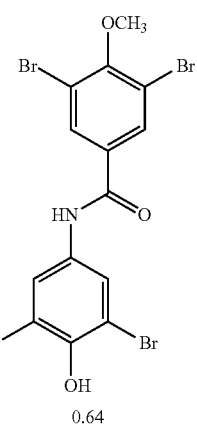
0.64
S19
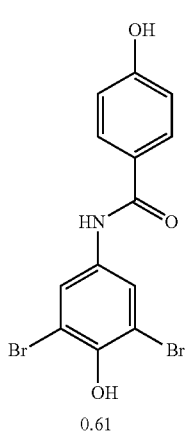
0.61
S20
S21
S22
S23

-continued

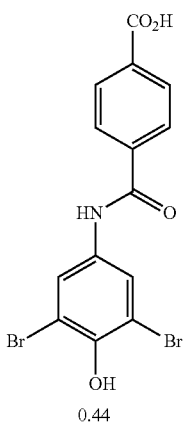
0.44

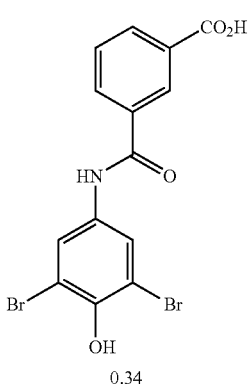
0.34

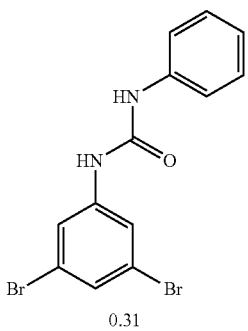
0.31

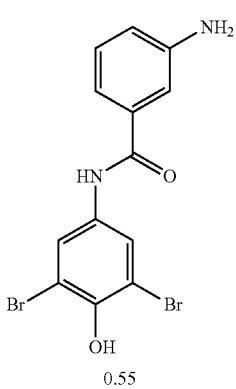
0.55

-continued

S24

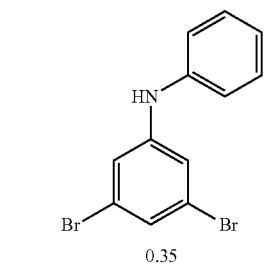
0.35

S28

Chemoselective Conjugation of A2 to WT-TTR in Buffer Creating Blue Fluorescence

The ability of compounds A1 and A2, auxochromic analogs of previously discussed stilbenes [Klabunde et al., Nat. Struct. Biol. 2000, 7, 312-321; Connelly et al., Curr. Opin. Struc. Biol. 2010, 20, 54-62; Johnson et al., J. Med. Chem. 2008, 51, 6348-6358; Choi et al., J. Am. Chem. Soc. 2010, 132, 1359-1370; Choi et al., Nat. Chem. Biol. 2010, 6, 133-139; and Baures et al., Bioorg. Med. Chem. 1998, 6, 1389-1401] to form a chemoselective amide bond with the K15 residue of TTR was assessed by reverse-phase-HPLC and liquid chromatography-mass spectrometry analysis. Incubating WT-TTR (3.6 μM) with A1 or A2 (7.2 μM, due to the two thyroxine binding sites per TTR homotetramer) in phosphate buffer (pH 7) exhibits two peaks of nearly equal intensity. Because only 2 of the 4 subunits comprising the tetramer can be modified by A2, an about 1:1 peak ratio is the expected result for binding and chemoselective conjugation (the change in molar absorbtivity of the conjugate was accounted for, note the slightly increased intensity of the conjugate). Analogous incubation of A1 or A2 with the K15A-TTR homotetramer followed by HPLC analysis revealed no conjugation, consistent with the K15 TTR residue being essential for chemoselective conjugation (Figure S1A and S1B, right panels). The binding of the covalent modifier A2 to K15A-TTR (in the absence of amide bond conjugation) was confirmed by incubating A2 with K15A-TTR in phosphate buffer (pH 7) followed by K15A immunoisolation using a Sepharose® resin-conjugated anti-TTR polyclonal antibody [Purkey et al., Proc. Natl. Acad. Sci. U.S.A. 2001, 98, 5566-5571]. After the dissociation of K15A-TTR and bound A2 at high pH, HPLC analysis showed that 0.88 equivalents out of maximum 2 equivalents of A2 were non-covalently bound to K15A-TTR, an underestimation of bound A2 owing to the washing steps preceding dissociation.

Furthermore, compound A2 was evaluated to determine its ability to bind selectively to and then react chemoselectively with TTR over the 4000+ other proteins in human blood plasma. Compound A2 (10.8 μM) was incubated with human blood plasma (TTR concentration is 3.6-5.4 μM) for 24 hours at 37° C. before immunoisolating human TTR using a Sepharose® resin-conjugated anti-TTR polyclonal antibody [Purkey et al., Proc. Natl. Acad. Sci. U.S.A. 2001, 98, 5566-5571]. After dissociation of TTR from the resin-linked antibody at high pH, HPLC analysis revealed the ratio of TTR monomer and TTR monomer covalently attached to the benzoyl portion of A2 via amide bond formation is effectively 1:1 (taking into account the differences in molar absorbtivity).

Compound A2 must exhibit very high binding selectivity to TTR in human plasma in order to chemoselectively label 48% of the TTR subunits through amide bond formation, as only 2 of the 4 subunits comprising the tetramer can be modified, corresponding to maximal subunit labeling of 50%. Mass spectrometric analysis of the conjugate showed the expected masses [Choi et al., *Nat. Chem. Biol.* 2010, 6, 133-139]. It is clear that these second generation auxochromic stilbenes exhibit exceptional binding selectivity and amide bond forming chemoselectivity to TTR, comparable to the first generation stilbenes. This will be important for determination of plasma TTR concentration and kinetic stabilizer binding stoichiometry to TTR (see discussion) [Choi et al., *Nat. Chem. Biol.* 2010, 6, 133-139].

Although incubation of recombinant WT-TTR with A1 or A2 in phosphate buffer (pH 7) for 18 hours produced bright blue fluorescence resulting from amide bond conjugation, barely detectable fluorescence resulted from A1 or A2 alone in buffer. Notably, no significant fluorescence increase was observed when A2 was incubated with the recombinant K15A-TTR homotetramer, which binds A2, but cannot amide bond conjugate. A red shift in the weak, but detectable fluorescence of A1 was observed with K15A-TTR, providing evidence that it is binding to the $T_4$ binding sites within K15A-TTR, but not reacting.

Incubation of unreactive B2 (7.2 μM), comprising a built-in amide bond, with WT-TTR (3.6 μM) for 10 minutes reveals a significant increase in fluorescence intensity. Collectively, these data support the hypothesis that amide bond linkage of the benzoyl portion of A1 or A2 to TTR enhances WT-TTR-(stilbene)$_2$ conjugate fluorescence. In stark contrast to A2 which remains non-fluorescent upon binding to K15A-TTR, B2 exhibited an approximately 4-fold increase in fluorescence intensity upon binding to K15A-TTR, providing additional evidence that this family of stilbenes binds to K15A-TTR. The fluorescence intensity was diminished relative to WT-TTR binding, presumably due to changes in the $T_4$ binding site environment or dynamics associated with the K15A mutant [Hammarstrom et al., *Biochemistry* 2001, 40, 11453-11459].

We also incubated A2 with recombinant WT- or K15A-TTR and the resulting solution fluorescence was detected using a hand-held UV lamp (365 nm). Although intense blue fluorescence resulted from the incubation of WT-TTR with A2, no fluorescence was observed when K15A-TTR was incubated with A2. In contrast, intense blue fluorescence was produced when amide B2 was incubated with either WT-TTR or K15A-TTR. The reaction chemoselectivity of A2 for WT-TTR was further demonstrated by the observation that WT-TTR, but not K15A-TTR, was detected by conjugate fluorescence on an SDS-PAGE gel.

Investigating the Mechanism by which Stilbene Conjugation to TTR Creates Blue Fluorescence The data outlined above and presented below suggest that amide bond conjugation is required for the observation of TTR-(stilbene)$_{n\leq2}$ conjugate fluorescence. As mentioned above, it is unusual that stilbenes remain dark when bound to proteins, including TTR, and in this regard we hypothesize that stilbene A2 could be especially useful for cellular imaging.

What makes A2 atypical in this regard? To answer this question, it is useful to consider the excited state relaxation mechanism available to most stilbenes [Gorner, H.; Kuhn, H. J. *Adv. Photochem.* 1995, 19, 1-117; Malkin et al., *J. Phys. Chem.* 1964, 68, 1153-1163; Saltiel, J. *J. Am. Chem. Soc.* 1967, 89, 1036-1037; Saltiel et al., *J. Am. Chem. Soc.* 1972, 94, 6445-6457; Saltiel et al., *J. Am. Chem. Soc.* 1979, 101, 2982-2996; and Saltiel et al., *J. Am. Chem. Soc.* 1968, 90, 4759-4760].

Upon promotion of an electron from the stilbene HOMO to the LUMO, a singlet excited state is formed that repopulates the ground state in solution primarily by isomerization to a cis-stilbene, and to a lesser extent by stilbene fluorescence [Gorner, H.; Kuhn, H. J. *Adv. Photochem.* 1995, 19, 1-117; Malkin et al., *J. Phys. Chem.* 1964, 68, 1153-1163; Saltiel, J. *J. Am. Chem. Soc.* 1967, 89, 1036-1037; Saltiel et al., *J. Am. Chem. Soc.* 1972, 94, 6445-6457; Saltiel et al., *J. Am. Chem. Soc.* 1979, 101, 2982-2996; and Saltiel et al., *J. Am. Chem. Soc.* 1968, 90, 4759-4760]. The trans form of the singlet excited state can twist about the central C—C bond orienting the planes of the two aryl rings perpendicular to each other, affording a mixture of cis and trans isomers after internal conversion and conformational relaxation [Gorner, H.; Kuhn, H. J. *Adv. Photochem.* 1995, 19, 1-117; Malkin et al., *J. Phys. Chem.* 1964, 68, 1153-1163; Saltiel, J. *J. Am. Chem. Soc.* 1967, 89, 1036-1037; Saltiel et al., *J. Am. Chem. Soc.* 1972, 94, 6445-6457; Saltiel et al., *J. Am. Chem. Soc.* 1979, 101, 2982-2996; and Saltiel et al., *J. Am. Chem. Soc.* 1968, 90, 4759-4760].

Although TTR can bind to small molecules composed of two aromatic rings when the tethered rings are up to 40° out of plane {based on TTR-stilbene crystal structures [Klabunde et al., *Nat. Struct. Biol.* 2000, 7, 312-321; Connelly et al., *Curr. Opin. Struc. Biol.* 2010, 20, 54-62; Johnson et al., *J. Med. Chem.* 2008, 51, 6348-6358; Choi et al., *J. Am. Chem. Soc.* 2010, 132, 1359-1370; Choi et al., *Nat. Chem. Biol.* 2010, 6, 133-139; Baures et al., *Bioorg. Med. Chem.* 1998, 6, 1389-1401; and Baures et al., *Bioorg. Med. Chem.* 1999, 7, 1339-1347]}, it would be energetically unfavorable to bind the excited singlet state in a conformation where the two aryl rings are oriented perpendicular to one another. Thus, we propose that the increase in fluorescence quantum yield of B2 from 0.09 in buffer to 0.55 in complex with TTR results from the resculpted excited singlet state energy surface of the stilbene in complex with TTR, such that the trans-conformer is the only state of relatively low potential energy [Gorner, H.; Kuhn, H. J. *Adv. Photochem.* 1995, 19, 1-117; Malkin et al., *J. Phys. Chem.* 1964, 68, 1153-1163; Saltiel, J. *J. Am. Chem. Soc.* 1967, 89, 1036-1037; Saltiel et al., *J. Am. Chem. Soc.* 1972, 94, 6445-6457; Saltiel et al., *J. Am. Chem. Soc.* 1979, 101, 2982-2996; and Saltiel et al., *J. Am. Chem. Soc.* 1968, 90, 4759-4760] inhibiting photoisomerization-based relaxation of B2. That B2 binding to TTR inhibits B2 photoisomerization is consistent with the observation that the irradiation of B2 in buffer (Life Technologies, TFX-35M, 312 nm) for 10 seconds affords 60% of the cis isomer, along with other minor photoreaction products, whereas irradiation of B2 bound to TTR yields only 20% cis isomer.

It appears that the increase in fluorescence quantum yield of A2 from 0.00 in buffer to 0.27 in the TTR-(stilbene)$_{n\leq2}$ conjugate is only partly explained by the mechanism proposed for B2 [Gorner, H.; Kuhn, H. J. *Adv. Photochem.* 1995, 19, 1-117; Malkin et al., *J. Phys. Chem.* 1964, 68, 1153-1163; Saltiel, J. *J. Am. Chem. Soc.* 1967, 89, 1036-1037; Saltiel et al., *J. Am. Chem. Soc.* 1972, 94, 6445-6457; Saltiel et al., *J. Am. Chem. Soc.* 1979, 101, 2982-2996; and Saltiel et al., *J. Am. Chem. Soc.* 1968, 90, 4759-4760]. That A2 is different from B2 is supported by observation that A2 does not readily form the cis isomer or undergo photoreactions upon irradiation in buffer for 10 seconds. Nor does A2 fluoresce upon binding to K15A-TTR. It is also notable that the fluorescence intensity of A2 does not increase appreciably in dichloromethane, unlike B2, which is an environmentally sensitive fluorophore.

The very low fluorescence intensity of A2 combined with its resistance to photoisomerization suggests that the thioester comprising A2 quenches its fluorescence, both in solution and when bound to K15A-TTR. However, upon amide bond formation with TTR, the conjugate derived from A2 becomes fluorescent because the stilbene is no longer quenched by the thioester functionality and because the perpendicular excited singlet state conformation cannot be accommodated in the TTR-(stilbene)$_{n\leq2}$ conjugate structure, inhibiting the photoisomerization-based relaxation.

The formation of the perpendicular excited singlet state conformation required for photoisomerization is envisioned to be even more energetically inaccessible in the amide bond conjugate, as the aryl ring occupying the inner $T_4$ binding subsite is rigidly held through complementary non-covalent interactions [Klabunde et al., Nat. Struct. Biol. 2000, 7, 312-321; Connelly et al., Curr. Opin. Struc. Biol. 2010, 20, 54-62; Johnson et al., J. Med. Chem. 2008, 51, 6348-6358; Choi et al., J. Am. Chem. Soc. 2010, 132, 1359-1370; Choi et al., Nat. Chem. Biol. 2010, 6, 133-139; Baures et al., Bioorg. Med. Chem. 1998, 6, 1389-1401; Baures et al., Bioorg. Med. Chem. 1999, 7, 1339-1347; Petrassi et al., J. Am. Chem. Soc. 2000, 122, 2178-2192; Razavi et al., Angew. Chem. Int. Ed. Engl. 2003, 42, 2758-2761; Purkey et al., Chem. Biol. 2004, 11, 1719-1728; Johnson et al., J. Med. Chem. 2008, 51, 260-270; Johnson et al., J. Med. Chem. 2009, 52, 1115-1125; Petrassi et al., J. Am. Chem. Soc. 2005, 127, 6662-6671; Wiseman et al., J. Am. Chem. Soc. 2005, 127, 5540-5551; Adamski-Werner et al., J. Med. Chem. 2004, 47, 355-374; Green et al., J. Am. Chem. Soc. 2003, 125, 13404-13414; Oza et al., Bioorg. Med. Chem. Lett. 1999, 9, 1-6; Oza et al., J. Med. Chem. 2002, 45, 321-332; Miller et al., Lab. Invest. 2004, 84, 545-552; and Johnson et al., J. Med. Chem. 2005, 48, 1576-1587] and the ring occupying the outer $T_4$ binding subsite is covalently tethered to the protein through a m-amide linkage [Choi et al., Nat. Chem. Biol. 2010, 6, 133-139]. The thioester stilbene quenching hypothesis is supported by observations that A1 and B2 are quenched, dose dependently, by the addition of mM concentrations of thiophenol.

Antibodies that bind to stilbenes and have aromatic side chains in their stilbene binding sites can form either fluorescence exciplexes or charge-transfer-based luminescent antibody-stilbene complexes [Simeonov et al., Science 2000, 290, 307-313; Debler et al., Science 2008, 319, 1232-1235]. However, the TTR stilbene binding sites do not comprise any aromatic residues, making an exciplex fluorescence or charge-transfer luminescence explanation unlikely [Simeonov et al., Science 2000, 290, 307-313; Debler et al., Science 2008, 319, 1232-1235]

Summing up the mechanistic details; A2 remains dark, even if bound to proteins, including TTR, because of a thioester quenching mechanism. Upon amide bond conjugation to TTR, the fluorescence quantum yield of the blue conjugate is reasonably high because the trans-to-cis photoisomerization mechanism is energetically disfavored owing to TTR binding and photobleaching is minimized by the lower energy excitation and emission resulting from the dimethylamino auxochromic substituent on one of the aromatic rings.

Kinetics of TTR Fluorescent Conjugate Formation at 37° C. in Human Cell Lysate

Because the one-chain, one-binding-site TTR tag being created is envisioned to be useful for doing pulse-chase studies in the secretory pathway of eukaryotic cells, the kinetics of WT-TTR modification by A2 in concentrated cell lysate was investigated. HeLa cell lysate was employed because these cells do not make transthyretin. We added WT-TTR at a final concentration of 2 µM (tetramer) to the HeLa cell lysate (2 µg/µL total protein concentration) to which A2 (6 µM) was added. At 37° C., the conjugate formed with a $t_{50}$ of 18 minutes, within experimental error of the $t_{50}$ (19 minutes) of TTR (2 µM) conjugate formation with A2 (6 µM) in phosphate buffer (pH 7). That A2 remains dark, even if bound to other proteins in the absence of TTR, is demonstrated by the HeLa cell lysate (2 µg/µL total protein concentration) incubated with A2 (2 µM) for 180 minutes.

Selectivity of the A2 TTR Conjugation Reaction at 37° C. in Human Cell Lysate

The ability of A2 to form a chemoselective amide bond with the K15 residue of TTR in cell lysate was assessed by RP-HPLC and LC-MS analysis. Incubating WT-TTR (5 µM) with A2 (15 µM) in 900 µL of HeLa cell lysate (2 µg/µL total protein concentration, excluding TTR) exhibits peaks of nearly equal intensity (the molar absorptivity changes associated with benzoylation were accounted for) demonstrating high binding selectivity and a highly chemoselective amide bond forming reaction with TTR (49% out of a maximum of 50% of the subunits were modified). Immunoisolation of TTR affords the expected mass resulting from conjugate formation (14,185 m/z [M+H] for benzoylation by A2). The equal rates of TTR conjugate formation in HeLa cell lysate and in buffer demonstrate that the binding selectivity of A2 to TTR and the chemoselectivity of amide bond conjugation to TTR are excellent in complicated biological environments.

Detection of WT-TTR in Transfected HeLa Cells and in Huh-7 Human Liver Cells

Having demonstrated that A2 is a non-fluorescent stilbene in solution and in HeLa cell lysate not containing TTR, we next investigated whether specific labeling of TTR could be achieved in the complex environment of the eukaryotic cellular secretory pathway.

Secreted WT-TTR was produced in HeLa cells by transient transfection and the cells were treated with A2 for 1 hour prior to imaging using confocal fluorescence microscopy. The expression of WT-TTR in the HeLa cells after transient transfection was confirmed using western blot analysis, as was the absence of TTR in the empty vector control. Only HeLa cells expressing WT-TTR, and not cells transfected with empty vector (control), afforded strong conjugate fluorescence upon A2 treatment. Indirect TTR immunofluorescence afforded an analogous image, revealing that TTR was being imaged by A2 treatment. TTR conjugate fluorescence co-localized with calnexin indirect immunofluorescence, a marker for the endoplasmic reticulum (ER), confirming that WT-TTR within the secretory pathway is being observed. TTR conjugate fluorescence is also expected in the Golgi and in secretory vesicles, explaining why TTR conjugate fluorescence is observed in organelles in addition to the ER.

We also demonstrated that endogenous TTR could be detected with A2-derived fluorescence in a common cell line secreting TTR, which is challenging, as the low quantities of TTR being detected are undergoing folding and tetramerization in the endoplasmic reticulum, vesicular trafficking to the Golgi, followed by vesicular trafficking to the plasma membrane and release into the media [Sekijima et al., Cell 2005, 121, 73-85].

Although A2 treatment gave no significant fluorescence in human fibroblasts, consistent with reports that these cells do not make TTR [Su et al., Proc. Natl. Acad. Sci. USA 2004, 101, 6062-6067], the A2-treated Huh-7 human liver (hepatoma) cells afforded strong fluorescence that colocalized with calnexin immunofluorescence. The confocal fluorescence observations are consistent with substantial evidence that the liver secretes the vast majority, if not all, of the TTR into the human bloodstream [Felding et al., Biochimica et Biophysica Acta 1982, 716, 446-9]. That TTR could be visualized in the secretory pathway addresses the sensitivity of A2-derived TTR fluorescent conjugate-based detection [Sekijima et al., Cell 2005, 121, 73-85].

Pulse-Chase Study Demonstrating WT-TTR Secretion from HeLa Cells

Because imaging WT-TTR in the secretory pathway of HeLa cells post-transfection employing A2 is feasible and A2 conjugation kinetics in HeLa cell lysate is sufficiently rapid, we next utilized A2-based fluorescence to label WT-TTR in a pulse-chase study in living, transiently transfected HeLa cells. WT-TTR in HeLa cells (48 hours post-transfection) was labeled using a 20 µM A2 pulse for 30 minutes, followed by a chase employing C1, below,

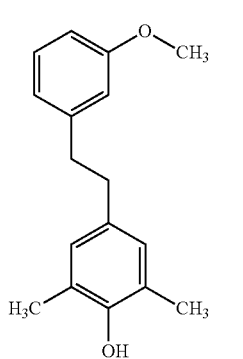

C1

(10 µM) over a 2 hour time course. C1 is a non-fluorescent, highly selective, non-covalent, dihydrostilbene-based TTR binder [Choi et al., *J. Am. Chem. Soc.* 2010, 132, 1359-1370]. Although notable TTR conjugate fluorescence was observed 30 and 60 minutes into the chase period, no conjugate fluorescence was detected after 120 minutes, indicating that the WT-TTR has been secreted out of the cells over that period. The movement of TTR through the secretory pathway in our pulse-chase study is consistent with previous data from BHK and MMH cells transiently over expressing WT-TTR demonstrating that WT-TTR secretion takes about 90 minute [Sekijima et al., *Cell* 2005, 121, 73-85]. It appears that the 20 minute $t_{50}$ for TTR fluorescent conjugate formation observed in HeLa cell lysate is a reasonable facsimile for what happens in a transiently transfected living HeLa cell, as a 30 minute pulse afforded a strong signal in the pulse-chase study that disappeared over time as a consequence of the C1 chase and secretion on the expected 2 hour scale, with TTR secretion into the medium being confirmed. The reaction kinetics of A2 would become problematic if higher time resolution than tens of minutes were required for a particular application.

Discussion

A non-fluorescent, second generation, auxochromic stilbene A2 is described that very selectively binds to transthyretin in the eukaryotic cellular secretory pathway (remains dark in mammalian cells lacking TTR) and then chemoselectively reacts with a pKa perturbed Lys-15 ε-amino group in TTR-creating a bright blue fluorescent conjugate. Stilbene A2 exhibits sufficiently rapid TTR conjugation kinetics at 37° C. to enable pulse-chase studies to be performed within the secretory pathway of HeLa cells, demonstrating that transthyretin can be imaged as it transits through the secretory pathway. The progress reported is viewed as a first and necessary step toward our long-term goal of creating a one-chain, one-binding-site transthyretin tag that can be used in the eukaryotic secretory pathway to follow protein secretion and turnover utilizing A2, or an analogous molecule. A1 though the reaction kinetics of A2 with TTR are well-suited for studying the folding, trafficking, secretion and degradation of TTR and TTR-tagged proteins, other thiol containing functional groups (required to keep the latent fluorophores dark) with faster reaction kinetics are being explored to carry out pulse-chase studies with higher time resolution.

An immediate application of A2 is to utilize the conjugate fluorescence to quantify TTR concentration in human plasma. The TTR concentration in plasma is an established metric of nutritional status and is an often used clinical laboratory test [Ingenbleek, *Ann. Rev. Nutrition* 1994, 14, 495-453]. A2 demonstrates sufficient binding selectivity to TTR in human plasma and amide bond reaction chemoselectivity with Lys-15 in TTR to create a new method that would replace the error-prone immunoprecipitation-turbidity assay widely used in clinical laboratories today to quantify TTR plasma levels.

Another immediate application of A2 is the quantification of kinetic stabilizer binding stoichiometry to rare variants of TTR in human plasma [Purkey et al., *Proc. Natl. Acad. Sci. U.S.A.* 2001, 98, 5566-5571]. Tafamidis, below,

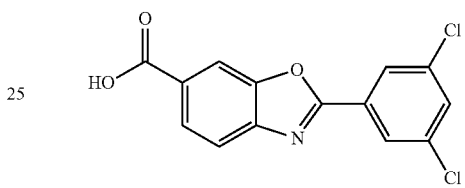

a TTR kinetic stabilizer disclosed in Kelly et al. U.S. Pat. No. 7,214,695 [Razavi et al., *Angew. Chem. Int. Ed. Engl.* 2003, 42, 2758-2761], has recently been shown in a phase II/III placebo-controlled clinical trial to halt the progression of familial amyloid polyneuropathy (FAP). Negatively cooperative binding of Tafamidis to one of the two $T_4$ binding sites in the TTR tetramer is sufficient to increase the kinetic barrier for tetramer dissociation (through selective ground state stabilization) such that it becomes insurmountable under physiological conditions-inhibiting amyloidogenesis that causes FAP [Johnson et al., *Acc. Chem. Res.* 2005, 38, 911-921; Hammarstrom et al., *Science* 2003, 299, 713-716; Hammarstrom et al., *Science* 2001, 293, 2459-62; and Lai et al., *Biochemistry* 1997, 36, 10230-10239].

Although the human oral dose required for occupancy of more than one TTR binding site is known for the most common TTR FAP-associated mutations, this has not been established for all mutations. It is now feasible to utilize A2-derived conjugate fluorescence to measure the stoichiometry of kinetic stabilizers, such as Tafamidis, bound to TTR in patient plasma using an A2-kinetic stabilizer competition assay. After assay optimization, physicians could use such an approach to titrate the dose of kinetic stabilizer to be used in patients with rare mutations to be sure that the kinetic stabilizer occupies at least one TTR binding site per tetramer [Wiseman et al., *J. Am. Chem. Soc.* 2005, 127, 5540-5551]. Because there are over one hundred TTR mutations that cause FAP, developing the A2 method for determining kinetic stabilizer TTR binding stoichiometry is important and especially timely, because Tafamidis, the first kinetic stabilizer to be shown to be efficacious, is expected to become a regulatory agency approved drug during the coming year [Razavi at al., *Angew. Chem. Int. Ed. Engl.* 2003, 42, 2758-2761; Wiseman et al., *J. Am. Chem. Soc.* 2005, 127, 5540-5551; Hammarstrom at al., *Science* 2003, 299, 713-716; and Hammarstrom et al., *Science* 2001, 293, 2459-2462].

Methods

Reverse Phase HPLC Analysis.

Recombinant WT-TTR was expressed as described previously [Lashuel et al., *Biochemistry* 38:13560-13573 (1999)]. For analysis of test compounds with TTR, each compound (1.5 μL in DMSO, 1.44 mM) was added to 300 μL of WT-TTR or K15A mutant TTR (3.6 μM, 10 mM sodium phosphate, 100 mM KCl, 1 mM EDTA, pH 7.0). The samples were vortexed, and incubated for 18 hours at 25° C. Reverse phase high performance liquid chromatography (RP-HPLC) was performed on a Water 600 E multi-solvent delivery system, using a Waters 486 tunable absorbance detector, a 717 autosampler, and a ThermoHypersil Keystone Betabasic-18 column μ150 Å pore size, 3 μm particle size, and mobile phase A; 0.1% TFA in 95% $H_2O$+5% $CH_3CN$ and mobile phase B, 0.1% TFA in 95% $CH_3CN$+5% $H_2O$). Linear gradients were run from 100:0 to 0:100 A:B for 27 minutes.

Fibril Formation of Transthyretin

Compounds (5 μL of 1.44 mM solution in DMSO) were added to 495 μL of TTR (7.2 μM, in 10 mM sodium phosphate, 100 mM KCl, 1 mM EDTA, pH 7.0). The mixtures were vortexed and incubated (maintained) for 18 hours at 25° C. An acidic buffer solution (500 μL, 100 mM acetate, 100 mM KCl, 1 mM EDTA, pH 4.2) was added to obtain a final pH value of 4.4, and the mixtures were incubated at 37° C. for 72 hours without agitation. The solutions were vortexed to evenly distribute any precipitate, and turbidity was measured at 400 nm using a Hewlett Packard model 8453 UV-VIS Spectrophotometer.

Modification of WT-TTR and K15A-TTR by Test Compounds in Human Plasma

The modification ratio of TTR by kinetic stabilizers in human plasma was evaluated as described [Purkey et al., *Proc. Natl. Acad. Sci. U.S.A.* 98:5566-5571 (2001)] with minor modifications. Briefly, compounds (7.5 μL of 1.44 mM solution in DMSO) were added to 1 mL of human plasma and incubated at 37° C. for 24 hours on a rocker (30 rpm). A 1:1 (v/v) slurry of unfunctionalized Sepharose® resin in 10 mM Tris, 140 mM NaCl, pH 8.0 (TSA) was added and the solutions were incubated for 1 hour at 4° C. on a rocker plate, followed by brief centrifugation.

Two 400 μL aliquots of the supernatants were added to 300 μL of 1:1 (v:v) slurry of anti-TTR antibody-conjugated Sepharose® resin in TSA. The solutions were gently rocked at 4° C. for 20 minutes (30 rpm), centrifuged, and supernatants were removed. The resin was washed by shaking for 1 minute in 1 mL of TSA solution containing 0.05% saponin (three times) and then 1 mL of TSA solution (twice). The TTR and bound test compound were dissociated from the resin by adding 155 μL of triethylamine (100 mM, pH 11.5) and vortexing for 1 minute. After centrifugation, 135 μL of solution containing test compound and TTR was analyzed by RP-HPLC as described above except that the linear gradients were run from 100:0 to 0:100 A:B for 45 minutes.

Urea-Induced Dissociation Kinetics Study

Compounds (at 1.25, 2.5, 5, 7.5, and 10 mM in DMSO) were diluted 10 fold in EtOH. Such stocks (7.2 μL) were added to 200 μL of TTR (18 μM, 10 mM sodium phosphate, 100 mM KCl, 1 mM EDTA, pH 7.0) to afford final concentrations of 4.5, 9, 18, 27, and 36 μM. These mixtures were briefly vortexed and incubated for 18 hours at 25° C., before adding 100 μL to 900 μL of 6.67 M urea solution (10 mM sodium phosphate, 100 mM KCl, 1 mM EDTA, pH 7.0). The mixtures were vortexed and incubated in the dark at 25° C. without agitation. CD spectra were measured at 215-218 nm (0.5 nm steps, 5 times, 3 s averages) at the indicated times.

Cell-Based Assay

The human neuroblastoma IMR-32 cell line (CCL-127 ATCC) was maintained in Opti-MEM® medium (Invitrogen), supplemented with 5% FBS, 1 mM Hepes buffer, 2 mM L-glutamine, 100 units/mL penicillin, 100 μg/mL streptomycin and 0.05 mg/mL $CaCl_2$ (complete cell medium). Cells were seeded in black wall, clear bottom, tissue culture treated 96-well plates (Costar) at a density of 6,000 cells/well in complete cell medium and incubated overnight (about 18 hours) at 37° C.

Recombinant WT-TTR purified in the cold was used as the cytotoxic insult. The protein was buffer-exchanged in Hanks' Balanced Salt Solution (HBSS, Mediatech, Manassas, Va.) at 10° C. using a Centriprep® filter device (10 kDa MWCO, Millipore). Compounds (16 mM in DMSO) were diluted 1:1000 with WT-TTR (16 μM in HBSS, filter sterilized) or with HBSS only, vortexed and incubated for 18 hours at 37° C. WT-TTR (16 μM in HBSS) containing the same amount of DMSO was prepared in parallel and incubated under the same conditions.

The medium was removed from the cells and replaced immediately by the TTR/compound mixtures or HBSS previously diluted 1:1 in Opti-MEM® supplemented with 0.8 mg/mL BSA, 1 mM Hepes buffer, 4 mM L-glutamine, 200 units/mL penicillin, 200 μg/mL streptomycin and 0.1 mg/mL $CaCl_2$. The cells were incubated 24 hours at 37° C. Cell viability was evaluated by a resazurin reduction assay.

Briefly, 10 μL of resazurin (500 μM, PBS) was added to each well and fluorescence quantified in a plate reader (Ex/Em 530/590 nm, Tecan Safire 2, Austria) after 1 hour of incubation at 37° C. Cell viability was calculated as percentage of fluorescence relative to cells treated only with vehicle (100% viability) after subtraction of blank fluorescence (wells without cells). Averages and standard errors from 2 independently performed studies, each performed at least in triplicate, were calculated using GraphPrism (San Diego, Calif., US).

Crystallization and Structure of the WT-TTR-(Benzoyl Substructure of Compound 4)$_2$ Complex WT-TTR concentrated to 4 mg/mL in 10 mM sodium phosphate buffer, 100 mM KCl (pH 7.6) was incubated at room temperature with a 5-fold molar excess of Compound 4. The vapor-diffusion sitting drop method was employed for crystallization. Crystals from TTR with Compound 4 grew from 1.395 M sodium citrate, 3.5% v/v glycerol at pH 5.5.

The crystals were cryo-protected with 10% v/v glycerol. Data were collected at beamline GM/CA-CAT 23-IDB at the APS (Advanced Photon Source) at a wavelength of 1.0333 Å. All data sets were integrated and scaled using HKL2000 [Otwinowski et al., *Methods Enzymol.* 276:307-326 (1997)]. The diffraction data from the crystal were indexed in orthorhombic space group $P2_12_12$ with two subunits (one dimer) per asymmetric unit.

Refinement of the Crystal Structure of WT-TTR-(Benzoyl Substructure of 4)$_2$ Complex The crystal structure was determined by molecular replacement using the model coordinates of 2FBR [Green et al., *J. Am. Chem. Soc.* 125:13404-13414 (2003)] with the program Phaser. [Storoni et al., *Acta Crystallogr. D Biol. Crystallogr.* 60:432-438 (2004)] Further model building and refinement were completed using Refmac[3]. [Murshudo et al., *Crystallogr.* 53:240-255 (1997)] Hydrogens were added during refinement and anisotropic B-values calculated. Final models were validated using the JCSG quality control server incorporating Molprobity [Lovell et al., *Proteins* 50:437-450 (2003)], ADIT (rcsb-deposit.rutgers.edu/validate) WHATIF [Vriend, *J. Mol. Graph.* 8:52-56 (1990)], Resolve [Terwilliger, *Acta Crystallogr. D Biol. Crystallogr.* 59:38-44 (2003)], and Procheck [Laskowski et al., *J. Appl. Crystallogr.* 26:283-291 (1993)]. Data collection and refinement statistics are described in Table 2, below. Coordinates and structure factors for the WT-TTR-(benzoyl substructure of Compound 4)$_2$ complex structure have been deposited in the Protein Data Bank (accession code 3HJ0).

TABLE 2

Data collection and refinement statistics for the crystal structure of the WT-TTR-(benzoyl substructure of 4)$_2$ conjugate

| Data Collection | |
| --- | --- |
| Beamline | APS GM/CA-CAT 23-IDB |
| Wavelength (Å) | 1.033 |
| Resolution (Å) | 1.34-50.00 (1.34-1.39) |
| Space group | P2$_1$2$_1$2 |
| a, b, c (Å) | 42.65, 85.46, 63.97 |
| No. of molecules in asymmetric unit | 2 |
| No. of observations | 373,782 (30,010) |
| No. of unique reflections | 52,436 (4,547) |
| Completeness (%) | 98.1 (86.4) |
| R$_{sym}$ (%)$^b$ | 4.9 (24.9) |
| Average I/□ | 33.0 (7.9) |
| Redundancy | 7.1 (6.6) |
| Refinement statistics | |
| Resolution (Å) | 85.44-1.34 |
| No. of reflections (working set) | 49,727 (3,537) |
| No. of reflections (test set) | 2,668 (204) |
| R$_{cryst}$ (%)$^c$ | 14.7 (17.6) |
| R$_{free}$ (%)$^d$ | 18.1 (19.8) |
| Average B-values | (Å$^2$) |
| TTR | 13.0 |
| Ligand | 17.4 |
| Wilson B-value | 14.7 |
| Ramachandran plot | |
| Most favored (%) | 92.5 |
| Additionally allowed (%) | 7.5 |
| Generously allowed (%) | 0 |
| Disallowed (%) | 0 |
| R.M.S deviations | |
| Bond lengths (Å) | 0.016 |
| Angles (°) | 1.62 |

$^a$Numbers in parentheses are for highest resolution shell of data.
$^b$R$_{sym}$ = Σ$_{hkl}$|I − <I>|/Σ$_{hkl}$ I
$^c$R$_{cryst}$ = Σ$_{hkl}$|F$_o$ − F$_c$|/Σ$_{hkl}$ F$_o$
$^d$R$_{free}$ is the same as R$_{cryst}$, but for 5% of data excluded from the refinement.

Competition Assay

Figure 4C:
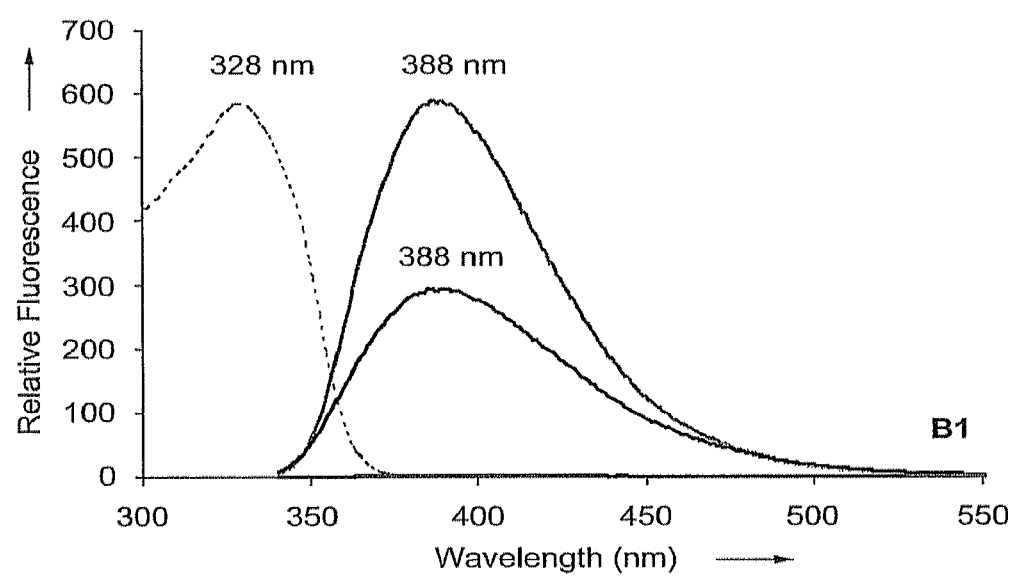

One L of each candidate kinetic stabilizer (0.72 mM in DMSO) was added to 100 μL of recombinant WT-TTR (3.6 μM) in 10 mM sodium phosphate buffer, 100 mM KCl, with 1 mM EDTA (pH 7.0) in a 96-well plate (Costar black, clear bottom). The plate was sealed and vortexed slowly for 4 hours at 25° C., and then 1 μL of covalent TTR modifier Compound 4 (0.72 mM in DMSO) was added to each well. The fluorescence changes were monitored using a microplate spectrophotometer reader (Gemini SpectraMax®, Molecular Devices, Sunnyvale, Calif.) over an 8 hour time course at 37° C. Fluorescence ($\lambda_{ex}$=328 nm and $\lambda_{em}$=384 nm) was measured from the bottom of the plate at 10 minute intervals without shaking (FIGS. 4A-4C).

Fluorimetric Assay with Recombinant Wild Type Transthyretin

WT-TTR was expressed in an *E. coli* expression system and purified as described previously. [Lashuel et al., *Biochemistry* 1999, 38, 13560-13573] The covalent TTR modifiers (A1 or A2) or the non-covalent TTR ligand B2 (5 μL of a 1.44 mM solution in DMSO, final concentration: 7.2 μM) were added to 1 mL of a solution of WT-TTR homotetramer (0.2 mg/mL, 3.6 μM) in 10 mM phosphate, 100 mM KCl and 1 mM EDTA (pH 7.0 phosphate buffer) in a 2 mL Eppendorf tube. The samples were vortexed, and incubated for 18 h at 25° C. The fluorescence changes were monitored using a Varian Cary 50 spectrofluorometer at 20° C. in a 1 cm path length quartz cell. The excitation slit was set at 5 nm and the emission slit was set at 5 mm. The samples were excited at 328 nm and the emission spectra were collected from 350 to 550 nm.

Kinetics of the A2-TTR Conjugation Reaction

The covalent TTR modifier A2 (1 μL of 0.6 mM solution in DMSO, final concentration: 6 μM) was added to 90 μL of HeLa cell lysate (final protein concentration: 2 μg/μL) and 10 μL of WT-TTR (20 μM in pH 7.0 phosphate buffer, final concentration: 2 μM). The time-dependent fluorescence change of the conjugate derived from A2 was monitored utilizing a microplate spectrophotometer reader (Gemini SpectraMax®, Molecular Devices, Sunnyvale, Calif.) for 3 hours at 37° C. The fluorescence ($\lambda_{ex}$=328 nm and $\lambda_{em}$=430 nm) was measured from the bottom of the plate without shaking.

Binding Stoichiometry of A2 to WT- and K15A-TTR

To 1 mL of WT- or K15A-TTR (5 μM in pH 7.0 phosphate buffer) in a 2 mL Eppendorf tube was added A2 (5 μL of a 2 mM solution in DMSO, final concentration: 10 μM) and then the solution was incubated at 37° C. for 24 hours on a rocker plate (30 rpm). A 1:1 (v/v) slurry of unfunctionalized Sepharose® resin in 10 mM Tris, 140 mM NaCl, pH 8.0 (TSA) buffer was added and the solution was incubated for 1 hour at 4° C. on a rocker plate (18 rpm). The solution was then centrifuged and the supernatant was divided into two 400 μL aliquots, which were added to 200 μL of 1:1 (v:v) slurry of anti-TTR antibody conjugated Sepharose® resin in TSA. The solution was gently rocked (18 rpm) at 4° C. for 20 minutes, then centrifuged and the supernatant removed. The resin was washed three times by shaking for 1 minute with 1 mL of TSA. After centrifugation to remove the supernatant, 155 μL of triethylamine (100 mM, pH 11.5) was added to the Sepharose® resin to dissociate the TTR and bound test compound from the resin and the suspension was vortexed for 1 minute. After centrifugation, the supernatant was analyzed by reverse phase HPLC on a Water 600 E multi-solvent delivery system, using a Waters 486 tunable absorbance detector, a 717 autosampler, and a ThermoHypersil Keystone Betabasic-18 column (150 Å pore size, 3 μm particle size). The "A" mobile phase comprises 0.1% TFA in 94.9% H$_2$O+5% CH$_3$CN and the "B" mobile phase is made up of 0.1% TFA in 94.9% CH$_3$CN+5% H$_2$O. Linear gradients were run from 100:0 A:B to 0:100 A:B for 10 minutes.

Quantum Yield Measurement

The covalent TTR modifier A1 or A2 or the non-covalent TTR ligand B2 (15 μL of a 1.44 mM solution in DMSO, final concentration: 7.2 μM) was added to 3 mL of a solution of WT-TTR homotetramer (0.2 mg/mL, 3.6 μM) in 10 mM phosphate, 100 mM KCl and 1 mM EDTA (pH 7.0 phosphate buffer). The samples were vortexed, and incubated for 18 hours at 25° C. Quantum yields were measured by following the instructions at the web site: jobinyvon.com/usadivisions/Fluorescence/applications/quantumyieldstrad.pdf. Quinine bisulfate in 0.5 M H$_2$SO$_4$ was used as a reference for comparison ($\Phi_f$=0.546). [Crosby et al., *J. Phys. Chem.* 1971, 75, 991-1024.]

Indirect Immunofluorescence Detection of TTR

HeLa cells were plated on cover slips in DMEM containing 10% FBS at 37° C. under 5% $CO_2$ the day before they were transfected with pcDNA3.1(+)-empty vector or pcDNA3.1 (+)-WT-TTR using FIG. 6 (Roche) according to the manufacturer's instructions. After 48 hours, the cells were washed with PBS twice before adding fresh DMEM (without FBS) with A2 (final concentration: 10 μM), and the cells were incubated at 37° C. for 1 hour. After two washes with PBS, the cells were fixed at 25° C. for 15 minutes with 3.7% (w/v) paraformaldehyde in PBS. After two washes with PBS, the cells were permeabilized with 0.2% saponin (w/v) in PBS at 25° C. for 15 minutes, followed by blocking at 25° C. for 30 minutes with blocking buffer (10% goat serum (v/v), 0.2% saponin (w/v) in PBS). Cells were incubated for 1 h with anti-TTR (a kind gift from Dr. E. Masliah at UCSD, diluted 1:100) and anti-calnexin (Stressgen, diluted 1:200), washed three times with PBS, and incubated for 1 hour with Alexa Fluor 546 goat anti-rabbit IgG and Alexa Fluor 488 goat anti-mouse IgG (Molecular Probes, A11035 and A11029, respectively) for WT-TTR and calnexin staining. After mounting, microscopic images were acquired by using a fully tunable filter-based emission collection system (Bio-Rad (Zeiss) Radiance 2100 Rainbow laser scanning confocal microscope) that enables the precise collection of 420-460 nm for compound detection (from a 405 nm laser line). Image analyses were performed using either Zen 2008 Light Edition software (Carl Zeiss MicroImaging) or ImageJ software (NIH).

Plasmid Constructs Harboring TTR

The pcDNA3.1(+)-WT-TTR plasmid was produced by ligating the WT-TTR cDNA (excised from the pCMV5-WT-TTR plasmid [Sekijima et al., Cell 2005, 121, 73-85] using HindIII and XhoI restriction sites) into the pcDNA3.1(+) plasmid (Invitrogen). A point mutation in the WT-TTR at position 133 (A>G) was corrected using Quikchange II site-directed mutagenesis (Stratagene) using the following primers (5' to 3'): CCGAGGCAGTCCTGCCATCAATGTGGC (SEQ ID NO:1) and GCCACATTGATGGCAGGACTGC-CTCGG (SEQ ID NO:2). The proper construction of all plasmids was confirmed by DNA sequencing. Restriction endonucleases and Pfu Turbo DNA polymerase were purchased from New England Biolabs and Stratagene, respectively. TTR plasmid DNA was isolated with a QIAprep Spin Miniprep kit (Qiagen Inc.).

Labeling of Endogenous TTR in Cells

Huh-7 cells or Gaucher's patient-derived fibroblasts (Coriell Cell Repositories, GM08760) were maintained in DMEM containing 10% FBS at 37° C. under 5% $CO_2$. The cells were plated the day before compound treatment and imaging. Cells were washed twice with PBS and then treated with A2 (final concentration: 10 μM) for 30 minutes at 37° C. in a $CO_2$ incubator. After two washes, cells were fixed at 25° C. for 15 minutes with 3.7% paraformaldehyde (w/v) in PBS and microscopic images were acquired as described above.

Monitoring Secretion of WT-TTR from HeLa Cells Utilizing a Pulse-Chase Study

HeLa cells were transfected with pcDNA3.1(+)-WT-TTR using Fugene 6 (Roche). After 48 hours post-transfection, the cells were washed with PBS twice before adding fresh DMEM (without FBS) with A2 (final concentration: 20 μM). The cells were incubated at 37° C. for 30 min (pulse) to label the synthesized WT-TTR, followed by the chase using 10 μM C1 [Choi et al., J. Am. Chem. Soc. 2010, 132, 1359-1370] over a time course of 2 hours. After two

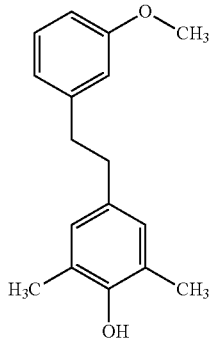

C1 washes, cells were fixed at 25° C. for 15 minutes with 3.7% paraformaldehyde (w/v) in PBS at the indicated times and microscopic images were acquired as described above. The cell culture media was collected at the indicated time points during the pulse-chase experiment and the proteins were precipitated using a methanol/chloroform mixture (4:1 v/v). The protein pellet was solubilized in 8 M urea (pH 8) and half of the mixture was analyzed for the presence of TTR in the media using western blot analysis.

Compound Syntheses

Unless otherwise indicated, all reactions were run under argon gas. Anhydrous solvents were obtained via passage through an activated alumina column and from commercial suppliers. $^1$H and $^{13}$C NMR spectra were recorded on a Bruker 500 MHz spectrometer. Chemical shifts are reported relative to internal $CDCl_3$ ($Me_4Si$, δ 0.0) and DMSO-$d_6$ (δ 2.50 for $^1$H and δ 39.52 for $^{13}$C). Reverse phase high performance liquid chromatography (RP-HPLC) was performed on a Water 600 E multi-solvent delivery system, using a Waters 486 tunable absorbance detector, a 717 autosampler, and a ThermoHypersil Keystone Betabasic-18 column (150 Å pore size, 3 μm particle size, and mobile phase A; 0.1% TFA in 94.9% $H_2O$+5% $CH_3CN$ and mobile phase B, 0.1% TFA in 94.9% $CH_3CN$+5% $H_2O$). Final compound purities were determined by analytical RP-HPLC and were >95% in purity. All mass spectrometry data were collected at The Scripps Research Institute Center for Mass Spectrometry (ESI-MS; Agilent Technologies and LC/MSD TOF G1969A).

Procedure for Horner-Wittig Reaction: Preparation of (E)-ethyl 3-(4-(methoxy-methoxy)-3,5-dimethylstyryl)benzoate The general synthetic approach for the preparation of stilbenes is shown below in Scheme 2 that is followed by illustrative syntheses.

Scheme 2

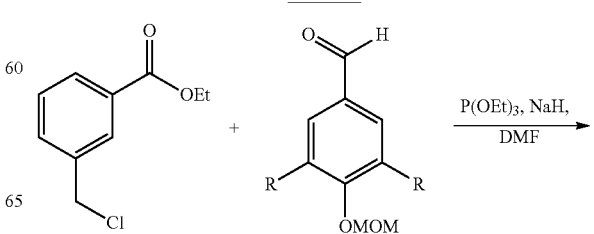

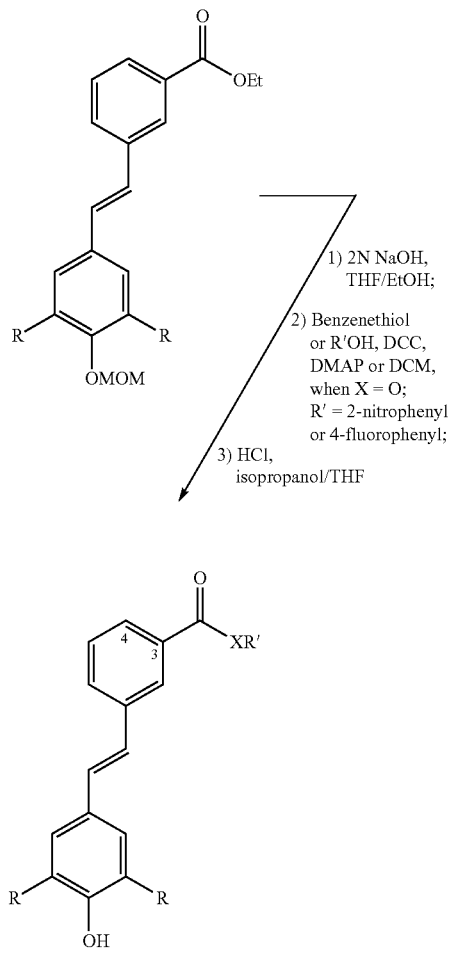

R = Br, CH₃

Ethyl 3-(chloromethyl)benzoate (1.192 g, 6 mmol) and triethylphosphite (1.273 mL, 7.2 mmol) were heated to 150° C. for 4 hours. The reaction mixture was cooled to 0° C. and then DMF was added. NaH (60% in oil, 0.252 g, 6.3 mmol) was added to the solution at 0° C. After stirring for 20 minutes, the solution of 4-(methoxymethoxy)-3,5-dimethylbenzaldehyde (4-MOMO-3,5-dimethylbenzaldehyde; 0.583 g, 3 mmol) in DMF was added to the mixture dropwise at 0° C. After 18 hours, the mixture was diluted with ethyl acetate (EtOAc) and the solution was washed with 10% citric acid and brine. After drying on Na₂SO₄, the organic layer was filtered and concentrated under reduced pressure. The compound was purified by column chromatography (9.5:0.5 Hexane:EtOAc) to afford (E)-ethyl 3-[4-(methoxymethoxy)-3,5-dimethylstyryl]-benzoate (0.726 g, 71%).

Procedure for Hydrolysis of Ethyl Ester: Preparation of (E)-3-(4-(methoxymethoxy)-3,5-dimethylstyryl)benzoic acid To a solution of (E)-ethyl 3-[4-(methoxymethoxy)-3,5-dimethylstyryl]benzoate (0.6 g, 1.762 mmol) in THF and EtOH (⅔ mL) was added 2N NaOH (1.762 mL, 3.524 mmol) at room temperature. The reaction mixture was stirred overnight (about 18 hours) at room temperature and diluted with EtOAc and acidified with 5% citric acid. The solution was washed with saturated brine and dried with Na₂SO₄. The solution was filtered and concentrated. (E)-3-[4-(methoxymethoxy)-3,5-dimethylstyryl]benzoic acid (0.533 g, 97%) was obtained without further purification (TLC indicated a pure compound).

Procedure for Esterification: Preparation of (E)-S-phenyl 3-(4-(methoxymethoxy)-3,5-dimethylstyryl)benzothioate To a solution of (E)-3-[4-(methoxymethoxy)-3,5-dimethylstyryl]benzoic acid (0.1 g, 0.320 mmol) in DCM (5 mL) were added DCC (72.6 mg, 0.352 mmol), DMAP (7.9 mg, 0.064 mmol), and benzenethiol (65.7 μL, 0.640 mmol) at room temperature. The reaction mixture was stirred overnight (about 18 hours) and filtered through Celite. The filtrate was washed with 10% citric acid, brine, and dried with Na₂SO₄. The solution was filtered and concentrated. The compound was purified by column chromatography (9:1 Hexane:EtOAc) to afford (E)-S-phenyl 3-(4-(methoxymethoxy)-3,5-dimethylstyryl)benzothioate in quantitative yield.

Procedure for Deprotection of MOM group: Preparation of (E)-S-phenyl 3-(4-hydroxy-3,5-dimethylstyryl)benzothioate To a solution of (E)-S-phenyl 3-(4-(methoxymethoxy)-3,5-dimethylstyryl)benzothioate (80 mg, 0.198 mmol) in i-PrOH and THF (½ mL) was added 0.5 mL of concentrated HCl. The reaction mixture was stirred overnight (about 18 hours). After removal of solvent under reduced pressure, the residue was dissolved in EtOAc. The solution was washed with brine and dried with Na₂SO₄. The solution was filtered and concentrated. The compound was purified by column chromatography (9:1 Hexane:EtOAc) to afford (E)-S-phenyl 3-(4-hydroxy-3,5-dimethylstyryl)-benzothioate in quantitative yield. Azo-linked compounds of Formula I are prepared following usual syntheses for preparing aromatic or heteroaromatic azo compounds. A typical scheme is shown in Scheme 3.

Scheme 3

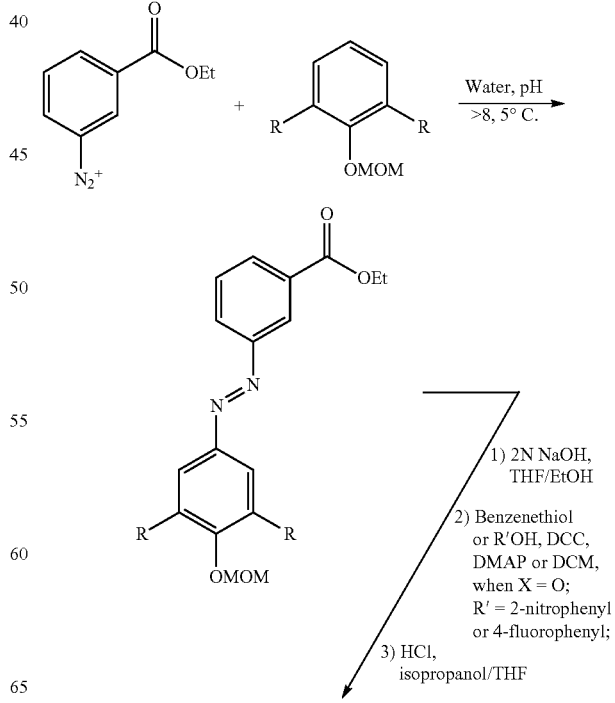

-continued

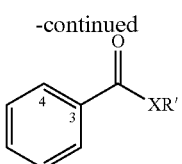

R = Br, CH₃

(E)-ethyl 3-(3,5-dibromo-4-(methoxymethoxy)styryl)benzoate

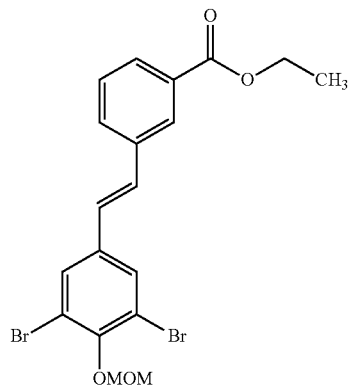

¹H-NMR (500 MHz, CDCl₃) δ 8.16 (s, 1H), 7.95 (d, J=7.8 Hz, 1H), 7.66 (s, 2H), 7.64 (d, J=7.8 Hz, 1H), 7.43 (dd, J=7.8, 7.8 Hz, 1H), 7.04 (d, J=16.3 Hz, 1H), 6.97 (d, J=16.3 Hz, 1H), 5.19 (s, 2H), 4.40 (q, J=7.1 Hz, 2H), 3.73 (s, 3H), 1.42 (t, J=7.1 Hz, 3H); ¹³C-NMR (125 MHz, CDCl₃) δ 166.28, 150.85, 136.68, 135.91, 131.06, 130.75, 130.58, 129.63, 129.07, 128.78, 127.58, 126.22, 118.65, 99.71, 61.12, 58.47, 14.32; ESI-MS: m/z (MH⁺): 468.9645 (calculated), 468.9645 (found).

(E)-3-(3,5-dibromo-4-(methoxymethoxy)-styryl)benzoic acid

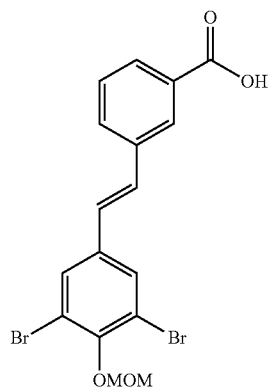

¹H-NMR (500 MHz, DMSO-d₆) δ 13.03 (s, 1H), 8.17 (s, 1H), 7.98 (s, 2H), 7.82-7.86 (m, 2H), 7.53 (dd, J=7.8, 7.8 Hz, 1H), 7.47 (d, J=16.5 Hz, 1H), 7.30 (d, J=16.5 Hz, 1H), 5.15 (s, 2H), 3.62 (s, 3H); ¹³C-NMR (125 MHz, DMSO-d₆) δ 167.03, 149.90, 136.86, 136.30, 131.22, 130.61, 130.56, 129.71, 128.95, 128.62, 127.33, 125.89, 118.08, 99.30, 57.84; ESI-MS: m/z ([M−H]⁻): 438.9186 (calculated), 38.9179 (found).

(E)-S-phenyl 3-(3,5-dibromo-4-(methoxymethoxy)styryl)benzothioate

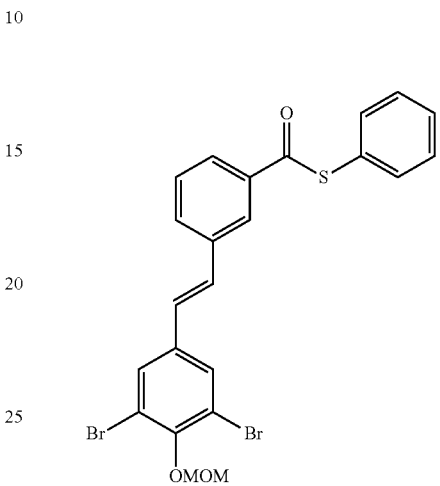

¹H-NMR (500 MHz, CDCl₃) δ 8.09 (s, 1H), 7.92 (d, J=7.8 Hz, 1H), 7.68 (d, J=7.8 Hz, 1H), 7.65 (s, 2H), 7.51-7.53 (m, 2H), 7.44-7.48 (m, 4H), 7.03 (d, J=16.3 Hz, 1H), 6.96 (d, J=16.3 Hz, 1H), 5.18 (s, 2H), 3.72 (s, 3H); ¹³C-NMR (125 MHz, CDCl₃) δ 189.82, 150.99, 137.20, 137.15, 135.70, 134.99, 131.38, 130.65, 129.55, 129.28, 129.24, 129.17, 127.15, 126.95, 126.73, 125.41, 118.68, 99.71, 58.46; ESI-MS: m/z (MH⁺): 532.9416 (calculated), 532.9397 (found).

(E)-S-phenyl 3-(3,5-dibromo-4-hydroxystyryl)benzothioate (1)

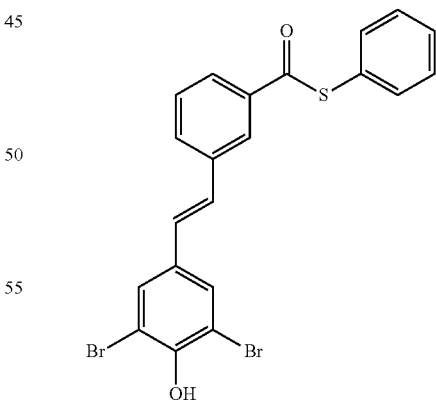

¹H-NMR (500 MHz, DMSO-d₆) δ 10.11 (s, 1H), 8.11 (dd, J=1.6, 1.6 Hz, 1H), 7.93 (d, J=7.8 Hz, 1H), 7.85-7.88 (m, 3H), 7.61 (dd, J=7.8, 7.8 Hz, 1H), 7.52-7.57 (m, 5H), 7.39 (d, J=16.5 Hz, 1H), 7.28 (d, J=16.5 Hz, 1H); ¹³C-NMR (125 MHz, DMSO-d₆) δ 189.05, 150.25, 137.93, 136.36, 134.88, 131.52, 131.29, 130.27, 129.69, 129.58, 129.37, 127.19, 127.06, 126.55, 125.95, 124.88, 112.22; ESI-MS: m/z (MH⁺): 488.9154 (calculated), 488.9157 (found).

(E)-ethyl 3-(4-(methoxymethoxy)-3,5-dimethyl-styryl)benzoate

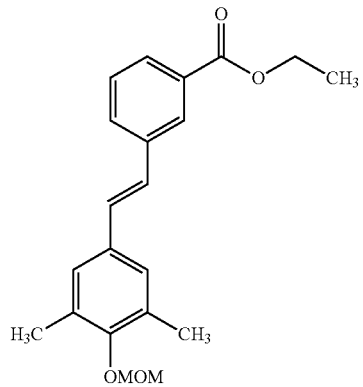

¹H-NMR (500 MHz, CDCl₃) δ 8.16 (s, 1H), 7.91 (d, J=7.7 Hz, 1H), 7.65 (d, J=8.1 Hz, 1H), 7.41 (dd, J=7.7 Hz, 1H), 7.20 (s, 2H), 7.09 (d, J=16.3 Hz, 1H), 7.02 (d, J=16.3 Hz, 1H), 4.98 (s, 2H), 4.40 (q, J=7.4 Hz, 2H), 3.62 (s, 3H), 2.32 (s, 6H), 1.42 (t, J=7.4 Hz, 3H); ¹³C-NMR (125 MHz, CDCl₃) δ 166.57, 154.86, 137.83, 132.86, 131.33, 130.93, 130.46, 129.37, 128.63, 128.25, 127.34, 127.15, 126.68, 99.12, 61.03, 57.40, 16.99, 14.36; ESI-MS: m/z (MH⁺): 341.1747 (calculated), 341.1747 (found).

(E)-3-(4-(methoxymethoxy)-3,5-dimethylstyryl) benzoic acid

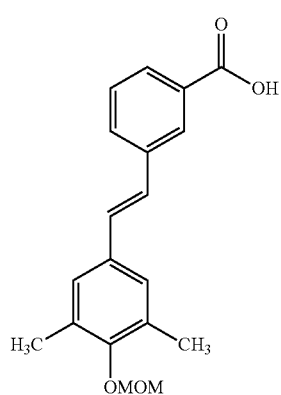

¹H-NMR (500 MHz, DMSO-d₆) δ 13.00 (s, 1H), 8.12 (s, 1H), 7.82 (d, J=1.7 Hz, 1H), 7.81 (d, J=1.7 Hz, 1H), 7.50 (dd, J=7.7, 7.7 Hz, 1H), 7.32 (s, 2H), 7.22 (s, 2H), 4.95 (s, 2H), 3.51 (s, 3H), 2.55 (s, 6H); ¹³C-NMR (125 MHz, DMSO-d₆) δ 167.11, 154.34, 137.51, 132.34, 131.16, 130.67, 130.16, 128.89, 128.85, 127.92, 126.97, 126.90, 126.36, 98.50, 56.71, 16.53; ESI-MS: m/z (MH⁺): 313.1434 (calculated), 313.1429 (found).

(E)-S-phenyl 3-(4-(methoxymethoxy)-3,5-dimethyl-styryl)benzothioate

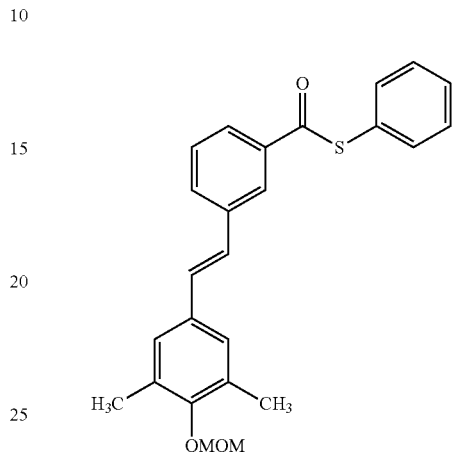

¹H-NMR (500 MHz, CDCl₃) δ 8.11 (s, 1H), 7.89 (d, J=7.8 Hz, 1H), 7.71 (d, J=7.8 Hz, 1H), 7.53-7.55 (m, 2H), 7.44-7.48 (m, 4H), 7.21 (s, 2H), 7.10 (d, J=16.3 Hz, 1H), 7.03 (d, J=16.3 Hz, 1H), 4.98 (s, 2H), 3.62 (s, 3H), 2.33 (s, 6H); ¹³C-NMR (125 MHz, CDCl₃) δ 190.10, 154.99, 138.33, 137.13, 135.06, 132.67, 131.37, 131.14, 129.92, 129.52, 129.25, 129.04, 127.38, 127.23, 126.33, 126.15, 125.17, 99.12, 57.39, 16.99; ESI-MS: m/z (MH⁺): 405.1519 (calculated), 405.1517 (found).

(E)-S-phenyl 3-(4-hydroxy-3,5-dimethylstyryl)ben-zothioate (2)

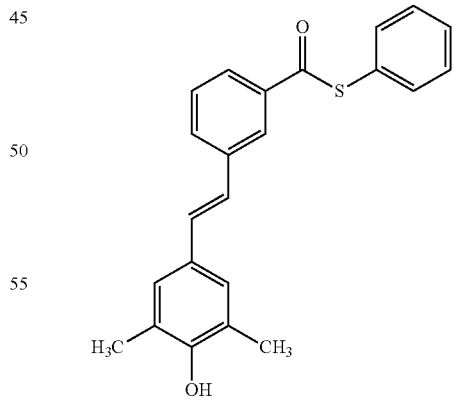

¹H-NMR (500 MHz, DMSO-d₆) δ 8.46 (s, 1H), 8.06 (s, 1H), 7.91 (d, J=7.8 Hz, 1H), 7.81 (d, J=7.8 Hz, 1H), 7.52-7.58 (m, 6H), 7.24 (s, 2H), 7.22 (d, J=16.8 Hz, 1H), 7.15 (d, J=16.4 Hz, 1H), 2.19 (s, 6H); ³³C-NMR (125 MHz, DMSO-d₆) δ 189.10, 153.57, 138.68, 136.34, 134.87, 130.89, 130.36, 129.63, 129.47, 129.33, 127.55, 126.94, 126.63, 125.18, 124.33, 124.28, 123.49, 16.54; ESI-MS: m/z (MH+): 361.1257 (calculated), 361.1254 (found).

(E)-2-nitrophenyl 3-(4-(methoxymethoxy)-3,5-dimethylstyryl)benzoate

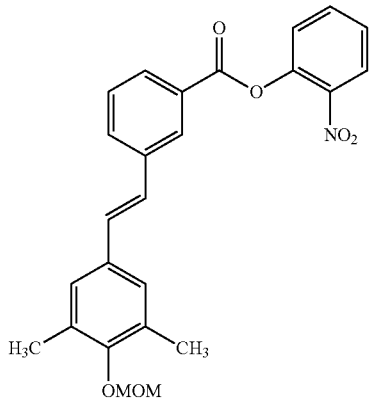

¹H-NMR (500 MHz, CDCl₃) δ 8.31 (s, 1H), 8.16 (dd, J=1.6, 8.2 Hz, 1H), 8.06 (d, J=7.8 Hz, 1H), 7.76 (d, J=7.8 Hz, 1H), 7.71 (dd, J=8.0, 8.0 Hz, 1H), 7.50 (dd, J=7.8, 7.8 Hz, 1H), 7.45 (dd, J=7.8, 7.8 Hz, 1H), 7.41 (dd, J=1.2, 8.2 Hz, 1H), 7.21 (s, 2H), 7.12 (d, J=16.3 Hz, 1H), 7.05 (d, J=16.3 Hz, 1H), 4.96 (s, 2H), 3.62 (s, 3H), 2.32 (s, 6H); ¹³C-NMR (125 MHz, CDCl₃) δ 164.33, 154.96, 144.36, 141.99, 138.30, 134.67, 132.68, 131.72, 131.35, 129.92, 129.09, 129.03, 128.88, 128.21, 127.23, 126.64, 126.24, 125.87, 125.38, 99.11, 57.39, 16.98; ESI-MS: m/z (MH+): 434.1598 (calculated), 434.1594 (found).

(E)-2-nitrophenyl 3-(4-hydroxy-3,5-dimethylstyryl) benzoate (3)

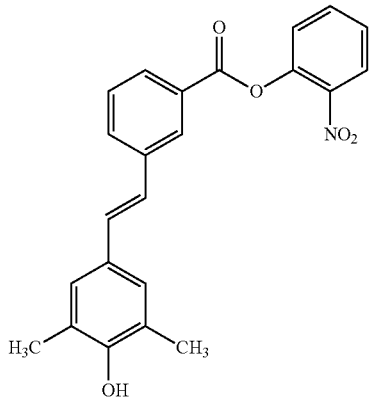 [SMILES: Cc1cc(/C=C/c2cccc(C(=O)Oc3ccccc3[N+](=O)[O-])c2)cc(C)c1O]

¹H-NMR (500 MHz, CDCl₃) δ 8.46 (s, 1H), 8.27 (s, 1H), 8.23 (dd, J=1.6, 8.2 Hz, 1H), 7.96 (dd, J=7.8, 7.8 Hz, 1H), 7.91 (dd, J=7.8, 7.8 Hz, 1H), 7.68 (dd, J=1.3, 8.1 Hz, 1H), 7.59-7.64 (m, 2H), 7.22-7.26 (m, 3H), 7.16 (d, J=16.4 Hz, 1H), 2.19 (s, 6H); ¹³C-NMR (125 MHz, CDCl₃) δ 163.80, 153.56, 143.23, 141.51, 138.57, 135.54, 131.37, 130.31, 129.36, 128.31, 128.09, 127.57, 127.38, 127.31, 126.93, 125.65, 125.42, 124.28, 123.44, 16.54; ESI-MS: m/z (MH+): 390.1336 (calculated), 390.1334 (found).

(E)-4-fluorophenyl 3-(4-(methoxymethoxy)-3,5-dimethylstyryl)benzoate

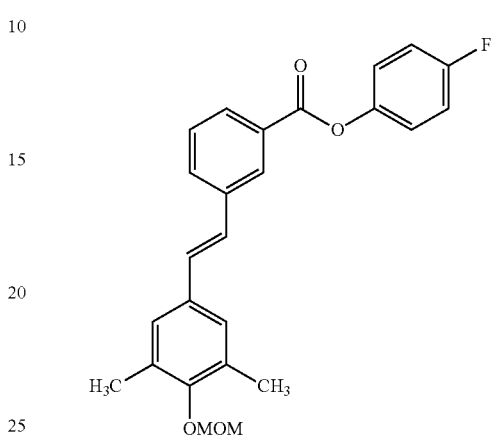

¹H-NMR (500 MHz, CDCl₃) δ 8.30 (s, 1H), 8.05 (d, J=7.7 Hz, 1H), 7.74 (d, J=7.8 Hz, 1H), 7.49 (dd, J=7.7, 7.7 Hz, 1H), 7.19-7.21 (m, 4H), 7.10-7.14 (m, 3H), 7.05 (d, J=16.3 Hz, 1H), 4.96 (s, 2H), 3.62 (s, 3H), 2.33 (s, 6H); ¹³C-NMR (125 MHz, CDCl₃) δ 165.15, 161.28, 159.34, 154.98, 146.74, 138.19, 132.69, 131.38, 131.30, 129.79, 129.72, 128.93, 128.77, 127.88, 127.21, 126.32, 123.14, 123.08, 116.25, 116.06, 99.13, 57.40, 17.00; ESI-MS: m/z (MH+): 407.1653 (calculated), 407.1659 (found).

(E)-4-fluorophenyl 3-(4-hydroxy-3,5-dimethylstyryl) benzoate (4)

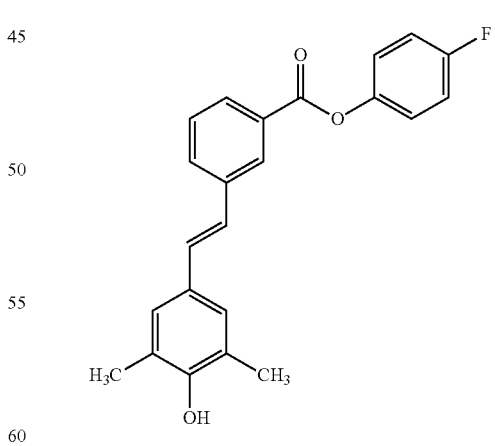

¹H-NMR (500 MHz, CDCl₃) δ 8.45 (s, 1H), 8.25 (s, 1H), 7.95 (d, J=7.8 Hz, 1H), 7.91 (d, J=7.8 Hz, 1H), 7.58 (d, J=7.8 Hz, 1H), 7.30-7.39 (m, 4H), 7.21 (m, 3H), 7.15 (d, J=16.5 Hz, 1H), 2.19 (s, 6H); ¹³C-NMR (125 MHz, CDCl₃) δ 164.53, 160.57, 158.64, 153.52, 146.62, 138.38, 130.87, 130.09, 129.17, 127.85, 127.61, 127.08, 126.88, 124.28, 123.68, 123.60, 116.13, 115.94, 16.53; ESI-MS: m/z (MH+): 363.1391 (calculated), 363.1392 (found).

(E)-3-(4-hydroxy-3,5-dimethylstyryl)-N-propylbenzamide (B1)

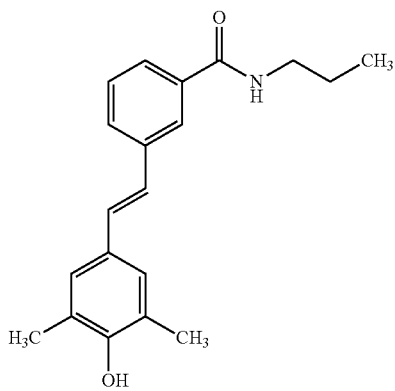

B1

To a solution of (E)-3-(4-(methoxymethoxy)-3,5-dimethylstyryl)benzoic acid (0.1 g, 0.32 mmol), EDC (0.125 g, 0.64 mmol), 1-hydroxy-7-azabenzo-triazole (HOAT; 87.1 mg, 0.64 mmol), and DMAP (7.8 mg, 0.064 mmol) in 2 mL of DMF was added propylamine (54 µL, 0.64 mmol) at room temperature. The reaction mixture was stirred overnight (about 18 hours) and diluted with EtOAc. The solution was washed with brine and dried with $Na_2SO_4$. The solution was filtered and concentrated.

MOM Deprotection

To a solution of crude (E)-3-(4-(methoxymethoxy)-3,5-dimethylstyryl)-N-propylbenzamide in 2 mL of THF and 1 mL of MeOH was added 0.5 mL of concentrated HCl. The reaction mixture was refluxed overnight (about 18 hours) and was diluted in EtOAc. The solution was washed with brine and dried with $Na_2SO_4$. The solution was filtered and concentrated. The residue was subjected to chromatography over silica gel (Hexanes/EtOAc=2.5/1) to provide Compound B1 (97 mg, 98% in 2 steps). $^1$H-NMR (500 MHz, $CDCl_3$) δ 7.88 (s, 1H), 7.57 (dd, J=7.8, 7.8 Hz, 2H), 7.38 (dd, J=7.7, 7.7 Hz, 1H), 7.16 (s, 2H), 7.06 (d, J=16.3 Hz, 1H), 6.95 (d, J=16.3 Hz, 1H), 6.16 (s, 1H), 4.84 (s, 1H), 3.44 (m, 2H), 2.28 (s, 6H), 1.66 (m, 2H), 1.01 (t, J=7.4 Hz, 3H); $^{13}$C-NMR (125 MHz, $CDCl_3$) δ 167.68, 152.46, 138.35, 135.24, 129.74, 129.10, 128.89, 128.76, 127.05, 125.03, 124.97, 124.69, 123.40, 41.81, 22.93, 15.99, 11.45; ESI-MS: m/z (MH+): 310.1801 (calc'd), 310.1806 (found).

A reaction scheme for the preparation of Compounds A1, A2 and B2 is shown below in Scheme 4, followed by the details for the synthesis of those compounds. The compound numbers shown in the scheme are used for illustrative purposes in that scheme and the following synthetic discussion and are not the numbers used for identification of contemplated compounds of the invention that are discussed previously.

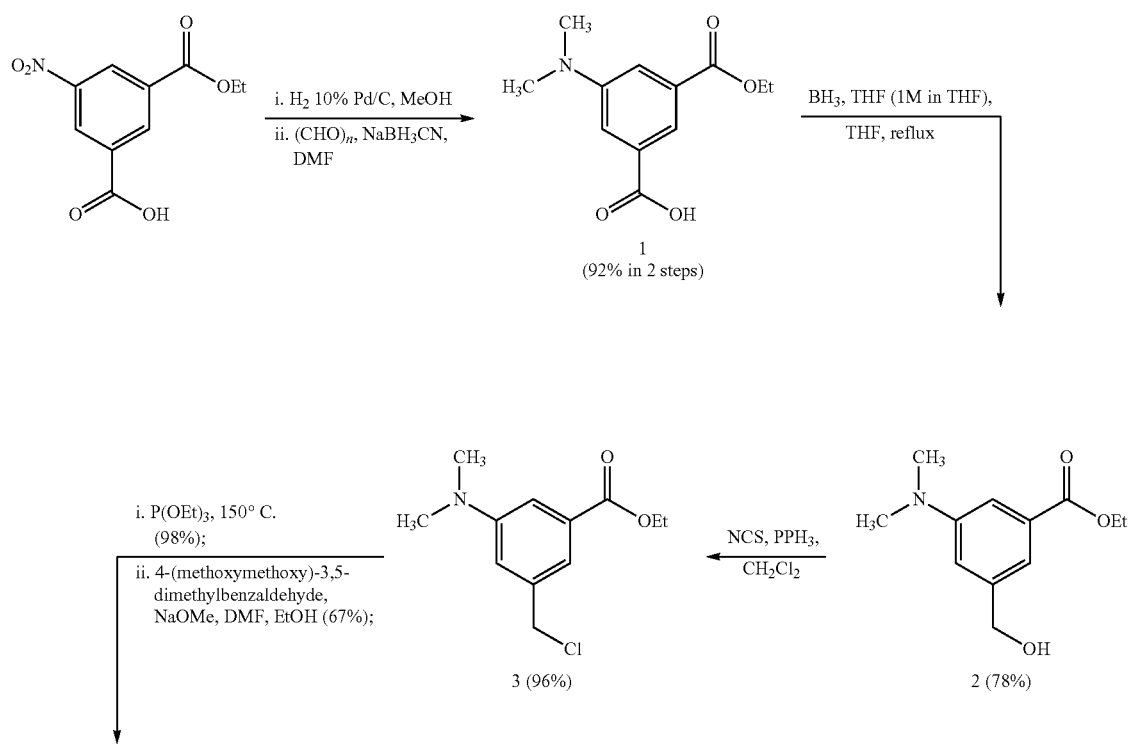

Scheme 4

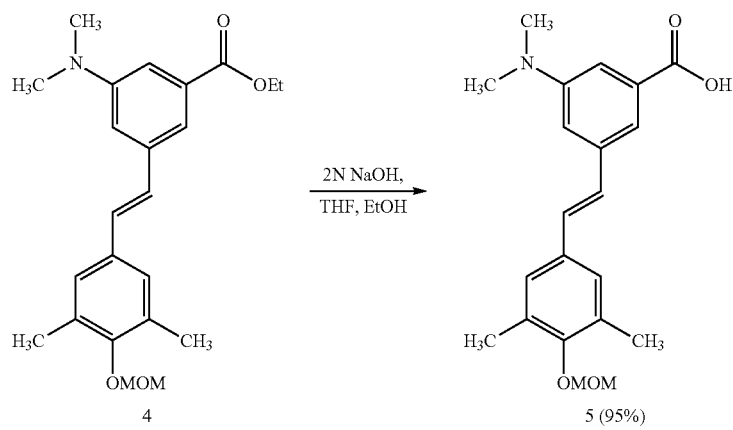

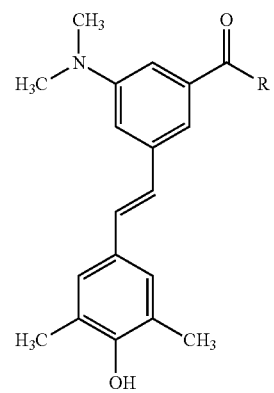

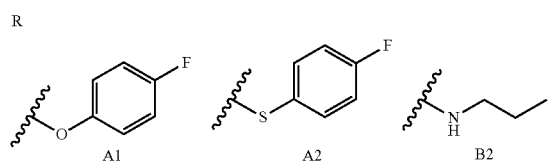

3-(Dimethylamino)-5-(ethoxycarbonyl)benzoic acid (1)

A mixture of 3-(ethoxycarbonyl)-5-nitrobenzoic acid (5 g, 20.905 mmol) and 10% Pd/C (1.11 g, 1.045 mmol) in 100 mL of MeOH was stirred under $H_2$ gas at room temperature. After 4 hours, the mixture was filtered through Celite and concentrated to give 3-amino-5-(ethoxycarbonyl)benzoic acid. To a solution of 3-amino-5-(ethoxycarbonyl)benzoic acid (2 g, 9.56 mmol) in 10 mL of DMF was added formaldehyde (about 37% wt % in $H_2O$, 7.118 mL, 95.60 mmol) at room temperature. After 10 minutes, the solution was cooled to 0° C. and $NaBH_3CN$ (1.897 g, 28.68 mmol) was added. The mixture was stirred at room temperature for 3 hours. The solution was diluted with EtOAc. The solution was washed with 5% citric acid and saturated brine and dried with $Na_2SO_4$. The solution was filtered and concentrated to give 3-(Dimethylamino)-5-(ethoxycarbonyl)benzoic acid Compound 1 (2.1 g, 92% in two steps). $^1$H-NMR (500 MHz, DMSO-$d_6$) δ 7.78 (s, 1H), 7.44 (s, 1H), 7.41 (s, 1H), 4.32 (q, J=7.1 Hz, 2H), 2.99 (s, 6H), 1.33 (t, J=7.1 Hz, 3H); $^{13}$C-NMR (125 MHz, DMSO-$d_6$) δ 166.99, 165.54, 150.14, 131.76, 130.79, 116.89, 116.25, 115.59, 60.79, 39.84, 14.05; ESI-MS: m/z (MH$^+$): 238.1074 (calc'd), 238.1076 (found).

Ethyl 3-(dimethylamino)-5-(hydroxymethyl)benzoate (2)

To a solution of Compound 1 (4 g, 16.86 mmol) in 40 mL of THF was added $BH_3$·THF (1M in THF, 42.15 mL, 42.15 mmol) dropwise at 0° C. The mixture was refluxed for 4 hours and cooled to room temperature. The solvent was evaporated, diluted with EtOAc, and washed with saturated $NaHCO_3$ and brine and dried with $Na_2SO_4$. The solution was filtered and concentrated. The residue was subjected to chromatography over silica gel (Hexanes/EtOAc=2/1) to give Compound 2 (2.95 g, 78%). $^1$H-NMR (500 MHz, CDCl$_3$) δ 7.35 (s, 1H), 7.32 (s, 1H), 6.91 (s, 1H), 4.68 (s, 2H), 4.36 (q, J=7.1 Hz, 2H), 2.99 (s, 6H), 1.39 (t, J=7.1 Hz, 3H); $^{13}$C-NMR (125 MHz, CDCl$_3$) δ 167.15, 150.71, 141.93, 131.36, 115.87, 114.91, 112.57, 65.41, 60.89, 40.54, 14.32; ESI-MS: m/z (MH$^+$): 224.1281 (calc'd), 224.1283 (found).

Ethyl 3-(chloromethyl)-5-(dimethylamino)benzoate (3)

To a solution of Compound 2 (3.45 g, 15.452 mmol) and PPh$_3$ (6.14 g, 23.17 mmol) in 70 mL of DCM was added NCS (3.19 g, 23.178 mmol) at 0° C. The reaction mixture was stirred for 1.5 hours. After removal of solvent under reduced pressure, the residue was dissolved in Et$_2$O. The solution was washed with brine and dried with MgSO$_4$. The solution was filtered and concentrated. The residue was subjected to chromatography over silica gel (Hexanes/EtOAc=9.5/0.5) to give Compound 3 (3.585 g, 96%). $^1$H-NMR (500 MHz, CDCl$_3$) δ 7.38 (s, 1H), 7.35 (s, 1H), 6.89 (s, 1H), 4.57 (s, 2H), 4.37 (q, J=7.1 Hz, 2H), 3.00 (s, 6H), 1.39 (t, J=7.1 Hz, 3H); $^{13}$C-NMR (125 MHz, CDCl$_3$) δ 166.73, 150.63, 138.35, 131.59, 117.31, 116.20, 113.22, 60.95, 46.40, 40.43, 14.31; ESI-MS: m/z (MH$^+$): 242.0942 (calc'd), 242.0944 (found).

(E)-Ethyl 3-(dimethylamino)-5-(4-(methoxymethoxy)-3,5-dimethylstyryl)benzoate (4)

Compound 3 (1.224 g, 4.277 mmol) and triethylphosphite (1.512 mL, 8.555 mmol) were heated to 150° C. for 3 hours. The reaction mixture was cooled to 0° C. and then 6 mL of DMF and 6 mL of EtOH were added. NaOMe (486 mg, 8.554 mmol) and 4-(methoxymethoxy)-3,5-dimethylbenzaldehyde (0.831 g, 4.277 mmol) were added to the solution. After 18 hours, the mixture was diluted with EtOAc and the solution was washed with brine. After drying on Na$_2$SO$_4$, the organic layer was filtered and concentrated under reduced pressure. The residue was subjected to chromatography over silica gel (Hexanes/EtOAc=9/1) to give Compound 4 (1.10 g, 67%). $^1$H-NMR (500 MHz, CDCl$_3$) δ 7.56 (s, 1H), 7.30 (m, 1H), 7.20 (s, 2H), 7.06 (d, J=16.3 Hz, 1H), 6.99 (d, J=16.3 Hz, 1H), 6.97 (s, 1H), 4.96 (s, 2H), 4.39 (q, J=7.1 Hz, 2H), 3.62 (s, 3H), 3.03 (s, 6H), 2.32 (s, 6H), 1.42 (t, J=7.1 Hz, 3H); $^{13}$C-NMR (125 MHz, CDCl$_3$) δ 167.23, 154.65, 150.72, 138.36, 133.12, 131.48, 131.24, 128.70, 127.78, 127.07, 115.70, 114.53, 112.47, 99.11, 60.92, 57.39, 40.65, 16.99, 14.40; ESI-MS: m/z (MH$^+$): 384.2169 (calc'd), 384.2173 (found).

(E)-3-(dimethylamino)-5-(4-(methoxymethoxy)-3,5-dimethylstyryl)benzoic acid (5)

To a solution of Compound 4 (1.046 g, 2.728 mmol) in THF and EtOH (⅜ mL) was added 2 N NaOH (2.728 mL, 5.456 mmol) at room temperature. The reaction mixture was stirred overnight (about 18 hours) at room temperature and diluted with EtOAc and acidified with 5% citric acid. The solution was washed with saturated brine and dried with Na$_2$SO$_4$. The solution was filtered and concentrated. Compound 5 (0.94 g, 97%) was obtained without further purification (TLC indicated a pure compound). $^1$H-NMR (500 MHz, DMSO-d$_6$) δ 7.47 (s, 1H), 7.31 (s, 2H), 7.12-7.16 (m, 4H), 4.94 (s, 2H), 3.51 (s, 3H), 2.98 (s, 6H), 2.25 (s, 6H); $^{13}$C-NMR (125 MHz, DMSO-d$_6$) δ 167.75, 154.18, 150.47, 137.92, 132.56, 131.62, 130.63, 128.12, 127.43, 126.86, 114.89, 114.16, 111.62, 98.51, 56.71, 40.03, 16.55; ESI-MS: m/z (MH$^+$): 356.1856 (calc'd), 356.1854 (found).

(E)-4-fluorophenyl 3-(dimethylamino)-5-(4-hydroxy-3,5-dimethylstyryl)benzoate (A1)

To a solution of Compound 5 (80 mg, 0.225 mmol) in DCM (3 mL) were added DCC (70 mg, 0.338 mmol), DMAP (5.5 mg, 0.045 mmol), and 4-fluorophenol (61.5 mg, 0.450 mmol) at room temperature. The reaction mixture was stirred overnight (about 18 hours) and filtered through Celite. The filtrate was washed with brine, and dried with Na$_2$SO$_4$. The solution was filtered and concentrated. The residue was subjected to chromatography over silica gel (Hexanes/EtOAc=8/1) to give (E)-4-fluorophenyl 3-(dimethylamino)-5-(4-(methoxymethoxy)-3,5-dimethyl-styryl)benzoate.
MOM Deprotection
To a solution of (E)-4-fluorophenyl 3-(dimethylamino)-5-(4-(methoxymethoxy)-3,5-dimethylstyryl)-benzoate (81 mg, 0.180 mmol) in i-PrOH and THF (½ mL) was added 0.5 mL of concentrated HCl. The reaction mixture was stirred overnight (about 18 hours). After removal of solvent under reduced pressure, the residue was dissolved in EtOAc. The solution was washed with brine and dried with Na$_2$SO$_4$. The solution was filtered and concentrated. The compound was purified by column chromatography (5:1 Hexane:EtOAc) to give Compound A1 (81% in 2 steps). $^1$H-NMR (500 MHz, DMSO-d$_6$) δ 8.40 (s, 1H), 7.61 (s, 1H), 7.29-7.36 (m, 4H), 7.16-7.24 (m, 5H), 7.08 (d, J=16.4 Hz, 1H), 3.01 (s, 6H), 2.18 (s, 6H); $^{13}$C-NMR (125 MHz, DMSO-d$_6$) δ 165.15, 160.50, 158.58, 153.31, 150.61, 146.72, 138.77, 129.61, 129.32, 127.80, 126.75, 124.66, 124.24, 123.71, 123.64, 116.11, 115.92, 114.93, 114.80, 111.21, 40.02, 16.54; ESI-MS: m/z (MH$^+$): 406.1813 (calc'd), 406.1829 (found).

(E)-S-4-fluorophenyl 3-(dimethylamino)-5-(4-hydroxy-3,5-dimethylstyryl)-benzothioate (A2)

To a solution of Compound 5 (80 mg, 0.225 mmol) in DCM (3 mL) were added DCC (70 mg, 0.338 mmol), DMAP (5.5 mg, 0.045 mmol), and 4-fluorobenzenethiol (37 µL, 0.338 mmol) at room temperature. The reaction mixture was stirred overnight (about 18 hours) and filtered through Celite. The filtrate was washed with brine, and dried with Na$_2$SO$_4$. The solution was filtered and concentrated. The residue was subjected to chromatography over silica gel (Hexanes/EtOAc=8/1) to give (E)-S-4-fluorophenyl 3-(dimethylamino)-5-(4-(methoxymethoxy)-3,5-dimethylstyryl)benzothioate.
MOM Deprotection
To a solution of (E)-S-4-fluorophenyl 3-(dimethylamino)-5-(4-(methoxymethoxy)-3,5-dimethyl-styryl)benzothioate (80 mg, 0.172 mmol) in i-PrOH and THF (½ mL) was added 0.5 mL of concentrated HCl. The reaction mixture was stirred overnight. After removal of solvent under reduced pressure, the residue was dissolved in EtOAc. The solution was washed with brine and dried with Na$_2$SO$_4$. The solution was filtered and concentrated. The compound was purified by column chromatography (6:1 Hexane:EtOAc) to give Compound A2 (73% in 2 steps). $^1$H-NMR (500 MHz, DMSO-d$_6$) δ 8.42 (s, 1H), 7.57-7.60 (m, 2H), 7.42 (s, 1H), 7.37 (t, J=8.9 Hz, 2H), 7.23 (s, 2H), 7.16-7.20 (m, 2H), 7.07 (d, J=16.4 Hz, 1H), 7.02 (s, 1H), 3.00 (s, 6H), 2.19 (s, 6H); $^{13}$C-NMR (125 MHz, DMSO-d$_6$) δ 189.74, 163.84, 161.87, 153.38, 150.65, 139.07, 137.30, 137.23, 136.94, 129.59, 127.72, 126.81, 124.50, 124.25, 122.76, 116.52, 116.35, 114.72, 112.26, 108.06, 39.92, 16.53; ESI-MS: m/z (MH$^+$): 422.1584 (calc'd), 42.1599 (found).

(E)-3-(dimethylamino)-5-(4-hydroxy-3,5-dimethylstyryl)-N-propylbenzamide (B2)

To a solution of 5 (80 mg, 0.225 mmol), EDC (88 mg, 0.45 mmol), HOAT (61.2 mg, 0.45 mmol), and DMAP (5.5 mg, 0.045 mmol) in 2 mL of DMF was added propylamine (37.8 □L, 0.45 mmol) at room temperature. The reaction mixture was stirred overnight (about 18 hours) and diluted with EtOAc. The solution was washed with brine and dried with Na$_2$SO$_4$. The solution was filtered and concentrated.
MOM Deprotection
To a solution of crude (E)-3-(dimethylamino)-5-(4-(methoxymethoxy)-3,5-dimethylstyryl)-N-propylbenzamide in 2 mL of THF and 1 mL of MeOH was added 0.5 mL of concentrated HCl. The reaction mixture was stirred overnight (about 187 hours). The solution was evaporated under reduced pressure and the remained water was lyophilized. The residue was subjected to chromatography over silica gel (Hexanes/EtOAc=6/4) to provide Compound B2 (68% in 2 steps). $^1$H-NMR (500 MHz, DMSO-$d_6$) δ 8.35-8.38 (m, 2H), 7.34 (s, 1H), 7.18 (s, 2H), 7.10 (d, J=16.4 Hz, 1H), 6.97-7.02 (m, 3H), 3.22 (q, J=6.7 Hz, 2H), 2.96 (s, 6H), 2.19 (s, 6H), 1.55 (m, 2H), 0.90 (t, J=7.1 Hz, 3H); $^{13}$C-NMR (125 MHz, DMSO-$d_6$) δ 166.63, 153.17, 150.42, 137.96, 135.66, 128.55, 127.96, 126.54, 125.42, 124.28, 112.60, 112.43, 109.77, 40.86, 40.12, 22.36, 16.55, 11.40; ESI-MS: m/z (MH$^+$): 352.2151 (calc'd), 352.4699 (found).

Fluorimetric Assay

WT-TTR was expressed and purified from an *E. coli* expression system as described previously. [Lashuel et al., *Biochemistry* 1999, 38:13560]. The covalent modifiers (Compounds 4 or 2) or the non-covalent TTR ligand Compound B2 (5 μL of a 1.44 mM solution in DMSO) were added to 1 mL of a solution of WT-TTR (0.2 mg/mL, 3.6 μM) in 10 mM phosphate, 100 mM KCl and 1 mM EDTA (pH 7.0) in a 2 mL Eppendorf tube. The samples were vortexed, and incubated for 18 hours at 25° C. The fluorescence changes were monitored using a Varian Cary 50 spectrofluorometer at 20° C. in a 1 cm path length quartz cell. The excitation slits was set at 5 nm and the emission slits was set at 10 mm. The samples were excited at 328 nm and the emission spectra were collected from 330 to 550 nm (FIG. 4). The time-dependent fluorescence changes were monitored in similar manner (FIG. 5).

Each of the patents, patent applications and articles cited herein is incorporated by reference. The use of the article "a" or "an" is intended to include one or more.

The foregoing description and the examples are intended as illustrative and are not to be taken as limiting. Still other variations within the spirit and scope of this invention are possible and will readily present themselves to those skilled in the art.

ASPECTS OF THE INVENTION

1. A compound corresponding in structure to Formula I

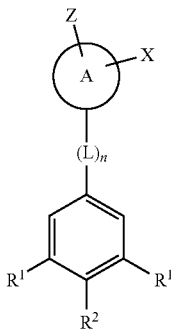

wherein
$R^1$ is a halide, a methyl, monofluoro-, difluoro- or trifluoromethyl group;
$R^2$ is H, OH or NH$_2$;
n is zero or one;
L is a linker that is Q=Q or CH$_2$—CH$_2$ when n is one and is absent when n is zero, so that the two depicted cyclic structures are bonded directly to each other, where Q=Q is N=N or HC=CH;
the circle A is an aromatic or heteroaromatic ring structure containing one 5- or 6-membered ring or a fused ring system containing one 5- and one 6-membered ring or two 6-membered rings;

X is a reactive substituent that reacts with an amine in an aqueous environment to bond the amine to the depicted compound; and Z is H, or a second linker, L$_2$, that is an X group that is the same or different from the previously mentioned X group, NR$^3$R$^4$, where R$^3$ and R$^4$ are the same or different and are H, methyl or ethyl, a 1,3-diketo group or a metal ion chelating group.

2. The compound according to aspect 1, wherein X is a carboxylic ester or thioester, an azetidin-2-one, a Michael acceptor, an epoxide, aziridine or thienyl group or a β-haloacetyl group.

3. The compound according to aspect 2, wherein n is one.

4. The compound according to aspect 3, wherein circle A is an aromatic or heteroaromatic ring structure containing one 5- or 6-membered ring.

5. The compound according to aspect 4, wherein said heterocyclic ring contains one to three heteroatoms that are oxygen, nitrogen, sulfur and mixtures thereof.

6. The compound according to aspect 5, wherein said heterocyclic ring contains 6-members and the heteroatom is nitrogen.

7. The compound according to aspect 3, wherein circle A is an aromatic or heteroaromatic ring structure containing two fused rings having one 5- and one 6-membered ring or two 6-membered rings.

8. The compound according to aspect 7, wherein said heterocyclic ring contains one to three heteroatoms that are oxygen, nitrogen, sulfur and mixtures thereof.

9. The compound according to aspect 1, wherein L is Q=Q.

10. The compound according to aspect 1, wherein Z is L$_2$.

11. The compound according to aspect 1, that corresponds in structure to Formula Ic, below,

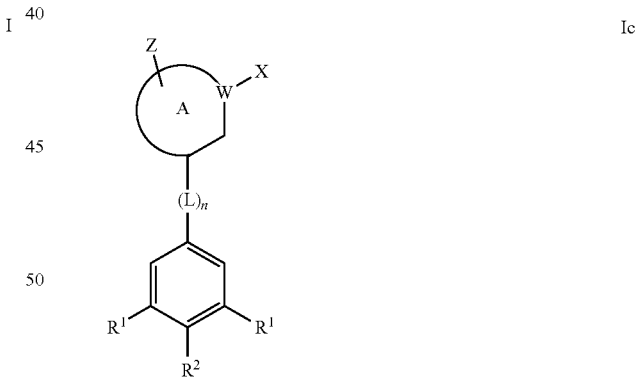

where L, n, X, Z, R$^1$ and R$^2$ are as defined before, W is N or C, preferably C, and the depicted structure A is an aromatic or heteroaromatic ring structure containing one 5- or 6-membered ring, and wherein L and X are in a 1,3-substitution relationship on the ring to which they are bonded.

12. The compound according to aspect 11, wherein structure A is a six-membered ring.

13. The compound according to aspect 12, wherein the six-membered ring is a hydrocarbyl ring.

14. The compound according to aspect 12, wherein Z is NR$^3$R$^4$.

15. A compound corresponding in structure to Formula Ia

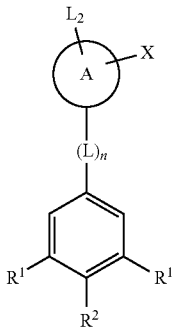

Ia wherein

R$^1$ is a halide, a methyl, monofluoro-, difluoro- or trifluoromethyl group;

R$^2$ is H, OH or NH$_2$;

n is zero or one;

L is a linker that is Q=Q or CH$_2$—CH$_2$ when n is one and is absent when n is zero, so that the two depicted cyclic structures are bonded directly to each other, where Q=Q is N=N or HC=CH;

the circle A is an aromatic or heteroaromatic ring structure containing one 5- or 6-membered ring or a fused ring system containing one 5- and one 6-membered ring or two 6-membered rings;

X is a reactive substituent that reacts with an amine in an aqueous environment to bond the amine to the depicted compound; and L$_2$ is an X group that is the same or different from the previously mentioned X group, NR$^3$R$^4$, where R$^3$ and R$^4$ are the same or different and are H, methyl or ethyl, a 1,3-diketo group or a metal ion chelating group.

16. The compound according to aspect 15, wherein L$_2$ is a metal ion chelating group.

17. The compound according to aspect 16, wherein said metal ion chelating group chelates a radionuclide.

18. The compound according to aspect 16, wherein said metal ion chelating group chelates a magnetic resonance imaging contrast ion.

19. The compound according to aspect 15, wherein L$_2$ is NR$^3$R$^4$.

20. The compound according to aspect 19, wherein R$^3$ and R$^4$ are both methyl.

21. A conjugate compound corresponding in structure to Formula Ib

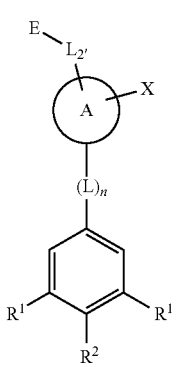

Ib wherein

R$^1$ is a halide, a methyl, monofluoro-, difluoro- or trifluoromethyl group;

R$^2$ is H, OH or NH$_2$;

n is zero or one;

L is a linker that is Q=Q or CH$_2$—CH$_2$ when n is one and is absent when n is zero, so that the two depicted cyclic structures are bonded directly to each other, where Q=Q is N=N or HC=CH;

the circle A is an aromatic or heteroaromatic ring structure containing one 5- or 6-membered ring or a fused ring system containing one 5- and one 6-membered ring or two 6-membered rings;

X is a reactive substituent that reacts with an amine in an aqueous environment to bond the amine to the depicted compound; and L$_{2'}$ is a reacted linker group that is an X group that is the same as or different from the previously mentioned X group, a 1,3-diketo group or a metal ion chelating group; and E is bonded to L$_{2'}$ as a conjugated small molecule drug, a peptide, a peptide hormone or a chelator for a metal ion that can be a radionuclide or contrast agent, but only one of E and L$_{2'}$ is a chelator for a metal ion.

22. The conjugate compound according to aspect 21, wherein E is a chelator for a radionuclide metal ion.

23. The conjugate compound according to aspect 21, wherein E is a chelator for a metal ion contrast agent.

24. A method for assaying for the presence of transthyretin (TTR) in a sample to be assayed that comprises the steps of:

a) admixing a binding/reaction sufficient amount compound of claim 1 with a sample to be assayed, b) maintaining that admixture for a time period sufficient for said compound to bind to TTR present in the sample, react therewith and form a protein-reacted compound, and c) determining the presence of reacted compound.

25. The method according to aspect 24, wherein the sample to be assayed is blood plasma or serum.

26. The method according to aspect 24, wherein the presence of the protein-reacted compound is determined using mass spectral analysis.

27. The method according to aspect 24, wherein the presence of the protein-reacted compound is determined using fluorescence emitted by the protein-reacted compound.

28. The method according to aspect 24, wherein Q=Q is HC=CH.

29. A pharmaceutical composition that comprises a transthyretin (TTR) fibril formation-inhibiting amount of a compound of aspect 1 dissolved or dispersed in a pharmaceutically acceptable diluent.

30. A method of treating transthyretin (TTR) amyloidosis in a subject in need thereof that comprises administering to that subject a pharmaceutical composition according to aspect 29.

31. The method according to aspect 30 that comprises repeating said administration a plurality of times in one week.

32. A method of inhibiting transthyretin (TTR) fibril formation that comprises the steps of a) contacting an aqueous composition containing TTR with a stabilizing amount of a compound of aspect 1; and b) maintaining that contact for a time period sufficient for the compound to bind to, react with and thereby stabilize TTR.

33. A method for identifying a non-covalent transthyretin (TTR) kinetic stabilizer compound that comprises the steps of a) admixing a binding-sufficient amount of a candidate non-covalent transthyretin (TTR) kinetic stabilizer compound and an aqueous composition that contains a predetermined amount of TTR to form a first binding admixture;

b) maintaining the first binding admixture for a time period sufficient for the candidate compound to bind to TTR;

c) admixing a binding/reaction sufficient amount of a compound of aspect 1 wherein Q=Q is HC=CH with the first binding admixture to form a binding/reaction admixture;

d) maintaining the binding/reaction admixture for a time period sufficient for the compound of step c) to bind to and react with TTR; and e) determining whether the reaction of the compound of step c) with TTR has been inhibited, wherein the presence of reaction inhibition identifies the candidate as a non-covalent TTR kinetic stabilizer compound.

34. The method according to aspect 33 wherein whether the reaction of the compound of step c) with TTR has been inhibited is determined using fluorescence data.

35. The method according to aspect 33 wherein whether the reaction of the compound of step c) with TTR has been inhibited is determined using liquid chromatography-mass spectral data.

wherein the depicted structure Ar is a hydrocarbyl aromatic ring structure, $R^1$ is a halide, a methyl, monofluoro-, difluoro- or trifluoromethyl group;

$R^2$ is H, OH or $NH_2$;

n is one;

L is a linker that is HC=CH;

X is a reactive substituent that reacts with an amine in an aqueous environment to bond the amine to the depicted compound that is a carboxylic ester or thioester, an azetidin-2-one, a Michael acceptor, an epoxide, aziridine or thienyl group or a □-haloacetyl group, and L and X are in a 1,3-substitution relationship on the ring to which they are bonded; and Z is H, or a second linker, $L_2$, that is an X group that is the same as or different from the previously mentioned X

---

---

What is claimed:

1. A method for assaying for the presence of transthyretin (TTR) in a sample to be assayed that comprises the steps of:

a) admixing a binding/reaction sufficient amount of a covalent TTR kinetic stabilizer compound of Formula II with a sample to be assayed,

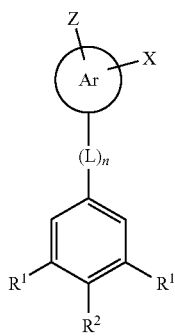

II group, a $NR^3R^4$ group, where $R^3$ and $R^4$ are the same or different and are H, methyl or ethyl, a 1,3-diketo group or a metal ion chelating group;

b) maintaining that admixture for a time period sufficient for said compound to bind to TTR present in the sample, react therewith and form a covalently-bound reacted compound, and c) determining the presence of said reacted compound.

2. The method according to claim 1, wherein the sample to be assayed is blood plasma or serum.

3. The method according to claim 1, wherein X substituent reactive group is a carboxylic acid ester or thioester prepared using an aromatic or heteroaromatic alcohol or thiol.

4. The method according to claim 1, wherein Z is $NR^3R^4$.

5. The method according to claim 4, wherein $R^3$ and $R^4$ are both methyl.

6. The method according to claim 1, wherein compound of Formula II has the structural formula
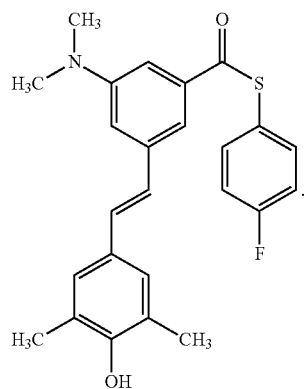 [SMILES: Cc1cc(/C=C/c2cc(C(=O)Sc3ccc(F)cc3)cc(N(C)C)c2)cc(C)c1O]
7. The method according to claim 1, wherein compound of Formula II has the structural formula
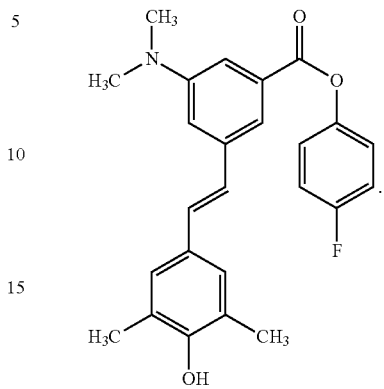
* * * * *

UNITED STATES PATENT AND TRADEMARK OFFICE
CERTIFICATE OF CORRECTION

PATENT NO.         : 8,703,815 B2
APPLICATION NO.    : 13/516963
DATED              : April 22, 2014
INVENTOR(S)        : Jeffery W. Kelly and Sungwook Choi Page 1 of 1

It is certified that error appears in the above-identified patent and that said Letters Patent is hereby corrected as shown below:

In the Specification:

Column 1, Lines 13-16; Change:

"The present invention was made with governmental support under Contract No. DK046335 awarded by the National Institutes of Health. The government has certain rights in this invention."

to

"This invention was made with government support under DK046335 awarded by the National Institutes of Health. The government has certain rights in the invention."

Signed and Sealed this
Fourteenth Day of June, 2016

Michelle K. Lee
*Director of the United States Patent and Trademark Office*

SEQUENCE LISTING

<160> NUMBER OF SEQ ID NOS: 2

<210> SEQ ID NO 1
<211> LENGTH: 27
<212> TYPE: DNA
<213> ORGANISM: Artificial sequence
<220> FEATURE:
<223> OTHER INFORMATION: synthetic sequence

<400> SEQUENCE: 1
ccgaggcagt cctgccatca atgtggc                                    27

<210> SEQ ID NO 2
<211> LENGTH: 27
<212> TYPE: DNA
<213> ORGANISM: Artificial sequence
<220> FEATURE:
<223> OTHER INFORMATION: synthetic sequence

<400> SEQUENCE: 2
gccacattga tggcaggact gcctcgg                                    27